US012643957B2

(12) United States Patent
Pritsker et al.

(10) Patent No.: US 12,643,957 B2
(45) Date of Patent: *Jun. 2, 2026

(54) ANTIBODIES TO PLASMINOGEN ACTIVATOR INHIBITOR-1 (PAI-1) AND USES THEREOF

(71) Applicant: Sanofi, Paris (FR)

(72) Inventors: Alla Pritsker, Bridgewater, NJ (US); Patrick Grailhe, Paris (FR); Alexey Rak, Paris (FR); Magali Mathieu, Paris (FR); Christopher Ryan Morgan, Bridgewater, NJ (US); Nicolas Baurin, Paris (FR); Bruno Poirier, Paris (FR); Cyril Daveu, Paris (FR); Francis Duffieux, Paris (FR); Han Li, Yardley, PA (US); Dorothea Kominos, Millington, NJ (US); Philip Janiak, Paris (FR)

(73) Assignee: Sanofi, Paris (FR)

( * ) Notice: Subject to any disclaimer, the term of this patent is extended or adjusted under 35 U.S.C. 154(b) by 273 days.

This patent is subject to a terminal disclaimer.

(21) Appl. No.: 17/843,777

(22) Filed: Jun. 17, 2022

(65) Prior Publication Data

US 2023/0015181 A1     Jan. 19, 2023

Related U.S. Application Data

(63) Continuation of application No. 16/533,048, filed on Aug. 6, 2019, now abandoned, which is a continuation of application No. 15/809,935, filed on Nov. 10, 2017, now abandoned, which is a continuation of application No. 14/911,429, filed as application No. PCT/US2014/050896 on Aug. 13, 2014, now Pat. No. 9,845,363.

(60) Provisional application No. 61/865,451, filed on Aug. 13, 2013.

(30) Foreign Application Priority Data

May 22, 2014   (EP) .................................... 14305757

(51) Int. Cl.
    *C07K 16/38*       (2006.01)
    *A61K 39/00*      (2006.01)

(52) U.S. Cl.
    CPC ........ *C07K 16/38* (2013.01); *A61K 2039/505* (2013.01); *C07K 2317/24* (2013.01); *C07K 2317/32* (2013.01); *C07K 2317/34* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 4,816,397 A | 3/1989 | Boss et al. | |
| 4,816,567 A | 3/1989 | Cabilly et al. | |
| 5,225,539 A | 7/1993 | Winter | |
| 5,314,995 A | 5/1994 | Fell et al. | |
| 5,460,785 A | 10/1995 | Rhodes et al. | |
| 5,530,101 A | 6/1996 | Queen et al. | |
| 5,565,332 A | 10/1996 | Hoogenboom et al. | |
| 5,585,089 A | 12/1996 | Queen et al. | |
| 5,639,641 A | 6/1997 | Pedersen et al. | |
| 5,648,260 A | 7/1997 | Winter et al. | |
| 5,739,277 A | 4/1998 | Presta et al. | |
| 5,807,715 A | 9/1998 | Morrison et al. | |
| 5,834,250 A | 11/1998 | Wells et al. | |
| 5,869,046 A | 2/1999 | Presta et al. | |
| 6,096,871 A | 8/2000 | Presta et al. | |
| 6,121,022 A | 9/2000 | Presta et al. | |
| 6,193,980 B1 | 2/2001 | Efstathiou et al. | |
| 6,194,551 B1 | 2/2001 | Idusogie et al. | |
| 6,242,195 B1 | 6/2001 | Idusogie et al. | |
| 6,271,352 B1 * | 8/2001 | Nielsen ................. | G01N 33/86 |
| | | | 530/388.1 |
| 6,277,375 B1 | 8/2001 | Ward | |
| 6,528,624 B1 | 3/2003 | Idusogie et al. | |

(Continued)

FOREIGN PATENT DOCUMENTS

| | | |
|---|---|---|
| DE | 2000153251 | 5/2002 |
| EP | 239400 | 9/1987 |

(Continued)

OTHER PUBLICATIONS

Kipriyanov et al., Mol Biotechnol. Jan. 2004;26(1):39-60. doi: 10.1385/MB:26:1:39. PMID: 14734823.*
Aertgeerts et al., "Crystallization and X-ray diffraction data of the cleaved form of plasminogen activator Inhibitor-1." Proteins 23(1):118-21 (Sep. 1995).
Artimo et al., "ExPASy: SIB bioinformatics resource portal." Nucleic Acids Res. 40(Web Server Issue): W597-603 (Jul. 2012; epub May 31, 2012).

(Continued)

*Primary Examiner* — Michael Szperka
(74) *Attorney, Agent, or Firm* — McDonnell Boehen Hulbert & Berghoff

(57) ABSTRACT

The invention provides antibodies that specifically bind to Plasminogen Activator inhibitor type-1 (PAI-1), The invention also provides pharmaceutical compositions, as well as nucleic acids encoding anti-PAI-1 antibodies, recombinant expression vectors and host cells for making such antibodies, or fragments thereof. Methods of using antibodies to modulate PAI-1 activity or detect PAI-1, either in vitro or in vivo, are also provided. The disclosure further provides methods of making antibodies that specifically bind to PAI-1 in the active conformational state.

19 Claims, 53 Drawing Sheets

Specification includes a Sequence Listing.

(56)                    References Cited

U.S. PATENT DOCUMENTS

| | | | |
|---|---|---|---|
| 6,538,124 B1 | 3/2003 | Idusogie et al. | |
| 6,737,056 B1 | 5/2004 | Presta | |
| 6,821,505 B2 | 11/2004 | Ward | |
| 6,994,840 B1 | 2/2006 | Chinn | |
| 6,998,253 B1 | 2/2006 | Presta et al. | |
| 7,083,784 B2 | 8/2006 | Dall'Acqua et al. | |
| 7,538,195 B2 | 5/2009 | Singh et al. | |
| 7,771,720 B2 | 8/2010 | Staunton et al. | |
| 9,845,363 B2 * | 12/2017 | Pritsker | A61P 17/00 |
| 2002/0102208 A1 | 8/2002 | Chinn et al. | |
| 2009/0136500 A1 | 5/2009 | Staunton et al. | |
| 2011/0027266 A1 | 2/2011 | Lee et al. | |
| 2011/0182817 A1 | 7/2011 | Matsuura et al. | |
| 2012/0114652 A1 | 5/2012 | Elvin | |

FOREIGN PATENT DOCUMENTS

| | | | |
|---|---|---|---|
| EP | 0 339 302 | 11/1989 | |
| EP | 396387 | 11/1990 | |
| EP | 519596 | 12/1992 | |
| EP | 592106 | 4/1994 | |
| JP | 10-014592 | 1/1998 | |
| WO | WO 88/07089 | 9/1988 | |
| WO | WO 89/12624 | 12/1989 | |
| WO | WO 91/09967 | 7/1991 | |
| WO | WO 91/14438 | 10/1991 | |
| WO | WO 92/08495 | 5/1992 | |
| WO | WO 96/14339 | 5/1996 | |
| WO | WO 98/05787 | 2/1998 | |
| WO | WO 98/23289 | 6/1998 | |
| WO | WO 98/52976 | 11/1998 | |
| WO | WO 99/51642 | 10/1999 | |
| WO | WO 99/58572 | 11/1999 | |
| WO | WO 00/09560 | 2/2000 | |
| WO | WO 00/32767 | 6/2000 | |
| WO | WO 00/34317 | 6/2000 | |
| WO | WO 00/42072 | 7/2000 | |
| WO | WO 02/34776 | 5/2002 | |
| WO | WO 02/44215 | 6/2002 | |
| WO | WO 02/060919 | 8/2002 | |
| WO | WO 03/074569 | 9/2003 | |
| WO | WO 2004/016750 | 2/2004 | |
| WO | WO 2004/029207 | 4/2004 | |
| WO | WO 2004/035752 | 4/2004 | |
| WO | WO 2004/063351 | 7/2004 | |
| WO | WO 2004/074455 | 9/2004 | |
| WO | WO 2004/099249 | 11/2004 | |
| WO | WO 2005/018572 | 3/2005 | |
| WO | WO 2005/040217 | 5/2005 | |
| WO | WO 2005/047327 | 5/2005 | |
| WO | WO 2005/070963 | 8/2005 | |
| WO | WO 2005/077981 | 8/2005 | |
| WO | WO 2005/092925 | 10/2005 | |
| WO | WO 2005/123780 | 12/2005 | |
| WO | WO 2006/019447 | 2/2006 | |
| WO | WO 2006/047350 | 5/2006 | |
| WO | WO 2006/085967 | 8/2006 | |
| WO | WO 2009/032661 | 3/2009 | |
| WO | WO-2009033095 A2 * | 3/2009 | A61P 9/00 |
| WO | WO 2009/131850 | 10/2009 | |
| WO | WO 2011/139973 | 11/2011 | |

OTHER PUBLICATIONS

Bauman et al., "The antifibrotic effects of plasminogen activation occur via prostaglandin E2 synthesis in humans and mice." J. Clin. Invest. 120(6):1950-60 (Jun. 2010; epub May 24, 2010).

Beebe & Aronson, "An automated fibrinolytic assay performed in microtiter plates." Thromb. Res. 47(1): 123-28 (Jul. 1987).

Beier et al., "Plasminogen activator inhibitor-1 deficient mice are protected from angiotensin II-induced fibrosis." Arch. Bioch. Biophys. 510(1):19-26 (Jun. 2011; epub Apr. 9, 2011).

Bergheim et al., "Critical role of plasminogen activator inhibitor-1 in cholestatic liver injury and fibrosis." J. Pharmacol. Exp. Ther. 316(2):592-600 (Feb. 2006; epub Oct. 12, 2005).

Berkenpas et al., "Molecular evolution of plasminogen activator inhibitor-1 functional stability." EMBO J., 14 (13);2969-77 (Jul. 1995).

Berry et al., "Antithrombotic activity of a monoclonal antibody inducing the substrate form of plasminogen activator Inhibitor type 1 in rat models of venous and arterial thrombosis", British Journal of Pharmacology, 125 (1):29-34 (Sep. 1998).

Blouse et al., "Interactions of plasminogen activator inhibitor-1 with vitronectin involve an extensive binding surface and induce mutual conformational rearrangements." Biochemistry, 48(8):1723-35 (Mar. 2009).

Bowie et al., "Deciphering the Message in Protein Sequences: Tolerance to Amino Acid Substitutions," Science, 247:1306-1310 (1990).

Brooks et al., "CHARMM: A program for macromolecular energy, minimization, and dynamics calculations" J. Comp. Chem. 4(2):187-217 (Jun. 1983).

Brummell et al., "Probing the combining site of an anti-carbohydrate antibody by saturation-mutagenesis: role of the heavy-chain CDR3 residues." Biochem. 32(4):1180-87 (Feb. 1993).

Burks et al., "In vitro scanning saturation mutagenesis of an antibody binding pocket." Proc. Nat'l. Acad. Sci. USA 94 (2):412-17 (Jan. 1997).

Cale and Lawrence, "Structure-function relationships of plasminogen activator inhibitor-1 and its potential as a therapeutic agent." Curr. Drug Targets 8(9):971-81 (Sep. 2007).

Case et al., "The Amber biomolecular simulation programs." J. Comp. Chem. 26(16):1668-88 (Dec. 2005).

Chapman, "PEGylated antibodies and antibody fragments for improved therapy: a review" Advances in Drug Delivery Reviews 54(4):531-45 (Jun. 2002).

Chothia & Lesk, "Canonical structures for the hypervariable regions of immunoglobulins." J. Mol. Biol. 196 (4):901-17 (Aug. 1987).

Chuang-Tsai et al., "Reduction in fibrotic tissue formation in mice genetically deficient in plasminogen activator Inhibitor-1." Am. J. Pathol 163(2):445-52 (Aug. 2003).

Courey et al., "The vitronectin-binding function of PAI-1 exacerbates lung fibrosis in mice." Blood 118(8):2313-21 (Aug. 2011; epub Jul. 6, 2011).

Cunningham & Wells, "High-resolution epitope mapping of hGH-receptor interactions by alanine-scanning mutagenesis." Science 244(4908):1081-85 (Jun. 1989).

Dawson et al., "Genetic variation at the plasminogen activator inhibitor-1 locus is associated with altered levels of plasma plasminogen activator inhibitor-1 activity." Arterioscler Thromb. 11(1):183-90 (Jan.-Feb. 1991).

De Armas et al., "Study of Recombinant Antibody Fragments and PAI-1 Complexes Combining Protein-Protein Docking and Results from Site-Directed Mutagenesis", Structure, 15(9):1105-16 (Sep. 2007).

De Taeye et al., "The story of the serpin plasminogen activator inhibitor 1: is there any need for another mutant?" Thromb. Haemost. 92(5):898-924 (Nov. 2004).

Debrock & Declerck, Identification of a functional epitope in plasminogen activator inhibitor-1, not localized in the reactive center loop. Thromb. Haemost. 79(3):597-601 (Mar. 1998).

Debrock & Declerck, "Neutralization of plasminogen activator inhibitor-1 inhibitory properties: identification of two different mechanisms." Biochimica Biophysica Acta, 1337(2):257-66 (Feb. 1997).

Dewilde et al., "Subtle structural differences between human and mouse PAI-1 reveal the basis for biochemical differences." J Struct. Biol. 171(1):95-101 (Jul. 2010; epub Mar. 15, 2010).

Eddy, "Serine proteases, inhibitors and receptors in renal fibrosis." Thromb. Haemost. 101(4):656-64 (Apr. 2009).

Ehrenmann et al. "IMGT/DomainGapAlign: IMGT Standardized Analysis of Amino Acid Sequences of Variable, Constant, and Groove Domains (IG, TR, MH, IgSF, MhSF)." Cold Spring Harbor Protocols 2011 (6):737-49 (Jun. 2011).

Eitzman et al., "Bleomycin-induced pulmonary fibrosis in transgenic mice that either lack or overexpress the murine plasminogen activator inhibitor-1 gene." J. Clin. Invest. 97(1):232-37 (Jan. 1996).

(56)          References Cited

OTHER PUBLICATIONS

Foote & Winter, "Antibody framework residues affecting the conformation of the hypervariable loops." J. Mol.Biol., 224(2):487-99 (Mar. 1992).

Freedberg et al., "Flexibility and Function in HIV Protease: Dynamics of the HIV-1 Protease Bound to the Asymmetric Inhibitor Kynostatin 272 (KNI-272)." J. Am. Chem. Soc. 120(31):7916-23 (Jul. 1998).

Ghosh and Vaughan, "PAI-1 in tissue fibrosis." J. Cell Physiol. 227(2):493-507 (Feb. 2012).

Gillies et al., High-level expression of chimeric antibodies using adapted cDNA variable region cassettes. J. Immunol Methods. 125(1-2):191-202 (Dec. 1989).

Gils and Declerk, "The structural basis for the pathophysiological relevance of PAI-I in cardiovascular diseases and the development of potential PAI-I inhibitors." Thromb Haemost. 91(3):425-37 (Mar. 2004).

Gonzalez et al., "Delayed treatment with plasminogen activator inhibitor-1 decoys reduces tubulointerstitial fibrosis." Exp. Biol Med. 234(12):1511-18 (Dec. 2009).

Gorlatova et al., "Mapping of a Conformational Epitope on Plasminogen Activator Inhibitor-1 by Random Mutagenesis. Implications for Serpin Function", Journal of Biological Chemistry, 278 (18):16329-335 (Apr. 2003).

Grunberg et al., "Flexibility and conformational entropy in protein-protein binding." Structure 14(4):683-93 (Apr. 2006).

Haney A.F. et al., "Expanded-polytetrafluoroethylene but not oxidized regenerated cellulose prevents adhesion formation and reformation in a mouse uterine horn model of surgical injury," Fertility and Sterility, 60(3): 550-558 (1993).

Harris et al., "Commercial manufacturing scale formulation and analytical characterization of therapeutic recombinant antibodies." Drug Dev. Res. 61(3):137-54 (Mar. 2004).

Hattori et al., "Bleomycin-induced pulmonary fibrosis in fibrinogen-null mice." J Clin Invest. 106(11):1341-50 (Dec. 2000).

Hattori et al., "The plasminogen activation system reduces fibrosis in the lung by a hepatocyte growth factor-dependent mechanism." Am. J. Pathol. 164(3):1091-98 (Mar. 2004).

Houde et al., "The utility of hydrogen/deuterium exchange mass spectrometry in biopharmaceutical comparability studies." J. Pharm. Sci. 100(6):2071-86 (Jun. 2011; epub Dec. 29, 2010).

Hiu et al., "Adenovirus-mediated transfer of siRNA against PAI-1 mRNA ameliorates hepatic fibrosis in rats." J. Hepatol. 51(1):102-13 (Jul. 2009; epub Apr. 10, 2009).

Huang et al., "Noninhibitory PAI-1 enhances plasmin-mediated matrix degradation both in vitro and in experimental nephritis." Kidney Int. 70(3):515-22 (Aug. 2006, epub Jun. 21, 2006).

Huang et al., "Therapeutic value of small molecule inhibitor to plasminogen activator inhibitor-1 for lung fibrosis." Am. J. Respir. Cell Mol Biol. 46(1):87-95 (Jan. 2012).

International Search Report for International Application No. PCT/US2014/050896; mailed Dec. 23, 2014, pp. 1-10.

Izuhara et al., "Inhibition of plasminogen activator inhibitor-1: its mechanism and effectiveness on coagulation and fibrosis.Arierioscler." Thromb. Vase. Biol. 28(4):672-77 (Apr. 2008; epub Jan. 31, 2008).

Jambon, et al., "The SuMo server: 3D search for protein functional sites." Bioinformatics 21(20):3929-30 (Oct. 2005; epub Sep. 1, 2005).

James et al., "Antibody multispecificity mediated by conformational diversity." Science, 299(5611):1362-67 (Feb. 2003).

Jones et al., "Replacing the complementarity-determining regions in a human antibody with those from a mouse." Nature 321(6069):522-25 (May-Jun. 1986).

Tschumper & Carbon, "Sequence of a yeast DNA fragment containing a chromosomal replicator and the TRP1 gene." Gene, 10(2):157-66 (Jul. 1980).

Verbeke et al., "Cloning and paratope analysis of an antibody fragment, a rational approach for the design of a PAI-1 Inhibitor", Journal of Thrombosis and Haemostasis, 2(2):289-97 (Feb. 2004).

Verbeke et al., "Elucidation of the paratope of scFv-8H9D4, a PAI-1 neutralizing antibody derivative.", Thrombosis and Haemostasis, 89(1):74-82 (Jan. 2003).

Verbeke et al., "Inhibition of plasminogen activator inhibitor-1: antibody fragments and their unique sequences as a tool for the development of profibrinolytic drugs", Journal of Thrombosis and Haemostasis, 2(2):298-305 (Feb. 2004).

Verhamme et al., "Accelerated Conversion of Human Plasminogen Activator Inhibitor-1 to Its Latent Form by Antibody Binding", Journal of Biological Chemistry, 274(25):17511-17 (Jun. 1999).

Vita et al., "The immune epitope database 2.0" Nucleic Acids Res. 38(Database issue): D854-62 (Jan. 2010; epub Nov. 11, 2009).

Wang et al., "PAI-1 deficiency reduces liver fibrosis after bile duct ligation in mice through activation of tPA." FEBS Lett. 581(16):3098-104 (Jun. 2007; epub May 29, 2007).

Wang et al., "Transcriptional profiling after bile duct ligation identifies PAI-1 as a contributor to cholestatic injury in mice." Hepatology 42(5):1099-108 (Nov. 2005).

Wei et al., "Hydrogen/deuterium exchange mass spectrometry for probing higher order structure of protein therapeutics: methodology and applications." Drug Discovery Today, 19(1):95-102 (Jan. 2014; epub Aug. 6, 2013).

Weir et al., "Formatting antibody fragments to mediate specific therapeutic functions." Biochem. Soc. Transactions 30 (4):512-16 (Aug. 2002).

Wells, J.A., "Additivity of Mutational Effects in Proteins," Biochemistry, 29:8509-8517 (1990).

Wilson et al., "The structure of an antigenic determinant in a protein." Cell 37(3):767-78 (Jul. 1984).

Wind et al., "Epitope mapping for four monoclonal antibodies against human plasminogen activator inhibitor type-1 : Implications for antibody-mediated PAI-1-neutralization and vitronectin-binding", European Journal of Biochemistry, 268(4):1095-106 (Feb. 2001).

Xu et al., "Diversity in the CDR3 Region of VH Is Sufficient for Most Antibody Specificities," Immunity, 13:37-45 (Jul. 2000).

Xue et al., "Interfering with the inhibitory mechanism of serpins: crystal structure of a complex formed between cleaved plasminogen activator inhibitor type 1 and a reactive-centre loop peptide." Structure 6(5):627-36 (May 1998).

Zhou et al., "How vitronectin binds PAI-1 to modulate fibrinolysis and cell migration." Nat. Struct. Biol. 10(7):541-44 (Jul. 2003).

Jones, "Proteinase mutants of Saccharomyces cerevisiae." Genetics, 85(1):23-33 (Jan. 1977).

Jonsson et al., "Effect of Spatially Distributed Hydrophobic Surface Residues on Protein-Polymer Association" J. Phys. Chem. B, 107(23):5511-5518 (May 2003).

Kabat et al., "Unusual distributions of amino acids in complementarity-determining (hypervariable) segments of heavy and light chains of immunoglobulins and their possible roles in specificity of antibody-combining sites." J. Biol. Chem. 252(19):6609-16 (Oct. 1977).

Kim et al., "A plasminogen activator inhibitor-1 promoter polymorphism and idiopathic interstitial pneumonia." Mol. Med. 9(1-2):52-56 (Jan.-Feb. 2003).

Kingsman et al., "Replication in *Saccharomyces cerevisiae* of plasmid pBR313 carrying DNA from the yeast trpl region." Gene, 7(2):141-52 (Oct. 1979).

Kirschmann et al., "Naturally processed peptides from rheumatoid arthritis associated and non-associated HLA-DR alleles." J. Immun., 155(12):5655-62 (Dec. 1995).

Klinger, K.W. et al., "Plasminogen activator inhibitor type 1 gene is located at region q21.3-q22 of chromosome 7 and genetically linked with cystic fibrosis." Proc. Nat'l Acad. Sci. USA 84(23):8548-52 (Dec. 1987).

Knier et al., "Effect of the plasminogen-plasmin system on hypertensive renal and cardiac damage." J. Hypertens. 29 (8):1602-12 (Aug. 2011).

Kobayashi et al., "Tryptophan H33 plays an important role in pyrimidine (6-4) pyrimidone photoproduct binding by a high-affinity antibody." Protein Eng. 12(10):879-84 (Oct. 1999).

Kundu et al., "Dynamics of proteins in crystals: comparison of experiment with simple models." Biophys. J. 83 (2):723-32 (Aug. 2002).

(56)          References Cited

OTHER PUBLICATIONS

Lefranc et al., "IMGT unique numbering for immunoglobulin and T cell receptor variable domains and Ig superfamily V-like domains." Dev Comp. Immunol. 27(1):55-77 (Jan. 2003).

Leong et al., "Adapting pharmacokinetic properties of a humanized anti-interleukin-8 antibody for therapeutic applications using site-specific pegylation." Cytokine 16(3):106-19 (Nov. 2001).

Lindgren et al., "Tissue plasminogen activator and plasminogen activator inhibitor-1 in stroke patients." Stroke 27 (6):1066-71 (Jun. 1996).

Liu et al., "Characterization of the stability of a fully human monoclonal IgG after prolonged incubation at elevated temperature." J. Chromatography B, 837(1-2):35-43 (Jun. 2006; epub Apr. 27, 2006).

Loskutoff & Quigley, "PAI-1, fibrosis, and the elusive provisional fibrin matrix." J. Clin. Invest. 106(32):1441-43 (Dec. 2000).

Ma et al., "Multiple diverse ligands binding at a single protein site: A matter of pre-existing populations" Protein Science 11:184-87 (2002).

Ma et al., "PAI-1 and kidney fibrosis." Frontiers Biosci. 14:2028-41 (Jan. 2009).

Mac Callum et al., "Antibody-antigen Interactions: Contact Analysis and Binding Site Topography" J. Mol. Biol. 262 (5):732-45 (Oct. 1996).

Marcsisin & Engen, "Hydrogen exchange mass spectrometry: what is it and what can it tell us?" Anal Bioanal Chem. 397(3):967-72 (Jun. 2010; epub Mar. 1, 2010).

Matsuo et al., "Multifunctionality of PAI-1 in fibrogenesis: Evidence from obstructive nephropathy in PAI-1-overexpressing mice" Kidney Int. 67(6):2221-38 (Jun. 2005).

Mccoy et al., "Phaser crystallographic software." J. Appl. Cryst. 40(Pt 4): 658-74 (Aug. 2007; epub Jul. 13, 2007).

Molina-Molina et al., "Losartan attenuates bleomycin induced lung fibrosis by increasing prostaglandin E2 synthesis" Thorax 61(7):604-10 (epub Apr. 6, 2006).

Monsellier & Bedouelle, "Improving the stability of an antibody variable fragment by a combination of knowledge-based approaches: validation and mechanisms." J. Mol. Biol., 362(3):580-93 (epub Jul. 28, 2006).

Moriwaki et al., "Overexpression of urokinase by macrophages or deficiency of plasminogen activator inhibitor type 1 causes cardiac fibrosis in mice." Cric. Res. 95(6):637-44 (Sep. 2004; epub Aug. 5, 2004).

Morrison et al., "Chimeric human antibody molecules: mouse antigen-binding domains with human constant region domains." Proc. Natl. Acad. Sci. 81(21):6851-55 (Nov. 1984).

Morrison, "Transfectomas provide novel chimeric antibodies." Science 229(4719):1202-07 (Sep. 1985).

Mottonen et al., "Structural basis of latency in plasminogen activator inhibitor-1." Nature 355(6357):270-73 (Jan. 1992).

Naessens et al., "Elucidation of the epitope of a latency-inducing antibody: identification of a new molecular target for PAI-1 inhibition.", Thrombosis and Haemostasis, 90(1):52-58 (Jul. 2003).

Neuberger et al., "Recombinant antibodies possessing novel effector functions." Nature 312(5995):604-08 (Dec. 1984).

Nicholas et al., "Plasminogen activator inhibitor-1 deficiency retards diabetic nephropathy." Kidney Int. 67 (4):1297-307 (Apr. 2005).

Oda et al., "PAI-1 deficiency attenuates the fibrogenic response to ureteral obstruction." Kidney Int. 60(2):587-96 (Aug. 2001).

Oi & Morrison, "Chimeric Antiodies" BioTechniques 4(3):214-21 (1986).

Padlan, "A possible procedure for reducing the immunogenicity of antibody variable domains while preserving their ligand-binding properties" Molecular Immunology 28:489-98 (1991).

Peters et al., "The Immune Epitope Database and Analysis Resource: From Vision to Blueprint." PLoS Biol. 3 (3):379-381, e91 (Mar. 15, 2005).

Pietersz et al., "The use of monoclonal antibody conjugates for the diagnosis and treatment of cancer." Immunol. Cell Biol. 65(Pt 2):111-25 (Apr. 1987).

Rerolle et al., "PAI-1 donor polymorphism influences long-term kidney graft survival." Nephrol Dial Transplant 23(1):3325-32 (Oct. 2008; epub May 7, 2008).

Riechmann et al, "Reshaping human antibodies for therapy." Nature 332(6162):323-27 (Mar. 1988).

Rizzo et al., "Validation of a Model for the Complex of HIV-1 Reverse Transcriptase with Sustiva through Computation of Resistance Profiles" J. Am. Chem. Soc, 122(51):12898-12900 (Dec. 2000).

Roguska et al., "Humanization of murine monoclonal antibodies through variable domain resurfacing." PNAS 91 (3):969-73 (Feb. 1994).

Seco et al., "Binding site detection and druggability index from first principles." J. Med. Chem. 52(8):2363-71 (Apr. 2009).

Senoo et al., "Suppression of plasminogen activator inhibitor-1 by RNA interference attenuates pulmonary fibrosis." Thorax 65(4):334-40 (Apr. 2010).

Sharp et al., "The active conformation of plasminogen activator inhibitor 1, a target for drugs to control fibrinolysis and cell adhesion." Structure 7(2):111-18 (Feb. 1999).

Steipe et al., "Sequence statistics reliably predict stabilizing mutations in a protein domain." J. Mol. Biol. 240 (3):188-92 (Jul. 1994).

Stinchcomb et al., "Isolation and characterisation of a yeast chromosomal replicator." Nature, 282(5734):39-43 (Nov. 1979).

Studnicka et al., "Human-engineered monoclonal antibodies retain full specific binding activity by preserving non-CDR complementarity-modulating residues." Protein Engineering 7(6):805-14 (Jun. 1994).

Sundberg & Mariuzza, "Luxury accommodations: the expanding role of structural plasticity in protein-protein interactions." Structure 8(7):R137-R142 (Jul. 2000).

Suzuki et al., "Effects of specific chemical suppressors of plasminogen activator inhibitor-1 in cardiovascular diseases." Expert Opin. Investig. Drugs, 20(2):255-64 (Feb. 2011; epub Jan. 3, 2011).

Takeda et al., "Construction of chimaeric processed immunoglobulin genes containing mouse variable and human constant region sequences." Nature 314(6010):452-54 (Apr. 1985).

Takeshita et al., "Increased expression of plasminogen activator inhibitor-1 in cardiomyocytes contributes to cardiac fibrosis after myocardial infarction." Am. J. Pathol. 164(2):449-56 (Feb. 2004).

Tilley et al., "Measurement of factor v activity in human plasma using a microplate coagulation assay." J Vis. Exp. 67:e3822 pp. 1-7, (Sep. 2012).

* cited by examiner

% Neutralization 2.8 nM CYNO and 2.8 nM Mouse PAI-1 v. Mab's IMA-33B8 and A44

| | CYNO PAI-1-33B8 | CYNO PAI-1-A44 | mouse PAI-1-33B8 |
|---|---|---|---|
| HILLSLOPE | 0.9877 | 1.841 | 2.831 |
| EC50 | 1.303e-009 | 2.255e-010 | 2.395e-007 |

VL ALIGNMENT

```
A105: DVVMTQTPLTLSVTIGQPASISCKSSQSLLDSDGKTYLNWLLQRPGQSPQRLISLVSK
A39:  DIQMTHSPASLSASVGETVTITCRASENIY-----SYLAWYHQKQGKSPQLLVYNAKT
A44:  DIKMTQSPSSMYASLGERVTITCKASQDIN-----SYLSWLQQKPGKSPKTLIYRANR
A71:  DVVMTQTPLTLSVTIGQPASISCKSSQSLLDSDGKTYLYWLLQRPGQSPKRLIYLVSK
A75:  DVVMTQTPLTLSVTIGQPASI-CKSSQSLLDSEGKTYLNWLFQRPGQSPKRLIYLVCK
B109: DIVMTQSHKFEMSTSAGDRVSIPCKASQDVS-----SAVAWYQQKLGQSPKLLIYSASF
B28:  DIQLTQSPASLSASVGATVTITCRASENVY-----SYLAWYQQKQGKSPQLLVYNAKT
C45:  DIKMTQSPSSMYASLGERVTITCKASQDIN-----SYLSWFQQKPGKSPKTLIYRANR
E16:  DIVMTQSHKFEMSTSVGDRVNITCKASQDVS-----TAVGWYQQEPGQSPKLLIYSASN
E21:  DIQMTQTTSSLSASLGDRVTISCRASQDIS-----NYLNWYQQKPDGTVKLLIYTSR

A105: LDSGVPDRFTGSGSGTDFTLKLSRVEGADLGVYYCWQDRHFPRTFGGGTKLEIKRAD
A39:  LAEGVPSRFSGSGSGTQFSLNIKSLQPEDFGTFYCQHRYGSPWTFGGGTKLEIKRAD
A44:  SVDGVPSRFSGSGSGQDYSLTISSLEYEDMGIYYCLQYDEFPPTFGGGTKLEIKRAD
A71:  LDSGVPDRFTGSGSGTDFTLKISRVEAEDLGVYYCWQDTHFPRTFGGGTKLEIKRAD
A75:  LDCGVPDRFTGSGSGTDFTLKISRVEGEDLGVYYCWQGSHFPQTFGGGTKLEIKRAD
B109: RYTGVPDRFTGSGSGTDFTLKISSVQAEDLAVYYCQQHYSSPYTFGGGTNLEIKRAD
B28:  LAEGVPSRFSGSGSGTQFSLKINYLQPEDFGSYCQHYGTPPTFGGGTKVEIKRAD
C45:  LVDGVPSRFSGSGSGQDYSLTISSLEYEDMGIYYCLQYDEFPRTFGGGTKLEIK---
E16:  RHTGVPDRFTGSGSGTDFTFTISSVQAEDLAVYYCQQHYSSPWTFGGGTKLEIK---
E21:  LHSGVPSRFSGSGSGTDYSLTISNLEQEDIATYECQQGNTLPWTFGGGTKLEIK---
```

FIG. 11

VH ALIGNMENT

```
A105: QVQLQQSGAELMKPGASVKISCKATGFTFSTYWIEWVKQRPGL------------GLEWIGEILPGSGST
A39:  QVQLQQSGAELMKPGASVKISCKATGYTFNTYWIQWVKQRPGH------------GLEWIGEILPGSN-T
A44:  EMQLQESGPSLVKPSQTLSLTCSVTGDSMTNGYWNWIRKFPGN------------KLEYMGYIT-YSGST
A71:  QVQLQQSGAELMKPGASVKISCKATGFTFSTYWIEWIKQRPGH------------GLDWIGEILPGSGNT
A75:  QGQLQQSGAELMKPGASVKISCKASGFTFSTYWIAWLKQRPGH------------GLEWIAEILPGSGLT
B109: EVQLQQSGSVLARPGTSVKMSCKASGYSFTSYWMHWVKQRPGQGLEWMGAIYPGNSGQGLDWIGAIYPGNSDT
B28:  QVQLQQSGAELMKPGASVKISCKATGYTFSISWIEWIKQRPGL------------GLEWIGKILPGSGGA
C45:  QVQLQQSGGVELVRPGTSVKVSCKASGYAFTNYLIEWIKQRPGQ-----------GLEWIGVIHPGSGVT
E16:  EVKLVESGGGLVKPGGSIKLSCAASGFTFSNYGMSWVRQTPEK------------GLGWVASLRTGGN-T
E21:  EVQLQQSGAELVRSGASVKLSCTASGFNIKDYYMHWVKQRPEQ------------GLEWIGWIDPENGDT

A105: NYNEKFKGKATFTADTSSNTAFMQLSSLTSEDSAVYYCARG---GLYYDLDYWGQGTTLTVSSAKTTPP
A39:  NYNEKFKDKRATFTADTSSNTAVMQLSSLTSEDSAVYYCARLGI-GLRGALDYWGQGTSVTVSSAKTTPP
A44:  YYNPSLKGRISTTRNTSKMQYYLQLSSVTTEDTIATYYCARWMY-GSPYYFDYWGQGTTLTVSSAKTTPP
A71:  NYNEKFKGKATFTADTSSNTVYMQLSSLTSEDSAVYYCARG---GLYYNLDSWGQGTTLTVSSAKTTPP
A75:  NYNEIFRGKATFTADTSSNTAVMQLSSLTSEDSAVYYCARG---GLYYAMDYWGQGTSVTVSSAKTTAP
B109: TYNQKFEDKAKLTAVASASTAYMEVSSLTNEDSAVYYCTRG---LRRWGAMDYWGQGTSVTVSSAKTTPP
B28:  NYNEKFKGKATVTADTSSNTVYMQLSSLTSEDSAVYYCARLST-GTRGAFDYWGQGTTLTVSSAKTTPP
C45:  NYNEKFKGKAILTADKSSSTAYMQLSSLTSDSAVFFCARDYYGSSHGLMDYWGQGTSVTVSS------
E16:  YYSDSVKGRFTISRDNDRNILYLQMSSLTSEDTAVYYCARG--LRHWGYFDVWGAGTTVTVSS------
E21:  EYDPKFQAKATMTADTSSNTAVLQLSSLTSEDTAVYYCMYG---NYPYYFDYWGQGTLTVSS------
```

FIG. 12

Alignment of A44 LC with vk1:

```
A44: DIKMTQSPSS MYASLGERVT ITCKASQDIN SYLSWLQQKP GKSPKTLIYR
VK1: DIQMTQSPSS LSASVGDRVT ITCRASQSIS SYLNWYQQKP GKAPKLLIYA

A44: ANRSVDGVPS RFSGSGSGQD YSLTISSLEY EDMGIYYCLQ YDEFPPTFGG
VK1: ASSLQSGVPS RFSGSGSGTD FTLTISSLQP EDIATYYCQQ SYSTPPTFGQ

A44: GTKLEIK
VK1: GTKVEIK
```

Alignment of A44 LC with vlambda3:

```
A44: DIKMTQSPSS MYASLGERVT ITXKASQDIN SYLSWLQQKP GKSPKTLIYR
VL3: -SYELTQPPS VSVSPGQTAS ITXSGDKLGD KYASWYQQKP GQSPVLVIYQ

A44: ANRSVDGVPS RFSGSGSGQD YSLTISSLEY EDMGIYYXLQ YDEFPPTFGG
VL3: DSKRPSGIPE RFSGSNSGNT ATLTISGTQA MDEADYYXQA WDSSAVVFGG

A44: GTKLEIK
VL3: GTKLTVL
```

FIG. 13

Figure 14:
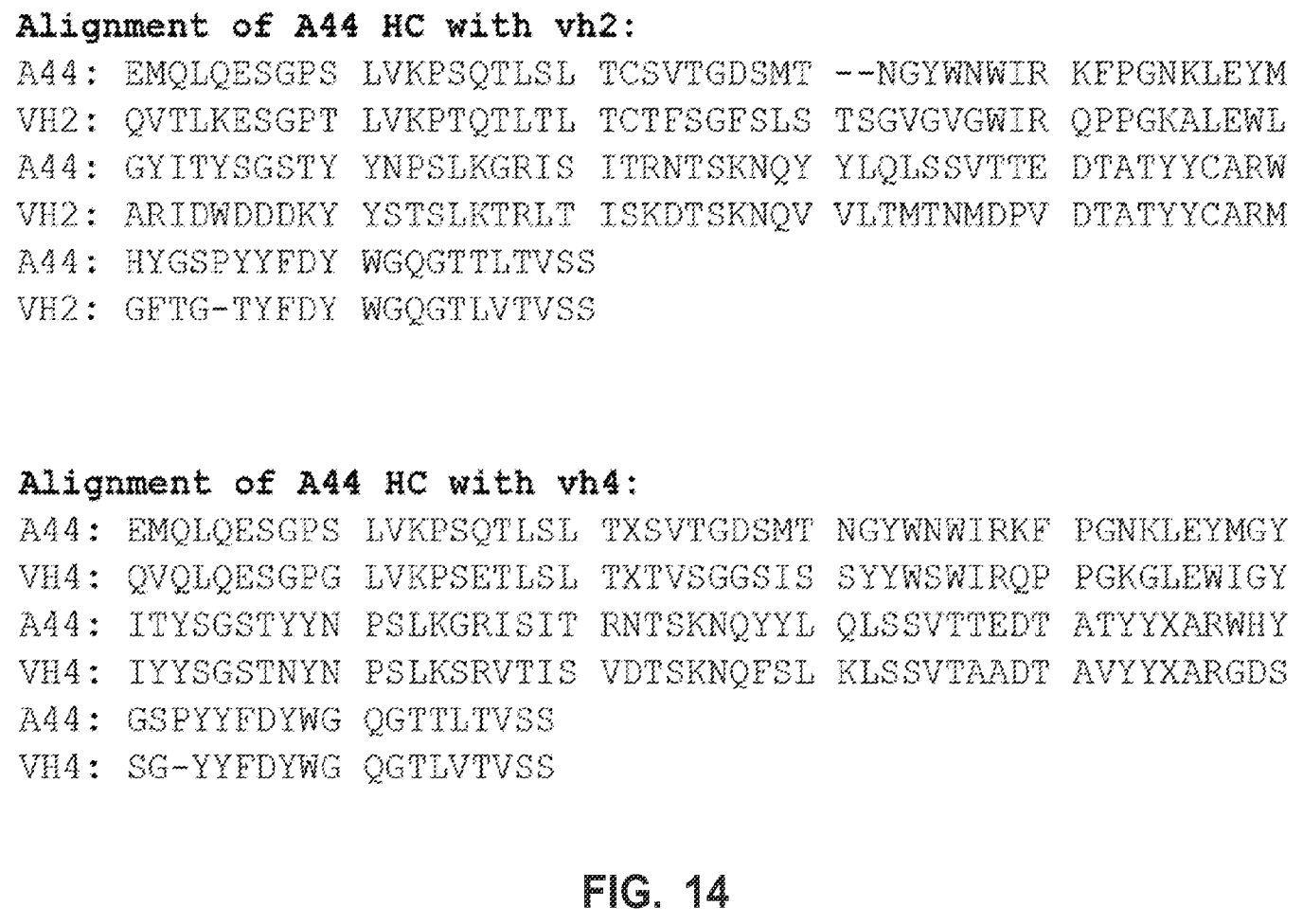

Alignment of A44 HC with vh2:

```
A44:  EMQLQESGPS LVKPSQTLSL TCSVTGDSMT --NGYWNWIR KFPGNKLEYM
VH2:  QVTLKESGPT LVKPTQTLTL TCTFSGFSLS TSGVGVGWIR QPPGKALEWL
A44:  GYITYSGSTY YNPSLKGRIS ITRNTSKNQY YLQLSSVTTE DTATYYCARW
VH2:  ARIDWDDDKY YSTSLKTRLT ISKDTSKNQV VLTMTNMDPV DTATYYCARM
A44:  HYGSPYYFDY WGQGTLLTVSS
VH2:  GFTG-TYFDY WGQGTLVTVSS
```

Alignment of A44 HC with vh4:

```
A44:  EMQLQESGPS LVKPSQTLSL TXSVTGDSMT NGYWNWIRKF PGNKLEYMGY
VH4:  QVQLQESGPG LVKPSETLSL TXTVSGGSIS SYYWSWIRQP PGKGLEWIGY
A44:  ITYSGSTYYN PSLKGRISIT RNTSKNQYYL QLSSVTTEDT ATYYXARWHY
VH4:  IYYSGSTNYN PSLKSRVTIS VDTSKNQESL KLSSVTAADT AVYYXARGDS
A44:  GSPYYFDYWG QGTLLTVSS
VH4:  SG-YYFDYWG QGTLVTVSS
```

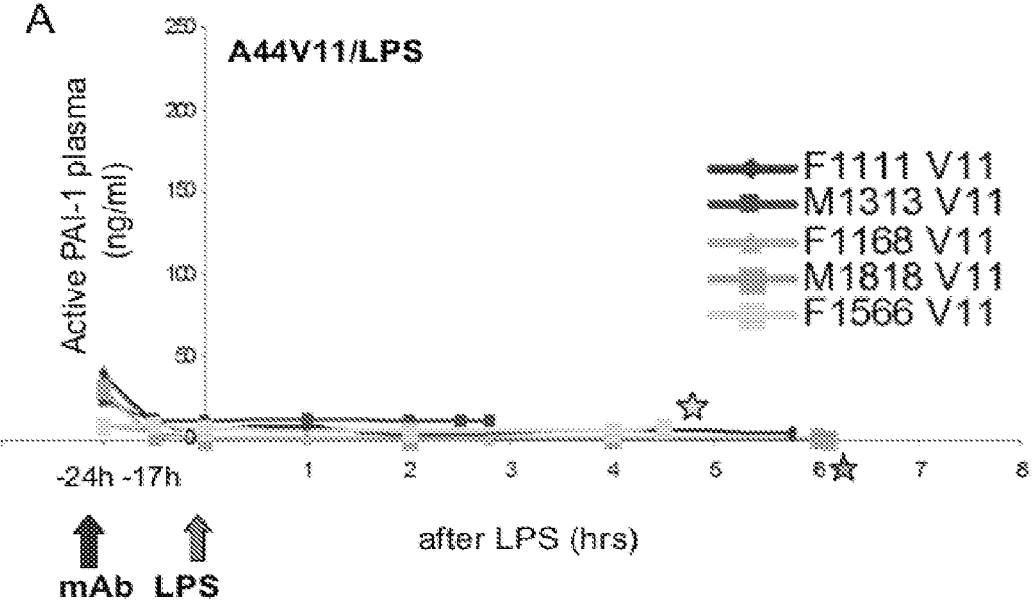
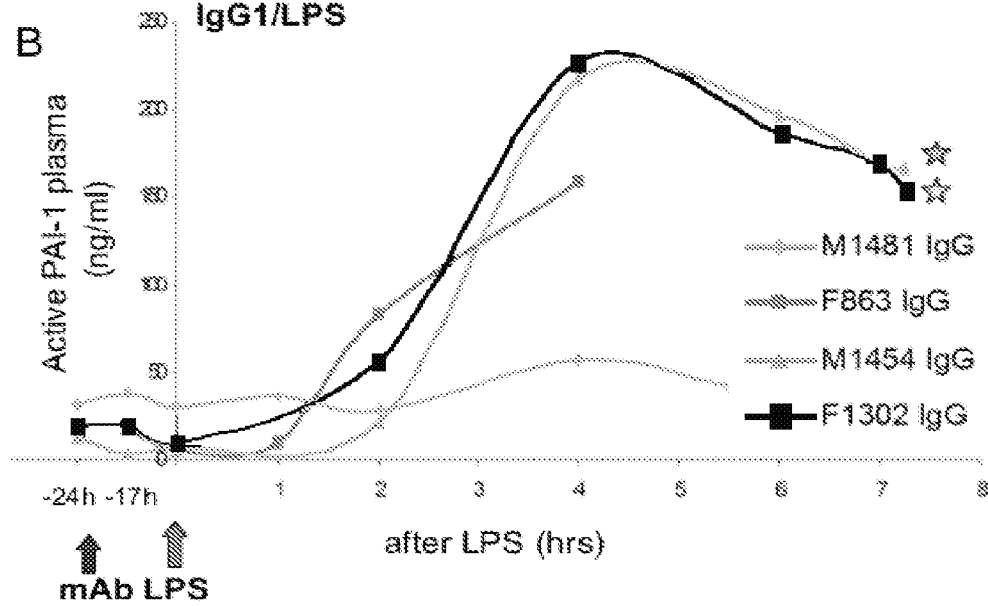
FIG. 32

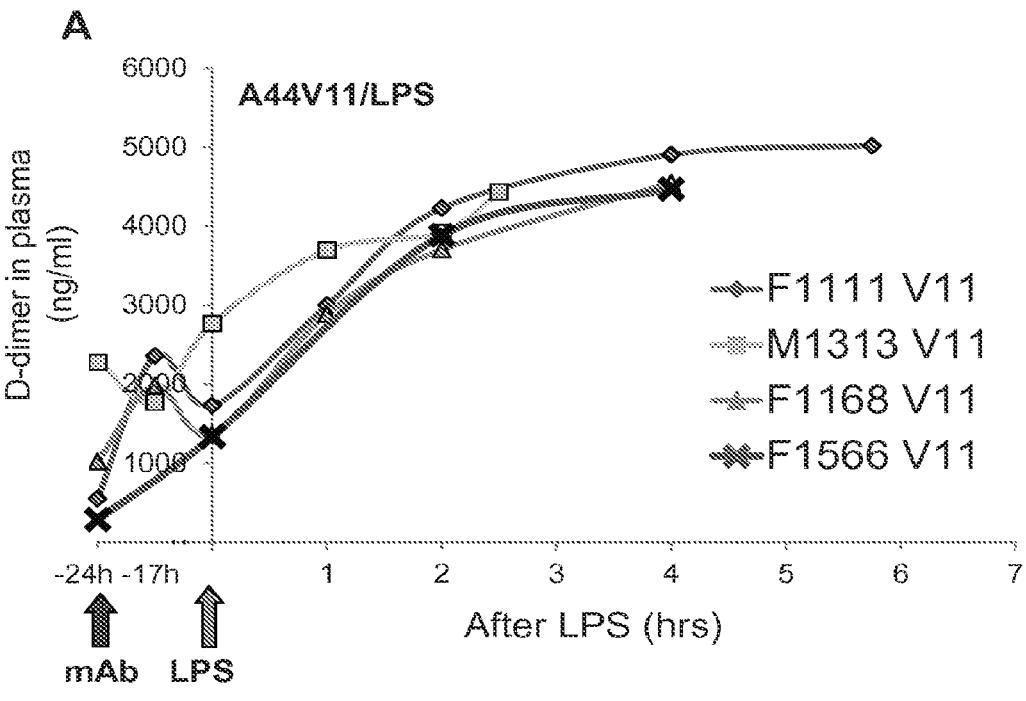
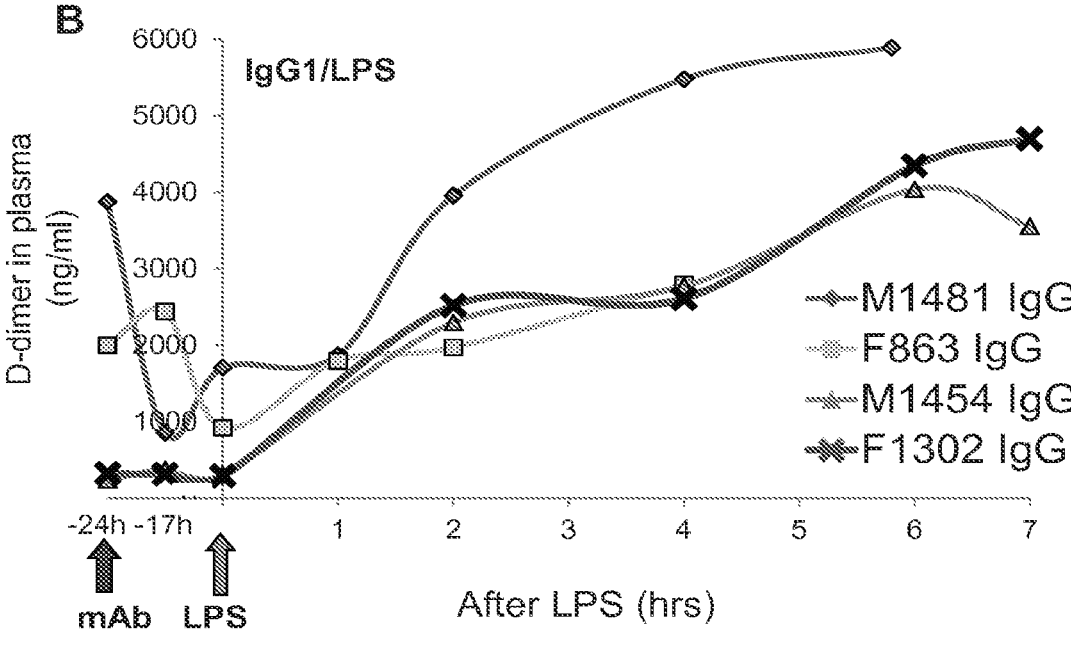
FIG. 34

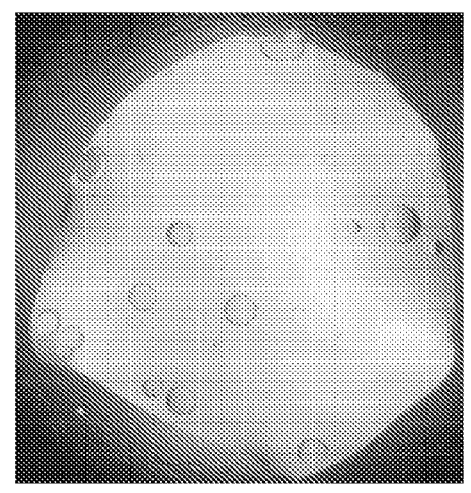
A
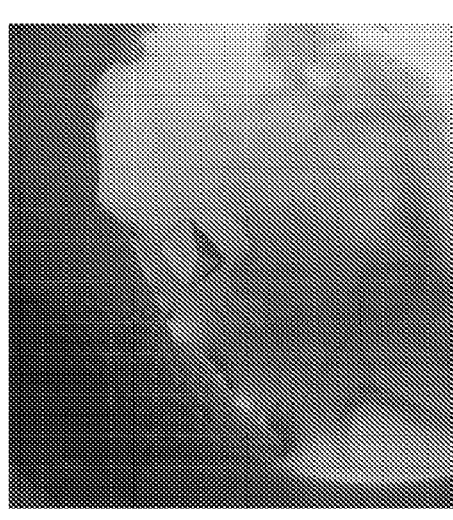
B
FIG. 39 somatomedin B
domain of
vibronectin

Total: 95.3% Coverage
4.44 Redundancy

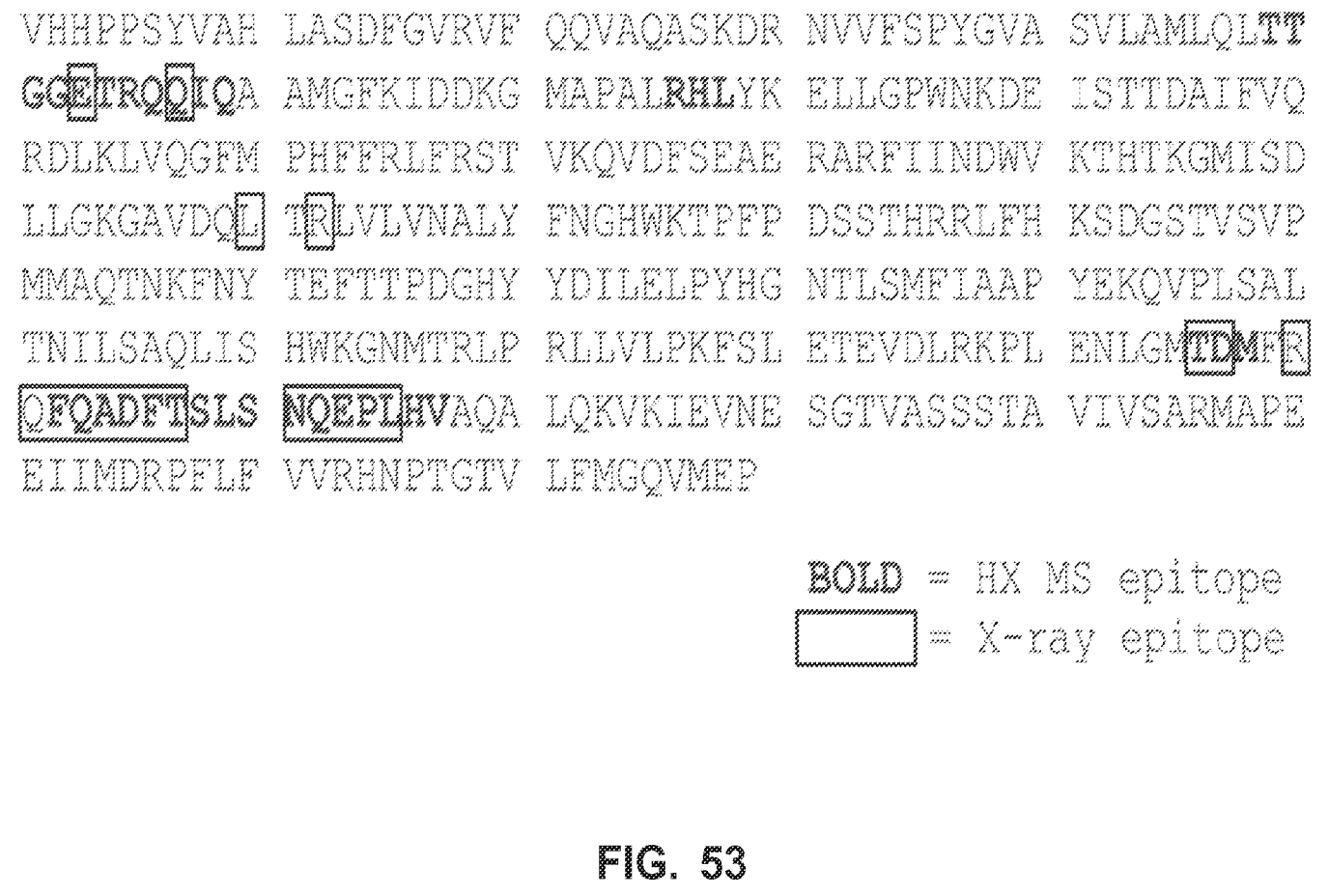

VHHPPSYVAH LASDFGVRVF QQVAQASKDR NVVFSPYGVA SVLAMLQLTT
GQETRQLQA AMGFKIDDKG MAPALRHLYK ELLGPWNKDE ISTTDAIFVQ
RDLKLVQGFM PHFRLFRSI VKQVDFSEAE RARFIINDWV KTHTKGMISD
LLGKGAVDQL TRLVLVNALY FNGHWKTPFP DSSTHRRLFH KSDGSTVSVP
MMAQTNKFNY TEFTTPDGHY YDILELPYHG NTLSMFIAAP YEKQVPLSAL
TNIISAQLIS HWKGNMTRLP RLLVLPKFSL ETEVDLRKPL ENLGMTDMFR
QFOADFTSLS NQEPLHVAQA LQKVKIEVNE SGTVASSSTA VTVSARMAPE
EITMDRPFLF LFMGQVMEP

BOLD = HX MS epitope

☐ = X-ray epitope

FIG. 53

SEQUENCE LISTING

<160> NUMBER OF SEQ ID NOS: 170

<210> SEQ ID NO 1
<211> LENGTH: 379
<212> TYPE: PRT
<213> ORGANISM: Homo sapiens

<400> SEQUENCE: 1

Val His His Pro Pro Ser Tyr Val Ala His Leu Ala Ser Asp Phe Gly
1               5                   10                  15

-continued

```
Val Arg Val Phe Gln Gln Val Ala Gln Ala Ser Lys Asp Arg Asn Val
            20                  25                  30

Val Phe Ser Pro Tyr Gly Val Ala Ser Val Leu Ala Met Leu Gln Leu
            35                  40                  45

Thr Thr Gly Gly Glu Thr Gln Gln Gln Ile Gln Ala Ala Met Gly Phe
        50                  55                  60

Lys Ile Asp Asp Lys Gly Met Ala Pro Ala Leu Arg His Leu Tyr Lys
65                  70                  75                  80

Glu Leu Met Gly Pro Trp Asn Lys Asp Glu Ile Ser Thr Thr Asp Ala
                85                  90                  95

Ile Phe Val Gln Arg Asp Leu Lys Leu Val Gln Gly Phe Met Pro His
            100                 105                 110

Phe Phe Arg Leu Phe Arg Ser Thr Val Lys Gln Val Asp Phe Ser Glu
            115                 120                 125

Val Glu Arg Ala Arg Phe Ile Ile Asn Asp Trp Val Lys Thr His Thr
        130                 135                 140

Lys Gly Met Ile Ser Asn Leu Leu Gly Lys Gly Ala Val Asp Gln Leu
145                 150                 155                 160

Thr Arg Leu Val Leu Val Asn Ala Leu Tyr Phe Asn Gly Gln Trp Lys
            165                 170                 175

Thr Pro Phe Pro Asp Ser Ser Thr His Arg Arg Leu Phe His Lys Ser
            180                 185                 190

Asp Gly Ser Thr Val Ser Val Pro Met Met Ala Gln Thr Asn Lys Phe
            195                 200                 205

Asn Tyr Thr Glu Phe Thr Thr Pro Asp Gly His Tyr Tyr Asp Ile Leu
        210                 215                 220

Glu Leu Pro Tyr His Gly Asp Thr Leu Ser Met Phe Ile Ala Ala Pro
225                 230                 235                 240

Tyr Glu Lys Glu Val Pro Leu Ser Ala Leu Thr Asn Ile Leu Ser Ala
            245                 250                 255

Gln Leu Ile Ser His Trp Lys Gly Asn Met Thr Arg Leu Pro Arg Leu
            260                 265                 270

Leu Val Leu Pro Lys Phe Ser Leu Glu Thr Glu Val Asp Leu Arg Lys
            275                 280                 285

Pro Leu Glu Asn Leu Gly Met Thr Asp Met Phe Arg Gln Phe Gln Ala
        290                 295                 300

Asp Phe Thr Ser Leu Ser Asp Gln Glu Pro Leu His Val Ala Gln Ala
305                 310                 315                 320

Leu Gln Lys Val Lys Ile Glu Val Asn Glu Ser Gly Thr Val Ala Ser
            325                 330                 335

Ser Ser Thr Ala Val Ile Val Ser Ala Arg Met Ala Pro Glu Glu Ile
            340                 345                 350

Ile Met Asp Arg Pro Phe Leu Phe Val Val Arg His Asn Pro Thr Gly
            355                 360                 365

Thr Val Leu Phe Met Gly Gln Val Met Glu Pro
        370                 375
```

<210> SEQ ID NO 2
<211> LENGTH: 124
<212> TYPE: PRT
<213> ORGANISM: Artificial Sequence
<220> FEATURE:
<223> OTHER INFORMATION: mA105 VH

<400> SEQUENCE: 2

-continued

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Phe Thr Phe Ser Ile Tyr
            20                  25                  30

Trp Ile Glu Trp Val Lys Gln Arg Pro Gly Leu Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Phe
65                  70                  75                  80

Met Gln Leu Ser Ser Leu Thr Ser Glu Asp Ser Ala Val Tyr Tyr Cys
                85                  90                  95

Ala Arg Gly Gly Leu Tyr Tyr Asp Leu Asp Tyr Trp Gly Gln Gly Thr
            100                 105                 110

Ile Leu Thr Val Ser Ser Ala Lys Thr Thr Pro Pro
        115                 120
```

<210> SEQ ID NO 3
<211> LENGTH: 115
<212> TYPE: PRT
<213> ORGANISM: Artificial Sequence
<220> FEATURE:
<223> OTHER INFORMATION: mA105 VL

<400> SEQUENCE: 3

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
            35                  40                  45

Pro Gln Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Lys Leu
65                  70                  75                  80

Ser Arg Val Glu Gly Ala Asp Leu Gly Val Tyr Tyr Cys Trp Gln Asp
                85                  90                  95

Arg His Phe Pro Arg Thr Phe Gly Gly Gly Thr Lys Leu Glu Ile Lys
            100                 105                 110

Arg Ala Asp
        115
```

<210> SEQ ID NO 4
<211> LENGTH: 125
<212> TYPE: PRT
<213> ORGANISM: Artificial Sequence
<220> FEATURE:
<223> OTHER INFORMATION: mA39 VH

<400> SEQUENCE: 4

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Asn Ile Tyr
            20                  25                  30

Trp Ile Gln Trp Val Lys Gln Arg Pro Gly His Gly Leu Glu Trp Ile
        35                  40                  45

Gly Glu Ile Leu Pro Gly Ser Asn Thr Asn Tyr Asn Glu Lys Phe Lys
    50                  55                  60
```

-continued

```
Asp Lys Ala Thr Phe Thr Ala Asp Ser Ser Ser Asn Thr Ala Tyr Met
65                  70                  75                  80

Gln Leu Ser Ser Leu Thr Ser Glu Asp Ser Ala Val Tyr Tyr Cys Ala
                85                  90                  95

Arg Leu Gly Ile Gly Leu Arg Gly Ala Leu Asp Tyr Trp Gly Gln Gly
            100                 105                 110

Thr Ser Val Thr Val Ser Ser Ala Lys Thr Thr Pro Pro
        115                 120                 125

<210> SEQ ID NO 5
<211> LENGTH: 110
<212> TYPE: PRT
<213> ORGANISM: Artificial Sequence
<220> FEATURE:
<223> OTHER INFORMATION: mA39 VL

<400> SEQUENCE: 5

Asp Ile Gln Met Thr His Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr His Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
        50                  55                  60

Ser Gly Ser Gly Thr Gln Phe Ser Leu Asn Ile Lys Ser Leu Gln Pro
65                  70                  75                  80

Glu Asp Phe Gly Thr Phe Tyr Cys Gln His Arg Tyr Gly Ser Pro Trp
                85                  90                  95

Thr Phe Gly Gly Gly Thr Lys Leu Glu Ile Lys Arg Ala Asp
            100                 105                 110

<210> SEQ ID NO 6
<211> LENGTH: 125
<212> TYPE: PRT
<213> ORGANISM: Artificial Sequence
<220> FEATURE:
<223> OTHER INFORMATION: mA44 VH

<400> SEQUENCE: 6

Glu Met Gln Leu Gln Glu Ser Gly Pro Ser Leu Val Lys Pro Ser Gln
1               5                   10                  15

Thr Leu Ser Leu Thr Cys Ser Val Thr Gly Asp Ser Met Thr Asn Gly
                20                  25                  30

Tyr Trp Asn Trp Ile Arg Lys Phe Pro Gly Asn Lys Leu Glu Tyr Met
            35                  40                  45

Gly Tyr Ile Thr Tyr Ser Gly Ser Thr Tyr Tyr Asn Pro Ser Leu Lys
        50                  55                  60

Gly Arg Ile Ser Ile Thr Arg Asn Thr Ser Lys Asn Gln Tyr Tyr Leu
65                  70                  75                  80

Gln Leu Ser Ser Val Thr Thr Glu Asp Thr Ala Thr Tyr Tyr Cys Ala
                85                  90                  95

Arg Trp His Tyr Gly Ser Pro Tyr Tyr Phe Asp Tyr Trp Gly Gln Gly
            100                 105                 110

Thr Thr Leu Thr Val Ser Ser Ala Lys Thr Thr Pro Pro
        115                 120                 125
```

```
<210> SEQ ID NO 7
<211> LENGTH: 110
<212> TYPE: PRT
<213> ORGANISM: Artificial Sequence
<220> FEATURE:
<223> OTHER INFORMATION: mA44 VL

<400> SEQUENCE: 7

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys Arg Ala Asp
            100                 105                 110

<210> SEQ ID NO 8
<211> LENGTH: 124
<212> TYPE: PRT
<213> ORGANISM: Artificial Sequence
<220> FEATURE:
<223> OTHER INFORMATION: mA71 VH

<400> SEQUENCE: 8

Gln Val Gln Leu Gln Gln Ser Gly Ala Glu Leu Met Lys Pro Gly Ala
1               5                   10                  15

Ser Val Lys Ile Ser Cys Lys Ala Thr Gly Phe Thr Phe Ser Thr Tyr
            20                  25                  30

Trp Ile Glu Trp Ile Lys Gln Arg Pro Gly His Gly Leu Asp Trp Ile
        35                  40                  45

Gly Glu Ile Leu Pro Gly Ser Gly Asn Thr Asn Tyr Asn Glu Lys Phe
    50                  55                  60

Lys Gly Lys Ala Thr Phe Thr Ala Asp Thr Ser Ser Asn Thr Val Tyr
65                  70                  75                  80

Met Gln Leu Ser Ser Leu Thr Ser Glu Asp Ser Ala Val Tyr Tyr Cys
                85                  90                  95

Ala Arg Gly Gly Leu Tyr Tyr Asn Leu Asp Ser Trp Gly Gln Gly Thr
            100                 105                 110

Thr Leu Thr Val Ser Ser Ala Lys Thr Thr Pro Pro
        115                 120

<210> SEQ ID NO 9
<211> LENGTH: 115
<212> TYPE: PRT
<213> ORGANISM: Artificial Sequence
<220> FEATURE:
<223> OTHER INFORMATION: mA71 VL

<400> SEQUENCE: 9

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30
```

-continued

```
Asp Gly Lys Thr Tyr Leu Tyr Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Asp
                85                  90                  95

Thr His Phe Pro Arg Thr Phe Gly Gly Gly Thr Lys Leu Glu Ile Lys
            100                 105                 110

Arg Ala Asp
        115

<210> SEQ ID NO 10
<211> LENGTH: 140
<212> TYPE: PRT
<213> ORGANISM: Artificial Sequence
<220> FEATURE:
<223> OTHER INFORMATION: mB109 VH

<400> SEQUENCE: 10

Glu Val Gln Leu Gln Gln Ser Gly Ser Val Leu Ala Arg Pro Gly Thr
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Met
        35                  40                  45

Gly Ala Ile Tyr Pro Gly Asn Ser Gly Gln Gly Leu Asp Trp Ile Gly
    50                  55                  60

Ala Ile Tyr Pro Gly Asn Ser Asp Thr Thr Tyr Asn Gln Lys Phe Glu
65                  70                  75                  80

Asp Lys Ala Lys Leu Thr Ala Val Ala Ser Ala Ser Thr Ala Tyr Met
                85                  90                  95

Glu Val Ser Ser Leu Thr Asn Glu Asp Ser Ala Val Tyr Tyr Cys Thr
            100                 105                 110

Arg Gly Leu Arg Arg Trp Gly Ala Met Asp Tyr Trp Gly Gln Gly Thr
            115                 120                 125

Ser Val Thr Val Ser Ser Ala Lys Thr Thr Pro Pro
    130                 135                 140

<210> SEQ ID NO 11
<211> LENGTH: 110
<212> TYPE: PRT
<213> ORGANISM: Artificial Sequence
<220> FEATURE:
<223> OTHER INFORMATION: mB109 VL

<400> SEQUENCE: 11

Asp Ile Val Met Thr Gln Ser His Lys Phe Met Ser Thr Ser Ala Gly
1               5                   10                  15

Asp Arg Val Ser Ile Pro Cys Lys Ala Ser Gln Asp Val Ser Ser Ala
            20                  25                  30

Val Ala Trp Tyr Gln Gln Lys Leu Gly Gln Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
```

```
65                    70                    75                    80

Glu Asp Leu Ala Val Tyr Tyr Cys Gln Gln His Tyr Ser Ser Pro Tyr
                     85                    90                    95

Thr Phe Gly Gly Gly Thr Asn Leu Glu Ile Lys Arg Ala Asp
             100                   105                   110
```

```
<210> SEQ ID NO 12
<211> LENGTH: 125
<212> TYPE: PRT
<213> ORGANISM: Artificial Sequence
<220> FEATURE:
<223> OTHER INFORMATION: mB28 VH

<400> SEQUENCE: 12

Gln Val Gln Leu Gln Gln Ser Gly Ala Glu Leu Met Lys Pro Gly Ala
1                   5                     10                    15

Ser Val Lys Ile Ser Cys Lys Ala Thr Gly Tyr Thr Phe Ser Ile Ser
                    20                    25                    30

Trp Ile Glu Trp Ile Lys Gln Arg Pro Gly Gly Leu Glu Trp Ile Gly
            35                    40                    45

Lys Ile Leu Pro Gly Ser Gly Gly Ala Asn Tyr Asn Glu Lys Phe Lys
    50                    55                    60

Gly Lys Ala Thr Val Thr Ala Asp Thr Ser Ser Asn Thr Val Tyr Met
65                    70                    75                    80

Gln Leu Ser Ser Leu Thr Ser Glu Asp Ser Ala Val Tyr Tyr Cys Ala
                    85                    90                    95

Arg Leu Ser Thr Gly Thr Arg Gly Ala Phe Asp Tyr Trp Gly Gln Gly
            100                   105                   110

Thr Thr Leu Thr Val Ser Ser Ala Lys Thr Thr Pro Pro
            115                   120                   125
```

```
<210> SEQ ID NO 13
<211> LENGTH: 110
<212> TYPE: PRT
<213> ORGANISM: Artificial Sequence
<220> FEATURE:
<223> OTHER INFORMATION: mB28 VL

<400> SEQUENCE: 13

Asp Ile Gln Leu Thr Gln Ser Pro Ala Ser Leu Ser Ala Ser Val Gly
1                   5                     10                    15

Ala Thr Val Thr Ile Thr Cys Arg Ala Ser Glu Asn Val Tyr Ser Tyr
                    20                    25                    30

Leu Ala Trp Tyr Gln Gln Lys Gln Gly Lys Ser Pro Gln Leu Leu Val
            35                    40                    45

Tyr Asn Ala Lys Thr Leu Ala Glu Gly Val Pro Ser Arg Phe Ser Gly
    50                    55                    60

Ser Gly Ser Gly Thr Gln Phe Ser Leu Lys Ile Asn Tyr Leu Gln Pro
65                    70                    75                    80

Glu Asp Phe Gly Ser Tyr Tyr Cys Gln His His Tyr Gly Thr Pro Pro
                    85                    90                    95

Thr Phe Gly Gly Gly Thr Lys Val Glu Ile Lys Arg Ala Asp
            100                   105                   110
```

```
<210> SEQ ID NO 14
<211> LENGTH: 121
<212> TYPE: PRT
<213> ORGANISM: Artificial Sequence
<220> FEATURE:
```

<223> OTHER INFORMATION: mC45 VH

<400> SEQUENCE: 14

Gln Val Gln Leu Gln Gln Ser Gly Val Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Val Ile His Pro Gly Ser Gly Val Thr Asn Tyr Asn Glu Lys Phe
    50                  55                  60

Lys Gly Lys Ala Ile Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Asp Tyr Tyr Gly Ser Ser His Gly Leu Met Asp Tyr Trp Gly
            100                 105                 110

Gln Gly Thr Ser Val Thr Val Ser Ser
        115                 120

<210> SEQ ID NO 15
<211> LENGTH: 107
<212> TYPE: PRT
<213> ORGANISM: Artificial Sequence
<220> FEATURE:
<223> OTHER INFORMATION: mC45 VL

<400> SEQUENCE: 15

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105

<210> SEQ ID NO 16
<211> LENGTH: 118
<212> TYPE: PRT
<213> ORGANISM: Artificial Sequence
<220> FEATURE:
<223> OTHER INFORMATION: mE16 VH

<400> SEQUENCE: 16

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Glu Lys Gly Leu Gly Trp Val
        35                  40                  45

Ala Ser Leu Arg Thr Gly Gly Asn Thr Tyr Tyr Ser Asp Ser Val Lys

```
           50                 55                 60

Gly Arg Phe Thr Ile Ser Arg Asp Asn Asp Arg Asn Ile Leu Tyr Leu
65                  70                  75                  80

Gln Met Ser Ser Leu Thr Ser Glu Asp Thr Ala Val Tyr Tyr Cys Ala
                85                  90                  95

Arg Gly Leu Arg His Trp Gly Tyr Phe Asp Val Trp Gly Ala Gly Thr
                100                 105                 110

Thr Val Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: mE16 VL

<400> SEQUENCE: 17

Asp Ile Val Met Thr Gln Ser His Lys Phe Met Ser Thr Ser Val Gly
1                   5                   10                  15

Asp Arg Val Asn Ile Thr Cys Lys Ala Ser Gln Asp Val Ser Thr Ala
                20                  25                  30

Val Gly Trp Tyr Gln Gln Glu Pro Gly Gln Ser Pro Lys Leu Leu Ile
            35                  40                  45

Tyr Ser Ala Ser Asn Arg His Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Trp
                85                  90                  95

Thr Phe Gly Gly Gly Thr Lys Leu Glu Ile Lys
                100                 105

<210> SEQ ID NO 18
<211> LENGTH: 118
<212> TYPE: PRT
<213> ORGANISM: Artificial Sequence
<220> FEATURE:
<223> OTHER INFORMATION: mE21 VH

<400> SEQUENCE: 18

Glu Val Gln Leu Gln Gln Ser Gly Ala Glu Leu Val Arg Ser Gly Ala
1                   5                   10                  15

Ser Val Lys Leu Ser Cys Thr Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asp Thr Glu Tyr Asp Pro Lys Phe
        50                  55                  60

Gln Ala Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Met Tyr Gly Asn Tyr Pro Tyr Tyr Phe Asp Tyr Trp Gly Gln Gly Thr
                100                 105                 110

Thr Leu Thr Val Ser Ser
        115
```

<210> SEQ ID NO 19
<211> LENGTH: 107
<212> TYPE: PRT
<213> ORGANISM: Artificial Sequence
<220> FEATURE:
<223> OTHER INFORMATION: mE21 VL

<400> SEQUENCE: 19

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 20
<211> LENGTH: 11
<212> TYPE: PRT
<213> ORGANISM: Artificial Sequence
<220> FEATURE:
<223> OTHER INFORMATION: mA105 HCDR3

<400> SEQUENCE: 20

```
Ala Arg Gly Gly Leu Tyr Tyr Asp Leu Asp Tyr
1               5                   10
```

<210> SEQ ID NO 21
<211> LENGTH: 8
<212> TYPE: PRT
<213> ORGANISM: Artificial Sequence
<220> FEATURE:
<223> OTHER INFORMATION: mA105 HCDR2

<400> SEQUENCE: 21

```
Ile Leu Pro Gly Ser Gly Ser Thr
1               5
```

<210> SEQ ID NO 22
<211> LENGTH: 8
<212> TYPE: PRT
<213> ORGANISM: Artificial Sequence
<220> FEATURE:
<223> OTHER INFORMATION: mA105 HCDR1

<400> SEQUENCE: 22

```
Gly Phe Thr Phe Ser Ile Tyr Trp
1               5
```

<210> SEQ ID NO 23
<211> LENGTH: 9
<212> TYPE: PRT
<213> ORGANISM: Artificial Sequence
<220> FEATURE:
<223> OTHER INFORMATION: mA105 LCDR3

<400> SEQUENCE: 23

Trp Gln Asp Arg His Phe Pro Arg Thr
1               5

<210> SEQ ID NO 24
<211> LENGTH: 3
<212> TYPE: PRT
<213> ORGANISM: Artificial Sequence
<220> FEATURE:
<223> OTHER INFORMATION: mA105 LCDR2

<400> SEQUENCE: 24

Leu Val Ser
1

<210> SEQ ID NO 25
<211> LENGTH: 11
<212> TYPE: PRT
<213> ORGANISM: Artificial Sequence
<220> FEATURE:
<223> OTHER INFORMATION: mA105 LCDR1

<400> SEQUENCE: 25

Gln Ser Leu Leu Asp Ser Asp Gly Lys Thr Tyr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: mA39 HCDR3

<400> SEQUENCE: 26

Ala Arg Leu Gly Ile Gly Leu Arg Gly Ala Leu Asp Tyr
1               5                   10

<210> SEQ ID NO 27
<211> LENGTH: 7
<212> TYPE: PRT
<213> ORGANISM: Artificial Sequence
<220> FEATURE:
<223> OTHER INFORMATION: mA39 HCDR2

<400> SEQUENCE: 27

Ile Leu Pro Gly Ser Asn Thr
1               5

<210> SEQ ID NO 28
<211> LENGTH: 8
<212> TYPE: PRT
<213> ORGANISM: Artificial Sequence
<220> FEATURE:
<223> OTHER INFORMATION: mA39 HCDR1

<400> SEQUENCE: 28

Gly Tyr Thr Phe Asn Ile Tyr Trp
1               5

<210> SEQ ID NO 29
<211> LENGTH: 9
<212> TYPE: PRT
<213> ORGANISM: Artificial Sequence
<220> FEATURE:
<223> OTHER INFORMATION: mA39 LCDR3

<400> SEQUENCE: 29

Gln His Arg Tyr Gly Ser Pro Trp Thr
1               5

<210> SEQ ID NO 30
<211> LENGTH: 3
<212> TYPE: PRT
<213> ORGANISM: Artificial Sequence
<220> FEATURE:
<223> OTHER INFORMATION: mA39 LCDR2

<400> SEQUENCE: 30

Asn Ala Lys
1

<210> SEQ ID NO 31
<211> LENGTH: 6
<212> TYPE: PRT
<213> ORGANISM: Artificial Sequence
<220> FEATURE:
<223> OTHER INFORMATION: mA38 LCDR1

<400> SEQUENCE: 31

Glu Asn Ile Tyr Ser Tyr
1               5

<210> SEQ ID NO 32
<211> LENGTH: 13
<212> TYPE: PRT
<213> ORGANISM: Artificial Sequence
<220> FEATURE:
<223> OTHER INFORMATION: mA44 HCDR3

<400> SEQUENCE: 32

Ala Arg Trp His Tyr Gly Ser Pro Tyr Tyr Phe Asp Tyr
1               5                   10

<210> SEQ ID NO 33
<211> LENGTH: 7
<212> TYPE: PRT
<213> ORGANISM: Artificial Sequence
<220> FEATURE:
<223> OTHER INFORMATION: mA44 HCDR2

<400> SEQUENCE: 33

Ile Thr Tyr Ser Gly Ser Thr
1               5

<210> SEQ ID NO 34
<211> LENGTH: 8
<212> TYPE: PRT
<213> ORGANISM: Artificial Sequence
<220> FEATURE:
<223> OTHER INFORMATION: mA44 HCDR1

<400> SEQUENCE: 34

Gly Asp Ser Met Thr Asn Gly Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: mA44 LCDR3

<400> SEQUENCE: 35

Leu Gln Tyr Asp Glu Phe Pro Pro Thr

```
1               5
```

```
<210> SEQ ID NO 36
<211> LENGTH: 3
<212> TYPE: PRT
<213> ORGANISM: Artificial Sequence
<220> FEATURE:
<223> OTHER INFORMATION: mA44 LCDR2

<400> SEQUENCE: 36

Arg Ala Asn
1

<210> SEQ ID NO 37
<211> LENGTH: 6
<212> TYPE: PRT
<213> ORGANISM: Artificial Sequence
<220> FEATURE:
<223> OTHER INFORMATION: mA44 LCDR1

<400> SEQUENCE: 37

Gln Asp Ile Asn Ser Tyr
1               5

<210> SEQ ID NO 38
<211> LENGTH: 11
<212> TYPE: PRT
<213> ORGANISM: Artificial Sequence
<220> FEATURE:
<223> OTHER INFORMATION: mA71 HCDR3

<400> SEQUENCE: 38

Ala Arg Gly Gly Leu Tyr Tyr Asn Leu Asp Ser
1               5                   10

<210> SEQ ID NO 39
<211> LENGTH: 8
<212> TYPE: PRT
<213> ORGANISM: Artificial Sequence
<220> FEATURE:
<223> OTHER INFORMATION: mA71 HCDR2

<400> SEQUENCE: 39

Ile Leu Pro Gly Ser Gly Asn Thr
1               5

<210> SEQ ID NO 40
<211> LENGTH: 8
<212> TYPE: PRT
<213> ORGANISM: Artificial Sequence
<220> FEATURE:
<223> OTHER INFORMATION: mA71 HCDR1

<400> SEQUENCE: 40

Gly Phe Thr Phe Ser Thr Tyr Trp
1               5

<210> SEQ ID NO 41
<211> LENGTH: 9
<212> TYPE: PRT
<213> ORGANISM: Artificial Sequence
<220> FEATURE:
<223> OTHER INFORMATION: mA71 LCDR3

<400> SEQUENCE: 41

Trp Gln Asp Thr His Phe Pro Arg Thr
1               5
```

```
<210> SEQ ID NO 42
<211> LENGTH: 3
<212> TYPE: PRT
<213> ORGANISM: Artificial Sequence
<220> FEATURE:
<223> OTHER INFORMATION: mA71 LCDR2

<400> SEQUENCE: 42

Leu Val Ser
1

<210> SEQ ID NO 43
<211> LENGTH: 11
<212> TYPE: PRT
<213> ORGANISM: Artificial Sequence
<220> FEATURE:
<223> OTHER INFORMATION: mA71 LCDR1

<400> SEQUENCE: 43

Gln Ser Leu Leu Asp Ser Asp Gly Lys Thr Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: mA75 HCDR3

<400> SEQUENCE: 44

Ala Arg Gly Gly Leu Tyr Tyr Ala Met Asp Tyr
1               5                   10

<210> SEQ ID NO 45
<211> LENGTH: 8
<212> TYPE: PRT
<213> ORGANISM: Artificial Sequence
<220> FEATURE:
<223> OTHER INFORMATION: mA75 HCDR2

<400> SEQUENCE: 45

Ile Leu Pro Gly Ser Gly Leu Thr
1               5

<210> SEQ ID NO 46
<211> LENGTH: 8
<212> TYPE: PRT
<213> ORGANISM: Artificial Sequence
<220> FEATURE:
<223> OTHER INFORMATION: mA75 HCDR1

<400> SEQUENCE: 46

Gly Phe Thr Phe Ser Thr Tyr Trp
1               5

<210> SEQ ID NO 47
<211> LENGTH: 9
<212> TYPE: PRT
<213> ORGANISM: Artificial Sequence
<220> FEATURE:
<223> OTHER INFORMATION: mA75 LCDR3

<400> SEQUENCE: 47

Trp Gln Gly Ser His Phe Pro Gln Thr
1               5
```

```
<210> SEQ ID NO 48
<211> LENGTH: 3
<212> TYPE: PRT
<213> ORGANISM: Artificial Sequence
<220> FEATURE:
<223> OTHER INFORMATION: mA75 LCDR2

<400> SEQUENCE: 48

Leu Val Cys
1

<210> SEQ ID NO 49
<211> LENGTH: 11
<212> TYPE: PRT
<213> ORGANISM: Artificial Sequence
<220> FEATURE:
<223> OTHER INFORMATION: mA75 LCDR1

<400> SEQUENCE: 49

Gln Ser Leu Leu Asp Ser Glu Gly Lys Thr Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: mB109 HCDR3

<400> SEQUENCE: 50

Thr Arg Gly Leu Arg Arg Trp Gly Ala Met Asp Tyr
1               5                   10

<210> SEQ ID NO 51
<211> LENGTH: 8
<212> TYPE: PRT
<213> ORGANISM: Artificial Sequence
<220> FEATURE:
<223> OTHER INFORMATION: mB109 HCDR2

<400> SEQUENCE: 51

Ile Leu Pro Gly Ser Gly Leu Thr
1               5

<210> SEQ ID NO 52
<211> LENGTH: 8
<212> TYPE: PRT
<213> ORGANISM: Artificial Sequence
<220> FEATURE:
<223> OTHER INFORMATION: mB109 HCDR1

<400> SEQUENCE: 52

Gly Phe Thr Phe Ser Thr Tyr Trp
1               5

<210> SEQ ID NO 53
<211> LENGTH: 9
<212> TYPE: PRT
<213> ORGANISM: Artificial Sequence
<220> FEATURE:
<223> OTHER INFORMATION: mB109 LCDR3

<400> SEQUENCE: 53

Gln Gln His Tyr Ser Ser Pro Tyr Thr
1               5
```

```
<210> SEQ ID NO 54
<211> LENGTH: 3
<212> TYPE: PRT
<213> ORGANISM: Artificial Sequence
<220> FEATURE:
<223> OTHER INFORMATION: mB109 LCDR2

<400> SEQUENCE: 54

Ser Ala Ser
1

<210> SEQ ID NO 55
<211> LENGTH: 6
<212> TYPE: PRT
<213> ORGANISM: Artificial Sequence
<220> FEATURE:
<223> OTHER INFORMATION: mB109 LCDR1

<400> SEQUENCE: 55

Gln Asp Val Ser Ser Ala
1               5

<210> SEQ ID NO 56
<211> LENGTH: 13
<212> TYPE: PRT
<213> ORGANISM: Artificial Sequence
<220> FEATURE:
<223> OTHER INFORMATION: mB28 HCDR3

<400> SEQUENCE: 56

Ala Arg Leu Ser Thr Gly Thr Arg Gly Ala Phe Asp Tyr
1               5                   10

<210> SEQ ID NO 57
<211> LENGTH: 8
<212> TYPE: PRT
<213> ORGANISM: Artificial Sequence
<220> FEATURE:
<223> OTHER INFORMATION: mB28 HCDR2

<400> SEQUENCE: 57

Ile Leu Pro Gly Ser Gly Gly Ala
1               5

<210> SEQ ID NO 58
<211> LENGTH: 8
<212> TYPE: PRT
<213> ORGANISM: Artificial Sequence
<220> FEATURE:
<223> OTHER INFORMATION: mB28 HCDR1

<400> SEQUENCE: 58

Gly Tyr Thr Phe Ser Ile Ser Trp
1               5

<210> SEQ ID NO 59
<211> LENGTH: 9
<212> TYPE: PRT
<213> ORGANISM: Artificial Sequence
<220> FEATURE:
<223> OTHER INFORMATION: mB28 LCDR3

<400> SEQUENCE: 59

Gln His His Tyr Gly Thr Pro Pro Thr
1               5

<210> SEQ ID NO 60
```

```
<211> LENGTH: 3
<212> TYPE: PRT
<213> ORGANISM: Artificial Sequence
<220> FEATURE:
<223> OTHER INFORMATION: mB28 LCDR2

<400> SEQUENCE: 60

Asn Ala Lys
1

<210> SEQ ID NO 61
<211> LENGTH: 6
<212> TYPE: PRT
<213> ORGANISM: Artificial Sequence
<220> FEATURE:
<223> OTHER INFORMATION: mB28 LCDR1

<400> SEQUENCE: 61

Glu Asn Val Tyr Ser Tyr
1               5

<210> SEQ ID NO 62
<211> LENGTH: 14
<212> TYPE: PRT
<213> ORGANISM: Artificial Sequence
<220> FEATURE:
<223> OTHER INFORMATION: mC45 HCDR3

<400> SEQUENCE: 62

Ala Arg Asp Tyr Tyr Gly Ser Ser His Gly Leu Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: mC45 HCDR2

<400> SEQUENCE: 63

Ile His Pro Gly Ser Gly Val Thr
1               5

<210> SEQ ID NO 64
<211> LENGTH: 8
<212> TYPE: PRT
<213> ORGANISM: Artificial Sequence
<220> FEATURE:
<223> OTHER INFORMATION: mC45 HCDR1

<400> SEQUENCE: 64

Gly Tyr Ala Phe Thr Asn Tyr Leu
1               5

<210> SEQ ID NO 65
<211> LENGTH: 9
<212> TYPE: PRT
<213> ORGANISM: Artificial Sequence
<220> FEATURE:
<223> OTHER INFORMATION: mC45 LCDR3

<400> SEQUENCE: 65

Leu Gln Tyr Asp Glu Phe Pro Arg Thr
1               5

<210> SEQ ID NO 66
<211> LENGTH: 3
```

```
<212> TYPE: PRT
<213> ORGANISM: Artificial Sequence
<220> FEATURE:
<223> OTHER INFORMATION: mC45 LCDR2

<400> SEQUENCE: 66

Arg Ala Asn
1

<210> SEQ ID NO 67
<211> LENGTH: 6
<212> TYPE: PRT
<213> ORGANISM: Artificial Sequence
<220> FEATURE:
<223> OTHER INFORMATION: mC45 LCDR1

<400> SEQUENCE: 67

Gln Asp Ile Asn Ser Tyr
1               5

<210> SEQ ID NO 68
<211> LENGTH: 12
<212> TYPE: PRT
<213> ORGANISM: Artificial Sequence
<220> FEATURE:
<223> OTHER INFORMATION: mE16 HCDR3

<400> SEQUENCE: 68

Ala Arg Gly Leu Arg His Trp Gly Tyr Phe Asp Val
1               5                   10

<210> SEQ ID NO 69
<211> LENGTH: 7
<212> TYPE: PRT
<213> ORGANISM: Artificial Sequence
<220> FEATURE:
<223> OTHER INFORMATION: mE16 HCDR2

<400> SEQUENCE: 69

Leu Arg Thr Gly Gly Asn Thr
1               5

<210> SEQ ID NO 70
<211> LENGTH: 8
<212> TYPE: PRT
<213> ORGANISM: Artificial Sequence
<220> FEATURE:
<223> OTHER INFORMATION: mE16 HCDR1

<400> SEQUENCE: 70

Gly Phe Thr Phe Ser Asn Tyr Gly
1               5

<210> SEQ ID NO 71
<211> LENGTH: 9
<212> TYPE: PRT
<213> ORGANISM: Artificial Sequence
<220> FEATURE:
<223> OTHER INFORMATION: mE16 LCDR3

<400> SEQUENCE: 71

Gln Gln His Tyr Ser Ser Pro Trp Thr
1               5

<210> SEQ ID NO 72
<211> LENGTH: 3
<212> TYPE: PRT
```

-continued

```
<213> ORGANISM: Artificial Sequence
<220> FEATURE:
<223> OTHER INFORMATION: mE16 LCDR2

<400> SEQUENCE: 72

Ser Ala Ser
1

<210> SEQ ID NO 73
<211> LENGTH: 6
<212> TYPE: PRT
<213> ORGANISM: Artificial Sequence
<220> FEATURE:
<223> OTHER INFORMATION: mE16 LCDR1

<400> SEQUENCE: 73

Gln Asp Ile Ser Asn Tyr
1               5

<210> SEQ ID NO 74
<211> LENGTH: 11
<212> TYPE: PRT
<213> ORGANISM: Artificial Sequence
<220> FEATURE:
<223> OTHER INFORMATION: mE21 HCDR3

<400> SEQUENCE: 74

Met Tyr Gly Asn Tyr Pro Tyr Tyr Phe Asp Tyr
1               5                   10

<210> SEQ ID NO 75
<211> LENGTH: 8
<212> TYPE: PRT
<213> ORGANISM: Artificial Sequence
<220> FEATURE:
<223> OTHER INFORMATION: mE21 HCDR2

<400> SEQUENCE: 75

Ile Asp Pro Glu Asn Gly Asp Thr
1               5

<210> SEQ ID NO 76
<211> LENGTH: 8
<212> TYPE: PRT
<213> ORGANISM: Artificial Sequence
<220> FEATURE:
<223> OTHER INFORMATION: mE21 HCDR1

<400> SEQUENCE: 76

Gly Phe Asn Ile Lys Asp Tyr Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: mE21 LCDR3

<400> SEQUENCE: 77

Gln Gln Gly Asn Thr Leu Pro Trp Thr
1               5

<210> SEQ ID NO 78
<211> LENGTH: 3
<212> TYPE: PRT
<213> ORGANISM: Artificial Sequence
```

```
<220> FEATURE:
<223> OTHER INFORMATION: mE21 LCDR2

<400> SEQUENCE: 78

Tyr Thr Ser
1

<210> SEQ ID NO 79
<211> LENGTH: 6
<212> TYPE: PRT
<213> ORGANISM: Artificial Sequence
<220> FEATURE:
<223> OTHER INFORMATION: mE21 LCDR1

<400> SEQUENCE: 79

Gln Asp Ile Ser Asn Tyr
1               5

<210> SEQ ID NO 80
<211> LENGTH: 124
<212> TYPE: PRT
<213> ORGANISM: Artificial Sequence
<220> FEATURE:
<223> OTHER INFORMATION: mA75 VH

<400> SEQUENCE: 80

Gln Gly Gln Leu Gln Gln Ser Gly Ala Glu Leu Met Lys Pro Gly Ala
1               5                   10                  15

Ser Val Lys Ile Ser Cys Lys Ala Ser Gly Phe Thr Phe Ser Thr Tyr
            20                  25                  30

Trp Ile Ala Trp Leu Lys Gln Arg Pro Gly His Gly Leu Glu Trp Ile
        35                  40                  45

Ala Glu Ile Leu Pro Gly Ser Gly Leu Thr Asn Tyr Asn Glu Ile Phe
    50                  55                  60

Arg Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Leu Tyr Tyr Ala Met Asp Tyr Trp Gly Gln Gly Thr
            100                 105                 110

Ser Val Thr Val Ser Ser Ala Lys Thr Thr Ala Pro
        115                 120

<210> SEQ ID NO 81
<211> LENGTH: 114
<212> TYPE: PRT
<213> ORGANISM: Artificial Sequence
<220> FEATURE:
<223> OTHER INFORMATION: mA75 VL

<400> SEQUENCE: 81

Asp Val Val Met Thr Gln Thr Pro Leu Thr Leu Ser Val Thr Ile Gly
1               5                   10                  15

Gln Pro Ala Ser Ile Cys Lys Ser Ser Gln Ser Leu Leu Asp Ser Glu
            20                  25                  30

Gly Lys Thr Tyr Leu Asn Trp Leu Phe Gln Arg Pro Gly Gln Ser Pro
        35                  40                  45

Lys Arg Leu Ile Tyr Leu Val Cys Lys Leu Asp Cys Gly Val Pro Asp
    50                  55                  60

Arg Phe Thr Gly Ser Gly Ser Gly Thr Asp Phe Thr Leu Lys Ile Ser
65                  70                  75                  80
```

-continued

Arg Val Glu Gly Glu Asp Leu Gly Val Tyr Tyr Cys Trp Gln Gly Ser
            85                  90                  95

His Phe Pro Gln Thr Phe Gly Gly Gly Thr Lys Leu Glu Ile Lys Arg
            100                 105                 110

Ala Asp

<210> SEQ ID NO 82
<211> LENGTH: 119
<212> TYPE: PRT
<213> ORGANISM: Artificial Sequence
<220> FEATURE:
<223> OTHER INFORMATION: HC1a

<400> SEQUENCE: 82

Glu Met Thr Leu Lys Glu Ser Gly Pro Thr Leu Val Lys Pro Thr Gln
1               5                   10                  15

Thr Leu Ser Leu Thr Cys Ser Val Thr Gly Asp Ser Met Thr Asn Gly
            20                  25                  30

Tyr Trp Asn Trp Ile Arg Lys Phe Pro Gly Lys Ala Leu Glu Tyr Met
            35                  40                  45

Gly Tyr Ile Thr Tyr Ser Gly Ser Thr Tyr Tyr Asn Pro Ser Leu Lys
            50                  55                  60

Gly Arg Ile Ser Ile Thr Arg Asn Thr Ser Lys Asn Gln Tyr Tyr Leu
65                  70                  75                  80

Thr Leu Ser Ser Val Thr Thr Val Asp Thr Ala Thr Tyr Tyr Cys Ala
            85                  90                  95

Arg Trp His Tyr Gly Ser Pro Tyr Tyr Phe Asp Tyr Trp Gly Gln Gly
            100                 105                 110

Thr Thr Leu Thr Val Ser Ser
        115

<210> SEQ ID NO 83
<211> LENGTH: 119
<212> TYPE: PRT
<213> ORGANISM: Artificial Sequence
<220> FEATURE:
<223> OTHER INFORMATION: HC1b

<400> SEQUENCE: 83

Glu Met Gln Leu Gln Glu Ser Gly Pro Gly Leu Val Lys Pro Ser Glu
1               5                   10                  15

Thr Leu Ser Leu Thr Cys Ser Val Thr Gly Asp Ser Met Thr Asn Gly
            20                  25                  30

Tyr Trp Asn Trp Ile Arg Lys Phe Pro Gly Lys Gly Leu Glu Tyr Met
            35                  40                  45

Gly Tyr Ile Thr Tyr Ser Gly Ser Thr Tyr Tyr Asn Pro Ser Leu Lys
            50                  55                  60

Gly Arg Ile Ser Ile Thr Arg Asn Thr Ser Lys Asn Gln Tyr Tyr Leu
65                  70                  75                  80

Lys Leu Ser Ser Val Thr Thr Ala Asp Thr Ala Thr Tyr Tyr Cys Ala
            85                  90                  95

Arg Trp His Tyr Gly Ser Pro Tyr Tyr Phe Asp Tyr Trp Gly Gln Gly
            100                 105                 110

Thr Thr Leu Thr Val Ser Ser
        115

<210> SEQ ID NO 84

<211> LENGTH: 119
<212> TYPE: PRT
<213> ORGANISM: Artificial Sequence
<220> FEATURE:
<223> OTHER INFORMATION: HC2a

<400> SEQUENCE: 84

Glu Met Thr Leu Lys Glu Ser Gly Pro Thr Leu Val Lys Pro Thr Gln
1               5                   10                  15

Thr Leu Ser Leu Thr Cys Ser Val Thr Gly Glu Ser Met Thr Gln Gly
            20                  25                  30

Tyr Trp Asn Trp Ile Arg Lys Phe Pro Gly Lys Ala Leu Glu Tyr Met
        35                  40                  45

Gly Tyr Ile Thr Tyr Ser Gly Ser Thr Tyr Tyr Asn Pro Ser Leu Lys
    50                  55                  60

Gly Arg Ile Ser Ile Thr Arg Gln Thr Ser Lys Asn Gln Tyr Tyr Leu
65                  70                  75                  80

Thr Leu Ser Ser Val Thr Thr Val Glu Thr Ala Thr Tyr Tyr Cys Ala
            85                  90                  95

Arg Trp His Tyr Gly Ser Pro Tyr Tyr Phe Asp Tyr Trp Gly Gln Gly
            100                 105                 110

Thr Thr Leu Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: HC2b

<400> SEQUENCE: 85

Glu Met Thr Leu Lys Glu Ser Gly Pro Thr Leu Val Lys Pro Thr Gln
1               5                   10                  15

Thr Leu Ser Leu Thr Cys Ser Val Thr Gly Asp Ser Met Thr Gln Gly
            20                  25                  30

Tyr Trp Asn Trp Ile Arg Lys Phe Pro Gly Lys Ala Leu Glu Tyr Met
        35                  40                  45

Gly Tyr Ile Thr Tyr Ser Gly Ser Thr Tyr Tyr Asn Pro Ser Leu Lys
    50                  55                  60

Gly Arg Ile Ser Ile Thr Arg Asn Thr Ser Lys Asn Gln Tyr Tyr Leu
65                  70                  75                  80

Thr Leu Ser Ser Val Thr Thr Val Asp Thr Ala Thr Tyr Tyr Cys Ala
            85                  90                  95

Arg Trp His Tyr Gly Ser Pro Tyr Tyr Phe Asp Tyr Trp Gly Gln Gly
            100                 105                 110

Thr Thr Leu Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: HC3

<400> SEQUENCE: 86

Gln Met Thr Leu Lys Glu Ser Gly Pro Thr Leu Val Lys Pro Thr Gln
1               5                   10                  15

```
Thr Leu Ser Leu Thr Cys Ser Val Ser Gly Asp Ser Met Thr Asn Gly
        20                  25                  30

Tyr Trp Asn Trp Ile Arg Gln Phe Pro Gly Lys Ala Leu Glu Tyr Met
        35                  40                  45

Gly Tyr Ile Thr Tyr Ser Gly Ser Thr Tyr Tyr Asn Pro Ser Leu Lys
        50                  55                  60

Gly Arg Ile Thr Ile Thr Arg Asp Thr Ser Lys Asn Gln Tyr Tyr Leu
65                  70                  75                  80

Thr Leu Ser Ser Val Thr Thr Val Asp Thr Ala Thr Tyr Tyr Cys Ala
                85                  90                  95

Arg Trp His Tyr Gly Ser Pro Tyr Tyr Phe Asp Tyr Trp Gly Gln Gly
        100                 105                 110

Thr Thr Leu Thr Val Ser Ser
        115
```

<210> SEQ ID NO 87
<211> LENGTH: 119
<212> TYPE: PRT
<213> ORGANISM: Artificial Sequence
<220> FEATURE:
<223> OTHER INFORMATION: HC4

<400> SEQUENCE: 87

```
Gln Met Thr Leu Lys Glu Ser Gly Pro Thr Leu Val Lys Pro Thr Gln
1               5                   10                  15

Thr Leu Ser Leu Thr Cys Ser Val Ser Gly Glu Ser Met Thr Gln Gly
        20                  25                  30

Tyr Trp Asn Trp Ile Arg Gln Phe Pro Gly Lys Ala Leu Glu Tyr Met
        35                  40                  45

Gly Tyr Ile Thr Tyr Ser Gly Ser Thr Tyr Tyr Asn Pro Ser Leu Lys
        50                  55                  60

Gly Arg Ile Thr Ile Thr Arg Gln Thr Ser Lys Asn Gln Tyr Tyr Leu
65                  70                  75                  80

Thr Leu Ser Ser Val Thr Thr Val Glu Thr Ala Thr Tyr Tyr Cys Ala
                85                  90                  95

Arg Trp His Tyr Gly Ser Pro Tyr Tyr Phe Asp Tyr Trp Gly Gln Gly
        100                 105                 110

Thr Thr Leu Thr Val Ser Ser
        115
```

<210> SEQ ID NO 88
<211> LENGTH: 119
<212> TYPE: PRT
<213> ORGANISM: Artificial Sequence
<220> FEATURE:
<223> OTHER INFORMATION: HC5a

<400> SEQUENCE: 88

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Met Thr Asn Gly
        20                  25                  30

Tyr Trp Asn Trp Ile Arg Gln Pro Pro Gly Lys Gly Leu Glu Tyr Met
        35                  40                  45

Gly Tyr Ile Thr Tyr Ser Gly Ser Thr Tyr Tyr Asn Pro Ser Leu Lys
        50                  55                  60

Ser Arg Ile Thr Ile Ser Arg Asn Thr Ser Lys Asn Gln Tyr Ser Leu
65                  70                  75                  80
```

```
Lys Leu Ser Ser Val Thr Ala Ala Asp Thr Ala Val Tyr Tyr Cys Ala
                85                  90                  95

Arg Trp His Tyr Gly Ser Pro Tyr Tyr Phe Asp Tyr Trp Gly Gln Gly
            100                 105                 110

Thr Leu Val Thr Val Ser Ser
        115

<210> SEQ ID NO 89
<211> LENGTH: 119
<212> TYPE: PRT
<213> ORGANISM: Artificial Sequence
<220> FEATURE:
<223> OTHER INFORMATION: HC5b

<400> SEQUENCE: 89

Gln Met Gln Leu Gln Glu Ser Gly Pro Gly Leu Val Lys Pro Ser Glu
1               5                   10                  15

Thr Leu Ser Leu Thr Cys Thr Val Ser Gly Asp Ser Met Thr Asn Gly
            20                  25                  30

Tyr Trp Asn Trp Ile Arg Gln Pro Pro Gly Lys Gly Leu Glu Tyr Met
        35                  40                  45

Gly Tyr Ile Thr Tyr Ser Gly Ser Thr Tyr Tyr Asn Pro Ser Leu Lys
    50                  55                  60

Ser Arg Ile Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Trp His Tyr Gly Ser Pro Tyr Tyr Phe Asp Tyr Trp Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: HC5c

<400> SEQUENCE: 90

Gln Met Gln Leu Gln Gln Ser Gly Pro Gly Leu Val Lys Pro Ser Gln
1               5                   10                  15

Thr Leu Ser Leu Thr Cys Ala Ile Ser Gly Asp Ser Met Thr Asn Gly
            20                  25                  30

Tyr Trp Asn Trp Ile Arg Gln Ser Pro Ser Arg Gly Leu Glu Tyr Met
        35                  40                  45

Gly Tyr Ile Thr Tyr Ser Gly Ser Thr Tyr Tyr Ala Val Ser Val Lys
    50                  55                  60

Ser Arg Ile Thr Ile Asn Arg Asp Thr Ser Lys Asn Gln Tyr Ser Leu
65                  70                  75                  80

Gln Leu Ser Ser Val Thr Pro Glu Asp Thr Ala Val Tyr Tyr Cys Ala
                85                  90                  95

Arg Trp His Tyr Gly Ser Pro Tyr Tyr Phe Asp Tyr Trp Gly Gln Gly
            100                 105                 110

Thr Leu Val Thr Val Ser Ser
        115
```

-continued

```
<210> SEQ ID NO 91
<211> LENGTH: 107
<212> TYPE: PRT
<213> ORGANISM: Artificial Sequence
<220> FEATURE:
<223> OTHER INFORMATION: LC1a

<400> SEQUENCE: 91

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: LC1b

<400> SEQUENCE: 92

Asp Ile Lys Met Thr Gln Ser Pro Ser Ser Val Ser Val Ser Pro Gly
1               5                   10                  15

Gln Thr Val Thr Ile Thr Cys Lys Ala Ser Gln Asp Ile Asn Ser Tyr
            20                  25                  30

Leu Ser Trp Leu Gln Gln Lys Pro Gly Gln Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Gln Ala
65                  70                  75                  80

Met Asp Glu Gly Ile Tyr Tyr Cys Leu Gln Tyr Asp Glu Phe Pro Pro
                85                  90                  95

Thr Phe Gly Gly Gly Thr Lys Leu Thr Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: LC2

<400> SEQUENCE: 93

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45
```

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: LC3

<400> SEQUENCE: 94

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
            35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Ala Thr Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: LC4

<400> SEQUENCE: 95

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
            35                  40                  45

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Ala Thr Tyr Tyr Cys Leu Gln Tyr Asp Glu Phe Pro Pro
                85                  90                  95

Thr Phe Gly Gly Gly Thr Lys Leu Glu Ile Lys
            100                 105

<210> SEQ ID NO 96
<211> LENGTH: 107
<212> TYPE: PRT

```
<213> ORGANISM: Artificial Sequence
<220> FEATURE:
<223> OTHER INFORMATION: LC5a

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ala Pro Lys Leu Leu Ile
        35                  40                  45

Tyr Arg Ala Asn Arg Ser Val Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Glu Phe Pro Pro
                85                  90                  95

Thr Phe Gly Gly Gly Thr Lys Val Glu Ile Lys
            100                 105

<210> SEQ ID NO 97
<211> LENGTH: 107
<212> TYPE: PRT
<213> ORGANISM: Artificial Sequence
<220> FEATURE:
<223> OTHER INFORMATION: LC5b

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ala Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Tyr Asp Glu Phe Pro Pro
                85                  90                  95

Thr Phe Gly Gly Gly Thr Lys Val Glu Ile Lys
            100                 105

<210> SEQ ID NO 98
<211> LENGTH: 107
<212> TYPE: PRT
<213> ORGANISM: Artificial Sequence
<220> FEATURE:
<223> OTHER INFORMATION: LC5c

<400> SEQUENCE: 98

Glu Ile Val Met Thr Gln Ser Pro Ala Thr Leu Ser Leu Ser Pro Gly
1               5                   10                  15

Glu Arg Ala Thr Leu Ser Cys Lys Ala Ser Gln Asp Ile Asn Ser Tyr
            20                  25                  30

Leu Ser Trp Leu Gln Gln Lys Pro Gly Gln Ala Pro Arg Thr Leu Ile
        35                  40                  45

Tyr Arg Ala Asn Arg Ser Val Asp Gly Ile Pro Ala Arg Phe Ser Gly
    50                  55                  60
```

-continued

```
Ser Gly Ser Gly Gln Asp Tyr Thr Leu Thr Ile Ser Ser Leu Glu Pro
65                  70                  75                  80

Glu Asp Phe Ala Val Tyr Tyr Cys Leu Gln Tyr Asp Glu Phe Pro Pro
                85                  90                  95

Thr Phe Gly Gly Gly Thr Lys Val Glu Ile Lys
            100                 105
```

```
<210> SEQ ID NO 99
<211> LENGTH: 255
<212> TYPE: PRT
<213> ORGANISM: Artificial Sequence
<220> FEATURE:
<223> OTHER INFORMATION: CH

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe
                245                 250                 255
```

```
<210> SEQ ID NO 100
<211> LENGTH: 107
<212> TYPE: PRT
<213> ORGANISM: Artificial Sequence
<220> FEATURE:
<223> OTHER INFORMATION: CL

<400> SEQUENCE: 100

Arg Thr Val Ala Ala Pro Ser Val Phe Ile Phe Pro Pro Ser Asp Glu
```

-continued

```
1                5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 101
<211> LENGTH: 107
<212> TYPE: PRT
<213> ORGANISM: Artificial Sequence
<220> FEATURE:
<223> OTHER INFORMATION: vk1

<400> SEQUENCE: 101

Asp Ile Gln Met Thr Gln Ser Pro Ser Ser Leu Ser Ala Ser Val Gly
1                5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Ser Thr Pro Pro
                85                  90                  95

Thr Phe Gly Gln Gly Thr Lys Val Glu Ile Lys
                100                 105

<210> SEQ ID NO 102
<211> LENGTH: 106
<212> TYPE: PRT
<213> ORGANISM: Artificial Sequence
<220> FEATURE:
<223> OTHER INFORMATION: vlambda3
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid

<400> SEQUENCE: 102

Ser Tyr Glu Leu Thr Gln Pro Pro Ser Val Ser Val Ser Pro Gly Gln
1                5                   10                  15

Thr Ala Ser Ile Thr Xaa Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
```

-continued

```
            50                55                60

Asn Ser Gly Asn Thr Ala Thr Leu Thr Ile Ser Gly Thr Gln Ala Met
65                70                75                80

Asp Glu Ala Asp Tyr Tyr Xaa Gln Ala Trp Asp Ser Ser Ala Val Val
                85                90                95

Phe Gly Gly Gly Thr Lys Leu Thr Val Leu
            100               105

<210> SEQ ID NO 103
<211> LENGTH: 120
<212> TYPE: PRT
<213> ORGANISM: Artificial Sequence
<220> FEATURE:
<223> OTHER INFORMATION: vh2

<400> SEQUENCE: 103

Gln Val Thr Leu Lys Glu Ser Gly Pro Thr Leu Val Lys Pro Thr Gln
1               5                 10                15

Thr Leu Thr Leu Thr Cys Thr Phe Ser Gly Phe Ser Leu Ser Thr Ser
            20                25                30

Gly Val Gly Val Gly Trp Ile Arg Gln Pro Pro Gly Lys Ala Leu Glu
            35                40                45

Trp Leu Ala Arg Ile Asp Trp Asp Asp Asp Lys Tyr Tyr Ser Thr Ser
            50                55                60

Leu Lys Thr Arg Leu Thr Ile Ser Lys Asp Thr Ser Lys Asn Gln Val
65                70                75                80

Val Leu Thr Met Thr Asn Met Asp Pro Val Asp Thr Ala Thr Tyr Tyr
                85                90                95

Cys Ala Arg Met Gly Phe Thr Gly Thr Tyr Phe Asp Tyr Trp Gly Gln
            100               105               110

Gly Thr Leu Val Thr Val Ser Ser
            115               120

<210> SEQ ID NO 104
<211> LENGTH: 118
<212> TYPE: PRT
<213> ORGANISM: Artificial Sequence
<220> FEATURE:
<223> OTHER INFORMATION: vh4
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid

<400> SEQUENCE: 104

Gln Val Gln Leu Gln Glu Ser Gly Pro Gly Leu Val Lys Pro Ser Glu
1               5                 10                15

Thr Leu Ser Leu Thr Xaa Thr Val Ser Gly Gly Ser Ile Ser Ser Tyr
            20                25                30

Tyr Trp Ser Trp Ile Arg Gln Pro Pro Gly Lys Gly Leu Glu Trp Ile
            35                40                45

Gly Tyr Ile Tyr Tyr Ser Gly Ser Thr Asn Tyr Asn Pro Ser Leu Lys
            50                55                60

Ser Arg Val Thr Ile Ser Val Asp Thr Ser Lys Asn Gln Phe Ser Leu
65                70                75                80

Lys Leu Ser Ser Val Thr Ala Ala Asp Thr Ala Val Tyr Tyr Xaa Ala
```

```
                    85              90              95

Arg Gly Asp Ser Ser Gly Tyr Tyr Phe Asp Tyr Trp Gly Gln Gly Thr
            100             105             110

Leu Val Thr Val Ser Ser
        115

<210> SEQ ID NO 105
<211> LENGTH: 21
<212> TYPE: DNA
<213> ORGANISM: Artificial Sequence
<220> FEATURE:
<223> OTHER INFORMATION: Heavy Chain 3'- Primer

<400> SEQUENCE: 105
tatgcaaggc ttacaaccac a                                          21

<210> SEQ ID NO 106
<211> LENGTH: 24
<212> TYPE: DNA
<213> ORGANISM: Artificial Sequence
<220> FEATURE:
<223> OTHER INFORMATION: Light Chain 3'- Primer

<400> SEQUENCE: 106
ctcattcctg ttgaagctct tgag                                       24

<210> SEQ ID NO 107
<211> LENGTH: 107
<212> TYPE: PRT
<213> ORGANISM: Artificial Sequence
<220> FEATURE:
<223> OTHER INFORMATION: IGKV1-33-01_IGKJ4-01

<400> SEQUENCE: 107

Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
            20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Tyr Asp Asn Leu Pro Leu
                85              90              95

Thr Phe Gly Gly Gly Thr Lys Val Glu Ile Lys
            100             105

<210> SEQ ID NO 108
<211> LENGTH: 119
<212> TYPE: PRT
<213> ORGANISM: Artificial Sequence
<220> FEATURE:
<223> OTHER INFORMATION: IGHV4-59-02_IGHD6-13-01_IGHJ4-02

<400> SEQUENCE: 108

Gln Val Gln Leu Gln Glu Ser Gly Pro Gly Leu Val Lys Pro Ser Glu
1               5               10              15

Thr Leu Ser Leu Thr Cys Thr Val Ser Gly Gly Ser Val Ser Ser Tyr
            20              25              30
```

-continued

```
Tyr Trp Ser Trp Ile Arg Gln Pro Pro Gly Lys Gly Leu Glu Trp Ile
        35              40              45

Gly Tyr Ile Tyr Tyr Ser Gly Ser Thr Asn Tyr Asn Pro Ser Leu Lys
    50              55              60

Ser Arg Val Thr Ile Ser Val Asp Thr Ser Lys Asn Gln Phe Ser Leu
65              70              75              80

Lys Leu Ser Ser Val Thr Ala Ala Asp Thr Ala Val Tyr Tyr Cys Ala
            85              90              95

Arg Gly Tyr Ser Ser Ser Trp Tyr Tyr Phe Asp Tyr Trp Gly Gln Gly
            100             105             110

Thr Leu Val Thr Val Ser Ser
        115
```

```
<210> SEQ ID NO 109
<211> LENGTH: 226
<212> TYPE: PRT
<213> ORGANISM: Artificial Sequence
<220> FEATURE:
<223> OTHER INFORMATION: A44-hv1LC1a x HC1a

<400> SEQUENCE: 109

Asp Ile Lys Met Thr Gln Ser Pro Ser Ser Leu Ser Ala Ser Val Gly
1               5               10              15

Asp Arg Val Thr Ile Thr Cys Lys Ala Ser Gln Asp Ile Asn Ser Tyr
            20              25              30

Leu Ser Trp Leu Gln Gln Lys Pro Gly Lys Ser Pro Lys Thr Leu Ile
        35              40              45

Tyr Arg Ala Asn Arg Ser Val Asp Gly Val Pro Ser Arg Phe Ser Gly
    50              55              60

Ser Gly Ser Gly Gln Asp Tyr Ser Leu Thr Ile Ser Ser Leu Gln Pro
65              70              75              80

Glu Asp Leu Gly Ile Tyr Tyr Cys Leu Gln Tyr Asp Glu Phe Pro Pro
            85              90              95

Thr Phe Gly Gly Gly Thr Lys Leu Glu Ile Lys Glu Met Thr Leu Lys
            100             105             110

Glu Ser Gly Pro Thr Leu Val Lys Pro Thr Gln Thr Leu Ser Leu Thr
        115             120             125

Cys Ser Val Thr Gly Asp Ser Met Thr Asn Gly Tyr Trp Asn Trp Ile
    130             135             140

Arg Lys Phe Pro Gly Lys Ala Leu Glu Tyr Met Gly Tyr Ile Thr Tyr
145             150             155             160

Ser Gly Ser Thr Tyr Tyr Asn Pro Ser Leu Lys Gly Arg Ile Ser Ile
            165             170             175

Thr Arg Asn Thr Ser Lys Asn Gln Tyr Tyr Leu Thr Leu Ser Ser Val
            180             185             190

Thr Thr Val Asp Thr Ala Thr Tyr Tyr Cys Ala Arg Trp His Tyr Gly
        195             200             205

Ser Pro Tyr Tyr Phe Asp Tyr Trp Gly Gln Gly Thr Thr Leu Thr Val
        210             215             220

Ser Ser
225
```

```
<210> SEQ ID NO 110
<211> LENGTH: 226
<212> TYPE: PRT
<213> ORGANISM: Artificial Sequence
<220> FEATURE:
```

<223> OTHER INFORMATION: A44-hv2LC1b x HC1b

<400> SEQUENCE: 110

Asp Ile Lys Met Thr Gln Ser Pro Ser Ser Val Ser Val Ser Pro Gly
1               5                   10                  15

Gln Thr Val Thr Ile Thr Cys Lys Ala Ser Gln Asp Ile Asn Ser Tyr
            20                  25                  30

Leu Ser Trp Leu Gln Gln Lys Pro Gly Gln Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Gln Ala
65                  70                  75                  80

Met Asp Glu Gly Ile Tyr Tyr Cys Leu Gln Tyr Asp Glu Phe Pro Pro
                85                  90                  95

Thr Phe Gly Gly Gly Thr Lys Leu Thr Ile Lys Glu Met Gln Leu Gln
            100                 105                 110

Glu Ser Gly Pro Gly Leu Val Lys Pro Ser Glu Thr Leu Ser Leu Thr
            115                 120                 125

Cys Ser Val Thr Gly Asp Ser Met Thr Asn Gly Tyr Trp Asn Trp Ile
    130                 135                 140

Arg Lys Phe Pro Gly Lys Gly Leu Glu Tyr Met Gly Tyr Ile Thr Tyr
145                 150                 155                 160

Ser Gly Ser Thr Tyr Tyr Asn Pro Ser Leu Lys Gly Arg Ile Ser Ile
                165                 170                 175

Thr Arg Asn Thr Ser Lys Asn Gln Tyr Tyr Leu Lys Leu Ser Ser Val
                180                 185                 190

Thr Thr Ala Asp Thr Ala Thr Tyr Tyr Cys Ala Arg Trp His Tyr Gly
        195                 200                 205

Ser Pro Tyr Tyr Phe Asp Tyr Trp Gly Gln Gly Thr Thr Leu Thr Val
    210                 215                 220

Ser Ser
225

<210> SEQ ID NO 111
<211> LENGTH: 226
<212> TYPE: PRT
<213> ORGANISM: Artificial Sequence
<220> FEATURE:
<223> OTHER INFORMATION: A44-hv3LC2 x HC2a

<400> SEQUENCE: 111

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys Glu Met Thr Leu Lys
            100                 105                 110

```
Glu Ser Gly Pro Thr Leu Val Lys Pro Thr Gln Thr Leu Ser Leu Thr
        115                 120                 125

Cys Ser Val Thr Gly Glu Ser Met Thr Gln Gly Tyr Trp Asn Trp Ile
    130                 135                 140

Arg Lys Phe Pro Gly Lys Ala Leu Glu Tyr Met Gly Tyr Ile Thr Tyr
145                 150                 155                 160

Ser Gly Ser Thr Tyr Tyr Asn Pro Ser Leu Lys Gly Arg Ile Ser Ile
                165                 170                 175

Thr Arg Gln Thr Ser Lys Asn Gln Tyr Tyr Leu Thr Leu Ser Ser Val
                180                 185                 190

Thr Thr Val Glu Thr Ala Thr Tyr Tyr Cys Ala Arg Trp His Tyr Gly
            195                 200                 205

Ser Pro Tyr Tyr Phe Asp Tyr Trp Gly Gln Gly Thr Thr Leu Thr Val
    210                 215                 220

Ser Ser
225

<210> SEQ ID NO 112
<211> LENGTH: 226
<212> TYPE: PRT
<213> ORGANISM: Artificial Sequence
<220> FEATURE:
<223> OTHER INFORMATION: A44-hv4LC1a x HC2b

<400> SEQUENCE: 112

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys Glu Met Thr Leu Lys
        100                 105                 110

Glu Ser Gly Pro Thr Leu Val Lys Pro Thr Gln Thr Leu Ser Leu Thr
        115                 120                 125

Cys Ser Val Thr Gly Asp Ser Met Thr Gln Gly Tyr Trp Asn Trp Ile
    130                 135                 140

Arg Lys Phe Pro Gly Lys Ala Leu Glu Tyr Met Gly Tyr Ile Thr Tyr
145                 150                 155                 160

Ser Gly Ser Thr Tyr Tyr Asn Pro Ser Leu Lys Gly Arg Ile Ser Ile
                165                 170                 175

Thr Arg Asn Thr Ser Lys Asn Gln Tyr Tyr Leu Thr Leu Ser Ser Val
                180                 185                 190

Thr Thr Val Asp Thr Ala Thr Tyr Tyr Cys Ala Arg Trp His Tyr Gly
            195                 200                 205

Ser Pro Tyr Tyr Phe Asp Tyr Trp Gly Gln Gly Thr Thr Leu Thr Val
    210                 215                 220

Ser Ser
225
```

-continued

```
<210> SEQ ID NO 113
<211> LENGTH: 226
<212> TYPE: PRT
<213> ORGANISM: Artificial Sequence
<220> FEATURE:
<223> OTHER INFORMATION: A44-hv5LC2 x HC2b

<400> SEQUENCE: 113

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
            35                  40                  45

Tyr Arg Ala Gln Arg Ser Val Glu Gly Val Pro Ser Arg Phe Ser Gly
        50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys Glu Met Thr Leu Lys
            100                 105                 110

Glu Ser Gly Pro Thr Leu Val Lys Pro Thr Gln Thr Leu Ser Leu Thr
            115                 120                 125

Cys Ser Val Thr Gly Asp Ser Met Thr Gln Gly Tyr Trp Asn Trp Ile
        130                 135                 140

Arg Lys Phe Pro Gly Lys Ala Leu Glu Tyr Met Gly Tyr Ile Thr Tyr
145                 150                 155                 160

Ser Gly Ser Thr Tyr Tyr Asn Pro Ser Leu Lys Gly Arg Ile Ser Ile
            165                 170                 175

Thr Arg Asn Thr Ser Lys Asn Gln Tyr Tyr Leu Thr Leu Ser Ser Val
            180                 185                 190

Thr Thr Val Asp Thr Ala Thr Tyr Tyr Cys Ala Arg Trp His Tyr Gly
        195                 200                 205

Ser Pro Tyr Tyr Phe Asp Tyr Trp Gly Gln Gly Thr Thr Leu Thr Val
    210                 215                 220

Ser Ser
225

<210> SEQ ID NO 114
<211> LENGTH: 226
<212> TYPE: PRT
<213> ORGANISM: Artificial Sequence
<220> FEATURE:
<223> OTHER INFORMATION: A44-hv6LC3 x HC3

<400> SEQUENCE: 114

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
            35                  40                  45

Tyr Arg Ala Asn Arg Ser Val Asp Gly Val Pro Ser Arg Phe Ser Gly
        50                  55                  60

Ser Gly Ser Gly Gln Asp Tyr Ser Leu Thr Ile Ser Ser Leu Gln Pro
```

-continued

```
65                    70                    75                    80

Glu Asp Leu Ala Thr Tyr Tyr Cys Leu Gln Tyr Asp Glu Phe Pro Pro
                    85                    90                    95

Thr Phe Gly Gly Gly Thr Lys Leu Glu Ile Lys Gln Met Thr Leu Lys
                100                   105                   110

Glu Ser Gly Pro Thr Leu Val Lys Pro Thr Gln Thr Leu Ser Leu Thr
                115                   120                   125

Cys Ser Val Ser Gly Asp Ser Met Thr Asn Gly Tyr Trp Asn Trp Ile
                130                   135                   140

Arg Gln Phe Pro Gly Lys Ala Leu Glu Tyr Met Gly Tyr Ile Thr Tyr
145                   150                   155                   160

Ser Gly Ser Thr Tyr Tyr Asn Pro Ser Leu Lys Gly Arg Ile Thr Ile
                165                   170                   175

Thr Arg Asp Thr Ser Lys Asn Gln Tyr Tyr Leu Thr Leu Ser Ser Val
                180                   185                   190

Thr Thr Val Asp Thr Ala Thr Tyr Tyr Cys Ala Arg Trp His Tyr Gly
                195                   200                   205

Ser Pro Tyr Tyr Phe Asp Tyr Trp Gly Gln Gly Thr Thr Leu Thr Val
        210                   215                   220

Ser Ser
225
```

```
<210> SEQ ID NO 115
<211> LENGTH: 226
<212> TYPE: PRT
<213> ORGANISM: Artificial Sequence
<220> FEATURE:
<223> OTHER INFORMATION: A44-hv7LC4 x HC4

<400> SEQUENCE: 115

Asp Ile Lys Met Thr Gln Ser Pro Ser Ser Leu Ser Ala Ser Val Gly
1                   5                     10                    15

Asp Arg Val Thr Ile Thr Cys Lys Ala Ser Gln Asp Ile Asn Ser Tyr
                20                    25                    30

Leu Ser Trp Leu Gln Gln Lys Pro Gly Lys Ser Pro Lys Thr Leu Ile
                35                    40                    45

Tyr Arg Ala Gln Arg Ser Val Glu Gly Val Pro Ser Arg Phe Ser Gly
        50                    55                    60

Ser Gly Ser Gly Gln Asp Tyr Ser Leu Thr Ile Ser Ser Leu Gln Pro
65                    70                    75                    80

Glu Asp Leu Ala Thr Tyr Tyr Cys Leu Gln Tyr Asp Glu Phe Pro Pro
                    85                    90                    95

Thr Phe Gly Gly Gly Thr Lys Leu Glu Ile Lys Gln Met Thr Leu Lys
                100                   105                   110

Glu Ser Gly Pro Thr Leu Val Lys Pro Thr Gln Thr Leu Ser Leu Thr
                115                   120                   125

Cys Ser Val Ser Gly Glu Ser Met Thr Gln Gly Tyr Trp Asn Trp Ile
                130                   135                   140

Arg Gln Phe Pro Gly Lys Ala Leu Glu Tyr Met Gly Tyr Ile Thr Tyr
145                   150                   155                   160

Ser Gly Ser Thr Tyr Tyr Asn Pro Ser Leu Lys Gly Arg Ile Thr Ile
                165                   170                   175

Thr Arg Gln Thr Ser Lys Asn Gln Tyr Tyr Leu Thr Leu Ser Ser Val
                180                   185                   190

Thr Thr Val Glu Thr Ala Thr Tyr Tyr Cys Ala Arg Trp His Tyr Gly
```

-continued

```
                195                 200                 205
Ser Pro Tyr Tyr Phe Asp Tyr Trp Gly Gln Gly Thr Thr Leu Thr Val
    210                 215                 220

Ser Ser
225

<210> SEQ ID NO 116
<211> LENGTH: 226
<212> TYPE: PRT
<213> ORGANISM: Artificial Sequence
<220> FEATURE:
<223> OTHER INFORMATION: A44-hv8LC5a x HC5a

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30

Leu Ser Trp Leu Gln Gln Lys Pro Gly Lys Ala Pro Lys Leu Leu Ile
        35                  40                  45

Tyr Arg Ala Asn Arg Ser Val Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Glu Phe Pro Pro
                85                  90                  95

Thr Phe Gly Gly Gly Thr Lys Val Glu Ile Lys Gln Val Gln Leu Gln
                100                 105                 110

Glu Ser Gly Pro Gly Leu Val Lys Pro Ser Glu Thr Leu Ser Leu Thr
            115                 120                 125

Cys Thr Val Ser Gly Asp Ser Met Thr Asn Gly Tyr Trp Asn Trp Ile
    130                 135                 140

Arg Gln Pro Pro Gly Lys Gly Leu Glu Tyr Met Gly Tyr Ile Thr Tyr
145                 150                 155                 160

Ser Gly Ser Thr Tyr Tyr Asn Pro Ser Leu Lys Ser Arg Ile Thr Ile
                165                 170                 175

Ser Arg Asn Thr Ser Lys Asn Gln Tyr Ser Leu Lys Leu Ser Ser Val
            180                 185                 190

Thr Ala Ala Asp Thr Ala Val Tyr Tyr Cys Ala Arg Trp His Tyr Gly
            195                 200                 205

Ser Pro Tyr Tyr Phe Asp Tyr Trp Gly Gln Gly Thr Leu Val Thr Val
    210                 215                 220

Ser Ser
225

<210> SEQ ID NO 117
<211> LENGTH: 226
<212> TYPE: PRT
<213> ORGANISM: Artificial Sequence
<220> FEATURE:
<223> OTHER INFORMATION: A44-hv9LC5b x HC5b

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
                20                  25                  30
```

-continued

```
Leu Ser Trp Leu Gln Gln Lys Pro Gly Lys Ala Pro Lys Thr Leu Ile
        35                  40                  45

Tyr Arg Ala Asn Arg Ser Val Asp Gly Val Pro Ser Arg Phe Ser Gly
        50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Tyr Asp Glu Phe Pro Pro
                85                  90                  95

Thr Phe Gly Gly Gly Thr Lys Val Glu Ile Lys Gln Met Gln Leu Gln
            100                 105                 110

Glu Ser Gly Pro Gly Leu Val Lys Pro Ser Glu Thr Leu Ser Leu Thr
            115                 120                 125

Cys Thr Val Ser Gly Asp Ser Met Thr Asn Gly Tyr Trp Asn Trp Ile
        130                 135                 140

Arg Gln Pro Pro Gly Lys Gly Leu Glu Tyr Met Gly Tyr Ile Thr Tyr
145                 150                 155                 160

Ser Gly Ser Thr Tyr Tyr Asn Pro Ser Leu Lys Ser Arg Ile Thr Ile
                165                 170                 175

Ser Arg Asp Thr Ser Lys Asn Gln Tyr Ser Leu Lys Leu Ser Ser Val
            180                 185                 190

Thr Ala Ala Asp Thr Ala Val Tyr Tyr Cys Ala Arg Trp His Tyr Gly
            195                 200                 205

Ser Pro Tyr Tyr Phe Asp Tyr Trp Gly Gln Gly Thr Leu Val Thr Val
        210                 215                 220

Ser Ser
225
```

```
<210> SEQ ID NO 118
<211> LENGTH: 226
<212> TYPE: PRT
<213> ORGANISM: Artificial Sequence
<220> FEATURE:
<223> OTHER INFORMATION: A44-hv10LC5c x HC5c

<400> SEQUENCE: 118
```

```
Glu Ile Val Met Thr Gln Ser Pro Ala Thr Leu Ser Leu Ser Pro Gly
1                   5                   10                  15

Glu Arg Ala Thr Leu Ser Cys Lys Ala Ser Gln Asp Ile Asn Ser Tyr
            20                  25                  30

Leu Ser Trp Leu Gln Gln Lys Pro Gly Gln Ala Pro Arg Thr Leu Ile
        35                  40                  45

Tyr Arg Ala Asn Arg Ser Val Asp Gly Ile Pro Ala Arg Phe Ser Gly
        50                  55                  60

Ser Gly Ser Gly Gln Asp Tyr Thr Leu Thr Ile Ser Ser Leu Glu Pro
65                  70                  75                  80

Glu Asp Phe Ala Val Tyr Tyr Cys Leu Gln Tyr Asp Glu Phe Pro Pro
                85                  90                  95

Thr Phe Gly Gly Gly Thr Lys Val Glu Ile Lys Gln Met Gln Leu Gln
            100                 105                 110

Gln Ser Gly Pro Gly Leu Val Lys Pro Ser Gln Thr Leu Ser Leu Thr
            115                 120                 125

Cys Ala Ile Ser Gly Asp Ser Met Thr Asn Gly Tyr Trp Asn Trp Ile
        130                 135                 140

Arg Gln Ser Pro Ser Arg Gly Leu Glu Tyr Met Gly Tyr Ile Thr Tyr
145                 150                 155                 160
```

-continued

```
Ser Gly Ser Thr Tyr Tyr Ala Val Ser Val Lys Ser Arg Ile Thr Ile
            165                 170                 175

Asn Arg Asp Thr Ser Lys Asn Gln Tyr Ser Leu Gln Leu Ser Ser Val
            180                 185                 190

Thr Pro Glu Asp Thr Ala Val Tyr Tyr Cys Ala Arg Trp His Tyr Gly
            195                 200                 205

Ser Pro Tyr Tyr Phe Asp Tyr Trp Gly Gln Gly Thr Leu Val Thr Val
    210                 215                 220

Ser Ser
225

<210> SEQ ID NO 119
<211> LENGTH: 226
<212> TYPE: PRT
<213> ORGANISM: Artificial Sequence
<220> FEATURE:
<223> OTHER INFORMATION: A44-hv11LC2 x HC3

<400> SEQUENCE: 119

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys Gln Met Thr Leu Lys
            100                 105                 110

Glu Ser Gly Pro Thr Leu Val Lys Pro Thr Gln Thr Leu Ser Leu Thr
            115                 120                 125

Cys Ser Val Ser Gly Asp Ser Met Thr Asn Gly Tyr Trp Asn Trp Ile
        130                 135                 140

Arg Gln Phe Pro Gly Lys Ala Leu Glu Tyr Met Gly Tyr Ile Thr Tyr
145                 150                 155                 160

Ser Gly Ser Thr Tyr Tyr Asn Pro Ser Leu Lys Gly Arg Ile Thr Ile
            165                 170                 175

Thr Arg Asp Thr Ser Lys Asn Gln Tyr Tyr Leu Thr Leu Ser Ser Val
            180                 185                 190

Thr Thr Val Asp Thr Ala Thr Tyr Tyr Cys Ala Arg Trp His Tyr Gly
            195                 200                 205

Ser Pro Tyr Tyr Phe Asp Tyr Trp Gly Gln Gly Thr Thr Leu Thr Val
    210                 215                 220

Ser Ser
225

<210> SEQ ID NO 120
<211> LENGTH: 226
<212> TYPE: PRT
<213> ORGANISM: Artificial Sequence
<220> FEATURE:
<223> OTHER INFORMATION: A44-hv12LC4 X HC3

<400> SEQUENCE: 120
```

```
Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Ala Thr Tyr Tyr Cys Leu Gln Tyr Asp Glu Phe Pro Pro
                85                  90                  95

Thr Phe Gly Gly Gly Thr Lys Leu Glu Ile Lys Gln Met Thr Leu Lys
            100                 105                 110

Glu Ser Gly Pro Thr Leu Val Lys Pro Thr Gln Thr Leu Ser Leu Thr
            115                 120                 125

Cys Ser Val Ser Gly Asp Ser Met Thr Asn Gly Tyr Trp Asn Trp Ile
            130                 135                 140

Arg Gln Phe Pro Gly Lys Ala Leu Glu Tyr Met Gly Tyr Ile Thr Tyr
145                 150                 155                 160

Ser Gly Ser Thr Tyr Tyr Asn Pro Ser Leu Lys Gly Arg Ile Thr Ile
            165                 170                 175

Thr Arg Asp Thr Ser Lys Asn Gln Tyr Tyr Leu Thr Leu Ser Ser Val
            180                 185                 190

Thr Thr Val Asp Thr Ala Thr Tyr Tyr Cys Ala Arg Trp His Tyr Gly
            195                 200                 205

Ser Pro Tyr Tyr Phe Asp Tyr Trp Gly Gln Gly Thr Thr Leu Thr Val
            210                 215                 220

Ser Ser
225

<210> SEQ ID NO 121
<211> LENGTH: 226
<212> TYPE: PRT
<213> ORGANISM: Artificial Sequence
<220> FEATURE:
<223> OTHER INFORMATION: A44-hv13LC2 x HC5b

<400> SEQUENCE: 121

Asp Ile Lys Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Gln Arg Ser Val Glu Gly Val Pro Ser Arg Phe Ser Gly
    50                  55                  60

Ser Gly Ser Gly Gln Asp Tyr Ser Leu Thr Ile Ser Ser Leu Gln Pro
65                  70                  75                  80

Glu Asp Leu Gly Ile Tyr Tyr Cys Leu Gln Tyr Asp Glu Phe Pro Pro
                85                  90                  95

Thr Phe Gly Gly Gly Thr Lys Leu Glu Ile Lys Gln Met Gln Leu Gln
            100                 105                 110

Glu Ser Gly Pro Gly Leu Val Lys Pro Ser Glu Thr Leu Ser Leu Thr
            115                 120                 125
```

-continued

```
Cys Thr Val Ser Gly Asp Ser Met Thr Asn Gly Tyr Trp Asn Trp Ile
    130             135             140

Arg Gln Pro Pro Gly Lys Gly Leu Glu Tyr Met Gly Tyr Ile Thr Tyr
145             150             155             160

Ser Gly Ser Thr Tyr Tyr Asn Pro Ser Leu Lys Ser Arg Ile Thr Ile
                165             170             175

Ser Arg Asp Thr Ser Lys Asn Gln Tyr Ser Leu Lys Leu Ser Ser Val
            180             185             190

Thr Ala Ala Asp Thr Ala Val Tyr Tyr Cys Ala Arg Trp His Tyr Gly
            195             200             205

Ser Pro Tyr Tyr Phe Asp Tyr Trp Gly Gln Gly Thr Leu Val Thr Val
    210             215             220

Ser Ser
225

<210> SEQ ID NO 122
<211> LENGTH: 226
<212> TYPE: PRT
<213> ORGANISM: Artificial Sequence
<220> FEATURE:
<223> OTHER INFORMATION: A44-hv14LC4 x HC5b

<400> SEQUENCE: 122

Asp Ile Lys Met Thr Gln Ser Pro Ser Ser Leu Ser Ala Ser Val Gly
1               5               10              15

Asp Arg Val Thr Ile Thr Cys Lys Ala Ser Gln Asp Ile Asn Ser Tyr
            20              25              30

Leu Ser Trp Leu Gln Gln Lys Pro Gly Lys Ser Pro Lys Thr Leu Ile
        35              40              45

Tyr Arg Ala Gln Arg Ser Val Glu Gly Val Pro Ser Arg Phe Ser Gly
    50              55              60

Ser Gly Ser Gly Gln Asp Tyr Ser Leu Thr Ile Ser Ser Leu Gln Pro
65              70              75              80

Glu Asp Leu Ala Thr Tyr Tyr Cys Leu Gln Tyr Asp Glu Phe Pro Pro
            85              90              95

Thr Phe Gly Gly Gly Thr Lys Leu Glu Ile Lys Gln Met Gln Leu Gln
        100             105             110

Glu Ser Gly Pro Gly Leu Val Lys Pro Ser Glu Thr Leu Ser Leu Thr
        115             120             125

Cys Thr Val Ser Gly Asp Ser Met Thr Asn Gly Tyr Trp Asn Trp Ile
    130             135             140

Arg Gln Pro Pro Gly Lys Gly Leu Glu Tyr Met Gly Tyr Ile Thr Tyr
145             150             155             160

Ser Gly Ser Thr Tyr Tyr Asn Pro Ser Leu Lys Ser Arg Ile Thr Ile
                165             170             175

Ser Arg Asp Thr Ser Lys Asn Gln Tyr Ser Leu Lys Leu Ser Ser Val
            180             185             190

Thr Ala Ala Asp Thr Ala Val Tyr Tyr Cys Ala Arg Trp His Tyr Gly
            195             200             205

Ser Pro Tyr Tyr Phe Asp Tyr Trp Gly Gln Gly Thr Leu Val Thr Val
    210             215             220

Ser Ser
225

<210> SEQ ID NO 123
```

```
<211> LENGTH: 255
<212> TYPE: DNA
<213> ORGANISM: Artificial Sequence
<220> FEATURE:
<223> OTHER INFORMATION: HC1a

<400> SEQUENCE: 123
gagatgaccc tgaaagagtc cggccccacc ctggtcaaac ccacccagac cctgagcctg       60
acctgcagcg tgaccggcga cagcatgacc aacggctact ggaactggat ccggaagttc      120
cccggcaagg ccctcgagta catgggctac atcacctaca gcggcagcac ctactacaac      180
cccagcctga agggccggat cagcatcacc cggaacacca gcaagaacca gtactacctg      240
accctgtcca gcgtg                                                       255

<210> SEQ ID NO 124
<211> LENGTH: 255
<212> TYPE: DNA
<213> ORGANISM: Artificial Sequence
<220> FEATURE:
<223> OTHER INFORMATION: HC1b

<400> SEQUENCE: 124
gagatgcagc tgcaggaaag cggccctggc ctggtcaaac ccagcgagac actgagcctg       60
acctgcagcg tgaccggcga cagcatgacc aacggctact ggaactggat ccggaagttc      120
cccggcaagg ccctcgagta catgggctac atcacctaca gcggcagcac ctactacaac      180
cccagcctga agggccggat cagcatcacc cggaacacca gcaagaacca gtactacctg      240
aagctgtcca gcgtg                                                       255

<210> SEQ ID NO 125
<211> LENGTH: 255
<212> TYPE: DNA
<213> ORGANISM: Artificial Sequence
<220> FEATURE:
<223> OTHER INFORMATION: HC2a

<400> SEQUENCE: 125
gagatgaccc tgaaagagtc cggccccacc ctggtcaaac ccacccagac cctgagcctg       60
acctgcagcg tgaccggcga gagcatgacc cagggctact ggaactggat ccggaagttc      120
cccggcaagg ccctcgagta catgggctac atcacctaca gcggcagcac ctactacaac      180
cccagcctga agggccggat cagcatcacc cggcagacca gcaagaacca gtactacctg      240
accctgtcca gcgtg                                                       255

<210> SEQ ID NO 126
<211> LENGTH: 255
<212> TYPE: DNA
<213> ORGANISM: Artificial Sequence
<220> FEATURE:
<223> OTHER INFORMATION: HC2b

<400> SEQUENCE: 126
gagatgaccc tgaaagagtc cggccccacc ctggtcaaac ccacccagac cctgagcctg       60
acctgcagcg tgaccggcga cagcatgacc cagggctact ggaactggat ccggaagttc      120
cccggcaagg ccctcgagta catgggctac atcacctaca gcggcagcac ctactacaac      180
cccagcctga agggccggat cagcatcacc cggaacacca gcaagaacca gtactacctg      240
accctgtcca gcgtg                                                       255
```

```
<210> SEQ ID NO 127
<211> LENGTH: 255
<212> TYPE: DNA
<213> ORGANISM: Artificial Sequence
<220> FEATURE:
<223> OTHER INFORMATION: HC3

<400> SEQUENCE: 127
cagatgaccc tgaaagagtc cggccccacc ctggtcaaac ccacccagac cctgagcctg        60
acctgcagcg tgtccggcga cagcatgacc aacggctact ggaactggat ccggcagttc       120
cccggcaagg ccctcgagta catgggctac atcacctaca gcggcagcac ctactacaac       180
cccagcctga agggccggat caccatcacc cgggacacca gcaagaacca gtactacctg       240
accctgagca gcgtg                                                         255

<210> SEQ ID NO 128
<211> LENGTH: 255
<212> TYPE: DNA
<213> ORGANISM: Artificial Sequence
<220> FEATURE:
<223> OTHER INFORMATION: HC4

<400> SEQUENCE: 128
cagatgaccc tgaaagagtc cggccccacc ctggtcaaac ccacccagac cctgagcctg        60
acctgcagcg tgtccggcga gagcatgacc cagggctact ggaactggat ccggcagttc       120
cccggcaagg ccctcgagta catgggctac atcacctaca gcggcagcac ctactacaac       180
cccagcctga agggccggat caccatcacc cggcagacca gcaagaacca gtactacctg       240
accctgagca gcgtg                                                         255

<210> SEQ ID NO 129
<211> LENGTH: 255
<212> TYPE: DNA
<213> ORGANISM: Artificial Sequence
<220> FEATURE:
<223> OTHER INFORMATION: HC5a

<400> SEQUENCE: 129
caggtgcagc tgcaggaaag cggccctggc ctggtcaaac ccagcgagac actgagcctg        60
acctgcaccg tgtccggcga cagcatgacc aacggctact ggaactggat ccggcagccc       120
cctggcaagg gcctcgagta catgggctac atcacctaca gcggcagcac ctactacaac       180
cccagcctga agtcccggat caccatcagc cggaacacca gcaagaacca gtacagcctg       240
aagctgagca gcgtg                                                         255

<210> SEQ ID NO 130
<211> LENGTH: 255
<212> TYPE: DNA
<213> ORGANISM: Artificial Sequence
<220> FEATURE:
<223> OTHER INFORMATION: HC5b

<400> SEQUENCE: 130
cagatgcagc tgcaggaaag cggccctggc ctggtcaaac ccagcgagac actgagcctg        60
acctgcaccg tgtccggcga cagcatgacc aacggctact ggaactggat ccggcagccc       120
cctggcaagg gcctcgagta catgggctac atcacctaca gcggcagcac ctactacaac       180
cccagcctga agtcccggat caccatcagc cggacacca gcaagaacca gtacagcctg        240
aagctgagca gcgtg                                                         255
```

-continued

```
<210> SEQ ID NO 131
<211> LENGTH: 255
<212> TYPE: DNA
<213> ORGANISM: Artificial Sequence
<220> FEATURE:
<223> OTHER INFORMATION: HC5c

<400> SEQUENCE: 131
cagatgcagc tgcagcagag cggccctggc ctggtcaaac ccagccagac cctgagcctg      60
acctgcgcca tcagcggcga cagcatgacc aacggctact ggaactggat ccggcagagc     120
cccagcagag gcctcgagta catgggctac atcacctaca cgggcagcac ctactacgcc     180
gtgtccgtga agtcccggat caccatcaac cgggacacca gcaagaacca gtacagcctg     240
cagctgagca gcgtg                                                      255

<210> SEQ ID NO 132
<211> LENGTH: 255
<212> TYPE: DNA
<213> ORGANISM: Artificial Sequence
<220> FEATURE:
<223> OTHER INFORMATION: LC1a

<400> SEQUENCE: 132
gacatcaaga tgacccagag ccccagcagc ctgagcgcca gcgtgggcga cagagtgacc      60
atcacatgca aggccagcca ggacatcaac agctacctga gctggctgca gcagaagccc     120
ggcaagagcc ccaagaccct gatctaccgg gccaaccgca gcgtggacgg cgtgccaagc     180
agattttccg gcagcggcag cggccaggac tacagcctga ccatcagcag cctgcagccc     240
gaggacctgg gcatc                                                      255

<210> SEQ ID NO 133
<211> LENGTH: 255
<212> TYPE: DNA
<213> ORGANISM: Artificial Sequence
<220> FEATURE:
<223> OTHER INFORMATION: LC1b

<400> SEQUENCE: 133
gacatcaaga tgacccagag ccccagcagc gtgtccgtgt ctcctggcca gaccgtgacc      60
atcacatgca aggccagcca ggacatcaac agctacctga gctggctgca gcagaagccc     120
ggccagtccc ccaagaccct gatctaccgg gccaaccgca gcgtggacgg cgtgccaagc     180
agattttccg gcagcggcag cggccaggac tacagcctga ccatcagcag cctgcaggcc     240
atggacgagg gcatc                                                      255

<210> SEQ ID NO 134
<211> LENGTH: 255
<212> TYPE: DNA
<213> ORGANISM: Artificial Sequence
<220> FEATURE:
<223> OTHER INFORMATION: LC2

<400> SEQUENCE: 134
gacatcaaga tgacccagag ccccagcagc ctgagcgcca gcgtgggcga cagagtgacc      60
atcacatgca aggccagcca ggacatcaac agctacctga gctggctgca gcagaagccc     120
ggcaagagcc ccaagaccct gatctaccgg gcccagcgga gcgtggaagg cgtgccaagc     180
agattcagcg gcagcggctc cggccaggac tacagcctga ccatcagcag cctgcagccc     240
gaggacctgg gcatc                                                      255
```

```
<210> SEQ ID NO 135
<211> LENGTH: 255
<212> TYPE: DNA
<213> ORGANISM: Artificial Sequence
<220> FEATURE:
<223> OTHER INFORMATION: LC3

<400> SEQUENCE: 135
gacatcaaga tgacccagag ccccagcagc ctgagcgcca gcgtgggcga cagagtgacc        60
atcacatgca aggccagcca ggacatcaac agctacctga gctggctgca gcagaagccc       120
ggcaagagcc ccaagaccct gatctaccgg gccaaccgca gcgtggacgg cgtgccaagc       180
agattttccg gcagcggcag cggccaggac tacagcctga ccatcagcag cctgcagccc       240
gaggacctgg ccacc                                                        255

<210> SEQ ID NO 136
<211> LENGTH: 255
<212> TYPE: DNA
<213> ORGANISM: Artificial Sequence
<220> FEATURE:
<223> OTHER INFORMATION: LC4

<400> SEQUENCE: 136
gacatcaaga tgacccagag ccccagcagc ctgagcgcca gcgtgggcga cagagtgacc        60
atcacatgca aggccagcca ggacatcaac agctacctga gctggctgca gcagaagccc       120
ggcaagagcc ccaagaccct gatctaccgg gcccagcgga gcgtggaagg cgtgccaagc       180
agattcagcg gcagcggctc cggccaggac tacagcctga ccatcagcag cctgcagccc       240
gaggacctgg ccacc                                                        255

<210> SEQ ID NO 137
<211> LENGTH: 255
<212> TYPE: DNA
<213> ORGANISM: Artificial Sequence
<220> FEATURE:
<223> OTHER INFORMATION: LC5a

<400> SEQUENCE: 137
gacatccaga tgacccagag ccccagcagc ctgagcgcca gcgtgggcga cagagtgacc        60
atcacatgca aggccagcca ggacatcaac agctacctga gctggctgca gcagaagccc       120
ggcaaggccc ccaagctgct gatctaccgg gccaaccgca gcgtggacgg cgtgccaagc       180
agattttccg gcagcggctc cggcaccgac tacaccttca ccatcagcag cctgcagccc       240
gaggatatcg ccacc                                                        255

<210> SEQ ID NO 138
<211> LENGTH: 255
<212> TYPE: DNA
<213> ORGANISM: Artificial Sequence
<220> FEATURE:
<223> OTHER INFORMATION: LC5b

<400> SEQUENCE: 138
gacatccaga tgacccagag ccccagcagc ctgagcgcca gcgtgggcga cagagtgacc        60
atcacatgca aggccagcca ggacatcaac agctacctga gctggctgca gcagaagccc       120
ggcaaggccc ccaagaccct gatctaccgg gccaaccgca gcgtggacgg cgtgccaagc       180
agattttccg gcagcggcag cggccaggac tacaccttca ccatcagcag cctgcagccc       240
```

-continued gaggatatcg ccacc                                                    255

<210> SEQ ID NO 139
<211> LENGTH: 255
<212> TYPE: DNA
<213> ORGANISM: Artificial Sequence
<220> FEATURE:
<223> OTHER INFORMATION: LC5c

<400> SEQUENCE: 139
gagatcgtga tgacccagag ccccgccacc ctgtctctga gccctggcga gagagccacc        60
ctgagctgca aggccagcca ggacatcaac agctacctga gctggctgca gcagaagccc       120
ggccaggccc ccagaaccct gatctaccgg gccaacagaa gcgtggacgg catccccgcc       180
agattcagcg gcagcggctc cggccaggac tacaccctga ccatcagcag cctggaaccc       240
gaggacttcg ccgtg                                                    255

<210> SEQ ID NO 140
<211> LENGTH: 119
<212> TYPE: PRT
<213> ORGANISM: Artificial Sequence
<220> FEATURE:
<223> OTHER INFORMATION: mA44 VH

<400> SEQUENCE: 140

Glu Met Gln Leu Gln Glu Ser Gly Pro Ser Leu Val Lys Pro Ser Gln
1               5                   10                  15

Thr Leu Ser Leu Thr Cys Ser Val Thr Gly Asp Ser Met Thr Asn Gly
            20                  25                  30

Tyr Trp Asn Trp Ile Arg Lys Phe Pro Gly Asn Lys Leu Glu Tyr Met
        35                  40                  45

Gly Tyr Ile Thr Tyr Ser Gly Ser Thr Tyr Tyr Asn Pro Ser Leu Lys
    50                  55                  60

Gly Arg Ile Ser Ile Thr Arg Asn Thr Ser Lys Asn Gln Tyr Tyr Leu
65                  70                  75                  80

Gln Leu Ser Ser Val Thr Thr Glu Asp Thr Ala Thr Tyr Tyr Cys Ala
                85                  90                  95

Arg Trp His Tyr Gly Ser Pro Tyr Tyr Phe Asp Tyr Trp Gly Gln Gly
            100                 105                 110

Thr Thr Leu Thr Val Ser Ser
        115

<210> SEQ ID NO 141
<211> LENGTH: 107
<212> TYPE: PRT
<213> ORGANISM: Artificial Sequence
<220> FEATURE:
<223> OTHER INFORMATION: mA44 VL

<400> SEQUENCE: 141

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Glu Tyr

```
65                  70                  75                  80

Glu Asp Met Gly Ile Tyr Tyr Cys Leu Gln Tyr Asp Glu Phe Pro Pro
                    85                  90                  95

Thr Phe Gly Gly Gly Thr Lys Leu Glu Ile Lys
                    100                 105
```

<210> SEQ ID NO 142
<211> LENGTH: 118
<212> TYPE: PRT
<213> ORGANISM: Artificial Sequence
<220> FEATURE:
<223> OTHER INFORMATION: mA44 VL

<400> SEQUENCE: 142

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Leu Gln Gln Lys Pro Gly Lys Ser Pro Lys Thr Leu Ile
        35                  40                  45

Tyr Arg Ala Asn Arg Ser Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Pro
                    85                  90                  95

Thr Phe Gly Gly Gly Thr Lys Leu Glu Ile Lys Arg Ala Asp Ala Ala
                    100                 105                 110

Pro Thr Val Ser Ile Phe
        115
```

<210> SEQ ID NO 143
<211> LENGTH: 107
<212> TYPE: PRT
<213> ORGANISM: Artificial Sequence
<220> FEATURE:
<223> OTHER INFORMATION: IGKV3-11-02_IGKJ4-0

<400> SEQUENCE: 143

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Arg Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                    85                  90                  95

Thr Phe Gly Gly Gly Thr Lys Val Glu Ile Lys
                    100                 105
```

<210> SEQ ID NO 144
<211> LENGTH: 123
<212> TYPE: PRT
<213> ORGANISM: Artificial Sequence
<220> FEATURE:

```
<223> OTHER INFORMATION: IGHV6-1-02_IGHD6-13-01_IGHJ4-02

<400> SEQUENCE: 144

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Tyr Ser Ser Ser Trp Tyr Tyr Phe Asp Tyr
                100                 105                 110

Trp Gly Gln Gly Thr Leu Val Thr Val Ser Ser
        115                 120

<210> SEQ ID NO 145
<211> LENGTH: 3
<212> TYPE: PRT
<213> ORGANISM: Artificial Sequence
<220> FEATURE:
<223> OTHER INFORMATION: Synthetic

<400> SEQUENCE: 145

Arg Ala Gln
1

<210> SEQ ID NO 146
<211> LENGTH: 8
<212> TYPE: PRT
<213> ORGANISM: Artificial Sequence
<220> FEATURE:
<223> OTHER INFORMATION: Synthetic

<400> SEQUENCE: 146

Gly Glu Ser Met Thr Gln Gly Tyr
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic

<400> SEQUENCE: 147

Gly Asp Ser Met Thr Gln Gly Tyr
1               5

<210> SEQ ID NO 148
<211> LENGTH: 117
<212> TYPE: PRT
<213> ORGANISM: Artificial Sequence
<220> FEATURE:
<223> OTHER INFORMATION: Synthetic

<400> SEQUENCE: 148

Gln Val Lys Leu Gln Glu Ser Gly Pro Glu Leu Val Lys Pro Gly Ala
1               5                   10                  15
```

-continued

```
Ser Val Lys Ile Ser Cys Lys Ala Ser Gly Tyr Ser Phe Thr Asp Tyr
        20                  25                  30

Asn Met Asn Trp Val Lys Gln Ser Lys Gly Lys Ser Leu Glu Trp Ile
        35                  40                  45

Gly Ile Ile His Pro Asn Ser Gly Thr Thr Thr Tyr Asn Gln Lys Phe
    50                  55                  60

Lys Gly Lys Ala Thr Leu Thr Val Asp Gln Ser Ser Ser Thr Ala Tyr
65                  70                  75                  80

Leu Gln Leu Asn Ser Leu Thr Ser Glu Asp Ser Ala Val Tyr Tyr Cys
                85                  90                  95

Ala Arg Ser Lys Leu Arg Phe Phe Asp Tyr Trp Gly Gln Gly Thr Thr
        100                 105                 110

Val Thr Val Ser Ser
        115

<210> SEQ ID NO 149
<211> LENGTH: 107
<212> TYPE: PRT
<213> ORGANISM: Artificial Sequence
<220> FEATURE:
<223> OTHER INFORMATION: Synthetic

<400> SEQUENCE: 149

Asp Ile Lys Leu Thr Gln Ser Pro Ser Ser Met Tyr Ala Ser Leu Gly
1               5                   10                  15

Glu Arg Val Thr Ile Thr Cys Lys Ala Ser Gln Asp Ile Tyr Ser Tyr
        20                  25                  30

Leu Ser Trp Phe Gln Gln Lys Pro Gly Lys Ser Pro Lys Thr Leu Ile
        35                  40                  45

Tyr Arg Ala Asn Arg Leu Ile Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu His Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
        20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Cys
```

-continued

```
                 85                 90                 95

Ser Phe Gly Gln Gly Thr Lys Leu Glu Ile Lys
            100                105

<210> SEQ ID NO 151
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (99)..(103)
<223> OTHER INFORMATION: Xaa can be any naturally occurring amino acid

<400> SEQUENCE: 151

Gln Val Gln Leu Val Gln Ser Gly Ser Glu Leu Lys Lys Pro Gly Ala
1               5                  10                 15

Ser Val Lys Val Ser Cys Lys Ala Ser Gly Tyr Thr Phe Thr Ser Tyr
            20                 25                 30

Ala Met Asn Trp Val Arg Gln Ala Pro Gly Gln Gly Leu Glu Trp Met
         35                 40                 45

Gly Trp Ile Asn Thr Asn Thr Gly Asn Pro Thr Tyr Ala Gln Gly Phe
      50                 55                 60

Thr Gly Arg Phe Val Phe Ser Leu Asp Thr Ser Val Ser Thr Ala Tyr
65                 70                 75                 80

Leu Gln Ile Ser Ser Leu Lys Ala Glu Asp Thr Ala Val Tyr Tyr Cys
               85                 90                 95

Ala Arg Xaa Xaa Xaa Xaa Xaa Tyr Phe Asp Tyr Trp Gly Gln Gly Thr
            100                105                110

Leu Val Thr Val Ser Ser
         115

<210> SEQ ID NO 152
<211> LENGTH: 118
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (99)..(103)
<223> OTHER INFORMATION: Xaa can be any naturally occurring amino acid

<400> SEQUENCE: 152

Gln Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Ser Tyr
            20                 25                 30

Tyr Met His Trp Val Arg Gln Ala Pro Gly Gln Gly Leu Glu Trp Met
         35                 40                 45

Gly Ile Ile Asn Pro Ser Gly Gly Ser Thr Ser Tyr Ala Gln Lys Phe
      50                 55                 60

Gln Gly Arg Val Thr Met Thr Arg Asp Thr Ser Thr Ser Thr Val Tyr
65                 70                 75                 80

Met Glu Leu Ser Ser Leu Arg Ser Glu Asp Thr Ala Val Tyr Tyr Cys
               85                 90                 95

Ala Arg Xaa Xaa Xaa Xaa Xaa Tyr Phe Asp Tyr Trp Gly Gln Gly Thr
            100                105                110

Leu Val Thr Val Ser Ser
```

```
             115

<210> SEQ ID NO 153
<211> LENGTH: 107
<212> TYPE: PRT
<213> ORGANISM: Artificial Sequence
<220> FEATURE:
<223> OTHER INFORMATION: Synthetic

<400> SEQUENCE: 153

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Ile Tyr Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Ile Asp Gly Val Pro Ser Arg Phe Ser Gly
    50                  55                  60

Ser Gly Ser Gly Gln Asp Tyr Thr Phe Thr Ile Ser Ser Leu Gln Pro
65                  70                  75                  80

Glu Asp Ile Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 154
<211> LENGTH: 117
<212> TYPE: PRT
<213> ORGANISM: Artificial Sequence
<220> FEATURE:
<223> OTHER INFORMATION: Synthetic

<400> SEQUENCE: 154

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Ile
        35                  40                  45

Gly Ile Ile His Pro Asn Ser Gly Thr Thr Thr Tyr Asn Gln Lys Phe
    50                  55                  60

Lys Gly Arg Ala Val Leu Ser Val Asp Gln Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Leu Arg Phe Phe Asp Tyr Trp Gly Gln Gly Thr Leu
            100                 105                 110

Val Thr Val Ser Ser
        115

<210> SEQ ID NO 155
<211> LENGTH: 117
<212> TYPE: PRT
<213> ORGANISM: Artificial Sequence
<220> FEATURE:
<223> OTHER INFORMATION: Synthetic

<400> SEQUENCE: 155

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Ser Phe Thr Asp Tyr
          20                      25                      30

Asn Met Asn Trp Val Arg Gln Ala Pro Gly Gln Gly Leu Glu Trp Ile
          35                      40                      45

Gly Ile Ile His Pro Asn Ser Gly Thr Thr Thr Tyr Asn Gln Lys Phe
     50                      55                      60

Lys Gly Arg Ala Thr Leu Thr Val Asp Gln Ser Thr Ser Thr Ala Tyr
65                      70                      75                      80

Met Glu Leu Ser Ser Leu Arg Ser Glu Asp Thr Ala Val Tyr Tyr Cys
                    85                      90                      95

Ala Arg Ser Lys Leu Arg Phe Phe Asp Tyr Trp Gly Gln Gly Thr Leu
          100                     105                     110

Val Thr Val Ser Ser
          115

<210> SEQ ID NO 156
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 156

Glu Xaa Xaa Gln
1

<210> SEQ ID NO 157
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 157

Leu Xaa Arg
1

<210> SEQ ID NO 158
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 158

Thr Asp Xaa Xaa Arg Gln Phe Gln Ala Asp Phe Thr Xaa Xaa Ser Asp
1                   5                       10                      15

Gln Glu Pro Leu
          20

```
<210> SEQ ID NO 159
<211> LENGTH: 11
<212> TYPE: PRT
<213> ORGANISM: Artificial Sequence
<220> FEATURE:
<223> OTHER INFORMATION: Artificial Sequence

<400> SEQUENCE: 159

Thr Thr Gly Gly Glu Thr Arg Gln Gln Ile Gln
1               5                   10

<210> SEQ ID NO 160
<211> LENGTH: 3
<212> TYPE: PRT
<213> ORGANISM: Artificial Sequence
<220> FEATURE:
<223> OTHER INFORMATION: Artificial Sequence

<400> SEQUENCE: 160

Arg His Leu
1

<210> SEQ ID NO 161
<211> LENGTH: 22
<212> TYPE: PRT
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (4)..(6)
<223> OTHER INFORMATION: Xaa can be any naturally occurring amino acid

<400> SEQUENCE: 161

Thr Asp Met Xaa Xaa Xaa Phe Gln Ala Asp Phe Thr Ser Leu Ser Asn
1               5                   10                  15

Gln Glu Pro Leu His Val
            20

<210> SEQ ID NO 162
<211> LENGTH: 402
<212> TYPE: PRT
<213> ORGANISM: cynomolgus

<400> SEQUENCE: 162

Met Gln Met Ser Pro Ala Leu Ala Cys Leu Val Leu Gly Leu Ala Phe
1               5                   10                  15

Val Phe Gly Glu Gly Ser Thr Val His His Pro Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Arg Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Leu Gly Pro Trp Asn Lys Asp
            100                 105                 110

Glu Ile Ser Thr Thr Asp Ala Ile Phe Val Gln Arg Asp Leu Lys Leu
            115                 120                 125
```

```
Val Gln Gly Phe Met Pro His Phe Phe Arg Leu Phe Arg Ser Thr Val
    130                 135                 140

Lys Gln Val Asp Phe Ser Glu Ala Glu Arg Ala Arg Phe Ile Ile Asn
145                 150                 155                 160

Asp Trp Val Lys Thr His Thr Lys Gly Met Ile Ser Asp Leu Leu Gly
                165                 170                 175

Lys Gly Ala Val Asp Gln Leu Thr Arg Leu Val Leu Val Asn Ala Leu
                180                 185                 190

Tyr Phe Asn Gly His Trp Lys Thr Pro Phe Pro Asp Ser Ser Thr His
                195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asn Thr Leu
                245                 250                 255

Ser Met Phe Ile Ala Ala Pro Tyr Glu Lys Gln Val Pro Leu Ser Ala
                260                 265                 270

Leu Thr Asn Ile Leu Ser Ala Gln Leu Ile Ser His Trp Lys Gly Asn
                275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asn Gln Glu
                325                 330                 335

Pro Leu His Val Ala Gln Ala Leu Gln Lys Val Lys Ile Glu Val Asn
                340                 345                 350

Glu Ser Gly Thr Val Ala Ser Ser Ser Thr Ala Val Ile Val Ser Ala
                355                 360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385                 390                 395                 400

Glu Pro

<210> SEQ ID NO 163
<211> LENGTH: 402
<212> TYPE: PRT
<213> ORGANISM: Mus musculus

<400> SEQUENCE: 163

Met Gln Met Ser Ser Ala Leu Ala Cys Leu Ile Leu Gly Leu Val Leu
1               5                   10                  15

Val Ser Gly Lys Gly Phe Thr Leu Pro Leu Arg Glu Ser His Thr Ala
                20                  25                  30

His Gln Ala Thr Asp Phe Gly Val Lys Val Phe Gln Gln Val Val Gln
                35                  40                  45

Ala Ser Lys Asp Arg Asn Val Val Phe Ser Pro Tyr Gly Val Ser Ser
    50                  55                  60

Val Leu Ala Met Leu Gln Met Thr Thr Ala Gly Lys Thr Arg Arg Gln
65                  70                  75                  80

Ile Gln Asp Ala Met Gly Phe Lys Val Asn Glu Lys Gly Thr Ala His
                85                  90                  95
```

-continued

Ala Leu Arg Gln Leu Ser Lys Glu Leu Met Gly Pro Trp Asn Lys Asn
            100                 105                 110

Glu Ile Ser Thr Ala Asp Ala Ile Phe Val Gln Arg Asp Leu Glu Leu
            115                 120                 125

Val Gln Gly Phe Met Pro His Phe Phe Lys Leu Phe Gln Thr Met Val
            130                 135                 140

Lys Gln Val Asp Phe Ser Glu Val Glu Arg Ala Arg Phe Ile Ile Asn
145                 150                 155                 160

Asp Trp Val Glu Arg His Thr Lys Gly Met Ile Ser Asp Leu Leu Ala
                165                 170                 175

Lys Gly Ala Val Asp Glu Leu Thr Arg Leu Val Leu Val Asn Ala Leu
            180                 185                 190

Tyr Phe Ser Gly Gln Trp Lys Thr Pro Phe Leu Glu Ala Ser Thr His
            195                 200                 205

Gln Arg Leu Phe His Lys Ser Asp Gly Ser Thr Val Ser Val Pro Met
            210                 215                 220

Met Ala Gln Ser Asn Lys Phe Asn Tyr Thr Glu Phe Thr Thr Pro Asp
225                 230                 235                 240

Gly Leu Glu Tyr Asp Val Val Glu Leu Pro Tyr Gln Gly Asp Thr Leu
                245                 250                 255

Ser Met Phe Ile Ala Ala Pro Phe Glu Lys Asp Val His Leu Ser Ala
                260                 265                 270

Leu Thr Asn Ile Leu Asp Ala Glu Leu Ile Arg Gln Trp Lys Gly Asn
            275                 280                 285

Met Thr Arg Leu Pro Arg Leu Leu Ile Leu Pro Lys Phe Ser Leu Glu
            290                 295                 300

Thr Glu Val Asp Leu Arg Gly Pro Leu Glu Lys Leu Gly Met Pro Asp
305                 310                 315                 320

Met Phe Ser Ala Thr Leu Ala Asp Phe Thr Ser Leu Ser Asp Gln Glu
                325                 330                 335

Gln Leu Ser Val Ala Gln Ala Leu Gln Lys Val Arg Ile Glu Val Asn
            340                 345                 350

Glu Ser Gly Thr Val Ala Ser Ser Ser Thr Ala Phe Val Ile Ser Ala
            355                 360                 365

Arg Met Ala Pro Thr Glu Met Val Ile Asp Arg Ser Phe Leu Phe Val
            370                 375                 380

Val Arg His Asn Pro Thr Glu Thr Ile Leu Phe Met Gly Gln Val Met
385                 390                 395                 400

Glu Pro

<210> SEQ ID NO 164
<211> LENGTH: 402
<212> TYPE: PRT
<213> ORGANISM: Rattus norvegicus

<400> SEQUENCE: 164

Met Gln Met Ser Ser Ala Leu Thr Cys Leu Thr Leu Gly Leu Val Leu
1               5                   10                  15

Val Phe Gly Lys Gly Phe Ala Ser Pro Leu Pro Glu Ser His Thr Ala
            20                  25                  30

Gln Gln Ala Thr Asn Phe Gly Val Lys Val Phe Gln His Val Val Gln
        35                  40                  45

Ala Ser Lys Asp Arg Asn Val Val Phe Ser Pro Tyr Gly Val Ser Ser
        50                  55                  60

```
Val Leu Ala Met Leu Gln Leu Thr Thr Ala Gly Lys Thr Arg Gln Gln
65                  70                  75                  80

Ile Gln Asp Ala Met Gly Phe Asn Ile Ser Glu Arg Gly Thr Ala Pro
                85                  90                  95

Ala Leu Arg Lys Leu Ser Lys Glu Leu Met Gly Ser Trp Asn Lys Asn
                100                 105                 110

Glu Ile Ser Thr Ala Asp Ala Ile Phe Val Gln Arg Asp Leu Glu Leu
                115                 120                 125

Val Gln Gly Phe Met Pro His Phe Phe Lys Leu Phe Arg Thr Thr Val
            130                 135                 140

Lys Gln Val Asp Phe Ser Glu Val Glu Arg Ala Arg Phe Ile Ile Asn
145                 150                 155                 160

Asp Trp Val Glu Arg His Thr Lys Gly Met Ile Ser Asp Leu Leu Ala
                165                 170                 175

Lys Gly Ala Val Asn Glu Leu Thr Arg Leu Val Leu Val Asn Ala Leu
                180                 185                 190

Tyr Phe Asn Gly Gln Trp Lys Thr Pro Phe Leu Glu Ala Ser Thr His
                195                 200                 205

Gln Arg Leu Phe His Lys Ser Asp Gly Ser Thr Ile Ser Val Pro Met
            210                 215                 220

Met Ala Gln Asn Asn Lys Phe Asn Tyr Thr Glu Phe Thr Thr Pro Asp
225                 230                 235                 240

Gly His Glu Tyr Asp Ile Leu Glu Leu Pro Tyr His Gly Glu Thr Leu
                245                 250                 255

Ser Met Phe Ile Ala Ala Pro Phe Glu Lys Asp Val Pro Leu Ser Ala
                260                 265                 270

Ile Thr Asn Ile Leu Asp Ala Glu Leu Ile Arg Gln Trp Lys Ser Asn
                275                 280                 285

Met Thr Arg Leu Pro Arg Leu Leu Ile Leu Pro Lys Phe Ser Leu Glu
            290                 295                 300

Thr Glu Val Asp Leu Arg Gly Pro Leu Glu Lys Leu Gly Met Thr Asp
305                 310                 315                 320

Ile Phe Ser Ser Thr Gln Ala Asp Phe Thr Ser Leu Ser Asp Gln Glu
                325                 330                 335

Gln Leu Ser Val Ala Gln Ala Leu Gln Lys Val Lys Ile Glu Val Asn
                340                 345                 350

Glu Ser Gly Thr Val Ala Ser Ser Ser Thr Ala Ile Leu Val Ser Ala
                355                 360                 365

Arg Met Ala Pro Thr Glu Met Val Leu Asp Arg Ser Phe Leu Phe Val
            370                 375                 380

Val Arg His Asn Pro Thr Glu Thr Ile Leu Phe Met Gly Gln Leu Met
385                 390                 395                 400

Glu Pro
```

```
<210> SEQ ID NO 165
<211> LENGTH: 6
<212> TYPE: PRT
<213> ORGANISM: Artificial Sequence
<220> FEATURE:
<223> OTHER INFORMATION: Synthetic

<400> SEQUENCE: 165

Gln Asp Ile Tyr Ser Tyr
1               5
```

-continued

```
<210> SEQ ID NO 166
<211> LENGTH: 9
<212> TYPE: PRT
<213> ORGANISM: Artificial Sequence
<220> FEATURE:
<223> OTHER INFORMATION: Synthetic

<400> SEQUENCE: 166

Leu Gln Tyr Asp Glu Phe Pro Phe Thr
1               5

<210> SEQ ID NO 167
<211> LENGTH: 3
<212> TYPE: PRT
<213> ORGANISM: Artificial Sequence
<220> FEATURE:
<223> OTHER INFORMATION: Synthetic

<400> SEQUENCE: 167

Arg Ala Asn
1

<210> SEQ ID NO 168
<211> LENGTH: 8
<212> TYPE: PRT
<213> ORGANISM: Artificial Sequence
<220> FEATURE:
<223> OTHER INFORMATION: Synthetic

<400> SEQUENCE: 168

Gly Tyr Ser Phe Thr Asp Tyr Asn
1               5

<210> SEQ ID NO 169
<211> LENGTH: 9
<212> TYPE: PRT
<213> ORGANISM: Artificial Sequence
<220> FEATURE:
<223> OTHER INFORMATION: Synthetic

<400> SEQUENCE: 169

Leu Gln Tyr Asp Glu Phe Pro Phe Thr
1               5

<210> SEQ ID NO 170
<211> LENGTH: 3
<212> TYPE: PRT
<213> ORGANISM: Artificial Sequence
<220> FEATURE:
<223> OTHER INFORMATION: Synthetic

<400> SEQUENCE: 170

Arg Ala Asn
1
```

ANTIBODIES TO PLASMINOGEN ACTIVATOR INHIBITOR-1 (PAI-1) AND USES THEREOF

CROSS-REFERENCE TO RELATED APPLICATIONS

This application is a continuation of U.S. application Ser. No. 16/533,048, filed Aug. 6, 2019, which is a continuation of U.S. application Ser. No. 15/809,935, filed Nov. 10, 2017, which is a continuation of U.S. application Ser. No. 14/911, 429, filed Feb. 10, 2016, now U.S. Pat. No. 9,845,363, issued Dec. 19, 2017, which is a national stage application under 35 U.S.C. § 371 of International Application No. PCT/US2014/050896, filed Aug. 13, 2014, which claims priority to U.S. Provisional Application No. 61/865,451, filed Aug. 13, 2013, and European Application No. 14305757.8, filed May 22, 2014, all of which are incorporated by reference herein in their entirety.

SEQUENCE LISTING

The instant application contains a Sequence Listing which has been submitted electronically as a text file in ASCII format and is hereby incorporated by reference in its entirety. The name of the ASCII text file is "13-596-US-CON3_SequenceListing_ST25.txt," which was created on Jun. 9, 2022, and is 127,000 bytes in size.

BACKGROUND

Plasminogen Activator Inhibitor type-1 (PAI-1) is the main inhibitor of tissue-type plasminogen activator (tPA) and urokinase-type plasminogen activator (uPA), the key serine proteases responsible for plasmin generation. PAI-1 regulates fibrinolysis by inhibiting plasminogen activation in the vascular compartment. Fibrinolysis is a tightly coordinated process for degrading fibrin clots formed by activation of the coagulation cascade. Dysregulation of the coagulation/fibrinolysis balance leads to abnormal haemostasis events like bleeding or thrombotic diseases. PAI-1 is also a key regulator of plasminogen activation in the pericellular compartment (intravascular and tissular) where receptor bound plasminogen is activated mainly by urokinase bound to the urokinase receptor (uPAR). By inhibiting pericellular proteolysis, PAI-1 regulates numerous cellular functions like extracellular matrix (ECM) degradation, growth factors activation and release from ECM, matrix metalloproteinases (MMP) activation and cellular apoptosis. Recently, protease-independent effects of PAI-1 have been identified through its interaction with cofactors (like vitronectin, heparin, glycosaminoglycan), uPAR-urokinase complexes or cellular receptors (LRP: low-density Lipoprotein Receptor-related Protein) or integrins affecting cell functions like adhesion/de-adhesion, migration, proliferation and intracellular bioactivity. By these cellular mechanisms and anti-fibrinolytic effects, a pathogenic role of PAI-1 has been established in tumor growth and metastasis, fibrosis, acute myocardial infarction and metabolic disorders like atherosclerosis, obesity and diabetes.

The Human SERPINE1 (PAI-1) gene is localized to chromosome 7, consists of eight introns and nine exons, and has a size of 12,169 b (Klinger, K. W. et al. *Proc. Natl. Acad. Sci.* USA 84:8548, 1987). PAI-1 is a single chain glycoprotein of approximately 50 kDa (379 amino acids) from the SERPIN (serine protease inhibitor) superfamily that is synthesized in the active conformation but spontaneously becomes latent in the absence of vitronectin (Vn). Vitronectin, the main cofactor of PAI-1, stabilizes the active conformation with the Reactive Center Loop (RCL) which is approximately 20 amino acids that are exposed on the surface. The mechanism of inhibition of PAI-1's two main targets (tPA and uPA) is a suicide inhibition. The RCL region of PAI-1 bears the bait peptide bond (R346-M347, also called P1-P'1), which bears the cleavage site for this serine protease. A Michaelis complex with tPA or uPA forms first, then the catalytic triad reacts with the bait peptide bond to form an acyl-enzyme complex that, after cleavage of the P1-P'1 peptide bond, induces strong conformation changes. The conformational changes cause insertion of the cleaved RCL into a $3-strand with the protease staying covalently bound as an acyl enzyme with PAI-1. Under non-physiological circumstances, hydrolysis of this acyl-enzyme complex may induce release of the cleaved PAI-1 and free active protease (Blouse et al., Biochemistry, 48:1723, 2009).

PAI-1 circulates in blood at highly variable levels (nM range) and in excess over t-PA or uPA concentrations. PAI-1 exhibits structural flexibility and can be found in one of three conformations: (1) a latent conformation, (2) an active conformation, or (3) a substrate conformation (see FIG. 1). PAI-1 is mainly found as a noncovalent complex with vitronectin (Kd~1 nM) that decreases latency transition by 1.5 to 3 fold. Latent, cleaved or complexed PAI-1 affinity for vitronectin is significantly reduced. Matrix bound vitronectin also localizes with PAI-1 in the pericellular space. Endothelial cells, monocytes, macrophages and vascular smooth muscle cells synthesize this PAI-1 which then can be stored in large amounts under latent form by platelets (in the a granule). PAI-1 is a fast and specific inhibitor (with the second order rate constant of $10^6$ to $10^7$ $M^{-1}s^{-1}$) of tPA and uPA in solution, but inactive against protease bound either to fibrin or their cellular receptors. Other proteases like thrombin, plasmin, activated Protein C can be also inhibited by PAI-1 but less efficiently.

Several 3D structures of human PAI-1 have been solved since the first one described in 1992 (Mottonen et al., *Nature* 355:270, 1992) in the latent conformation. These 3D structures include mutant forms of PAI-1 in the substrate (Aert-geerts et al., *Proteins* 23:118, 1995), stabilized active conformation (Sharp et al., *Structure* 7:111, 1999), PAI complexed to Vitronectin-somatomedin B domain (Zhou et al., *Nat. Struct. Biol.* 10:541, 2003) or with inhibiting pentapeptide from the RCL loop (Xue et al., *Structure* 6:627, 1998). More recently, mouse PAI-1 structure in latent conformation was elucidated by Dewilde et al. (*J Struct. Biol.* 171:95, 2010) and revealed differences with human PAI-1 in the RCL position, gate region and position of α-helix A. Structure/function relationships in PAI-1 have been studied by using more than 600 mutant proteins (reviewed by De Taeye et al., *Thromb. Haemost.* 92:898, 2004) to localize domains involved in the various activities of this multifunctional serpin.

Since PAI-1 can be synthesized by almost every cell type including hepatocyte, adipocyte, mesangial cell, fibroblast, myofibroblast, and epithelial cell, its expression greatly varies under physiological (e.g., circadian variation of plasma PAI-1 level) and pathological conditions (e.g., obesity, metabolic syndrome, insulin resistance, infection, inflammatory diseases, cancer). PAI-1 is considered to be an acute phase protein. Transcriptional regulation of PAI-1 mRNA expression is induced by several cytokines and growth factors (e.g., TGFβ, TNFα, EGF, FGF, Insulin, angiotensin II & IV), hormones (e.g., aldosterone, glucocorticoids, PMA, high glucose) and stress factors (e.g., hypoxia, reactive oxygen species, lipopolysaccharides).

Moreover, a polymorphism in the promoter (position—675) of the PAI-1 gene affects expression level. The 4G allele increases PAI-1 level and the 4G/4G variant (occurring in around 25% of the population) induces an increase of approximately 25% of plasma PAI-1 level in comparison to 5G/5G (25% occurrence and 4G/5G 50% occurrence). The 4G/4G polymorphism has been linked to myocardial infarction (Dawson et al., *Arterioscler. Thromb.* 11:183, 1991), a specific type of pulmonary fibrosis (idiopathic interstitial pneumonia) (Kim et al., *Mol. Med.* 9:52, 2003) and the 4G/4G genotype donor group is an independent risk factor for kidney graft loss due to Interstitial Fibrosis &Tubular Atrophy (Rerolle et al., *Nephrol. Dial. Transplant* 23:3325, 2008).

Several pathogenic roles have been attributed to PAI-1 in thrombotic diseases such as arterial and venous thrombosis, acute myocardial infarction, and atherosclerosis. Its involvement in metabolic disorders like insulin resistance syndrome and obesity is well recognized. PAI-1 is also known as a profibrotic factor for several organs and has been shown to be over-expressed in fibrotic tissues (i.e., liver, lung, kidney, heart, abdominal adhesions, skin: scar or scleroderma) (reviewed by Ghosh and Vaughan, *J. Cell Physiol.* 227:493, 2012). PAI-1 knock-out (KO) mice are protected from fibrosis in different models, such as liver (bile duct ligation or xenobiotic), kidney (unilateral ureteral obstruction model (UUO)), lung (bleomycin inhalation) (Bauman et al., *J. Clin. Invest.* 120:1950, 2010; Hattori et al., *Am. J. Pathol.* 164: 1091, 2004; Chuang-Tsai et al., *Am. J. Pathol.* 163:445, 2003) whereas in heart this deletion is protected from induced fibrosis (Takeshita et al., *AM. J. Pathol.* 164:449, 2004) but prone to age-dependent cardiac selective fibrosis (Moriwaki et al., *Cric. Res.* 95:637, 2004). Down-regulation of PAI-1 expression by siRNA (Senoo et al., *Thorax* 65:334, 2010) or inhibition by chemical compounds (Izuhara et al., *Arterioscler. Thromb. Vasc. Biol.* 28:672, 2008; Huang et al., *Am. J. Respir. Cell Mol. Biol.* 46:87, 2012) have been reported to decrease lung fibrosis whereas PAI-1 overexpression of wild type (Eitzman et al., *J. Clin. Invest.* 97:232, 1996) or a PAI-1 mutant retaining only vitronectin binding but not tPA inhibitor function exacerbates lung fibrosis (Courey et al., *Blood* 118:2313, 2011).

Bile duct ligation (BDL) liver fibrosis is attenuated by antibody neutralizing PAI-1 (U.S. Pat. No. 7,771,720) whereas down-regulation by siRNA attenuates BDL and xenobiotic induced liver fibrosis (Hu et al., *J. Hepatol.* 51:102, 2009). PAI-1 KO mice were protected from cholestatic-induced liver damage and fibrosis in BDL (Bergheim et al., *J. Pharmacol. Exp. Ther.* 316:592, 2006; Wang et al., *FEBS Lett.* 581:3098, 2007; Wang et al., *Hepatology* 42:1099, 2005) and from angiotensin II induced liver fibrosis (Beier et al., *Arch. Bioch. Biophys.* 510:19, 2011).

PAI-1 KO mice are protected from renal fibrosis in the UUO model (Oda et al., *Kidney Int.* 60, 587, 2001), in diabetic nephropathy (Nicholas et al., *Kidney Int.* 67:1297, 2005) and in angiotensin II induced nephropathy (Knier et al., *J. Hypertens.* 29:1602, 2011; for reviews see Ma et al. *Frontiers Biosci.* 14:2028, 2009 and Eddy A. A. *Thromb. Haemost.* 101:656, 2009). In contrast, PAI-1 over expressing mice display more severe fibrosis and increased macrophage recruitment following UUO (Matsuo et al., *Kidney Int.* 67: 2221, 2005; Bergheim et al., *J. Pharmacol. Exp. Ther.* 316:592, 2006). Non-inhibitory PAI-1 mutant (PAI-1 R) has been shown to protect mice from the development of fibrosis in experimental glomerulonephritis (thy 1) in rat by decreasing urinary protein expression and glomerular matrix accumulation (Huang et al., *Kidney Int.* 70:515, 2006). Peptides blocking PAI-1 inhibit collagen 3, 4 and fibronectin accumulation in UUO mice (Gonzalez et al., *Exp. Biol. Med.* 234:1511, 2009).

PAI-1, as a target for numerous pathologies, has been the focus of intensive research to inhibit its activity or to regulate its expression for the last 20 years. Chemical compounds (Suzuki et al., *Expert Opin. Investig. Drugs* 20:255, 2011), monoclonal antibodies (Gils and Declerk, *Thromb Haemost;* 91:425, 2004), peptides, mutants (Cale and Lawrence, *Curr. Drug Targets* 8:971, 2007), siRNA or anti-sense RNA have been designed to inhibit its various function or to regulate its expression. However, despite the intensive research, the problem of developing a therapeutically effective modulator of PAI-1 still remains to be solved. Accordingly, there is a need in the art for novel agents that inhibit the PAI-1 activity for use in the treatment of PAI-1-mediated human pathologies.

SUMMARY OF THE DISCLOSURE

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 34), CDR2 (SEQ ID NO: 33), and CDR3 (SEQ ID NO: 32) of SEQ ID NO: 6, and a light chain variable region, said light chain variable region comprising CDR1 (SEQ ID NO: 37), CDR2 (SEQ ID NO: 36), and CDR3 (SEQ ID NO: 35) of SEQ ID NO: 7. In an additional aspect the heavy chain comprises a heavy chain variable region comprising SEQ ID NO: 6, and the light chain comprises a light chain variable region comprising SEQ ID NO: 7. In a further aspect, heavy chain variable region is 99%, 98%, 97%, 96%, 95%, 94%, 93%, 92%, 91%, or 90% identical to SEQ ID NO: 6, and the light chain variable region is 99%, 98%, 97%, 96%, 95%, 94%, 93%, 92%, 91%, or 90% identical to SEQ ID NO: 7. All % identity approximations indicate the minimum % identity; higher % identity than the recited values are also encompassed by the disclosure.

In another aspect, disclosed herein is an isolated monoclonal antibody that binds specifically to PAI-1, comprising: (a) heavy chain framework regions, a heavy chain CDR1 region comprising SEQ ID NO: 34, a heavy chain CDR2 region comprising SEQ ID NO: 33, and a heavy chain CDR3 region comprising SEQ ID NO: 32; and (b) light chain framework regions, a light chain CDR1 region comprising SEQ ID NO: 37, a light chain CDR2 region comprising SEQ ID NO: 36, and a light chain CDR3 region comprising SEQ ID NO: 35. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 6, and the antibody light chain comprises light chain framework regions that are 99%, 98%, 97%, 96%, 95%, 94%, 93%, 92%, 91%, or 90% identical to the framework regions of SEQ ID NO: 7.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 22), CDR2 (SEQ ID NO: 21), and CDR3 (SEQ ID NO: 20) of SEQ ID NO: 2, and a light chain variable region, said light chain variable region comprising CDR1 (SEQ ID NO: 25), CDR2

(SEQ ID NO: 24), and CDR3 (SEQ ID NO: 23) of SEQ ID NO: 3. In an additional aspect the heavy chain comprises a heavy chain variable region comprising SEQ ID NO: 2, and the light chain comprises a light chain variable region comprising SEQ ID NO: 3. In a further aspect, heavy chain variable region is 99%, 98%, 97%, 96%, 95%, 94%, 93%, 92%, 91%, or 90% identical to SEQ ID NO: 2, and the light chain variable region is 99%, 98%, 97%, 96%, 95%, 94%, 93%, 92%, 91%, or 90% identical to SEQ ID NO: 3.

In an additional aspect, disclosed herein is an isolated monoclonal antibody that binds specifically to PAI-1, comprising: (a) heavy chain framework regions, a heavy chain CDR1 region comprising SEQ ID NO: 22, a heavy chain CDR2 region comprising SEQ ID NO: 21, and a heavy chain CDR3 region comprising SEQ ID NO: 20; and (b) light chain framework regions, a light chain CDR1 region comprising SEQ ID NO: 25, a light chain CDR2 region comprising SEQ ID NO: 24, and a light chain CDR3 region comprising SEQ ID NO: 23. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 26, and the antibody light chain comprises light chain framework regions that are 99%, 98%, 97%, 96%, 95%, 94%, 93%, 92%, 91%, or 90% identical to the framework regions of SEQ ID NO: 3.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 28), CDR2 (SEQ ID NO: 27), and CDR3 (SEQ ID NO: 26) of SEQ ID NO: 4, and a light chain variable region, said light chain variable region comprising CDR1 (SEQ ID NO: 31), CDR2 (SEQ ID NO: 30), and CDR3 (SEQ ID NO: 29) of SEQ ID NO: 5. In an additional aspect the heavy chain comprises a heavy chain variable region comprising SEQ ID NO: 4, and the light chain comprises a light chain variable region comprising SEQ ID NO: 5. In a further aspect, heavy chain variable region is 99%, 98%, 97%, 96%, 95%, 94%, 93%, 92%, 91%, or 90% identical to SEQ ID NO: 4, and the light chain variable region is 99%, 98%, 97%, 96%, 95%, 94%, 93%, 92%, 91%, or 90% identical to SEQ ID NO: 5.

In an additional aspect, disclosed herein is an isolated monoclonal antibody that binds specifically to PAI-1, comprising: (a) heavy chain framework regions, a heavy chain CDR1 region comprising SEQ ID NO: 28, a heavy chain CDR2 region comprising SEQ ID NO: 27, and a heavy chain CDR3 region comprising SEQ ID NO: 26; and (b) light chain framework regions, a light chain CDR1 region comprising SEQ ID NO: 31, a light chain CDR2 region comprising SEQ ID NO: 30, and a light chain CDR3 region comprising SEQ ID NO: 29. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 4, and the antibody light chain comprises light chain framework regions that are 99%, 98%, 97%, 96%, 95%, 94%, 93%, 92%, 91%, or 90% identical to the framework regions of SEQ ID NO: 5.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 40), CDR2 (SEQ ID NO: 39), and CDR3 (SEQ ID NO: 38) of SEQ ID NO: 8, and a light chain variable region, said light chain variable region comprising CDR1 (SEQ ID NO: 43), CDR2 (SEQ ID NO: 42), and CDR3 (SEQ ID NO: 41) of SEQ ID NO: 9. In an additional aspect the heavy chain comprises a heavy chain variable region comprising SEQ ID NO: 8, and the light chain comprises a light chain variable region comprising SEQ ID NO: 9. In a further aspect, heavy chain variable region is 99%, 98%, 97%, 96%, 95%, 94%, 93%, 92%, 91%, or 90% identical to SEQ ID NO: 8, and the light chain variable region is 99%, 98%, 97%, 96%, 95%, 94%, 93%, 92%, 91%, or 90% identical to SEQ ID NO: 9.

In another aspect, disclosed herein is an isolated monoclonal antibody that binds specifically to PAI-1, comprising: (a) heavy chain framework regions, a heavy chain CDR1 region comprising SEQ ID NO: 40, a heavy chain CDR2 region comprising SEQ ID NO: 39, and a heavy chain CDR3 region comprising SEQ ID NO: 38; and (b) light chain framework regions, a light chain CDR1 region comprising SEQ ID NO: 43, a light chain CDR2 region comprising SEQ ID NO: 42, and a light chain CDR3 region comprising SEQ ID NO: 41. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 8, and the antibody light chain comprises light chain framework regions that are 99%, 98%, 97%, 96%, 95%, 94%, 93%, 92%, 91%, or 90% identical to the framework regions of SEQ ID NO: 9.

In one aspect, disclosed herein is An isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 52), CDR2 (SEQ ID NO: 51), and CDR3 (SEQ ID NO: 50) of SEQ ID NO: 10, and a light chain variable region, said light chain variable region comprising CDR1 (SEQ ID NO: 55), CDR2 (SEQ ID NO: 54), and CDR3 (SEQ ID NO: 53) of SEQ ID NO: 11. In an additional aspect the heavy chain comprises a heavy chain variable region comprising SEQ ID NO: 10, and the light chain comprises a light chain variable region comprising SEQ ID NO: 11. In a further aspect, heavy chain variable region is 99%, 98%, 97%, 96%, 95%, 94%, 93%, 92%, 91%, or 90% identical to SEQ ID NO: 10, and the light chain variable region is 99%, 98%, 97%, 96%, 95%, 94%, 93%, 92%, 91%, or 90% identical to SEQ ID NO: 11.

In an additional aspect, disclosed herein is an isolated monoclonal antibody that binds specifically to PAI-1, comprising: (a) heavy chain framework regions, a heavy chain CDR1 region comprising SEQ ID NO: 52, a heavy chain CDR2 region comprising SEQ ID NO: 51, and a heavy chain CDR3 region comprising SEQ ID NO: 50; and (b) light chain framework regions, a light chain CDR1 region comprising SEQ ID NO: 55, a light chain CDR2 region comprising SEQ ID NO: 54, and a light chain CDR3 region comprising SEQ ID NO: 53. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 10, and the antibody light chain comprises light chain framework regions that are 99%, 98%, 97%, 96%, 95%, 94%, 93%, 92%, 91%, or 90% identical to the framework regions of SEQ ID NO: 11.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 58), CDR2 (SEQ ID NO: 57), and CDR3 (SEQ ID NO: 56) of SEQ ID NO: 12, and a light chain variable region, said light chain variable region comprising CDR1 (SEQ ID NO: 61), CDR2 (SEQ ID NO: 60), and CDR3 (SEQ ID NO: 59) of SEQ ID NO: 13. In an additional aspect the heavy chain comprises a heavy chain variable region comprising SEQ ID NO: 12, and the light chain comprises a light chain variable region comprising SEQ ID NO: 13. In a further aspect, heavy chain variable region is 99%, 98%, 97%, 96%, 95%, 94%, 93%, 92%, 91%, or 90% identical to SEQ ID NO: 12, and the light chain variable region is 99%, 98%, 97%, 96%, 95%, 94%, 93%, 92%, 91%, or 90% identical to SEQ ID NO: 13.

In another aspect, disclosed herein is an isolated monoclonal antibody that binds specifically to PAI-1, comprising: (a) heavy chain framework regions, a heavy chain CDR1 region comprising SEQ ID NO: 58, a heavy chain CDR2 region comprising SEQ ID NO: 57, and heavy chain CDR3 region comprising SEQ ID NO: 56; and (b) light chain framework regions, a light chain CDR1 region comprising SEQ ID NO: 61, a light chain CDR2 region comprising SEQ ID NO: 60, and a light chain CDR3 region comprising SEQ ID NO: 59. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 12, and the antibody light chain comprises light chain framework regions that are 99%, 98%, 97%, 96%, 95%, 94%, 93%, 92%, 91%, or 90% identical to the framework regions of SEQ ID NO: 13.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 64), CDR2 (SEQ ID NO: 63), and CDR3 (SEQ ID NO: 62) of SEQ ID NO: 14, and a light chain variable region, said light chain variable region comprising CDR1 (SEQ ID NO: 67), CDR2 (SEQ ID NO: 66), and CDR3 (SEQ ID NO: 65) of SEQ ID NO: 15. In an additional aspect the heavy chain comprises a heavy chain variable region comprising SEQ ID NO: 14, and the light chain comprises a light chain variable region comprising SEQ ID NO: 15. In a further aspect, heavy chain variable region is 99%, 98%, 97%, 96%, 95%, 94%, 93%, 92%, 91%, or 90% identical to SEQ ID NO: 14, and the light chain variable region is 99%, 98%, 97%, 96%, 95%, 94%, 93%, 92%, 91%, or 90% identical to SEQ ID NO: 15.

In an additional aspect, disclosed herein is an isolated monoclonal antibody that binds specifically to PAI-1, comprising: (a) heavy chain framework regions, a heavy chain CDR1 region comprising SEQ ID NO: 64, a heavy chain CDR2 region comprising SEQ ID NO: 63, and a heavy chain CDR3 region comprising SEQ ID NO: 62; and (b) light chain framework regions, a light chain CDR1 region comprising SEQ ID NO: 67, a light chain CDR2 region comprising SEQ ID NO: 66, and a light chain CDR3 region comprising SEQ ID NO: 65. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 14, and the antibody light chain comprises light chain framework regions that are 99%, 98%, 97%, 96%, 95%, 94%, 93%, 92%, 91%, or 90% identical to the framework regions of SEQ ID NO: 15.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 70), CDR2

(SEQ ID NO: 69), and CDR3 (SEQ ID NO: 68) of SEQ ID NO: 16, and a light chain variable region, said light chain variable region comprising CDR1 (SEQ ID NO: 73), CDR2 (SEQ ID NO: 72), and CDR3 (SEQ ID NO: 71) of SEQ ID NO: 17.

In an additional aspect the heavy chain comprises a heavy chain variable region comprising SEQ ID NO: 16, and the light chain comprises a light chain variable region comprising SEQ ID NO: 17. In a further aspect, heavy chain variable region is 99%, 98%, 97%, 96%, 95%, 94%, 93%, 92%, 91%, or 90% identical to SEQ ID NO: 16, and the light chain variable region is 99%, 98%, 97%, 96%, 95%, 94%, 93%, 92%, 91%, or 90% identical to SEQ ID NO: 17.

In an additional aspect, disclosed herein is an isolated monoclonal antibody that binds specifically to PAI-1, comprising: (a) heavy chain framework regions, a heavy chain CDR1 region comprising SEQ ID NO: 70, a heavy chain CDR2 region comprising SEQ ID NO: 69, and a heavy chain CDR3 region comprising SEQ ID NO: 68; and (b) light chain framework regions, a light chain CDR1 region comprising SEQ ID NO: 73, a light chain CDR2 region comprising SEQ ID NO: 72, and a light chain CDR3 region comprising SEQ ID NO: 71. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 16, and the antibody light chain comprises light chain framework regions that are 99%, 98%, 97%, 96%, 95%, 94%, 93%, 92%, 91%, or 90% identical to the framework regions of SEQ ID NO: 17.

In one aspect, disclosed herein is an isolated monoclonal antibody that binds specifically to human Plasminogen Activator Inhibitor type-1 (PAI-1), wherein the antibody comprises a heavy chain variable region, said heavy chain variable region comprising CDR1 (SEQ ID NO: 46), CDR2 (SEQ ID NO: 45), and CDR3 (SEQ ID NO: 44) of SEQ ID NO: 80, and a light chain variable region, said light chain variable region comprising CDR1 (SEQ ID NO: 49), CDR2 (SEQ ID NO: 48), and CDR3 (SEQ ID NO: 47) of SEQ ID NO: 81.

In an additional aspect the heavy chain comprises a heavy chain variable region comprising SEQ ID NO: 80, and the light chain comprises a light chain variable region comprising SEQ ID NO: 81. In a further aspect, heavy chain variable region is 99%, 98%, 97%, 96%, 95%, 94%, 93%, 92%, 91%, or 90% identical to SEQ ID NO: 80, and the light chain variable region is 99%, 98%, 97%, 96%, 95%, 94%, 93%, 92%, 91%, or 90% identical to SEQ ID NO: 81.

In one aspect, disclosed herein is an isolated monoclonal antibody that binds specifically to PAI-1, comprising: (a) heavy chain framework regions, a heavy chain CDR1 region comprising SEQ ID NO: 46, a heavy chain CDR2 region comprising SEQ ID NO: 45, and a heavy chain CDR3 region comprising SEQ ID NO: 44; and (b) light chain framework regions, a light chain CDR1 region comprising SEQ ID NO: 49, a light chain CDR2 region comprising SEQ ID NO: 48, and a light chain CDR3 region comprising SEQ ID NO: 47. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 80, and the antibody light chain comprises light chain framework regions that are 99%, 98%, 97%, 96%, 95%, 94%, 93%, 92%, 91%, or 90% identical to the framework regions of SEQ ID NO: 81.

In another aspect, disclosed herein is an isolated monoclonal antibody that binds specifically to Plasminogen Activator Inhibitor type-1 (PAI-1), wherein the antibody comprises a heavy chain variable region, said heavy chain variable region comprising CDR1 (SEQ ID NO: 76), CDR2 (SEQ ID NO: 75), and CDR3 (SEQ ID NO: 74) of SEQ ID NO: 18, and a light chain variable region, said light chain variable region comprising CDR1 (SEQ ID NO: 79), CDR2 (SEQ ID NO: 78), and CDR3 (SEQ ID NO: 77) of SEQ ID 19. In an additional aspect the heavy chain comprises a heavy chain variable region comprising SEQ ID NO: 18, and the light chain comprises a light chain variable region comprising SEQ ID NO: 19. In a further aspect, heavy chain variable region is 99%, 98%, 97%, 96%, 95%, 94%, 93%, 92%, 91%, or 90% identical to SEQ ID NO: 18, and the light chain variable region is 99%, 98%, 97%, 96%, 95%, 94%, 93%, 92%, 91%, or 90% identical to SEQ ID NO: 19.

An isolated monoclonal antibody that binds specifically to PAI-1, comprising: (a) heavy chain framework regions, a heavy chain CDR1 region comprising SEQ ID NO: 76, heavy chain CDR2 region comprising SEQ ID NO: 75, and a heavy chain CDR3 region comprising SEQ ID NO: 74; and (b) light chain framework regions, a light chain CDR1 region comprising SEQ ID NO: 79, a light chain CDR2 region comprising SEQ ID NO: 78, and a light chain CDR3 region comprising SEQ ID NO: 77. In certain aspects, the antibody heavy chain comprises heavy chain framework regions that are 99%, 98%, 97%, 96%, 95%, 94%, 93%, 92%, 91%, or 90% identical to the heavy chain framework regions of SEQ ID NO: 18, and the antibody light chain comprises light chain framework regions that are 99%, 98%, 97%, 96%, 95%, 94%, 93%, 92%, 91%, or 90% identical to the framework regions of SEQ ID NO: 19.

In one aspect, disclosed herein is an isolated monoclonal antibody that binds specifically to PAI-1, comprising: (a) heavy chain framework regions, a heavy chain CDR1 region comprising SEQ ID NO: 33, heavy chain CDR2 region comprising SEQ ID NO: 146, and a heavy chain CDR3 region comprising SEQ ID NO: 32; and (b) light chain framework regions, a light chain CDR1 region comprising SEQ ID NO: 37, a light chain CDR2 region comprising SEQ ID NO: 145, and a light chain CDR3 region comprising SEQ ID NO: 35.

In one aspect, disclosed herein is an isolated monoclonal antibody that binds specifically to PAI-1, comprising: (a) heavy chain framework regions, a heavy chain CDR1 region comprising SEQ ID NO: 147, heavy chain CDR2 region comprising SEQ ID NO: 33, and a heavy chain CDR3 region comprising SEQ ID NO: 32; and (b) light chain framework regions, a light chain CDR1 region comprising SEQ ID NO: 37, a light chain CDR2 region comprising SEQ ID NO: 36, and a light chain CDR3 region comprising SEQ ID NO: 35.

In one aspect, disclosed herein is an isolated monoclonal antibody that binds specifically to PAI-1, comprising: (a) heavy chain framework regions, a heavy chain CDR1 region comprising SEQ ID NO: 147, heavy chain CDR2 region comprising SEQ ID NO: 33, and a heavy chain CDR3 region comprising SEQ ID NO: 32; and (b) light chain framework regions, a light chain CDR1 region comprising SEQ ID NO: 37, a light chain CDR2 region comprising SEQ ID NO: 145, and a light chain CDR3 region comprising SEQ ID NO: 35.

In one aspect, disclosed herein is an isolated monoclonal antibody that binds specifically to PAI-1, comprising: (a) heavy chain framework regions, a heavy chain CDR1 region comprising SEQ ID NO: 146, heavy chain CDR2 region comprising SEQ ID NO: 33, and a heavy chain CDR3 region comprising SEQ ID NO: 32; and (b) light chain framework regions, a light chain CDR1 region comprising SEQ ID NO:

37, a light chain CDR2 region comprising SEQ ID NO: 145, and a light chain CDR3 region comprising SEQ ID NO: 35.

In one aspect, disclosed herein is an isolated monoclonal antibody that binds specifically to PAI-1, comprising: (a) heavy chain framework regions, a heavy chain CDR1 region comprising SEQ ID NO: 34, heavy chain CDR2 region comprising SEQ ID NO: 33, and a heavy chain CDR3 region comprising SEQ ID NO: 32; and (b) light chain framework regions, a light chain CDR1 region comprising SEQ ID NO: 37, a light chain CDR2 region comprising SEQ ID NO: 145, and a light chain CDR3 region comprising SEQ ID NO: 35.

In an additional aspect, disclosed herein is an isolated monoclonal antibody that binds to essentially the same epitope on PAI-1 as an isolated monoclonal antibody, comprising a heavy chain variable region, wherein the heavy chain variable region comprises CDR1 (SEQ ID NO: 34), CDR2 (SEQ ID NO: 33), and CDR3 (SEQ ID NO: 32) of SEQ ID NO: 6, and a light chain variable region, wherein the light chain variable region comprises CDR1 (SEQ ID NO: 37), CDR2 (SEQ ID NO: 36), and CDR3 (SEQ ID NO: 35) of SEQ ID NO: 7.

In a certain aspect, disclosed herein is an isolated monoclonal antibody that binds specifically to PAI-1, comprising: (a) heavy chain framework regions, a heavy chain CDR1 region comprising SEQ ID NO: 76, heavy chain CDR2 region comprising SEQ ID NO: 75, and a heavy chain CDR3 region comprising SEQ ID NO: 74; and (b) light chain framework regions, a light chain CDR1 region comprising SEQ ID NO: 79, a light chain CDR2 region comprising SEQ ID NO: 78, and a light chain CDR3 region comprising SEQ ID NO: 77.

In one aspect, disclosed herein is a humanized monoclonal antibody that binds specifically to human PAI-1, wherein the antibody comprises: (a) a heavy chain having a heavy chain variable region comprising SEQ ID NO: 82, or an antigen-binding fragment thereof, and a light chain having a light chain variable region comprising SEQ ID NO: 91, or an antigen-binding fragment thereof; (b)

a heavy chain having a heavy chain variable region comprising SEQ ID NO: 83, or an antigen-binding fragment thereof, and a light chain having a light chain variable region comprising SEQ ID NO: 92, or an antigen-binding fragment thereof; (c) a heavy chain having a heavy chain variable region comprising SEQ ID NO: 84, or an antigen-binding fragment thereof, and a light chain having a light chain variable region comprising SEQ ID NO: 93, or an antigen-binding fragment thereof; (d) a heavy chain having a heavy chain variable region comprising SEQ ID NO: 85, or an antigen-binding fragment thereof, and a light chain having a light chain variable region comprising SEQ ID NO: 91, or an antigen-binding fragment thereof; (e) a heavy chain having a heavy chain variable region comprising SEQ ID NO: 85, or an antigen-binding fragment thereof, and a light chain having a light chain variable region comprising SEQ ID NO: 93, or an antigen-binding fragment thereof; (f) a heavy chain having a heavy chain variable region comprising SEQ ID NO: 86, or an antigen-binding fragment thereof, and a light chain having a light chain variable region comprising SEQ ID NO: 94, or an antigen-binding fragment thereof; (g) a heavy chain having a heavy chain variable region comprising SEQ ID NO: 87, or an antigen-binding fragment thereof, and a light chain having a light chain variable region comprising SEQ ID NO: 95, or an antigen-binding fragment thereof; (h) a heavy chain having a heavy chain variable region comprising SEQ ID NO: 88, or an antigen-binding fragment thereof, and a light chain having a light chain variable region comprising SEQ ID NO: 96, or an antigen-binding fragment thereof; (i) a heavy chain having a heavy chain variable region comprising SEQ ID NO: 89, or an antigen-binding fragment thereof, and a light chain having a light chain variable region comprising SEQ ID NO: 97, or an antigen-binding fragment thereof; j) a heavy chain having a heavy chain variable region comprising SEQ ID NO: 90, or an antigen-binding fragment thereof, and a light chain having a light chain variable region comprising SEQ ID NO: 98, or an antigen-binding fragment thereof; (k) a heavy chain having a heavy chain variable region comprising SEQ ID NO: 86, or an antigen-binding fragment thereof, and a light chain having a light chain variable region comprising SEQ ID NO: 93, or an antigen-binding fragment thereof; (1) a heavy chain having a heavy chain variable region comprising SEQ ID NO: 86, or an antigen-binding fragment thereof, and a light chain having a light chain variable region comprising SEQ ID NO: 95, or an antigen-binding fragment thereof; (m) a heavy chain having a heavy chain variable region comprising SEQ ID NO: 89, or an antigen-binding fragment thereof, and a light chain having a light chain variable region comprising SEQ ID NO: 93, or an antigen-binding fragment thereof; or (n) a heavy chain having a heavy chain variable region comprising SEQ ID NO: 89, or an antigen-binding fragment thereof, and a light chain having a light chain variable region comprising SEQ ID NO: 95, or an antigen-binding fragment thereof. In a further aspect, the humanized heavy chain variable region is 99%, 98%, 97%, 96%, 95%, 94%, 93%, 92%, 91%, or 90% identical to any of the previously disclosed human heavy chain variable regions, and the humanized light chain variable region is 99%, 98%, 97%, 96%, 95%, 94%, 93%, 92%, 91%, or 90% identical to any of the previously disclosed human light chain variable regions.

In one aspect, disclosed herein is an isolated monoclonal antibody that binds specifically to PAI-1 comprising: (a) a heavy chain framework region and a heavy chain variable region comprising SEQ ID NO: 86, and (b) a light chain framework region and a light chain variable region comprising SEQ ID NO: 93. In certain aspects, the isolated monoclonal heavy chain comprises heavy chain framework regions that are 99%, 98%, 97%, 96%, 95%, 94%, 93%, 92%, 91%, or 90% identical to the heavy chain framework regions of SEQ ID NO: 86, and the isolated monoclonal antibody light chain comprises light chain framework regions that are 99%, 98%, 97%, 96%, 95%, 94%, 93%, 92%, 91%, or 90% identical to the framework regions of SEQ ID NO: 93. In certain other aspects, the isolated monoclonal antibody heavy chain comprises heavy chain framework regions that are 95% identical to the heavy chain framework regions of SEQ ID NO: 86, and the isolated monoclonal antibody light chain comprises light chain framework regions that are 95% identical to the framework regions of SEQ ID NO: 93.

In another aspect, disclosed herein is a humanized monoclonal antibody that binds specifically to human PAI-1, wherein the antibody comprises a heavy chain having a heavy chain variable region comprising SEQ ID NO: 154, or an antigen-binding fragment thereof; and a light chain having a light chain variable region comprising SEQ ID NO: 153, or an antigen-binding fragment thereof. In another aspect, disclosed herein is a humanized monoclonal antibody that binds specifically to human PAI-1, wherein the antibody comprises a heavy chain having a heavy chain variable region comprising SEQ ID NO: 155, or an antigen-binding fragment thereof, and a light chain having a light chain variable region comprising SEQ ID NO: 153, or an antigen-binding fragment thereof. In a further aspect, the humanized heavy chain variable region is 99%, 98%, 97%, 96%, 95%, 94%, 93%, 92%, 91%, or 90% identical to any of the previously disclosed human heavy chain variable regions, and the humanized light chain variable region is 99%, 98%, 97%, 96%, 95%, 94%, 93%, 92%, 91%, or 90% identical to any of the previously disclosed human light chain variable regions.

In another aspect, disclosed herein is an isolated monoclonal antibody that binds specifically to PAI-1, wherein the antibody binds a polypeptide comprising SEQ ID NO: 158. In another embodiment, the isolate monoclonal antibody binds a fragment of a polypeptide comprising SEQ ID NO: 158. In yet another embodiment, the isolated monoclonal antibody that binds specifically to PAI-1 binds a polypeptide comprising SEQ ID NO: 156 and/or SEQ ID NO: 158. In another embodiment, the isolated monoclonal antibody that binds specifically to PAI-1 binds a polypeptide comprising SEQ ID NO: 156, SEQ ID NO: 158, and/or SEQ ID NO: 157. In still another embodiment, the isolated monoclonal antibody that binds specifically to PAI-1 comprises specific binding affinity for residues 160, 262, 296-297, 300-307, and/or $310^{-316}$ of SEQ ID NO: 1. In certain embodiments, the isolated monoclonal antibody disclosed herein interacts with at least residues 311, 312, and 313 (D-Q-E) of SEQ ID NO: 1. In certain embodiments, the PAI-1 bound by the antibody is human PAI-1. In other embodiments, the PAI-1 bound by the antibody is the active form of human PAI-1.

In other embodiments, the isolated monoclonal antibody that binds specifically to PAI-1 disclosed herein binds a polypeptide comprising SEQ ID NO: 161. In still other embodiments, the isolated monoclonal antibody binds a polypeptide comprising SEQ ID NO: 159 and/or SEQ ID NO: 161. In still other embodiments, the isolated monoclonal antibody binds a polypeptide comprising SEQ ID NO: 159, SEQ ID NO: 160, and/or SEQ ID NO: 161. In still another embodiment, the isolated monoclonal antibody that binds specifically to PAI-1 comprises specific binding affinity for residues 44-64 and/or residues 307-321 of cyno-PAI-1 (SEQ ID NO: 162). In certain embodiments, the PAI-1 bound by the antibody is cyno-PAI-1. In other embodiments, the PAI-1 bound by the antibody is the latent form of cyno-PAI-1.

In a further aspect, disclosed herein is an isolated monoclonal antibody that competitively inhibits binding of any of the disclosed antibodies to PAI-1. In an embodiment, disclosed herein is an isolated monoclonal antibody that competes for binding and/or competitively inhibits binding with any of the isolated monoclonal antibodies disclosed herein. In certain embodiments, the isolated monoclonal antibody competes or competitively inhibits binding to human PAI-1. In certain embodiments, the isolated monoclonal antibody competes or competitively inhibits binding to a polypeptide comprising SEQ ID NO: 156, SEQ ID NO: 157, and/or SEQ ID NO: 158. In another embodiment, the isolated monoclonal antibody competes or competitively inhibits binding to a polypeptide comprising SEQ ID NO: 159, SEQ ID NO: 160, and/or SEQ ID NO: 161. In an embodiment, the isolated antibody competes for binding to a polypeptide comprising SEQ ID NO: 156, 157, and/or 158 with an isolated monoclonal antibody comprising (a) heavy chain framework regions, a heavy chain CDR1 region comprising SEQ ID NO: 34, heavy chain CDR2 region comprising SEQ ID NO: 33, and a heavy chain CDR3 region comprising SEQ ID NO: 32; and (b) light chain framework regions, a light chain CDR1 region comprising SEQ ID NO: 37, a light chain CDR2 region comprising SEQ ID NO: 145, and a light chain CDR3 region comprising SEQ ID NO: 35.

In another aspect, disclosed herein are nucleotides encoding any of the isolated monoclonal antibodies disclosed herein.

In one aspect, disclosed herein is a method of treating a condition caused by increased expression of PAI-1 or increased sensitivity to PAI-1 comprising administering to a patient or other subject orally, parenterally by a solution for injection, by inhalation, or topically a pharmaceutically effective amount of a PAI-1 antibody.

In one aspect, disclosed herein is a method restoring plasmin generation comprising administering to a patient or other subject in need thereof orally, parenterally by a solution for injection, by inhalation, or topically a pharmaceutically effective amount of a PAI-1 antibody. Parenteral administration disclosed herein includes intravenous, drip, intraarterial, intraperitoneal, intramuscular, subcutaneous, rectal or vaginal, intravenous, intraarterial, subcutaneous, and intramuscular forms of parenteral administration. In some embodiments, the administration to a patient or other subject comprises multiple administrations. In another aspect, the method of restoring plasmin generation facilitates therapeutic treatment of a condition comprising increased levels of fibrotic tissue. In some aspects, the condition is characterized by fibrosis. In some aspects, the condition is fibrosis, skin fibrosis, systemic sclerosis, lung fibrosis, idiopathic pulmonary fibrosis, interstitial lung disease, and chronic lung disease. In other aspects, the plasmin generation facilitates therapeutic treatment of liver fibrosis, kidney fibrosis, including chronic kidney disease, thrombosis, venous and arterial thrombosis, deep vein thrombosis, peripheral limb ischemia, disseminated intravascular coagulation thrombosis, acute ischemic stroke with and without thrombolysis, or stent restenosis.

In another aspect, disclosed herein is the use of a pharmaceutically effective amount of a PAI-1 antibody for the manufacture of a medicament for treating a condition caused by increased expression of PAI-1 or increased sensitivity to PAI-1 comprising administering to a patient or other subject orally, parenterally by a solution for injection, by inhalation, or topically.

In one aspect, the medicament is for treating a condition comprising increased levels of fibrotic tissue. In some aspects, the condition is characterized by fibrosis. In some aspects, the condition is fibrosis, skin fibrosis, systemic sclerosis, lung fibrosis, idiopathic pulmonary fibrosis, interstitial lung disease, and chronic lung disease. In other aspects, the medicament is for treating a condition comprising liver fibrosis, kidney fibrosis, including chronic kidney disease, thrombosis, venous and arterial thrombosis, deep vein thrombosis, peripheral limb ischemia, disseminated intravascular coagulation thrombosis, acute ischemic stroke with and without thrombolysis, or stent restenosis.

In another aspect, disclosed herein is an isolated monoclonal antibody that binds specifically to PAI-1, wherein the antibody inhibits lung fibrosis. In certain embodiments, the antibody inhibits fibrosis in the lung of a subject. In certain embodiments, the antibody inhibits fibrosis in the lung of a subject with idiopathic pulmonary fibrosis (IPF). In some embodiments, the isolated monoclonal antibody disclosed herein induces an increase in fibrin degradation in a subject. In certain embodiments, the antibody increases fibrin degradation in the plasma of the subject. In some other embodiments, the isolated monoclonal antibody disclosed herein inhibits collagen accumulation in the lung of a subject. In some embodiments, the subject has IPF. In some other embodiments, the isolated monoclonal antibody disclosed herein increases D-dimer levels in the bronchoalveolar lavage fluid (BALF) of a subject. In some embodiments, the subject has IPF. In some other embodiments, the isolated monoclonal antibody disclosed herein binds specifically to PAI-1, wherein the antibody inhibits the increase in lung weight due to fibrosis in a subject. In one embodiment, the subject has IPF.

In another aspect, disclosed herein is the use of a pharmaceutically effective amount of a PAI-1 antibody for the manufacture of a medicament for treating a condition caused by increased expression of PAI-1 or increased sensitivity to PAI-1 comprising administering to a patient orally, parenterally by a solution for injection, by inhalation, or topically, wherein the condition is idiopathic pulmonary fibrosis.

In another aspect, disclosed herein is a method restoring plasmin generation comprising administering to a to a patient or other subject thereof orally, parenterally by a solution for injection, by inhalation, or topically a pharmaceutically effective amount of a PAI-1 antibody, wherein the plasmin generation facilitates therapeutic treatment of idiopathic pulmonary fibrosis.

In another aspect, disclosed herein is an isolated monoclonal antibody that binds specifically to PAI-1, wherein the antibody restores fibrinolytic activity in a subject. In certain embodiments, the antibody restores fibrinolytic activity in a subject with acute ischemic stroke. The acute ischemic stroke can be either with or without thrombolysis. In some embodiments, the isolated monoclonal antibody restores clot lysis. In certain embodiments, the antibody restores in vitro clot lysis. In still other embodiments, the antibody restores in vitro clot lysis with an $IC_{50}$ of about 2 nM.

In other aspects, disclosed herein is an isolated monoclonal antibody that binds specifically to PAI-1, wherein the antibody restores fibrin breakdown in a subject. In some embodiments, the subject has acute ischemic stroke.

In another aspect, disclosed herein is the use of a pharmaceutically effective amount of a PAI-1 antibody for the manufacture of a medicament for treating a condition caused by increased expression of PAI-1 or increased sensitivity to PAI-1 comprising administering to a patient orally, parenterally by a solution for injection, by inhalation, or topically, wherein the condition is acute ischemic stroke with and without thrombolysis.

In another aspect, disclosed herein is a method restoring plasmin generation comprising administering to a patient or other subject in need thereof orally, parenterally by a solution for injection, by inhalation, or topically a pharmaceutically effective amount of a PAI-1 antibody, wherein the plasmin generation facilitates therapeutic treatment of acute ischemic stroke with and without thrombolysis.

In another aspect, disclosed herein is an isolated monoclonal antibody that binds specifically to PAI-1, wherein the antibody inhibits formation of adhesions in a subject. In some embodiments, the adhesion formation is following surgery or injury to the subject. In some embodiments, the adhesion formation in the subject is abdominal. In other embodiments, the adhesion formation occurs in the shoulder, pelvis, heart, spine, hand, and other body regions of the subject.

In another aspect, disclosed herein is the use of a pharmaceutically effective amount of a PAI-1 antibody for the manufacture of a medicament for treating or preventing a condition caused by increased expression of PAI-1 or increased sensitivity to PAI-1 comprising administering to a patient orally, parenterally by a solution for injection, by inhalation, or topically, wherein the condition is abdominal adhesion formation.

In another aspect, disclosed herein is a method of restoring plasmin generation comprising administering to a to a patient or other subject in need thereof orally, parenterally by a solution for injection, by inhalation, or topically a pharmaceutically effective amount of a PAI-1 antibody, wherein the plasmin generation facilitates therapeutic treatment or prevention of adhesion formation. In some embodiments, the adhesion formation in the subject is abdominal.

In another aspect, disclosed herein is an isolated monoclonal antibody that binds to a PAI-1/vitronectin complex. In another aspect, disclosed herein is an isolated monoclonal antibody that neutralizes PAI-1 activity by inducing PAI-1 substrate conformation. In an embodiment, the antibody restores or is capable of restoring plasmin generation. In another embodiment, the isolated monoclonal antibody induces or is capable of inducing fibronectin degradation. In yet another embodiment, the isolated monoclonal antibody induces or is capable of inducing matrix metalloproteinases (MMP) activation.

In another aspect, the isolated monoclonal antibody disclosed herein is an antibody fragment. In some embodiments, the antibody is a single-chain Fv antibody. In other embodiments, the heavy chain and light chain are connected by a flexible linker to form a single-chain antibody. In other embodiments, the antibody is a Fab, Fab', or (Fab')$_2$ antibody.

In another aspect, disclosed herein is an isolated monoclonal antibody that binds specifically to PAI-1, wherein the antibody is a crystallized antibody. In an embodiment, disclosed herein is an isolated crystal comprising the Fab' fragment of monoclonal antibody A44, wherein the Fab' fragment consists of light chain sequence SEQ ID NO:7 and heavy chain sequence SEQ ID NO:6. In another embodiment, disclosed herein is an isolated crystal comprising a Fab' fragment comprising light chain sequence SEQ ID NO:93 and heavy chain sequence SEQ ID NO:86. In an embodiment, the isolated crystal comprises assimetric unit cell dimensions a=105 Å, b=152 Å and c=298 Å. In an embodiment, the isolated crystal belongs to P212121 space group. In another embodiment, the isolated crystal comprises a 3.3 Å resolution of x-ray diffraction. In an embodiment, the isolated crystal retains the biological activity of the crystallized antibody. In some embodiments, the isolated crystal has a greater half life in vivo than the soluble counterpart of the crystallized antibody.

In one aspect, disclosed herein is a pharmaceutical composition comprising: (a) the crystallized antibody that binds specifically to PAI-1 and (b) at least one pharmaceutical excipient which embeds or encapsulates the crystal.

In another aspect, disclosed herein is a pharmaceutical composition comprising a pharmaceutically acceptable carrier and a therapeutically effective amount of any of the antibodies disclosed herein.

In one aspect, disclosed herein is a method of generating an antibody against PAI-1 comprising immunizing a mammal with a complex composed of PAI-1, or a fragment thereof, and vitronectin.

In another aspect, disclosed herein is a method of screening a PAI-1 antibody in an ELISA for its ability to block PAI-1's function as a tPA activity inhibitor, comprising the steps of: (a) binding PAI-1 to an ELISA plate; (b) incubating the ELISA plate with the PAI-1 antibody; (c) incubating the ELISA plate with tPA; (d) incubating the ELISA plate with labeled anti-tPA antibody; and (e) measuring the OD$_{405}$ emitted by the labeled anti-tPA antibody; wherein a positive readout indicates that the PAI-1 antibody binds to PAI-1 but does not block formation of the covalent bond between PAI-1 and tPA, and a negative readout indicates that the PAI-1 antibody blocks tPA interaction with PAI-1.

In another aspect, disclosed herein is a method of screening hybridomas. In certain embodiments, the method of screening comprises a reverse screening method using anti-mouse immobilized anti-PAI-1 antibodies. In other embodiments, the method of screening comprises or a forward screening assay using free PAI-1 as a ligand or against immobilized vitronectin. In certain embodiments, the method is applied to determine the affinity of an antibody for a PAI-1/vitronectin complex. In some embodiments, the method comprises: immobilizing vitronectin to a surface; contacting PAI-1 with the vitronectin immobilized to the surface, thereby forming a complex; contacting the surface comprising the complex with the antibody; separating the antibody bound to the complex from unbound antibody; detecting the antibody bound to the complex, and analyzing the levels of antibody bound to the complex to determine the affinity of the antibody for the complex.

BRIEF DESCRIPTION OF THE DRAWINGS

FIG. 11 depicts the alignment of the light chain of the following murine antibodies: A105 (SEQ ID NO: 3), A39 (SEQ ID NO: 5), A44 (SEQ ID NO: 7), A71 (SEQ ID NO: 9), A75 (SEQ ID NO: 81), B109 (SEQ ID NO: 11), B28 (SEQ ID NO: 13), C45 (SEQ ID NO: 15), E16 (SEQ ID NO: 17), and E21 (SEQ ID NO: 19). CDRs are highlighted in bold.

FIG. 12 depicts the alignment of the heavy chain of the following murine antibodies: A105 (SEQ ID NO: 2), A39 (SEQ ID NO: 4), A44 (SEQ ID NO: 6), A71 (SEQ ID NO: 8), A75 (SEQ ID NO: 80), B109 (SEQ ID NO: 10), B28 (SEQ ID NO: 12), C45 (SEQ ID NO: 14), E16 (SEQ ID NO: 16), and E21 (SEQ ID NO: 18). CDRs, as defined by IMGT, are highlighted in bold.

FIG. 13 depicts the alignment of murine A44 light chain (SEQ ID NO: 7) with vk1 (SEQ ID NO: 101) and vlambda3 (SEQ ID NO: 102).

FIG. 14 depicts the alignment of murine A44 heavy chain (SEQ ID NO: 6) with vh2 (SEQ ID NO: 103) and vh4 (SEQ ID NO: 104).

FIG. 15 depicts clone A44 humanization VL with all constructs aligned. All aligned sequences (SEQ ID NOs: 91-98) are further described below in Table 25. Black boxes represent CDR domains. Highlighted residues vary in sequence from the residue directly above in the alignment. Residue numbering is as described by IMGT.

FIG. 16 depicts clone A44 humanization VH with all constructs aligned. All aligned sequences (SEQ ID NOs: 82-90) are further described below in Table 25. Black boxes represent CDR domains. Highlighted residues vary in sequence from the residue directly above in the alignment. Residue numbering is as described by IMGT.

FIG. 32 depicts active PAI-1 level in plasma from monkeys treated by A44V11 (A) mAb (n=5) or with IgG1 isotype control (B) (n=4) (5 mg/kg ip) 24 hours before LPS challenge (100 ug/kg iv). Blood samples were harvested at the indicated time point and active PAI-1 levels were determined in plasma using the ELISA (#HPAIKT from Molecular Innovation).

FIG. 34 depicts D-dimer level in plasma from monkeys treated by A44V11 (A) mAb (n=5) or with IgG1 isotype control (B) (n=4) (5 mg/kg ip) 24 hours before LPS challenge (100 ug/kg iv). Blood samples were harvested at the indicated time point and D-dimer levels were determined in plasma using the ELISA.

FIG. 39(*a*) depicts the complex crystallization of the Fab A44/PAI-1 complex, and FIG. 39 (*b*) depicts the best optimized crystals.

FIG. 53 depicts the cyno-PAI-1:A44v11 epitope determined by HDX MS. The residues of cynoPAI-1 (SEQ ID NO: 162) which show protection from exchange in the A44v11 antibody-bound state are shown in bold. The residues of cyno-PAI-1:A44v11 epitope determined from the crystallization studies is shown in boxes.

DETAILED DESCRIPTION

Figure 1:
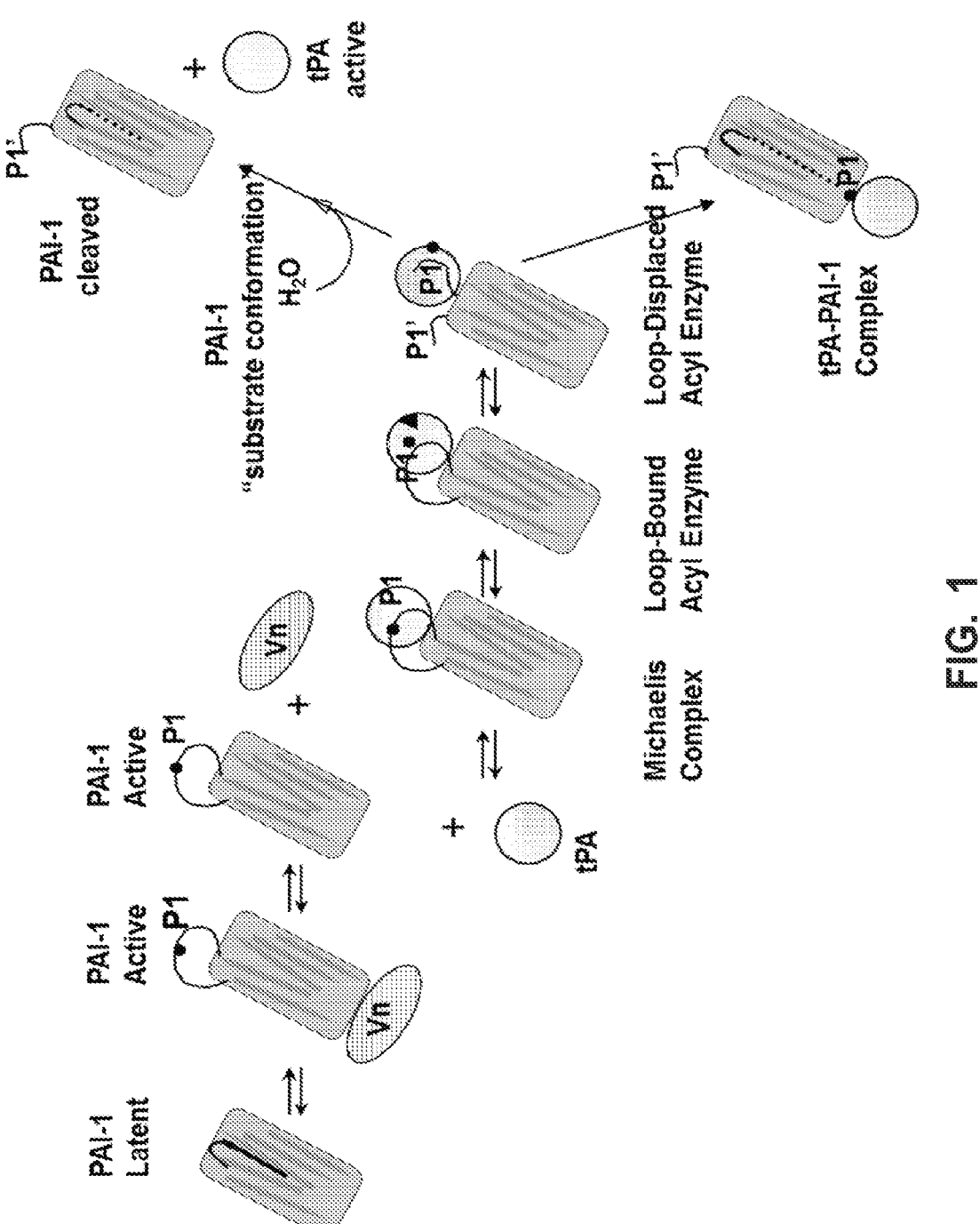
FIG. 1 depicts a schematic representation of the mechanisms between PAI-1 and the serine proteases tissue-type plasminogen activator (tPA) and urokinase-type plasminogen activator (uPA). PAI-1 exhibits structural flexibility and can occur in a latent conformation or an active conformation when it is bound to vitronectin (Vn). The RCL region of PAI-1 bears the bait peptide bond (also called P1-P1') that is the cleavage site by the serine protease. A Michaelis complex with tPA or uPA forms first, then the catalytic triad reacts with the bait peptide bond to form an acyl-enzyme complex that, after cleavage of the P1-P' 1 peptide bond, induces strong conformation changes. Acyl enzyme is a labile complex formed by covalent bond between the serine residue (black triangle) from catalytic triad from serine protease (tPA) and amino-acid from the substrate (black circle) that undergoes further hydrolysis. The conformational changes causes insertion of the cleaved RCL into a $-strand with the protease staying covalently bound as an acyl enzyme with PAI-1. Under non physiological circumstance, hydrolysis of this acyl-enzyme complex may induce release of the cleaved PAI-1 and free active protease.

The present invention provides antibodies and fragments thereof that specifically bind to human PAI-1 and modulate the biological functions of PAI-1. Such antibodies are particularly useful for treating PAI-1-associated disease or disorders (e.g., fibrosis). The invention also provides pharmaceutical compositions, as well as nucleic acids encoding PAI-1 antibodies, recombinant expression vectors and host cells for making such antibodies, or fragments thereof. Methods of using antibodies as disclosed herein to detect PAI-1 or to modulate PAI-1 activity, either in vitro or in vivo, are also encompassed by the invention.

I. Definitions

In order that the present invention may be more readily understood, certain terms are first defined.

As used herein, the term "human PAI-1" refers to a peptide comprising or consisting of the amino acid sequence listed below:

```
                                          (SEQ ID NO. 1)
VHHPPSYVAHLASDFGVRVFQQVAQASKDRNVVFSPYGVASVLAMLQLTT

GGETQQQIQAAMGFKIDDKGMAPALRHLYKELMGPWNKDEISTTDAIFVQ

RDLKLVQGFMPHFFRLFRSTVKQVDFSEVERARFIINDWVKTHTKGMISN

LLGKGAVDQLTRLVLVNALYFNGQWKTPFPDSSTHRRLFHKSDGSTVSVP

MMAQTNKFNYTEFTTPDGHYYDILELPYHGDTLSMFIAAPYEKEVPLSAL

TNILSAQLISHWKGNMTRLPRLLVLPKFSLETEVDLRKPLENLGMTDMFR
```

-continued

QFQADFTSLSDQEPLHVAQALQKVKIEVNESGTVASSSTAVIVSARMAPE

EIIMDRPFLFVVRHNPTGTVLFMGQVMEP, or a fragment thereof.

As used herein, the term "antibody" refers to immuno-globulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH or VH) and a heavy chain constant region ($C_H$ or CH). The heavy chain constant region comprises three domains, $C_H1$, $C_H2$ and $C_H3$. Each light chain comprises a light chain variable region (abbreviated $V_L$ or VL) and a light chain constant region ($C_L$ or CL). The light chain constant region comprises one domain ($C_L1$). The VH and $V_L$ regions can be further subdivided into regions of hyper-variability, termed complementarity determining regions (CDRs), interspersed with regions that are more conserved, termed framework regions (FR). Each VH and $V_L$ is com-posed of three CDRs and four FRs, arranged from amino-terminus to carboxy-terminus in the following order: FR1, CDR1, FR2, CDR2, FR3, CDR3, FR4.

As used herein, the term "antigen-binding fragment" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suit-able standard techniques such as proteolytic digestion or recombinant genetic engineering techniques involving the manipulation and expression of DNA encoding antibody variable and optionally constant domains. Non-limiting examples of antigen-binding portions include: (i) Fab frag-ments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determin-ing region (CDR)). Other engineered molecules, such as diabodies, triabodies, tetrabodies and minibodies, are also encompassed within the expression "antigen-binding frag-ment."

As used herein, the term "CDR" or "complementarity determining region" means the noncontiguous antigen com-bining sites found within the variable region of both heavy and light chain polypeptides. These particular regions have been described by Kabat et al., *J. Biol. Chem.* 252, 6609-6616 (1977) and Kabat et al., Sequences of protein of immunological interest. (1991), and by Chothia et al., *J. Mol. Biol.* 196:901-917 (1987) and by MacCallum et al., *J. Mol. Biol.* 262:732-745 (1996) where the definitions include overlapping or subsets of amino acid residues when com-pared against each other. The Kabat definition is based on sequence variability. The IMGT unique numbering for all IG and TR V-regions of all species relies on the high conser-vation of the structure of the variable region (Lefranc, Mp et al., *Dev comp. Immunol.* 27:55-77, 2003). IMGT number-ing, set up after aligning more than 5,000 sequences takes into account and combines the definition of the framework and CDRs. The Clothia definition is based on the location of the structural loop regions. The Contact definition (MacCa-llum et al.) is based on an analysis of the complex crystal structures and antibody-antigen interactions. The amino acid residues which encompass the CDRs as defined by each of the above cited references are set forth for comparison. In one embodiment disclosed herein, the term "CDR" is a CDR as defined by the Kabat definition. In another embodiment disclosed herein, the CDR is a CDR as defined by IMGT.

As used herein the term "framework (FR) amino acid residues" refers to those amino acids in the framework region of an Ig chain. The term "framework region" or "FR region" as used herein, includes the amino acid residues that are part of the variable region, but are not part of the CDRs (e.g., using the Contact definition of CDRs). Therefore, a variable region framework is between about 100-120 amino acids in length but includes only those amino acids outside of the CDRs.

The present invention also encompasses "conservative amino acid substitutions" in the CDR amino acid sequences of the antibodies disclosed herein, i.e., amino acid sequence modifications which do not abrogate the binding of the antibody to the antigen, i.e., PAI-1. A conservative substi-tution is a substitution of a native amino acid residue with a nonnative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine, as has been previously described for "alanine scanning mutagen-esis" (Cunningham et al., *Science* 244:1081-85 (1989)). Conservative amino acid substitutions include the substitu-tion of an amino acid in one class by an amino acid of the same class, where a class is defined by common physico-chemical amino acid side chain properties and high substi-tution frequencies in homologous proteins found in nature, as determined, for example, by a standard Dayhoff fre-quency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substi-tution. Thus, a predicted nonessential amino acid residue in a PAI-1 antibody is replaced with another amino acid residue from the same class. Methods of identifying amino acid conservative substitutions which do not eliminate antigen binding are well-known in the art (see, e.g., Brummell et al., *Biochem.* 32:1180, 1993; Kobayashi et al. *Protein Eng.* 12:879, 1999; and Burks et al. *Proc. Natl. Acad. Sci. USA* 94:412, 1997). General rules for conservative amino acid substitutions are set forth in Table 1 below.

TABLE 1

| Conservative Amino Acid Substitutions | | |
| --- | --- | --- |
| Original Residues | Exemplary Substitutions | Select Substitutions |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |

TABLE 1-continued

| Conservative Amino Acid Substitutions | | |
|---|---|---|
| Original Residues | Exemplary Substitutions | Select Substitutions |
| Met | Leu, Phe, Ile | Leu |
| Phe | Leu, Val, Ile, Ala, Tyr | Leu |
| Pro | Ala | Ala |
| Ser | Thr | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Conservative modifications to the amino acid sequence (and the corresponding modifications to the encoding nucleotides) are expected to produce PAI-1 antibodies having functional and chemical characteristics similar to those of naturally occurring PAI-1 antibodies. In contrast, substantial modifications in the functional or chemical characteristics of PAI-1 antibodies may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human PAI-1 antibody that are homologous with non-human PAI-1 antibody, or into the non-homologous regions of the molecule.

In certain aspects, the heavy or light chain variable regions may be 99%, 98%, 97%, 96%, 95%, 94%, 93%, 92%, 91%, or 90% identical to any of the variable region sequences disclosed herein.

As used herein, the term "specifically binds to" refers to the ability of an antibody or an antigen-binding fragment thereof to bind to an antigen with an Kd that is lower than $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or less. The term also encompasses refers to the ability of an antibody or an antigen-binding fragment thereof to bind to an antigen with an affinity that is at least two-fold greater than its affinity for a nonspecific antigen.

The disclosure also provides antibodies that competitively inhibit binding of an antibody to an epitope disclosed herein as determined by any method known in the art for determining competitive binding, for example, the immunoassays described herein. In certain embodiments, the antibody competitively inhibits binding to the epitope by at least 95%, at least 90%, at least 85%, at least 80%, at least 75%, at least 70%, at least 60%, or at least 50%.

As used herein, the term "antigen" refers to the binding site or epitope recognized by an antibody or antigen binding fragment thereof.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), which serve equivalent functions.

Numerous expression vector systems may be employed for the purposes of this invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals. In particular embodiments the cloned variable region genes are inserted into an expression vector along with the heavy and light chain constant region genes (e.g. human) synthetic as discussed above.

More generally, once a vector or DNA sequence encoding an antibody, or fragment thereof, has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Chapter 24.2, pp. 470-472 Vectors, Rodriguez and Denhardt, Eds. (Butterworths, Boston, Mass. 1988). An embodiment disclosed herein is plasmid introduction into the host via electroporation. The transformed cells are grown under conditions appropriate to the production of the light chains and heavy chains, and assayed for heavy or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

It should be understood that this term is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "treat," "treating," and "treatment" refer to therapeutic or preventative measures described herein. The methods of "treatment" employ administration to a subject, an antibody or antigen binding fragment disclosed herein, for example, a subject having a PAI-1-associated disease or disorder (e.g., a fibrotic disease) or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "PAI-1-associated disease or disorder" includes disease states with or without symptoms associated with a disease state, where altered levels or activity of PAI-1 are found. Exemplary PAI-1-associated diseases or disorders include various types of fibrosis.

As used herein, the term "effective amount" refers to that amount of an antibody or an antigen binding fragment thereof that binds PAI-1, which is sufficient to effect treatment, prognosis or diagnosis of a PAI-1-associated disease or disorder, as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 1 ug to about 5,000 mg, about 1 mg to about 1,000 mg, about 10 mg to about 100 mg, of an antibody or antigen binding fragment thereof, disclosed herein. Dosage regiments may be adjusted to provide the optimum therapeutic response. An effective amount is also one in which any toxic or detrimental effects (i.e., side effects) of an antibody or antigen binding fragment thereof are minimized or outweighed by the beneficial effects.

As used herein, the term "subject" or "mammal" includes any human or non-human animal.

As used herein, the term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain.

It is noted here that, as used in this specification and the appended claims, the singular forms "a," "an," and "the" include plural reference unless the context clearly dictates otherwise.

II. Anti-PAI-1 Antibodies

In one aspect the invention provides antibodies, or antigen binding fragments thereof, that specifically bind to human PAI-1. Exemplary VH, VL and CDR amino acid sequences and nucleotide sequences of the antibodies disclosed herein are set forth in Table 2. CDR regions shown in Table 2 are defined by IMGT.

TABLE 2

VH, VL and CDR amino acid sequences of exemplary anti-PAI-1 antibodies or fragments thereof

| ANTI-BODY | SEQUENCE | SEQ ID NO |
|---|---|---|
| mA105 VH | QVQLQQSGAELMKPGASVKISCKATGFTFSIYWIEW VKQRPGLGLEWIGEILPGSGSTNYNEKFKGKATFTA DTSSNTAFMQLSSLTSEDSAVYYCARGGLYYDLDYW GQGTILTVSSAKTTPP | 2 |
| mA105 VL | DVVMTQTPLTLSVTIGQPASISCKSSQSLLDSDGKT YLNWLLQRPGQSPQRLISLVSKLDSGVPDRFTGSGS GTDFTLKLSRVEGADLGVYYCWQDRHFPRTFGGGTK LEIKRAD | 3 |
| mA39 VH | QVQLQQSGAELMKPGASVKISCKATGYTFNIYWIQW VKQRPGHGLEWIGEILPGSNTNYNEKFKDKATFTAD SSSNTAYMQLSSLTSEDSAVYYCARLGIGLRGALDY WGQGTSVTVSSAKTTPP | 4 |
| mA39 VL | DIQMTHSPASLSASVGETVTITCRASENIYSYLAWY HQKQGKSPQLLVYNAKTLAEGVPSRFSGSGSGTQFS LNIKSLQPEDFGTFYCQHRYGSPWTFGGGTKLEIKR AD | 5 |
| mA44 VH | EMQLQESGPSLVKPSQTLSLTCSVTGDSMTNGYWNW IRKFPGNKLEYMGYITYSGSTYYNPSLKGRISITRN TSKNQYYLQLSSVTTEDTATYYCARWHYGSPYYFDY WGQGTTLTVSSAKTTPP | 6 |
| mA44 VL | DIKMTQSPSSMYASLGERVTITCKASQDINSYLSWL QQKPGKSPKTLIYRANRSVDGVPSRFSGSGSGQDYS LTISSLEYEDMGIYYCLQYDEFPPTFGGGTKLEIKR AD | 7 |
| mA71 VH | QVQLQQSGAELMKPGASVKISCKATGFTFSTYWIEW IKQRPGHGLDWIGEILPGSGNTNYNEKFKGKATFTA DTSSNTVYMQLSSLTSEDSAVYYCARGGLYYNLDSW GQGTTLTVSSAKTTPP | 8 |
| mA71 VL | DVVMTQTPLTLSVTIGQPASISCKSSQSLLDSDGKT YLYWLLQRPGQSPKRLIYLVSKLDSGVPDRFTGSGS GTDFTLKISRVEAEDLGVYYCWQDTHFPRTFGGGTK LEIKRAD | 9 |

TABLE 2-continued

VH, VL and CDR amino acid sequences of
exemplary anti-PAI-1 antibodies or
fragments thereof

| ANTI-BODY | SEQUENCE | SEQ ID NO |
|---|---|---|
| mA75 VH | QGQLQQSGAELMKPGASVKISCKASGFTFSTYWIAW LKQRPGHGLEWIAEILPGSGLTNYNEIFRGKATFTA DTSSNTAYMQLSSLTSEDSAVYYCARGGLYYAMDYW GQGTSVTVSSAKTTAP | 80 |
| mA75 VL | DVVMTQTPLTLSVTIGQPASICKSSQSLLDSEGKTY LNWLFQRPGQSPKRLIYLVCKLDCGVPDRFTGSGSG TDFTLKISRVEGEDLGVYYCWQGSHFPQTFGGGTKL EIKRAD | 81 |
| mB109 VH | EVQLQQSGSVLARPGTSVKMSCKASGYSFTSYWMHW VKQRPGQGLEWMGAIYPGNSGQGLDWIGAIYPGNSD TTYNQKFEDKAKLTAVASASTAYMEVSSLTNEDSAV YYCTRGLRRWGAMDYWGQGTSVTVSSAKTTPP | 10 |
| mB109 VL | DIVMTQSHKFMSTSAGDRVSIPCKASQDVSSAVAWY QQKLGQSPKLLIYSASFRYTGVPDRFTGSGSGTDFT FTISSVQAEDLAVYYCQQHYSSPYTFGGGTNLEIKR AD | 11 |
| mB28 VH | QVQLQQSGAELMKPGASVKISCKATGYTFSISWIEW IKQRPGGLEWIGKILPGSGGANYNEKFKGKATVTAD TSSNTVYMQLSSLTSEDSAVYYCARLSTGTRGAFDY WGQGTTLTVSSAKTTPP | 12 |
| mB28 VL | DIQLTQSPASLSASVGATVTITCRASENVYSYLAWY QQKQGKSPQLLVYNAKTLAEGVPSRFSGSGSGTQFS LKINYLQPEDFGSYYCQHHYGTPPTFGGGTKVEIKR AD | 13 |
| mC45 VH | QVQLQQSGVELVRPGTSVKVSCKASGYAFTNYLIEW IKQRPGQGLEWIGVIHPGSGVTNYNEKFKGKAILTA DKSSSTAYMQLSSLTSDDSAVYFCARDYYGSSHGLM DYWGQGTSVTVSS | 14 |
| mC45 VL | DIKMTQSPSSMYASLGERVTITCKASQDINSYLSWF QQKPGKSPKTLIYRANRLVDGVPSRFSGSGSGQDYS LTISSLEYEDMGIYYCLQYDEFPRTFGGGTKLEIK | 15 |
| mE16 VH | EVKLVESGGGLVKPGGSLKLSCAASGFTFSNYGMSW VRQTPEKGLGWVASLRTGGNTYYSDSVKGRFTISRD NDRNILYLQMSSLTSEDTAVYYCARGLRHWGYFDVW GAGTTVTVSS | 16 |
| mE16 VL | DIVMTQSHKFMSTSVGDRVNITCKASQDVSTAVGWY QQEPGQSPKLLIYSASNRHTGVPDRFTGSGSGTDFT FTISSVQAEDLAVYYCQQHYSSPWTFGGGTKLEIK | 17 |
| mE21 VH | EVQLQQSGAELVRSGASVKLSCTASGFNIKDYYMHW VKQRPEQGLEWIGWIDPENGDTEYDPKFQAKATMTA DTSSNTAYLQLSSLTSEDTAVYYCMYGNYPYYFDYW GQGTTLTVSS | 18 |
| mE21 VL | DIQMTQTTSSLSASLGDRVTISCRASQDISNYLNWY QQKPDGTVKLLIYYTSRLHSGVPSRFSGSGSGTDYS LTISNLEQEDIATYFCQQGNTLPWTFGGGTKLEIK | 19 |
| mA105 HCDR3 | ARGGLYYDLDY | 20 |
| mA105 HCDR2 | ILPGSGST | 21 |
| mA105 HCDR1 | GFTFSIYW | 22 |
| mA105 LCD3 | WQDRHFPRT | 23 |

TABLE 2-continued

VH, VL and CDR amino acid sequences of
exemplary anti-PAI-1 antibodies or
fragments thereof

| ANTI-BODY | SEQUENCE | SEQ ID NO |
|---|---|---|
| mA105 mA71 LCDR2 | LVS | 24 |
| mA105 mA71 LCDR1 | QSLLDSDGKTY | 25 |
| mA39 HCDR3 | ARLGIGLRGALDY | 26 |
| mA39 HCDR2 | ILPGSNT | 27 |
| mA39 HCDR1 | GYTFNIYW | 28 |
| mA39 LCDR3 | QHRYGSPWT | 29 |
| mA39 LCDR2 | NAK | 30 |
| mA39 LCDR1 | ENIYSY | 31 |
| mA44 HCDR3 | ARWHYGSPYYFDY | 32 |
| mA44 HCDR2 | ITYSGST | 33 |
| mA44 HCDR1 | GDSMTNGY | 34 |
| mA44 LCDR3 | LQYDEFPPT | 35 |
| mA44 LCDR2 | RAN | 36 |
| mA44 LCDR1 | QDINSY | 37 |
| mA71 HCDR3 | ARGGLYYNLDS | 38 |
| mA71 HCDR2 | ILPGSGNT | 39 |
| mA71 HCDR1 | GFTFSTYW | 40 |
| mA71 LCDR3 | WQDTHFPRT | 41 |
| mA71 LCDR2 | LVS | 42 |
| mA71 LCDR1 | QSLLDSDGKTY | 43 |
| mA75 HCDR3 | ARGGLYYAMDY | 44 |
| mA75 HCDR2 | ILPGSGLT | 45 |
| mA75 HCDR1 | GFTFSTYW | 46 |

TABLE 2-continued

VH, VL and CDR amino acid sequences of
exemplary anti-PAI-1 antibodies or
fragments thereof

| ANTI-BODY | SEQUENCE | SEQ ID NO |
|---|---|---|
| mA75 LCDR3 | WQGSHFPQT | 47 |
| mA75 LCDR2 | LVC | 48 |
| mA75 LCDR1 | QSLLDSEGKTY | 49 |
| mB109 HCDR3 | TRGLRRWGAMDY | 50 |
| mB109 HCDR2 | ILPGSGLT | 51 |
| mB109 HCDR1 | GFTFSTYW | 52 |
| mB109 LCDR3 | QQHYSSPYT | 53 |
| mB109 LCDR2 | SAS | 54 |
| mB109 LCDR1 | QDVSSA | 55 |
| mB28 HCDR3 | ARLSTGTRGAFDY | 56 |
| mB28 HCDR2 | ILPGSGGA | 57 |
| mB28 HCDR1 | GYTFSISW | 58 |
| mB28 LCDR3 | QHHYGTPPT | 59 |
| mB28 LCDR2 | NAK | 60 |
| mB28 LCDR1 | ENVYSY | 61 |
| mC45 HCDR3 | ARDYYGSSHGLMDY | 62 |
| mC45 HCDR2 | IHPGSGVT | 63 |
| mC45 HCDR1 | GYAFTNYL | 64 |
| mC45 LCDR3 | LQYDEFPRT | 65 |
| mC45 LCDR2 | RAN | 66 |
| mC45 LCDR1 | QDINSY | 67 |
| mE16 HCDR3 | ARGLRHWGYFDV | 68 |
| mE16 HCDR2 | LRTGGNT | 69 |
| mE16 HCDR1 | GFTFSNYG | 70 |

TABLE 2-continued

VH, VL and CDR amino acid sequences of
exemplary anti-PAI-1 antibodies or
fragments thereof

| ANTI-BODY | SEQUENCE | SEQ ID NO |
|---|---|---|
| mE16 LCDR3 | QQHYSSPWT | 71 |
| mE16 LCDR2 | SAS | 72 |
| mE16 LCDR1 | QDISNY | 73 |
| mE21 HCDR3 | MYGNYPYYFDY | 74 |
| mE21 HCDR2 | IDPENGDT | 75 |
| mE21 HCDR1 | GFNIKDYY | 76 |
| mE21 LCDR3 | QQGNTLPWT | 77 |
| mE21 LCDR2 | YTS | 78 |
| mE21 LCDR1 | QDISNY | 79 | m = murine; VH = variable heavy chain; VL = variable light chain;

In another embodiment, the present invention provides anti-PAI-1 antibodies that bind to the same epitope or competitively inhibit an antibody, or antigen binding fragment thereof comprising the VH and VL region amino acid sequences set forth in SEQ ID NO: 6 and 7 respectively. Such antibodies can be identified using routine competition binding assays including, for example, surface plasmon resonance (SPR)-based competition assays.

III. Modified Anti-PAI-1 Antibodies

In certain embodiments, anti-PAI-1 antibodies disclosed herein may comprise one or more modifications. Modified forms of anti-PAI-1 antibodies disclosed herein can be made using any techniques known in the art.
i) Reducing Immunogenicity
In certain embodiments, anti-PAI-1 antibodies, or antigen binding fragments thereof, disclosed herein are modified to reduce their immunogenicity using art-recognized techniques. For example, antibodies, or fragments thereof, can be chimerized, humanized, or deimmunized.

In one embodiment, an antibody, or antigen binding fragments thereof, disclosed herein may be chimeric. A chimeric antibody is an antibody in which different portions of the antibody are derived from different animal species, such as antibodies having a variable region derived from a murine monoclonal antibody and a human immunoglobulin constant region. Methods for producing chimeric antibodies, or fragments thereof, are known in the art. See e.g., Morrison, *Science* 229:1202, 1985; Oi et al., *BioTechniques* 4:214, 1986; Gillies et al., *J. Immunol. Methods* 125:191, 1989; U.S. Pat. Nos. 5,807,715; 4,816,567; and 4,816,397, which are incorporated herein by reference in their entireties. Techniques developed for the production of "chimeric antibodies" (Morrison et al., Proc. *Natl. Acad. Sci.* 81:851, 1984;

Neuberger et al., *Nature* 312:604, 1984; Takeda et al., *Nature* 314:452, 1985) may be employed for the synthesis of said molecules. For example, a genetic sequence encoding a binding specificity of a mouse anti-PAI-1 antibody molecule may be fused together with a sequence from a human antibody molecule of appropriate biological activity. As used herein, a chimeric antibody is a molecule in which different portions are derived from different animal species, such as those having a variable region derived from a murine monoclonal antibody and a human immunoglobulin constant region, e.g., humanized antibodies.

In another embodiment, an antibody, or antigen binding fragment thereof, as disclosed herein is humanized. Humanized antibodies have a binding specificity comprising one or more complementarity determining regions (CDRs) from a non-human antibody and framework regions from a human antibody molecule. Often, framework residues in the human framework regions will be substituted with the corresponding residue from the CDR donor antibody to alter, or improve, antigen binding. These framework substitutions are identified by methods well known in the art, e.g., by modeling of the interactions of the CDR and framework residues to identify framework residues important for antigen binding and sequence comparison to identify unusual framework residues at particular positions. See e.g. Queen et al., U.S. Pat. No. 5,585,089; Riechmann et al., *Nature* 332:323, 1988, which are incorporated herein by reference in their entireties. Antibodies can be humanized using a variety of techniques known in the art including, for example, CDR-grafting (EP 239,400; International Publication No. WO 91/09967; U.S. Pat. Nos. 5,225,539; 5,530,101; and 5,585,089), veneering or resurfacing (EP 592,106; EP 519,596; Padlan, *Molecular Immunology* 28:489, 1991; Studnicka et al., *Protein Engineering* 7:805, 1994; Roguska. et al., *PNAS* 91:969, 1994), and chain shuffling (U.S. Pat. No. 5,565,332).

In a particular embodiment, a humanization method is employed that is based on the impact of the molecular flexibility of the antibody during and at immune recognition (see International Publication No. WO2009/032661, which is incorporated herein by reference in its entirety). Protein flexibility is related to the molecular motion of the protein molecule. Protein flexibility is the ability of a whole protein, a part of a protein or a single amino acid residue to adopt an ensemble of conformations which differ significantly from each other. Information about protein flexibility can be obtained by performing protein X-ray crystallography experiments (see, for example, Kundu et al., *Biophys. J.* 83:723, 2002), nuclear magnetic resonance experiments (see, for example, Freedberg et al., *J. Am. Chem. Soc.* 120:7916, 1998) or by running molecular dynamics (MD) simulations. An MD simulation of a protein is done on a computer and allows one to determine the motion of all protein atoms over a period of time by calculating the physical interactions of the atoms with each other. The output of a MD simulation is the trajectory of the studied protein over the period of time of the simulation. The trajectory is an ensemble of protein conformations, also called snapshots, which are periodically sampled over the period of the simulation, e.g. every 1 picosecond (ps). It is by analyzing the ensemble of snapshots that one can quantify the flexibility of the protein amino acid residues. Thus, a flexible residue is one which adopts an ensemble of different conformations in the context of the polypeptide within which that residue resides. MD methods are known in the art, see, e.g., Brooks et al. "Proteins: A Theoretical Perspective of Dynamics, *Structure and Thermodynamics*"

(Wiley, New York, 1988). Several software enable MD simulations, such as Amber (see Case et al. *J. Comp. Chem.* 26:1668, 2005; Brooks et al. *J. Comp. Chem.* 4:187, 1983; and MacKerell et al. (1998) in "*The Encyclopedia of Computational Chemistry*" vol. 1:271-177, Schleyer et al., eds. Chichester: John Wiley & Sons) or Impact (see Rizzo et al. *J. Am. Chem. Soc.;* 122:12898, 2000).

Most protein complexes share a relatively large and planar buried surface and it has been shown that flexibility of binding partners provides the origin for their plasticity, enabling them to conformationally adapt to each other (Sundberg and Mariuzza, *Structure* 8, R137-R142, 2000). As such, examples of "induced fit" have been shown to play a dominant role in protein-protein interfaces. In addition, there is a steadily increasing body of data showing that proteins actually bind ligands of diverse shapes, sizes and composition (*Protein Science* 11:184-187, 2002) and that the conformational diversity appears to be an essential component of the ability to recognize different partners (James et al., *Science* 299:1362, 2003). Flexible residues are involved in the binding of protein-protein partners (Grunberg et al., Structure 14, 683, 2006).

The flexible residues can adopt a variety of conformations that provide an ensemble of interaction areas that are likely to be recognized by memory B cells and to trigger an immunogenic response. Thus, an antibody can be humanized by modifying a number of residues from the framework so that the ensemble of conformations and of recognition areas displayed by the modified antibody resemble as much as possible those adopted by a human antibody. That can be achieved by modifying a limited number of residues by: (1) building a homology model of the parent mAb and running an MD simulation; (2) analyzing the flexible residues and identification of the most flexible residues of a non-human antibody molecule, as well as identifying residues or motifs likely to be a source of heterogeneity or of degradation reaction; (3) identifying a human antibody which displays the most similar ensemble of recognition areas as the parent antibody; (4) determining the flexible residues to be mutated, residues or motifs likely to be a source of heterogeneity and degradation are also mutated; and (5) checking for the presence of known T cell or B cell epitopes. The flexible residues can be found using an MD calculation as taught herein using an implicit solvent model, which accounts for the interaction of the water solvent with the protein atoms over the period of time of the simulation.

Once the set of flexible residues has been identified within the variable light and heavy chains, a set of human heavy and light chain variable region frameworks that closely resemble that of the antibody of interest is identified. That can be done, for example, using a BLAST search on the set of flexible residues against a database of antibody human germ line sequence. It can also be done by comparing the dynamics of the parent mAb with the dynamics of a library of germ line canonical structures. The CDR residues and neighboring residues are excluded from the search to ensure high affinity for the antigen is preserved. Flexible residues then are replaced.

When several human residues show similar homologies, the selection is driven also by the nature of the residues that are likely to affect the solution behavior of the humanized antibody. For instance, polar residues will often occur in exposed flexible loops over hydrophobic residues. Residues which are a potential source of instability and heterogeneity are also mutated even if there are found in the CDRs. That will include exposed methionines as sulfoxide formation can result from oxygen radicals, proteolytic cleavage of acid labile bonds such as those of the Asp-Pro dipeptide (Drug Dev. Res. 61:137, 2004), deamidation sites found with an exposed asparagine residue followed by a small amino acid, such as Gly, Ser, Ala, H is, Asn or Cys (*J. Chromatog.* 837:35, 2006) and N-glycosylation sites, such as the Asn-X-Ser/Thr site. Typically, exposed methionines will be substituted by a Leu, exposed asparagines will be replaced by a glutamine or by an aspartate, or the subsequent residue will be changed. For the glycosylation site (Asn-X-Ser/Thr), either the Asn or the Ser/Thr residue will be changed.

The resulting composite antibody sequence is checked for the presence of known B cell or linear T-cell epitopes. A search is performed, for example, with the publicly available Immune Epitope Data Base (IEDB) (*PLOS Biol.* (2005) 3(3)e91). If a known epitope is found within the composite sequence, another set of human sequences is retrieved and substituted. Thus, unlike the resurfacing method of U.S. Pat. No. 5,639,641, both B-cell-mediated and T-cell-mediated immunogenic responses are addressed by the method. The method also avoids the issue of loss of activity that is sometimes observed with CDR grafting (U.S. Pat. No. 5,530,101). In addition, stability and solubility issues also are considered in the engineering and selection process, resulting in an antibody that is optimized for low immunogenicity, high antigen affinity and improved biophysical properties.

In some embodiments, de-immunization can be used to decrease the immunogenicity of and antibody, or antigen binding fragment thereof. As used herein, the term "de-immunization" includes alteration of an antibody, or antigen binding fragment thereof, to modify T cell epitopes (see, e.g., International Publication Nos. WO9852976A1, WO0034317A2). For example, VH and VL sequences from the starting antibody may be analyzed and a human T cell epitope "map" may be generated from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of PAI-1-specific antibodies or fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

ii) Effector Functions and Fc Modifications

Anti-PAI-1 antibodies disclosed herein may comprise an antibody constant region (e.g. an IgG constant region, a human IgG constant region, a human IgG1 or IgG4 constant region) which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In certain embodiments, the antibodies, or fragments thereof, disclosed herein bind to an Fc-gamma receptor. In alternative embodiments, anti-PAI-1 antibodies disclosed herein may comprise a constant region which is devoid of one or more effector functions (e.g., ADCC activity) or is unable to bind Fc receptor.

Certain embodiments disclosed herein include anti-PAI-1 antibodies in which at least one amino acid in one or more of the constant region domains has been deleted or otherwise altered so as to provide desired biochemical characteristics such as reduced or enhanced effector functions, the ability to non-covalently dimerize, increased ability to localize at a particular site in the body (e.g., the site of a tumor or to a particular organ), reduced serum half-life, or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, anti-PAI-1 antibodies comprise constant regions derived from different antibody isotypes (e.g., constant regions from two or more of a human IgG1, IgG2, IgG3, or IgG4). In other embodiments, anti-PAI-1 antibodies comprises a chimeric hinge (i.e., a hinge comprising hinge portions derived from hinge domains of different antibody isotypes, e.g., an upper hinge domain from an IgG4 molecule and an IgG1 middle hinge domain). In one embodiment, an anti-PAI-1 antibody comprises an Fc region or portion thereof from a human IgG4 molecule and a Ser228Pro mutation (Kabat numbering) in the core hinge region of the molecule.

In certain anti-PAI-1 antibodies, the Fc portion may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, biodistribution and serum half-life, may easily be measured and quantified using well know immunological techniques without undue experimentation.

In certain embodiments, an Fc domain employed in an antibody disclosed herein is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The antibodies disclosed herein may employ any art-recognized Fc variant which is known to impart an improvement (e.g., reduction or enhancement) in effector function or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834, 250; 5,869,046; 6,096,871; 6,121,022; 6,194,551; 6,242, 195; 6,277,375; 6,528,624; 6,538,124; 6,737,056; 6,821, 505; 6,998,253; and 7,083,784, each of which is incorporated by reference herein. In one exemplary embodiment, an antibody disclosed herein may comprise an Fc variant comprising an amino acid substitution at EU position 268 (e.g., H268D or H268E). In another exemplary embodiment, an antibody disclosed herein may comprise an amino acid substitution at EU position 239 (e.g., S239D or S239E) or EU position 332 (e.g., I332D or I332Q).

In certain embodiments, an antibody disclosed herein may comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, or liver is desired. In one exemplary embodiment, the altered antibodies disclosed herein exhibit reduced transport across the epithelium of kidney glomeruli from the vasculature. In another embodiment, the altered antibodies disclosed herein exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to Kabat numbering). Exemplary amino acid substitutions which altered FcRn binding activity are disclosed in International PCT Publication No. WO05/047327 which is incorporated by reference herein. In certain exemplary embodiments, the antibodies, or fragments thereof, disclosed herein comprise an Fc domain having one or more of the following substitutions: V284E, H285E, N286D, K290E and S304D (Kabat numbering).

In other embodiments, antibodies, for use in the diagnostic and treatment methods described herein have a constant region, e.g., an IgG1 or IgG4 heavy chain constant region, which is altered to reduce or eliminate glycosylation. For example, an antibody disclosed herein may also comprise an Fc variant comprising an amino acid substitution which alters the glycosylation of the antibody. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduce or altered glycosylation are disclosed in International PCT Publication No. WO05/018572, which is incorporated by reference herein. In certain embodiments, the antibodies, or fragments thereof, disclosed herein are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Exemplary agly antibodies, or fragments thereof, comprise an aglycosylated Fc region of an IgG4 antibody which is devoid of Fc-effector function thereby eliminating the potential for Fc mediated toxicity to the normal vital organs that express PAI-1. In yet other embodiments, antibodies, or fragments thereof, disclosed herein comprise an altered glycan. For example, the antibody may have a reduced number of fucose residues on an N-glycan at Asn297 of the Fc region, i.e., is afucosylated. In another embodiment, the antibody may have an altered number of sialic acid residues on the N-glycan at Asn297 of the Fc region.

iii) Covalent Attachment

Anti-PAI-1 antibodies disclosed herein may be modified, e.g., by the covalent attachment of a molecule to the antibody such that covalent attachment does not prevent the antibody from specifically binding to its cognate epitope. For example, but not by way of limitation, the antibodies, or fragments thereof, disclosed herein may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Antibodies, or fragments thereof, disclosed herein may further be recombinantly fused to a heterologous polypeptide at the N- or C-terminus or chemically conjugated (including covalent and non-covalent conjugations) to polypeptides or other compositions. For example, anti-PAI-1 antibodies may be recombinantly fused or conjugated to molecules useful as labels in detection assays and effector molecules such as heterologous polypeptides, drugs, radionuclides, or toxins. See, e.g., International PCT publication Nos. WO 92/08495; WO 91/14438; WO 89/12624; U.S. Pat. No. 5,314,995; and EP 396,387.

Anti-PAI-1 antibodies may be fused to heterologous polypeptides to increase the in vivo half-life or for use in immunoassays using methods known in the art. For example, in one embodiment, PEG can be conjugated to the anti-PAI-1 antibodies disclosed herein to increase their half-life in vivo. (Leong, S. R., et al., *Cytokine* 16:106, 2001; Adv. in Drug Deliv. Rev. 54:531, 2002; or Weir et al., Biochem. Soc. Transactions 30:512, 2002).

Moreover, anti-PAI-1 antibodies disclosed herein can be fused to marker sequences, such as a peptide to facilitate their purification or detection. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824, 1989, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767, 1984) and the "flag" tag.

Anti-PAI-1 antibodies disclosed herein may be used in non-conjugated form or may be conjugated to at least one of a variety of molecules, e.g., to improve the therapeutic properties of the molecule, to facilitate target detection, or for imaging or therapy of the patient. Anti-PAI-1 antibodies disclosed herein can be labeled or conjugated either before or after purification, when purification is performed. In particular, anti-PAI-1 antibodies disclosed herein may be conjugated to therapeutic agents, prodrugs, peptides, proteins, enzymes, viruses, lipids, biological response modifiers, pharmaceutical agents, or PEG.

The present invention further encompasses anti-PAI-1 antibodies conjugated to a diagnostic or therapeutic agent. The anti-PAI-1 antibodies can be used diagnostically to, for example, monitor the development or progression of a immune cell disorder (e.g., CLL) as part of a clinical testing procedure to, e.g., determine the efficacy of a given treatment or prevention regimen. Detection can be facilitated by coupling the anti-PAI-1 antibodies to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Non-limiting examples of suitable enzymes include horseradish peroxidase, alkaline phosphatase, beta-galactosidase, or acetylcholinesterase; non-limiting examples of suitable prosthetic group complexes include streptavidin/biotin and avidin/biotin; non-limiting examples of suitable fluorescent materials include umbelliferone, fluorescein, fluorescein isothiocyanate, rhodamine, dichlorotriazinylamine fluorescein, dansyl chloride or phycoerythrin; a non-limiting example of a luminescent material includes luminol; non-limiting examples of bioluminescent materials include luciferase, luciferin, and aequorin; and non-limiting examples of suitable radioactive material include 125I, 131I, 111In or 99Tc.

Anti-PAI-1 antibodies for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, an anti-PAI-1 antibody for use in the diagnostic and treatment methods disclosed herein can be conjugated to a molecule that decreases tumor cell growth. In other embodiments, the disclosed compositions may comprise antibodies, or fragments thereof, coupled to drugs or prodrugs. Still other embodiments disclosed herein comprise the use of antibodies, or fragments thereof, conjugated to specific biotoxins or their cytotoxic fragments such as ricin, gelonin, Pseudomonas exotoxin or diphtheria toxin. The selection of which conjugated or unconjugated antibody to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include: 90Y, 125I, 131I, 123I, 111In, 105Rh, 153Sm, 67Cu, 67Ga, 166Ho, 177Lu, 186Re and 188Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

IV. Expression of Anti-PAI-1 Antibodies, or
Antigen Binding Fragments Thereof

Following manipulation of the isolated genetic material to provide anti-PAI-1 antibodies disclosed herein as set forth above, the genes are typically inserted in an expression vector for introduction into host cells that may be used to produce the desired quantity of the claimed antibodies, or fragments thereof.

In other embodiments the anti-PAI-1 antibodies, or fragments thereof, disclosed herein may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides disclosed herein in eukaryotic host cells. Compatible IRES sequences are disclosed in U.S. Pat. No. 6,193,980, that is incorporated by reference herein. Those skilled in the art will appreciate that such expression systems may be used to effectively produce the full range of polypeptides disclosed in the instant application.

In one embodiment, the host cell line used for antibody expression is of mammalian origin; those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibodyexpressed therefrom (e.g., PER.C6® (Crucell) or FUT8-knock-out CHO cell lines (Potelligent® Cells) (Biowa, Princeton, N.J.)). In one embodiment NS0 cells may be used. CHO cells can be used in certain specific embodiments. Host cell lines are typically available from commercial services, the American Tissue Culture Collection or from published literature.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary or desired, the solutions of polypeptides can be purified by the customary chromatography methods, for example gel filtration, ion-exchange chromatography, chromatography over DEAE-cellulose or (immuno-)affinity chromatography.

Genes encoding the anti-PAI-1 antibodies, or fragments thereof, disclosed herein can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides can become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

V. Pharmaceutical Formulations and Methods of Administration of Anti-PAI-1 Antibodies In another aspect, the invention provides pharmaceutical compositions comprising an anti-PAI-1 antibody, or fragment thereof.

Methods of preparing and administering antibodies, or fragments thereof, disclosed herein to a subject are well known to or are readily determined by those skilled in the art. The route of administration of the antibodies, or fragments thereof, disclosed herein may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration can be used in certain embodiments. While all these forms of administration are clearly contemplated as being within the scope disclosed herein, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M (e.g. 0.05M) phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will in an embodiment be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In certain embodiments, isotonic agents are included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an antibody by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation can be vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259, 338 each of which is incorporated herein by reference. Such articles of manufacture will in an embodiment have labels or package inserts indicating that the associated compositions are useful for treating a subject suffering from, or predisposed to autoimmune or neoplastic disorders.

Effective doses of the stabilized antibodies, or fragments thereof, disclosed herein, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

For passive immunization with an antibody disclosed herein, the dosage may range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or in particular embodiments at least 1 mg/kg. Doses intermediate in the above ranges are also intended to be within the scope disclosed herein.

Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered may fall within the ranges indicated.

Antibodies or fragments thereof, disclosed herein can be administered on multiple occasions. Intervals between single dosages can be, e.g., daily, weekly, monthly or yearly. Intervals can also be irregular as indicated by measuring blood levels of polypeptide or target molecule in the patient. In some methods, dosage is adjusted to achieve a certain plasma antibody or toxin concentration, e.g., 1-1000 ug/ml or 25-300 ug/ml. Alternatively, antibodies, or fragments thereof, can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies. In one embodiment, the antibodies, or fragments thereof, disclosed herein can be administered in unconjugated form. In another embodiment, the antibodies disclosed herein can be administered multiple times in conjugated form. In still another embodiment, the antibodies, or fragments thereof, disclosed herein can be administered in unconjugated form, then in conjugated form, or vice versa.

The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and, in particular embodiments, until the patient shows partial or complete amelioration of symptoms of disease. Thereafter, the patient can be administered a prophylactic regime.

In one embodiment, a subject can be treated with a nucleic acid molecule encoding a polypeptide disclosed herein (e.g., in a vector). Doses for nucleic acids encoding polypeptides range from about 10 ng to 1 g, 100 ng to 100 mg, 1 ug to 10 mg, or 30-300 ug DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic or therapeutic treatment. Intramuscular injection or intravenous infusion can be used for administration of an antibody disclosed herein. In some methods, therapeutic antibodies, or fragments thereof, are injected directly into the cranium. In some methods, antibodies, or fragments thereof, are administered as a sustained release composition or device, such as a Medipad™ device.

Agents disclosed herein can optionally be administered in combination with other agents that are effective in treating the disorder or condition in need of treatment (e.g., prophylactic or therapeutic). Additional agents are those which are art recognized and are routinely administered for a particular disorder.

Effective single treatment dosages (i.e., therapeutically effective amounts) of 90Y-labeled antibodies disclosed herein range from between about 5 and about 75 mCi, and in an embodiment between about 10 and about 40 mCi. Effective single treatment non-marrow ablative dosages of 131I-labeled antibodies range from between about 5 and about 70 mCi, and in an embodiment between about 5 and about 40 mCi. Effective single treatment ablative dosages (i.e., may require autologous bone marrow transplantation) of 131I-labeled antibodies range from between about 30 and about 600 mCi, and in an embodiment between about 50 and less than about 500 mCi. In conjunction with a chimeric modified antibody, owing to the longer circulating half-life vis-a-vis murine antibodies, an effective single treatment non-marrow ablative dosages of iodine-131 labeled chimeric antibodies range from between about 5 and about 40 mCi, and in an embodiment, less than about 30 mCi. Imaging criteria for, e.g., the 11In label, are typically less than about 5 mCi.

While a great deal of clinical experience has been gained with 131I and 90Y, other radiolabels are known in the art and have been used for similar purposes. Still other radioisotopes are used for imaging. For example, additional radioisotopes which are compatible with the scope of the instant invention include, but are not limited to, 123I, 125I, 32P, 57Co, 64Cu, 67Cu, 77Br, 81Rb, 81Kr, 87Sr, 113In, 127Cs, 129Cs, 1321, 197Hg, 203Pb, 206Bi, 177Lu, 186Re, 212Pb, 212Bi, 47Sc, 105Rh, 109Pd, 153Sm, 188Re, 199Au, 225Ac, 211A 213Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include 125I, 123I, 99Tc, 43K, 52Fe, 67Ga, 68Ga, as well as 11In. Antibodies have also been labeled with a variety of radionuclides for potential use in targeted immunotherapy (Peirersz et al. Immunol. Cell Biol. 65: 111, 1987). These radionuclides include 188Re and 186Re as well as 199Au and 67Cu to a lesser extent. U.S. Pat. No. 5,460,785 provides additional data regarding such radioisotopes and is incorporated herein by reference.

As previously discussed, the antibodies, or fragments thereof, disclosed herein, can be administered in a pharmaceutically effective amount for the in vivo treatment of mammalian disorders. In this regard, it will be appreciated that the disclosed antibodies, or fragments thereof, will be formulated so as to facilitate administration and promote stability of the active agent. and In certain embodiments, pharmaceutical compositions in accordance with the present invention comprise a pharmaceutically acceptable, nontoxic, sterile carrier such as physiological saline, non-toxic buffers, preservatives and the like. For the purposes of the instant application, a pharmaceutically effective amount of an antibody disclosed herein, conjugated or unconjugated to a therapeutic agent, shall be held to mean an amount sufficient to achieve effective binding to a target and to achieve a benefit, e.g., to ameliorate symptoms of a disease or disorder or to detect a substance or a cell. In the case of tumor cells, the polypeptide will in certain embodiments be capable of interacting with selected immunoreactive antigens on neoplastic or immunoreactive cells and provide for an increase in the death of those cells. Of course, the pharmaceutical compositions disclosed herein may be administered in single or multiple doses to provide for a pharmaceutically effective amount of the polypeptide.

In keeping with the scope of the present disclosure, the antibodies disclosed herein may be administered to a human or other animal in accordance with the aforementioned methods of treatment in an amount sufficient to produce a therapeutic or prophylactic effect. The polypeptides disclosed herein can be administered to such human or other animal in a conventional dosage form prepared by combining the antibody disclosed herein with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VI. Methods of Treating PAI-1-Associated Disease or Disorders

The anti-PAI-1 antibodies, or fragments thereof, disclosed herein are useful for antagonizing PAI-1 activity. Accordingly, in another aspect, the invention provides methods for treating PAI-1-associated diseases or disorders by administering to a subject in need of thereof a pharmaceutical composition comprising one or more anti-PAI-1 antibodies, or antigen binding fragments thereof disclosed herein.

PAI-1-associated diseases or disorders amenable to treatment include, without limitation, pathophysiologic conditions such as kidney, liver or lung fibrosis or prevention of abdominal adhesion formation.

The occurrence of intra-abdominal adhesions is a major cause of human illness. Complications of adhesions may be as serious as a life-threatening bowel obstruction, but chronic pelvic pain and infertility in women are also common sequelae to peritoneal adhesions. The majority of adhesions is induced by surgery but in some cases also has been shown to be caused by inflammation, endometriosis, chemical peritonitis, radiotherapy, foreign body reaction, and continuous ambulatory peritoneal dialysis. Peritoneal damage causes a local inflammatory response that leads to fibrin deposition. It is assumed that a posttraumatic insufficiency in peritoneal fibrinolytic activity, caused by a decrease in tissue plasminogen activator (tPA) and an increase in the plasminogen activator inhibitors PAI-1 and PAI-2, permits the deposited fibrin to become organized into permanent adhesions.

Currently available and effective treatment option like Seprafilm® has limitations for use only in the open access (laparotomy) and cannot be used in the laparoscopy. The search for potential treatment is ongoing.

In certain exemplary embodiments, antibodies disclosed herein may be issued to treat renal fibrosis and associated acute kidney injury as well as chronic kidney diseases which are the main causes of end-stage renal failure.

One skilled in the art would be able, by routine experimentation, to determine what an effective, non-toxic amount of antibody (or additional therapeutic agent) would be for the purpose of treating a PAI-1-associated disease or disorder. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and in an embodiment from about 0.5 to 10, milligrams per kilogram body weight per day.

The different aspects disclosed herein and their embodiments can be combined with each other. In addition, any of the aspects and their embodiments described above can be combined with any of the particular aspects and embodiments described herein below.

Some particular aspects and embodiments that further serve to illustrate the present invention are given in the following:

DESCRIPTION OF PARTICULAR ASPECTS AND EMBODIMENTS

Claim 1. An isolated monoclonal antibody that binds specifically to PAI-1, comprising:

(a) a heavy chain framework region and a heavy chain variable region, the heavy chain variable region comprising a heavy chain CDR1 region comprising SEQ ID NO: 34, a heavy chain CDR2 region comprising SEQ ID NO: 33, and a heavy chain CDR3 region comprising SEQ ID NO: 32; and (b) a light chain framework region and a light chain variable region, the light chain variable region comprising a light chain CDR1 region comprising SEQ ID NO: 37, a light chain CDR2 region comprising SEQ ID NO: 145, and a light chain CDR3 region comprising SEQ ID NO: 35.

Claim 2. An isolated monoclonal antibody that binds specifically to PAI-1 comprising:

(a) a heavy chain framework region and a heavy chain variable region comprising SEQ ID NO: 86, and (b) a light chain framework region and a light chain variable region comprising SEQ ID NO: 93.

Claim 3. An isolated monoclonal antibody that binds specifically to PAI-1 comprising:

(a) a heavy chain variable region that is at least 95% identical to the heavy chain variable region of the antibody of claim 2, and/or (b) a light chain variable region that is at least 95% identical to the light chain variable region of the antibody of claim 2.

Claim 4. An isolated monoclonal antibody that binds to essentially the same epitope as the antibody of claim 1.

Claim 5. An isolated monoclonal antibody that binds specifically to PAI-1, comprising:

(a) a heavy chain framework region and a heavy chain variable region, the heavy chain variable region comprising a heavy chain CDR1 region comprising SEQ ID NO: 34, a heavy chain CDR2 region comprising SEQ ID NO: 33, and a heavy chain CDR3 region comprising SEQ ID NO: 32; and (b) a light chain framework region and a light chain variable region, the light chain variable region comprising a light chain CDR1 region comprising SEQ ID NO: 37, a light chain CDR2 region comprising SEQ ID NO: 36, and a light chain CDR3 region comprising SEQ ID NO: 35.

Claim 6. The antibody of claim 5, wherein the heavy chain variable region comprises SEQ ID NO: 6, and the light chain variable region comprises SEQ ID NO: 7.

Claim 7. An isolated monoclonal antibody that binds to essentially the same epitope as the antibody of claim 5.

Claim 8. A humanized monoclonal antibody that binds specifically to human PAI-1, wherein the antibody comprises:

(a) a heavy chain having a heavy chain variable region comprising SEQ ID NO: 82, or an antigen-binding fragment thereof, and a light chain having a light chain variable region comprising SEQ ID NO: 91, or an antigen-binding fragment thereof;

(b) a heavy chain having a heavy chain variable region comprising SEQ ID NO: 83, or an antigen-binding fragment thereof, and a light chain having a light chain variable region comprising SEQ ID NO: 92, or an antigen-binding fragment thereof;

(c) a heavy chain having a heavy chain variable region comprising SEQ ID NO: 84, or an antigen-binding fragment thereof, and a light chain having a light chain variable region comprising SEQ ID NO: 93, or an antigen-binding fragment thereof;

(d) a heavy chain having a heavy chain variable region comprising SEQ ID NO: 85, or an antigen-binding fragment thereof, and a light chain having a light chain variable region comprising SEQ ID NO: 91, or an antigen-binding fragment thereof;

(e) a heavy chain having a heavy chain variable region comprising SEQ ID NO: 85, or an antigen-binding fragment thereof, and a light chain having a light chain variable region comprising SEQ ID NO: 93, or an antigen-binding fragment thereof;

(f) a heavy chain having a heavy chain variable region comprising SEQ ID NO: 86, or an antigen-binding fragment thereof, and a light chain having a light chain variable region comprising SEQ ID NO: 94, or an antigen-binding fragment thereof;

(g) a heavy chain having a heavy chain variable region comprising SEQ ID NO: 87, or an antigen-binding fragment thereof, and a light chain having a light chain variable region comprising SEQ ID NO: 95, or an antigen-binding fragment thereof;

(h) a heavy chain having a heavy chain variable region comprising SEQ ID NO: 88, or an antigen-binding fragment thereof, and a light chain having a light chain variable region comprising SEQ ID NO: 96, or an antigen-binding fragment thereof;

(i) a heavy chain having a heavy chain variable region comprising SEQ ID NO: 89, or an antigen-binding fragment thereof, and a light chain having a light chain variable region comprising SEQ ID NO: 97, or an antigen-binding fragment thereof;

(j) a heavy chain having a heavy chain variable region comprising SEQ ID NO: 90, or an antigen-binding fragment thereof, and a light chain having a light chain variable region comprising SEQ ID NO: 98, or an antigen-binding fragment thereof;

(l) a heavy chain having a heavy chain variable region comprising SEQ ID NO: 86, or an antigen-binding fragment thereof, and a light chain having a light chain variable region comprising SEQ ID NO: 95, or an antigen-binding fragment thereof;

(m) a heavy chain having a heavy chain variable region comprising SEQ ID NO: 89, or an antigen-binding fragment thereof, and a light chain having a light chain variable region comprising SEQ ID NO: 93, or an antigen-binding fragment thereof; or (n) a heavy chain having a heavy chain variable region comprising SEQ ID NO: 89, or an antigen-binding fragment thereof, and a light chain having a light chain variable region comprising SEQ ID NO: 95, or an antigen-binding fragment thereof.

Claim 9. An isolated monoclonal antibody that binds specifically to PAI-1, comprising (a) a heavy chain variable region comprising a heavy chain CDR1 region comprising SEQ ID NO: 22, a heavy chain CDR2 region comprising SEQ ID NO: 21, and a heavy chain CDR3 region comprising SEQ ID NO: 20; and a light chain variable region comprising a light chain CDR1 region comprising SEQ ID NO: 25, a light chain CDR2 region comprising SEQ ID NO: 24, and a light chain CDR3 region comprising SEQ ID NO: 23, (b) a heavy chain variable region comprising a heavy chain CDR1 region comprising SEQ ID NO: 28, a heavy chain CDR2 region comprising SEQ ID NO: 27, and a heavy chain CDR3 region comprising SEQ ID NO: 26; and a light chain variable region comprising a light chain CDR1 region comprising SEQ ID NO: 31, a light chain CDR2 region comprising SEQ ID NO: 30, and a light chain CDR3 region comprising SEQ ID NO: 29, (c) a heavy chain variable region comprising a heavy chain CDR1 region comprising SEQ ID NO: 40, a heavy chain CDR2 region comprising SEQ ID NO: 39, and a heavy chain CDR3 region comprising SEQ ID NO: 38; and a light chain variable region comprising a light chain CDR1 region comprising SEQ ID NO: 43, a light chain CDR2 region comprising SEQ ID NO: 42, and a light chain CDR3 region comprising SEQ ID NO: 41, (d) a heavy chain variable region comprising a heavy chain CDR1 region comprising SEQ ID NO: 46, a heavy chain CDR2 region comprising SEQ ID NO: 45, and a heavy chain CDR3 region comprising SEQ ID NO: 44; and a light chain variable region comprising a light chain CDR1 region comprising SEQ ID NO: 49, a light chain CDR2 region comprising SEQ ID NO: 48, and a light chain CDR3 region comprising SEQ ID NO: 47, (e) a heavy chain variable region comprising a heavy chain CDR1 region comprising SEQ ID NO: 52, a heavy chain CDR2 region comprising SEQ ID NO: 51, and a heavy chain CDR3 region comprising SEQ ID NO: 50; and a light chain variable region comprising a light chain CDR1 region comprising SEQ ID NO: 55, a light chain CDR2 region comprising SEQ ID NO: 54, and a light chain CDR3 region comprising SEQ ID NO: 53, (f) a heavy chain variable region comprising a heavy chain CDR1 region comprising SEQ ID NO: 58, a heavy chain CDR2 region comprising SEQ ID NO: 57, and heavy chain CDR3 region comprising SEQ ID NO: 56; and a light chain variable region comprising a light chain CDR1 region comprising SEQ ID NO: 61, a light chain CDR2 region comprising SEQ ID NO: 60, and a light chain CDR3 region comprising SEQ ID NO: 59, (g) a heavy chain variable region comprising a heavy chain CDR1 region comprising SEQ ID NO: 64, a heavy chain CDR2 region comprising SEQ ID NO: 63, and a heavy chain CDR3 region comprising SEQ ID NO: 62; and a light chain variable region comprising a light chain CDR1 region comprising SEQ ID NO: 67, a light chain CDR2 region comprising SEQ ID NO: 66, and a light chain CDR3 region comprising SEQ ID NO: 65, (h) a heavy chain variable region comprising a heavy chain CDR1 region comprising SEQ ID NO: 70, a heavy chain CDR2 region comprising SEQ ID NO: 69, and a heavy chain CDR3 region comprising SEQ ID NO: 68; and a light chain variable region comprising a light chain CDR1 region comprising SEQ ID NO: 73, a light chain CDR2 region comprising SEQ ID NO: 72, and a light chain CDR3 region comprising SEQ ID NO: 71; or (i) a heavy chain variable region comprising a heavy chain CDR1 region comprising SEQ ID NO: 76, heavy chain CDR2 region comprising SEQ ID NO: 75, and a heavy chain CDR3 region comprising SEQ ID NO: 74; and a light chain variable region comprising a light chain CDR1 region comprising SEQ ID NO: 79, a light chain CDR2 region comprising SEQ ID NO: 78, and a light chain CDR3 region comprising SEQ ID NO: 77.

Claim 10. An isolated monoclonal antibody that binds specifically to PAI-1, that binds to essentially the same epitope on PAI-1 as the humanized monoclonal antibody of claim 8 or claim 9.

Claim 11. A method of restoring plasmin generation comprising administering to a subject in need thereof orally, parenterally by a solution for injection, by inhalation, or topically a pharmaceutically effective amount of a PAI-1 antibody.

Claim 12. The method of claim 11, wherein the method treats a condition comprising increased levels of fibrotic tissue.

Claim 13. The method of claim 12, wherein the condition is fibrosis, skin fibrosis, systemic sclerosis, lung fibrosis, idiopathic pulmonary fibrosis, interstitial lung disease, chronic lung disease, liver fibrosis, kidney fibrosis, chronic kidney disease, thrombosis, venous and arterial thrombosis, deep vein thrombosis, peripheral limb ischemia, disseminated intravascular coagulation thrombosis, acute ischemic stroke with and without thrombolysis, or stent restenosis.

Claim 14. The method of claim 11, 12, or 13 wherein the PAI-1 antibody comprises the antibody of any of the preceding claims.

Claim 15. Use of a pharmaceutically effective amount of a PAI-1 antibody for the manufacture of a medicament for treating a condition caused by increased levels of PAI-1 or increased sensitivity to PAI-1, comprising administering to a patient orally, parenterally by a solution for injection, by inhalation, or topically.

EXAMPLES

The present invention is further illustrated by the following examples which should not be construed as further limiting. The contents of Sequence Listing, Figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Example 1: Hybridoma Generation: Immunization of Mice with PAI-1 Protein and Antibody Generation Antibodies were developed that would be cross-reactive to human (h) and cynomolgus (cyno) monkey active PAI-1 (glycosylated or non-glycosylated form) and that would neutralize the inhibitory activity of PAI-1 and restore downstream production of plasmin thereby being an effective therapeutic for treatment of kidney, liver or lung fibrosis or prevention of abdominal adhesion formation and keloid scar formation. Neutralization of PAI-1 inhibitory function by monoclonal antibodies has been described to fall under three mechanisms: (1) blocking PAI-1 to tPA or uPA by steric hindrance, (2) converting PAI-1 into a latent conformation, or (3) converting PAI-1 into a substrate conformation.

a) Antigens

PAI-1 is secreted from the cells in an active conformation stabilized by its binding with subnanomolar affinity to vitronectin. PAI-1 undergoes spontaneous conformational change from active conformation into a latent conformation within minutes at 37° C. and within hours at room temperature. Once bound to vitronectin, PAI-1 becomes more resistant to the conformational change which prolongs the half-life of PAI-1 in active conformation from minutes to hours. To extend active conformation PAI-1 half-life in the immunized animals and to allow the mouse immune system to recognize the active PAI-1 conformation, a complex of vitronectin and PAI-1 was used for immunizations.

Human glycosylated PAI-1 produced in insect cells was purchased from Innovative Research (Cat #IGLYHPAI-A). Vitronectin (Cat #IHVN) and tPA (Cat #HTPA-TC) were also purchased from Innovative Research. To produce immunogens PAI-1 was incubated with vitronectin at a 1:1 molar ratio for 1 hour at room temperature, or with tPA at a 1:1 molar ratio for 15 minutes at 37° C. All immunogens were prepared using sterile saline as diluent.

b) Immunizations

Standard hybridoma production protocols known in the art were implemented to produce antibodies. Standard approaches previously described in the literature used PAI-1 only or PAI-1/tPA complex. The inventors instead generated antibodies against the active conformation of PAI-1. PAI-1/vitronectin complex was used as a novel approach to generating antibodies to PAI-1. A three-prong strategy, outlined below, was taken to generate antibodies:

(1) Classical immunization of mice with PAI-1/vitronectin complex to obtain mouse splenocytes for fusion with mouse myeloma cell line as a fusion partner to produce hybridoma;

(2) Classical immunization of mice with PAI-1/tPA complex to obtain mouse splenocytes for fusion with mouse myeloma cell line as a fusion partner to produce hybridoma; and (3) Classical immunization of mice with PAI-1 only to obtain mouse splenocytes for fusion with mouse myeloma cell line as a fusion partner to produce hybridoma.

Three mice per antigen (PAI-1 only, Vn/PAI-1 complex, tPA/PAI-1 complex) were used in the study. The mice were 9-20 week-old naïve female BALB/c Mice (Charles River, strain code 028). On day 0, nine mice were immunized intraperitoneally with PAI-1 alone, Vn/PAI-1 or tPA/PAI-1 complexes in phosphate-buffered saline (PBS). A total of 10 ug of antigen per mouse was mixed at 1:1 volume to volume ratio of Sigma Adjuvant System (Sigma cat #6322) in a total volume of 200 µl per mouse. On day 14, mice were boosted with the same amount of antigen and prepared the same way as on day 0. On day 21, blood samples were collected for PAI-1 specific antibody titer evaluation. Mice immunized with PAI-1/tPA complexes showed very low specific reactivity against PAI-1and high anti-tPA titers and were not used for downstream fusions.

On day 51, the mouse with the highest anti-PAI-1 specific antibody titer and the lowest titer against the protein that PAI-1 was complexed to (i.e., either Vn or tPA) while those having the highest titer against mouse and rat PAI-1 orthologs were selected for fusion. The mice selected for fusion were boosted with PAI-1 only or PAI-1/Vn complex in PBS as an antigen total of 10 ug per mouse mixed at 1:1 ratio of Sigma Adjuvant System (Sigma cat #6322) in a total volume of 200 µl per mouse as described above. At day 55 mice were sacrificed by $CO_2$ chamber, blood was collected through the cardiac puncture and spleen was harvested for hybridoma production. The other four mice underwent the same procedure at later times (2-4 months after the first mouse was used for fusion).

Serum titrations were performed on three mice for PAI-1 only and PAI-1/tPA and two mice for PAI-1/Vn using the ELISA protocol described in Example 2 (Binding ELISA).

TABLE 3

| Serum Titers for Mouse Immunized with PAI-1, PAI-1/Vn or PAI-1/tPA | | | | |
|---|---|---|---|---|
| | | Serum Titer Against PAI-1 ($OD_{405}$) | | |
| Immunogen | Mouse # | OD 1:100 | OD 1:1000 | OD 1:10000 |
| PAI-1 | 1 | 2.1 | 1.9 | 1 |
| PAI-1 | 2 | 2.1 | 1.4 | 1 |
| PAI-1 | 3 | 2.0 | 1.4 | 1 |
| PAI-1/Vn | 2 | 2.15 | 1.5 | 1 |
| PAI-1/Vn | 3 | 1.7 | 1.25 | 1 |
| PAI-1/tPA | 1 | 1.2 | 0.8 | 0.3 |
| PAI-1/tPA | 2 | 1.3 | 0.9 | 0.7 |
| PAI-1/tPA | 3 | 1.3 | 0.9 | 0.5 |
| NMS | n/a | 0.4 | 0.12 | 0.07 |

NMS = normal mouse serum;
n/a = not applicable
$OD_{405}$ using BioTek Synergy HT instrument The mice immunized with PAI-1/tPA complex did not reach high specific titer criteria and were not used for fusions (Table 3). Based on the serum titers presented in Table 3, a total of 5 mice with high specific titer against PAI-1 were selected for fusions.

b) Fusions

The five mice having the highest specific titer against PAI-1 were selected for fusions. On the day of the fusion, the mice were sacrificed in a $CO_2$ chamber, blood was collected through cardiac puncture and the spleens removed and placed into a Petri dish containing 10 ml of serum free Hybridoma Fusion Medium (IMDM; Iscove's Modified Dulbecco's Medium 500 ml (HyClone SH30259.01). Splenocytes were squeezed out of the fibroelastic coat by forceps and washed twice in 10 ml of serum free IMDM (including initial spin).

Cells were counted in a Countess Automated Cell Counter. Fusion partner cells (myeloma: FO (ATCC ref CRL- 1646)) and splenocytes were then combined in one 50 ml tube at ratio of 1:2 to 1:10 (by cell number) and spun down at 970 rpm for 10 min (slow spin) to form a loose pellet. Preheated (at 37° C.) 1 ml PEG (PEG 1500 in 75 mM Hepes 50% w/v, Roche cat #783641 (10783641001) was added drop by drop to the cell pellet over 1 minute period of time and cells were mixed after every drop of PEG was added. The pellet was incubated with PEG for another 1 minute followed by addition of 10 ml of serum-free IMDM medium over 1 minute, such that the first 1 ml out of 10 is added over 30 sec. Cells underwent slow spin at 970 rpm for 10 min to preserve viability. Fused cells were plated in 96-well plates at 200 ul in selection medium (200 ml Gibco Hybridoma (SFM #12045), 20 ml 10% HyClone SuperLow IgG Defined FBS (#SH30898.03), 2 ml penicillin/streptomycin, 4 ml (Hybridoma Fusion and Cloning Supplement (Roche Diagnostics 11 363 735 001 (50×)) and 4 ml of HAT (hypoxanthine-aminopterin-thymidine) (Sigma-Aldrich #H0262 (50×)). Fusions were ready for screening about 10 to 14 days later, or when medium in the wells turned yellow. Supernatants from the developed hybridomas were then tested by ELISA (Example 2) for the presence of antibodies binding to PAI-1 and PAI-1/Vn complexes.

Example 2: Binding ELISA for Hybridoma Supernatant Screening for Specificity to PAI-1-Vitronectin Complex Each fusion from the spleens of the five mice selected resulted in about 5000 clones that needed to be screened for binding to PAI-1/Vn complex as a first-step primary screen. Primary screening of the hybridoma supernatants was performed in parallel using ELISA against either PAI-1 or PAI-1-Vitronectin complexes to select hybridomas binding specifically to PAI-1 complexed to Vitronectin. The materials used for the ELISA were the following: Immulon 4 HBX ELISA plates (Dynax cat #N0541216); human monomeric Vitronectin at 5 ug/ml (Innovative Research cat #IHVN); glycosylated human PAI-1 (active form) (Molecular Innovations cat #GLYHPAI-A); non-glycosylated mouse PAI-1 in some fusions (Molecular Innovations cat #MPAI-A); a secondary antibody that was HRP-goat anti-mouse IgG (H+L) (Jackson ImmunoResearch Labs #115-035-166); and, ABTS substrate: Roche Diagnostics (#11 204 521 001). Control antibodies used were:

a) 33B8, a mouse monoclonal inhibitory antibody against PAI-1 (IgG1; Innovative Research cat #IMA-33B8);
b) 33H1, a mouse monoclonal inhibitory antibody against PAI-1 (IgG1; Innovative Research cat #IMA-33H1);
c) 31C9, a mouse monoclonal non-inhibitory antibody against PAI-1 (IgG1; Innovative Research cat #IMA-31C9); and
d) 1B7.11, a IgG1 isotype control antibody (anti-TNP mAb—produced in-house from hybridoma cell line purchased from ATCC (Cat #TIB-191)

The ELISA method was as follows: plates coated with 5 ug/ml Vn in PBS overnight at 4° C. at 50 ul/well; the next day plates were blocked 1 hour with 200 ul 1% bovine serum albumin in PBS (BSA/PBS); plates were washed four times with 200 ul/well PBS; active PAI-1 at 2 ug/ml in 1% BSA/PBS was added to the plates at 50 ul/well and incubated 1 hour; plates were washed four times with 200 ul/well PBS; antibody dilutions in 1% BSA/PBS or hybridoma supernatants from the original 96-well plates were added to ELISA plates at 50 ul/well; plates were incubated 1 hour at room temperature (RT); plates were washed four times with 200 ul/well PBS; HRP-anti-mouse IgG 50 ul 1:2000 in 1%

Figure 2:
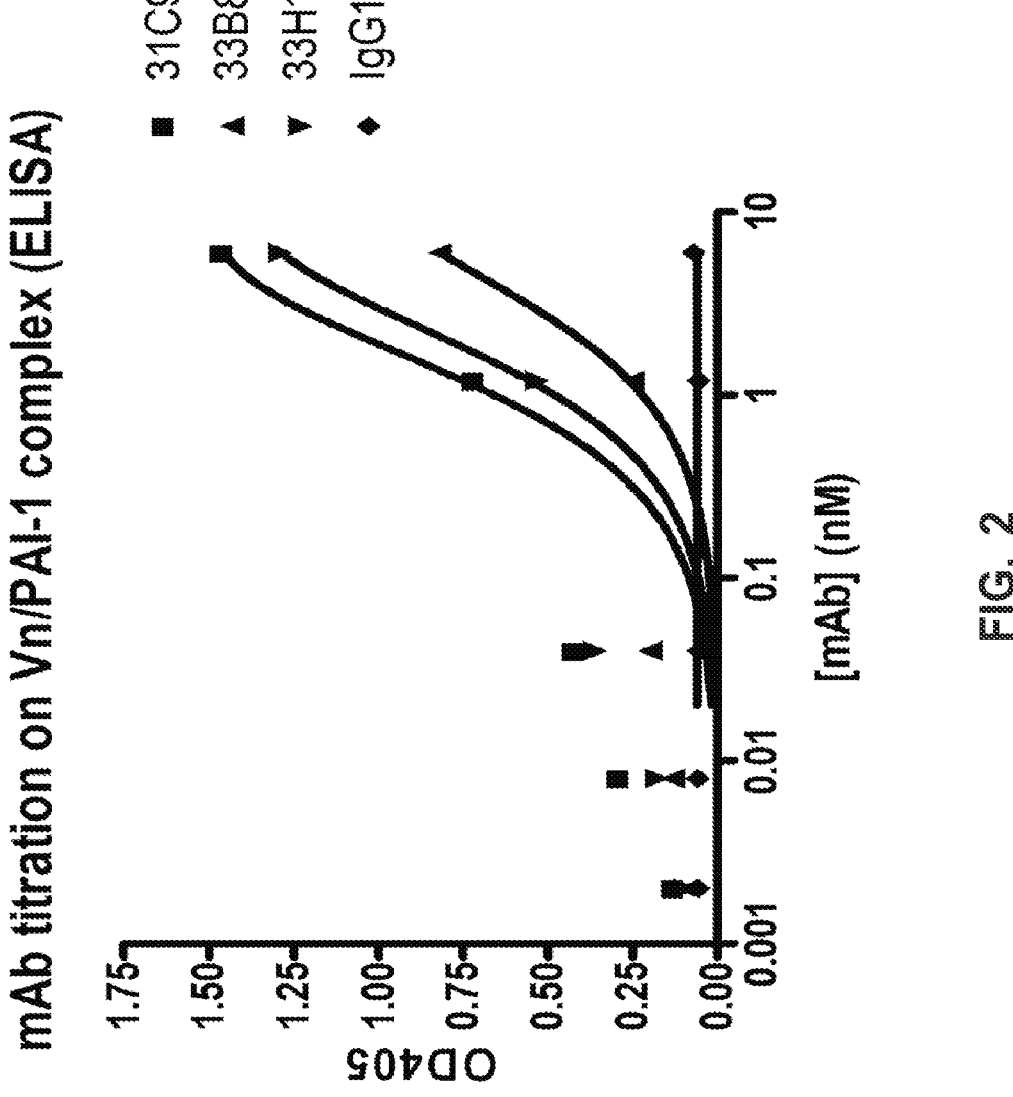
FIG. 2 depicts a typical standard curve for antibody titration in the binding ELISA as described in Example 2. The antibodies 31C9, 33B8 and 33H1 were positive controls and IgG1 was as a negative control.

BSA/PBS was added and incubated 1 hour at room temperature; plates were washed four times with 200 ul/well PBS; ABTS substrate (one pill dissolved in 5 ml) at 50 ul/well was added to the plates) and then plates were read on BioTek Synergy HT instrument using $OD_{405}$. A typical standard curve for antibody titration in the binding ELISA is shown in FIG. 2. The antibodies 31C9, 33B8 and 33H1 served as positive controls and IgG1 served as a negative control. Table 4 shows that of the about 5000 clones generated, 675 clones were positive for binding to both PAI-1 and PAI-1/Vn. These clones were then screened for PAI-1 affinity.

TABLE 4

Number of Clones Positive for Binding to Both PAI-1 and PAI-1/Vn

| Fusion | Immunogen | Mouse # | # of Clones Positive for Binding to Both PAI-1 and PAI-1/Vn |
|---|---|---|---|
| A | PAI-1/Vn | 2 | 131 |
| B | PAI-1 | 2 | 146 |
| C | PAI-1/Vn | 3 | 145 |
| D | PAI-1 | 3 | 104 |
| E | PAI-1 | 1 | 149 |

Example 3: Biacore Screening of Hybridoma Supernatants by Affinity Ranking

Further selection of a high affinity antibody with low off-rate was performed by Biacore. Biacore hybridoma supernatant screening was performed either by: (1) reverse screening using anti-mouse immobilized anti-PAI-1 antibodies or (2) forward screening assay using free PAI-1 as a ligand or against immobilized Vn.

The instruments used were the BIACORE 2000 or BIACORE 3000 (GE Healthcare), designed for biomolecular interaction analysis (BIA) in real time. The sensor chip used was the CM5 chip (GE Healthcare) with carboxymethylated dextran matrix on the surface. Each sensor chip has four parallel flow cells (Fc). Every flow cell was coupled with anti-mouse IgG Fc mAb via standard amine coupling according to the manufacture's protocol for chip preparation.

In the Biacore reverse screening assay, ELISA positive hybridoma supernatants were selected and filtered through 0.2 μm filters before being injected onto Biacore chip surface. Each hybridoma supernatant was injected onto one flow cell of flow cells Fc2-Fc4 and the IgG in the hybridoma supernatant would be captured to the chip surface by anti-mouse IgG Fc mAb, while Fc1 was left alone as reference cells. Human PAI-1 protein in PBS was then injected to Fc1 to Fc4. PBS buffer was also injected over the chip surface as a blank. After subtracting signals of Fc1 and blank buffer runs, the binding affinity (KD)/disassociation rate (kd) of the antibody from the supernatants to PAI-1 protein was analyzed and ranked using Scrubber 2 software.

In the Biacore forward screening assay, purified human vitronectin protein was immobilized to CM5 chip flow cells Fc1 to Fc4. Human or cyno PAI-1 were captured onto all flow cells. Filtered selected hybridoma supernatants then were injected over captured PAI-1 one per flow cell, except Fc1 which was reserved as the reference flow cell. PBS buffer was also injected over the chip surface as a blank. After subtracting signals of Fc1 and blank buffer runs, binding affinity of antibody in hybridoma supernatant to the vitronectin captured PAI-1 was analyzed and ranked using Scrubber 2 software (version 2.0a, 2005; BioLogic Software, BioLogic Software Rty Ltd., 116 Blamey Court, Campbell, ACT 2612 Australia).

Table 5 shows a selection of positive and negative antibody clones from the fusions A, B, C, D and E. Not all data was shown because of the large number of antibody clones that were screened. Only the antibody clones that demonstrated superior (kd<$10^{-4}$ 1/s) binding dissociation rate against human and cyno PAI-1 proteins were selected for the functional chromogenic assay.

TABLE 5

Hybridoma Supernatant Binding to Human PAI-1 Affinity/Off Rate Screening in Biacore Assay

| | Binding to hPAI-1 | | | | Binding to hPAI-1 | | |
|---|---|---|---|---|---|---|---|
| CLONE | Binding | Off-rate <= $10^{-4}$ | cyno PAI-1 | CLONE | Binding | Off-rate <= $10^{-4}$ | cyno PAI-1 |
| A9 | ND | ND | ND | C26 | + | − | − |
| A20 | + | − | − | C45 | + | + | +/− |
| A37 | + | − | − | C46 | + | + | + |
| A39 | + | + | − | C49 | + | +/− | ND |
| A41 | ND | ND | ND | C61 | + | +/− | +/− |
| A44 | + | + | + | C66 | + | − | − |
| A47 | + | + | + | C69 | + | + | +/− |
| A52 | ND | ND | ND | C76 | ND | ND | ND |
| A71 | + | + | + | C79 | + | − | − |
| A75 | + | +/− | +/− | C85 | ND | ND | ND |
| A83 | + | +/− | − | C109 | + | − | − |
| A89 | + | +/− | − | C118 | + | +/− | ND |
| A93 | + | +/− | − | C134 | ND | ND | ND |
| A98 | + | − | − | C145 | + | − | +/− |
| A99 | + | + | +/− | D4 | − | − | − |
| A105 | + | + | + | D12 | + | − | − |
| A107 | + | − | − | D13 | − | − | ND |
| A113 | + | + | + | D15 | − | − | ND |
| A119 | + | +/− | +/− | D31 | + | − | − |
| B16 | ND | ND | ND | D33 | + | +/− | − |
| B18 | + | − | − | D37 | + | − | − |
| B28 | + | + | − | D48 | + | + | +/− |
| B29 | + | − | − | D52 | + | + | + |
| B32 | + | + | + | E4 | + | + | − |
| B58 | + | + | − | E5 | + | + | − |
| B85 | ND | ND | ND | E11 | + | + | − |
| B89 | + | + | +/− | E16 | + | + | +/− |
| B99 | + | − | +/− | E20 | + | ND | ND |
| B105 | + | + | +/− | E21 | + | + | − |
| B109 | + | + | + | | | | |
| B118 | ND | ND | ND | | | | |

"+" = represents positive binding to h/cPAI-1 or an off-rate of less than or equal to $10^{-4}$
"+/−" = represents partial binding to h/cPAI-1 or an off-rate slightly higher than to $10^{-4}$
"−" = represents low or no binding to h/cPAI-1 or an off-rate higher than to $10^{-4}$
ND = not determined Example 4: Functional ELISA for Hybridoma Supernatant Screening to Select for Antibodies that Block the Interaction of PAI-1 with tPA To allow for selection of functional antibodies, a novel ELISA was developed to allow distinguishing between antibodies that only bind to PAI-1 versus those antibodies that blocked PAI-1's function as tPA inhibitor (functional ELISA).

Hybridoma supernatants were screened in a novel functional ELISA to identify hybridoma supernatant from different clones having the ability to block tPA-PAI-1 interaction. The design of the functional ELISA is as follows: (1) if the antibody binds to PAI-1 but the antibody binding does not block formation of the covalent bond between PAI-1 and tPA, the anti-tPA antibody will bind to the tPA that is bound to the plate through PAI-1 and gives a positive readout; (2) if the antibody blocks PAI-1 and thereby blocks the tPA interaction by either changing PAI-1 confirmation or by steric hindrance, the anti-tPA antibody will not be able to bind to the plate and readout will be negative (lower $OD_{405}$). In parallel, hybridoma supernatants were tested for binding to PAI-1 in the ELISA described in Example 2. Since the amount of antibody in the hybridoma supernatant is unknown, a lower than control reading (i.e., below the isotype control reading) was considered to be identifying an antibody of interest. Due to the variable antibody concentration in the supernatant, blocking in some cases was only partial.

Streptavidin coated plates (NUNC #436014) were incubated for 2 hours at RT with 2 ug/ml biotin-PAI-1 (human PAI-1 having N-terminal biotin labelled, active fraction; Molecular Innovations cat #NTBIOPAI-A) in 1% BSA/PBS at 50 ul/ml. Plates were blocked 1 hour with 200 ul 1% BSA/PBS at RT and washed four times with 200 ul/well PBS. Purified antibody dilutions and hybridoma supernatants were added to wells at 50 ul/well and incubated for 15 minutes. Plates were washed four times with 200 ul/well PBS. Two-chain tPA (Innovative Research cat #HTPA-TC) at 1 ug/ml was added to the plates at 50 ul/well and incubated for 30 minutes at RT. Plates were washed four times with 200 ul/well PBS. Anti-tPA HRP conjugated antibody (Life Span Technologies, cat #LS-C39721) at 1:3000 dilution were added to the plates and incubated for 45 minutes. Plates were washed four times with 200 ul/well PBS. ABTS substrate (one Tablet dissolved in 5 ml; Roche Diagnostics #11 204 521 001) at 50 ul/well was added to the plates and time allowed for color to develop. Plates were read on BioTek Synergy HT instrument using $OD_{405}$. ODs with the values that are lower than IgG isotype control indicate blocking of tPA binding to PAI-1.

Figure 3:
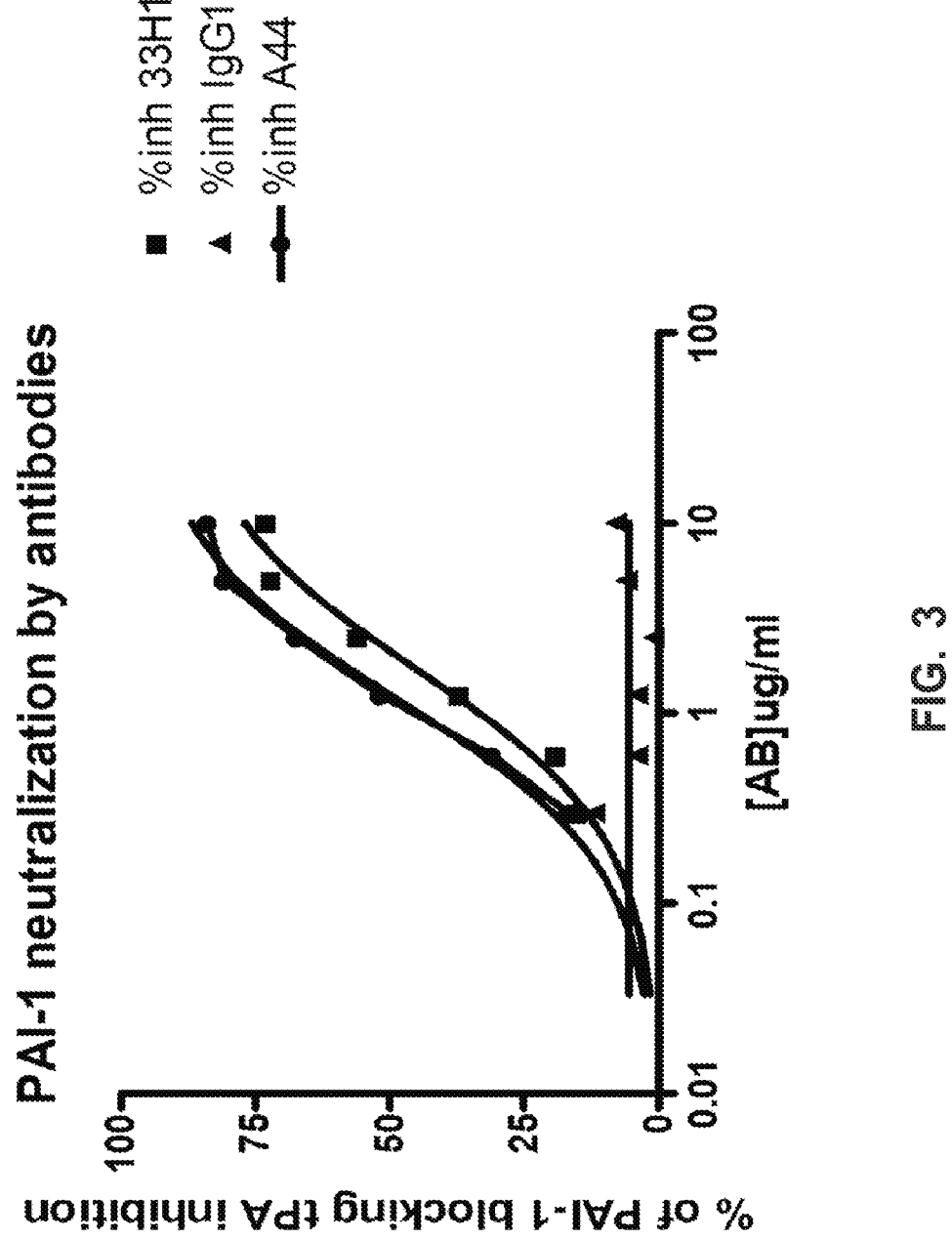
FIG. 3 depicts a representation curve for a functional ELISA to select antibodies that block the interaction of PAI-1 with tPA as described in Example 4. The antibody 33H1 is a positive control, IgG1 is a negative control and A44 was identified as a positive antibody clone.

In some cases functional ELISA was performed prior to Biacore supernatant screening and served as a selection step that was more important for hybridoma development. A representation curve with 33H1 as positive control, IgG1 as negative control and A44 as an identified positive antibody clone is shown in FIG. 3.

TABLE 6

Functional ELISA for Hybridoma Supernatant Screening to Select for Antibodies that Block the Interaction of PAI-1 with tPA

| CLONE | PAI-1 ELISA | tPA/PAI-1 Binding Inhibition | Selected | CLONE | PAI-1 ELISA | tPA/PAI-1 Binding Inhibition | Selected |
|---|---|---|---|---|---|---|---|
| A9 | + | − | no | C26 | + | + | yes |
| A20 | + | − | no | C45 | + | + | yes |
| A37 | + | + | yes | C46 | + | − | no |
| A39 | + | +/− | yes | C49 | + | − | no |

TABLE 6-continued

Functional ELISA for Hybridoma Supernatant Screening to Select for Antibodies that
Block the Interaction of PAI-1 with tPA

| CLONE | PAI-1 ELISA | tPA/PAI-1 Binding Inhibition | Selected | CLONE | PAI-1 ELISA | tPA/PAI-1 Binding Inhibition | Selected |
|-------|-------------|------------------------------|----------|-------|-------------|------------------------------|----------|
| A41 | + | + | yes | C61 | + | + | yes |
| A44 | + | + | yes | C66 | + | + | yes |
| A47 | + | + | yes | C69 | + | + | yes |
| A52 | + | - | no | C76 | + | − | no |
| A71 | + | + | yes | C79 | + | + | yes |
| A73 | + | - | no | C85 | + | − | no |
| A75 | + | + | yes | C109 | + | + | yes |
| A83 | + | + | yes | C118 | + | + | yes |
| A89 | + | + | yes | C134 | + | − | no |
| A93 | + | − | no | C145 | + | + | yes |
| A98 | + | + | yes | D4 | + | − | no |
| A99 | + | − | no | D12 | + | + | yes |
| A105 | + | + | yes | D13 | + | + | yes |
| A107 | + | + | yes | D15 | + | + | yes |
| A113 | + | + | yes | D31 | + | + | yes |
| A119 | + | + | yes | D33 | + | + | yes |
| B16 | + | − | no | D37 | + | + | yes |
| B18 | + | + | yes | D44 | + | + | yes |
| B28 | + | +/− | yes | D47 | + | + | yes |
| B29 | + | + | yes | D48 | + | + | yes |
| B32 | + | + | yes | D52 | + | + | yes |
| B58 | + | + | yes | D55 | + | + | yes |
| B85 | + | − | no | E4 | + | − | no |
| B89 | + | + | yes | E5 | + | − | no |
| B99 | + | + | yes | E11 | + | + | yes |
| B105 | + | + | yes | E16 | + | + | yes |
| B109 | + | + | yes | E20 | + | − | no |
| B118 | + | + | yes | E21 | + | + | yes |

PAI-1 ELISA = a "+" represents binding to PAI-1 (see Example 2)
tPA/PAI-1 Binding Inhibition = a "+" score represents the interaction of tPA with PAI-1 is inhibited;
+/− = partial inhibition of the interaction of tPA with PAI-1

Over 200 supernatants were screened. Table 6 shows a selection of positive and negative hybridoma supernatants. About 10 hybridomas per fusion showed ability to block PAI-1 from binding to tPA in functional ELISA. Based on the data from the hybridoma supernatants, hybridomas were selected for sequencing and medium scale antibody production. Even though D4 did not bind well to non-glycosylated PAI-1, it was selected for purification and sequencing based on its Biacore binding to glycosylated PAI-1. The purified antibodies were further characterized in Biacore for affinity kinetics, and in chromogenic and cellular assays for potency in comparison to the commercially available antibodies.

Example 5: Sequencing by 5'-RACE (Rapid Amplification of cDNA Ends) and Mouse Antibody Purification Antibodies for a specific target generated from a series of fusions could have the same sequences. By performing antibody gene sequencing at an early stage of antibody generation, any possibly redundant antibodies were eliminated and the correct antibody gene sequences guided antibody selection and humanization as well as chimeric antibody construction.

5'-RACE is a procedure for amplification of nucleic acid sequences from a messenger RNA template between a defined internal site and unknown sequences at the 3' or the 5' end of the mRNA. This methodology of amplification with single-sided specificity has been described as "one-sided" PCR or "anchored" PCR. The original variable murine anti-human PAI-1 antibody sequence of the lead antibody was determined by 5'-RACE cDNA sequencing and confirmed by N-terminal protein sequencing.

To determine variable heavy (VH) and light chain (VL) IgG sequences, total RNA from hybridoma cells was isolated using RNeasy Mini Kit (QIAGEN, Cat No. 74104) according to the manufacturer's instructions. Briefly, cells (5×106 cells) were lysed in 350 ul of the kit's RLT buffer followed by capturing total RNAs on spin column. RNA was eluted in the kit's TE buffer and stored on ice.

First-strand cDNA was prepared using SMARTer™ RACE cDNA Amplification Kit (ClonTech, Cat No. 634923). The 5'-RACE protocol was performed according to the manufacturer's instructions. VH and VL chain cDNAs were separately amplified by polymerase chain reaction (PCR) using the 5'-primers supplied with the SMARTer™ kit and the 3' VH and VL gene specific primers listed below:

```
                                   (SEQ ID NO: 105)
    Heavy Chain 3'- Primer:
    5'-TATGCAAGGCTTACAACCACA-3'

(SEQ ID NO: 106)
    Light Chain 3'- Primer:
    5'-CTCATTCCTGTTGAAGCTCTTGAG-3'
```

The amplified VH and VL genes were separately cloned into TOPO vector using TOPO TA cloning Kit (Invitrogen, Cat No. K4520-01). The procedures were performed according to the manufacturer's instructions. To transform bacteria, reaction mixtures were added into competent E. coli cells and incubated on ice for 20 minutes. The tubes, which contained the E. coli cells and the reaction mixture, were heated at 42° C. for 40 seconds and added 250 microliters of lit's SOC medium. After incubating the E. coli at 37° C. for 60 minutes with shaking at 300 rpm, the bacteria were spread on LB agar plate containing 100 micrograms per ml of ampicillin followed by incubating at 37° C., overnight.

Upon confirmation of the inserted VH and VL gene by PCR, five bacteria clones were selected and propagated in LB broth containing 100 micrograms per ml of ampicillin for plasmid DNA preparation. The plasmid DNAs were isolated using QIAprep Spin Miniprep Kit (QIAGEN, Cat No. 27104) according to manufacturer's instructions. The VH and VL IgG genes of hybridomas were sequenced by the Sanger method and the CDRs were determined using the Contact definition (MacCallum et al.).

Monoclonal antibodies were produced in CELLine biore-actor flasks (Wilson Wolf Manufacturing Corp.; Cat. #CL350 or Cat #CL1000) according to the manufacturer's instructions in serum-free medium (Gibco Cat. #12045) and purified by Protein A/G chromatography (GE Healthcare Life Sciences, Cat. #28-4083-47 and #28-4082-53). Purified antibodies were further characterized in Biacore for affinity kinetics, and in chromogenic and cellular assays for potency in comparison to the commercially available antibodies.

Example 6: Functional Chromogenic Assay Using Purified Antibody

Purified antibodies were tested in a chromogenic assay for the ability to block PAI-1. PAI-1 inhibits tPA function, therefore, antibodies that block PAI-1 will result in restoring tPA function. Chromogenic assays utilize proteolytic enzymes that act on their natural substrates (proteins and peptides) by hydrolyzing one or more peptide bond(s). This process is usually highly specific in the sense that only peptide bonds adjacent to certain amino acids are cleaved. Chromogenic substrates are peptides that react with prote-olytic enzymes resulting in the formation of color which is quantifiable. Chromogenic substrates are made synthetically and are designed to possess selectivity similar to that of the natural substrate for the enzyme. Attached to the peptide part of the chromogenic substrate is a chemical group which when released after the enzyme cleavage gives rise to color. The color change can be followed spectrophotometrically and is proportional to the proteolytic activity.

A chromogenic assay was used to confirm the ability of the antibody to neutralize PAI-1 function as a tPA inhibitor. tPA is able to release pNA from the chromogenic substrate S2288. S228 in solution has no color, but after being exposed to tPA and subsequent release of pNA, the solution develops a yellow color that can be read at $OD_{405}$. Color formation can be observed over 2-3 hours to determine kinetics of the enzymatic reaction. PAI-1 is able to block the enzymatic activity of tPA in a concentration dependent manner.

Figure 4:
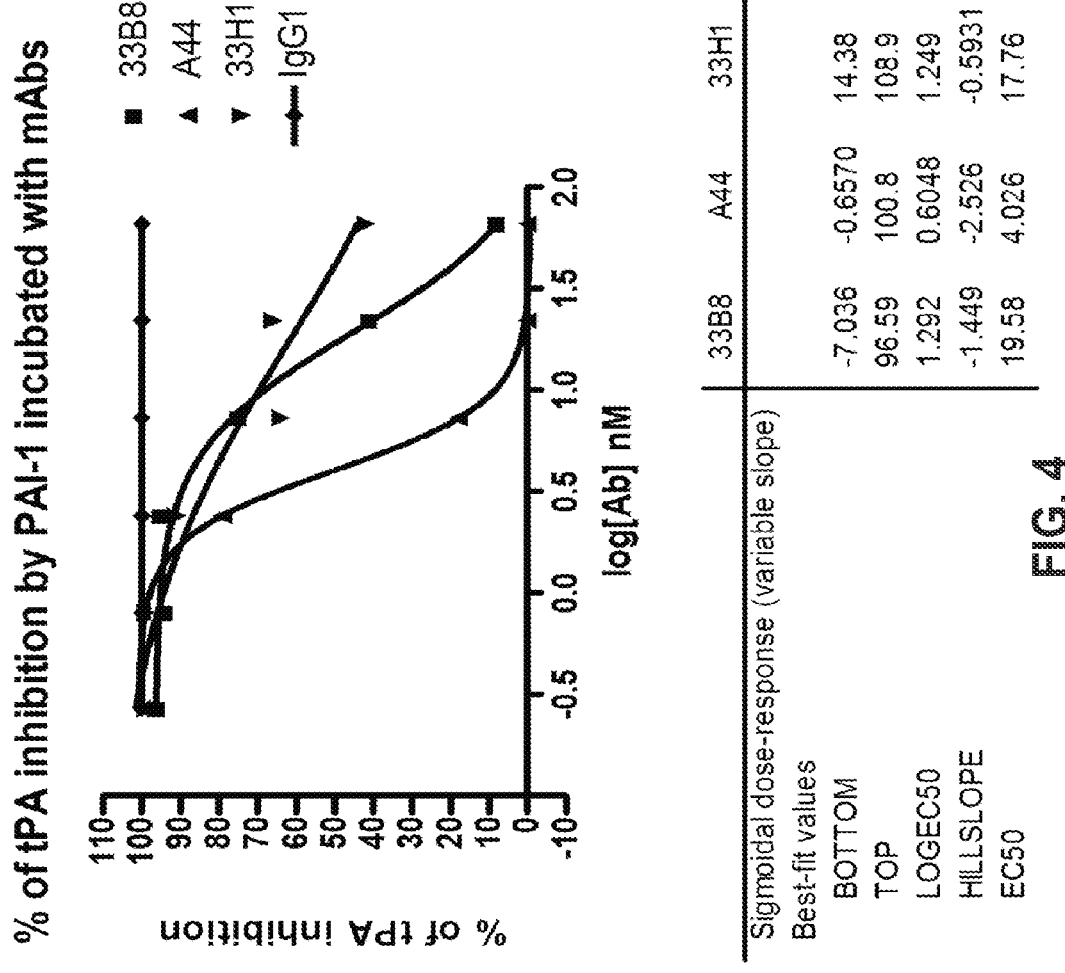
FIG. 4 depicts neutralization of human PAI-1 blocking activity of tPA by A44 and commercially available antibodies (33B8 and 33H1) in the chromogenic assay described in Example 4.

A two-step chromogenic assay was performed. All reagents are at 10× concentration until the step when they were added to substrate solution. In the first step, PAI-1 potency in tPA inhibition was measured using the chro-mogenic assay (PAI-1 titration with fixed tPA concentra-tion). The PAI-1 titration curve was analyzed to determine IC50 for PAI-1 blocking tPA activity. Afterward, the IC80 calculated from the curve was selected for further antibody interrogation for ability to neutralize PAI-1 blocking func-tion and restore tPA enzymatic activity. Equal volumes (25 ul) of tPA (at 14 nM) (Innovative Research, Cat. No. IHTPA-TC) and glycosylated (active form) human PAI-1 (Molecular Innovations, Cat. No. GLYHPAI-A) or non-glycosylated (active form) mouse PAI-1 (Molecular Inno-vations Cat. #IMPAI) were combined and incubated using 3-fold serial dilutions of PAI-1 starting at 108 nM and fixed concentration of tPA. All protein dilutions were made with 1% BSA/PBS. The mixture was incubated in the wells of a 96-well microtiter plate for 15 minutes at room temperature. Then 200 ul chromogenic substrate S2288 (1.25 mM) (Chromogenix, Cat. No. S-820852) diluted according to manufacturer's instructions is added to the wells and $OD_{405}$ absorbance change at 405 nm over 2 hours every 10 minutes is recorded to measure the residual tPA activity. For controls, background was measured in the absence of tPA (no enzy-matic reaction), a positive control was no PAI-1 (100% tPA activity) and a negative control was PAI-1 at 10-fold excess of tPA (complete blocking of tPA activity). See FIG. 4 for representative curves for 33B8, A44, 33H1 and IgG1.

Figure 5:
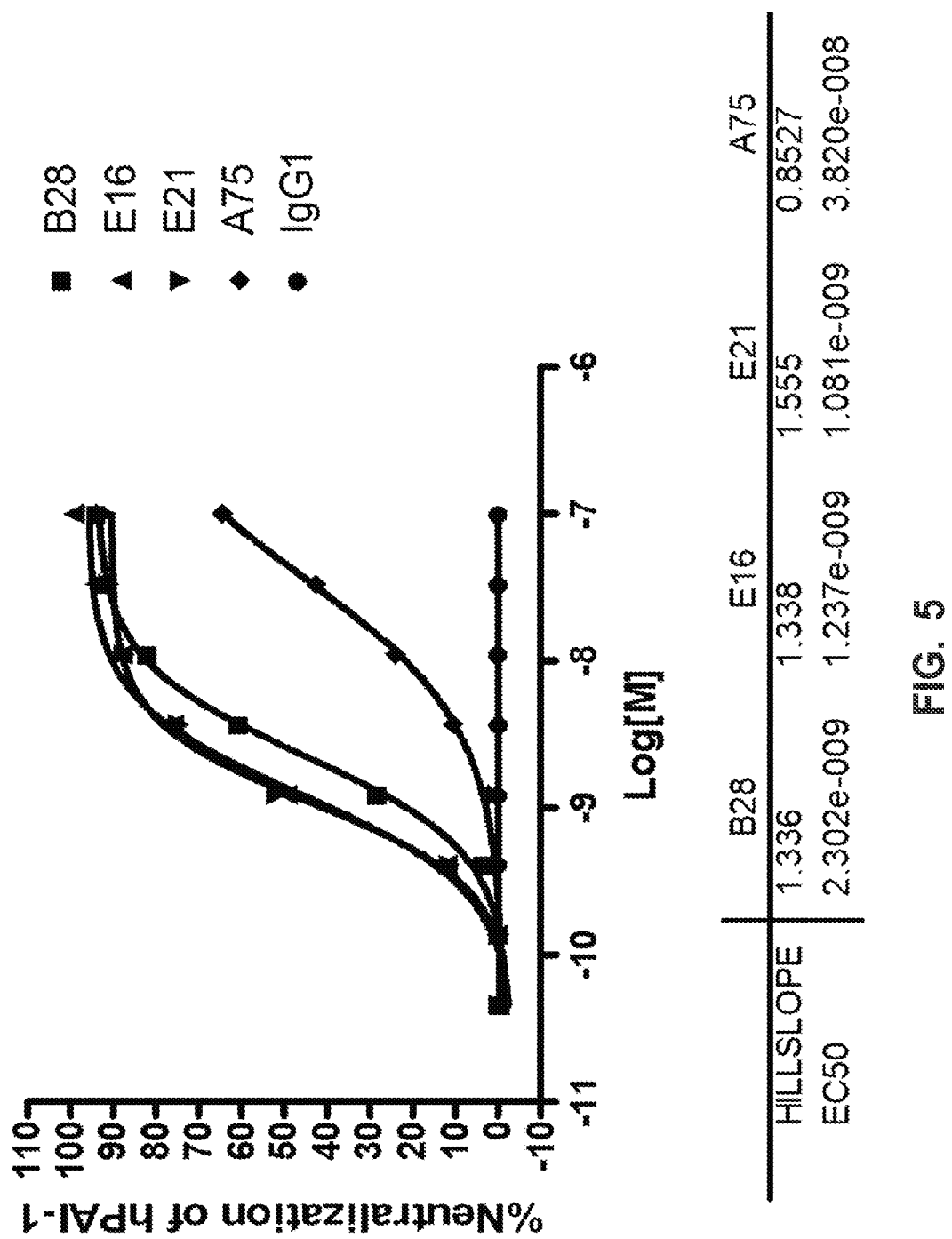
FIG. 5 depicts neutralization of human PAI-1 blocking activity of tPA by a selection of antibodies produced from different fusions (see Example 4).

For the second step, the functional properties of the antibodies were determined by assessing their ability to inhibit active PAI-1 and restore tPA function utilizing the PAI-1 neutralization assay. For this step, active PAI-1 12.5 ul (at 56 nM) was incubated with an equal volume of either PBS (Invitrogen, Cat. No. 14190-144) containing 1% BSA (Sigma, Cat. No. A3059) or with serial 3-fold dilutions of antibody starting at 2 uM. Control and unknown antibodies were incubated at concentrations (5 fold dilutions) ranging from 0.1 to 300 nM with 3 nM PAI-1 and tPA was added to the mixture. All the ingredients were incubated at 10× concentration at room temperature and further diluted 10 fold with tPA substrate S2288 which upon cleavage by tPA changes color from clear to yellow. Samples were read at OD 405 for 2 hours every 10 minutes at 37° C. The mixture was allowed to react in the wells of a 96-well microtiter plate for 30 minutes at room temperature to achieve antibody-antigen complex formation. Then 25 ul of tPA (at 14 nM which corresponds to $IC_{50}$ inhibition of tPA activity) was added to the wells and incubated for 15 minutes at room temperature. Finally, 200 ul 1.25 mM substrate S2288 diluted according to manufacturer's instructions was added to the mix. The absorbance change at 405 nm is recorded to measure the residual tPA activity for 2 hours every 10 min. One hundred percent PAI-1 activity is defined as the PAI-1 activity observed in the absence of antibody. Neutralization of PAI-1 activity by the antibody is calculated from the residual PAI-1 activity measured in the presence of the antibody. Controls were IgG1 as an isotype control (nega-tive) and 33H1 mAb and 33B8 mAb as positive controls. See FIG. 5 for representative curves for B28, E16, E21, A75 and IgG1.

Figure 6:
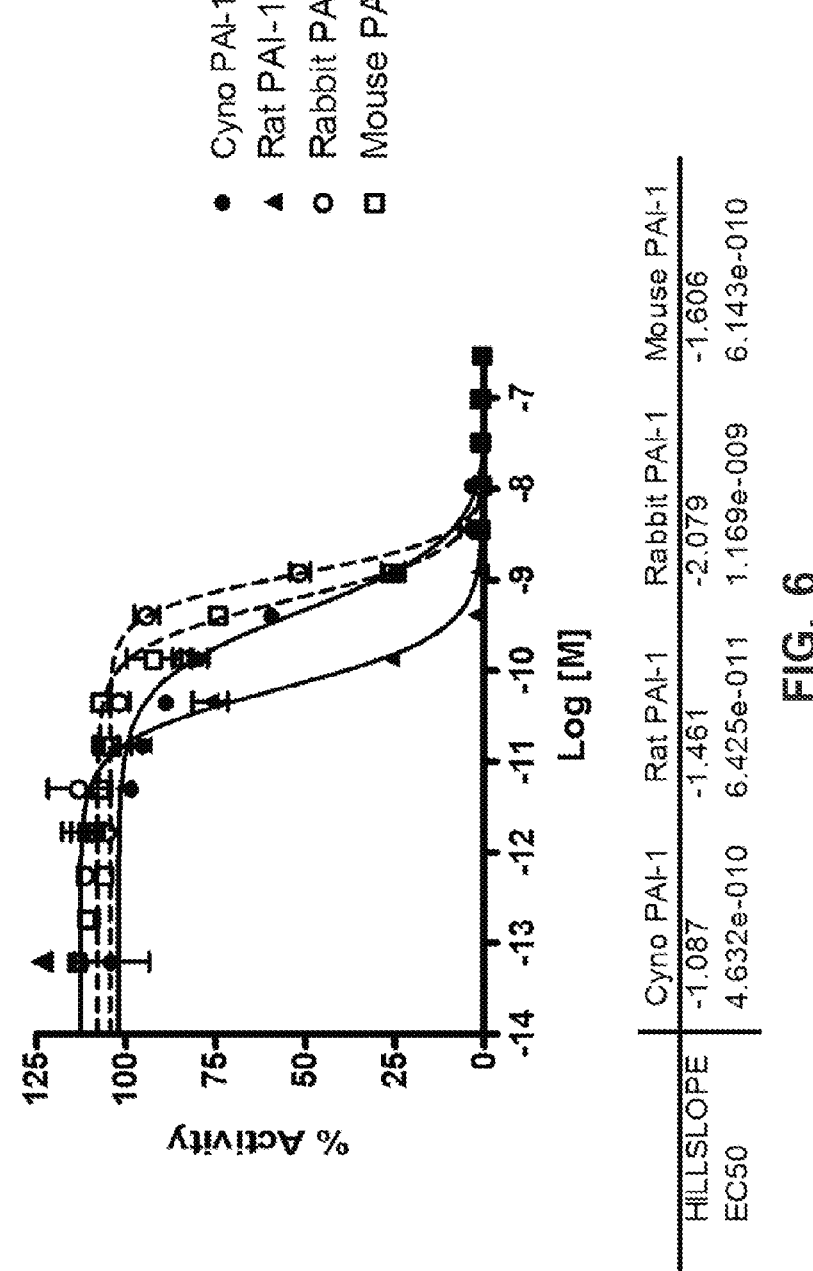
FIG. 6 depicts human PAI-1 and its orthologs block human tPA activity in chromogenic assay with the similar potency.
Figure 7:
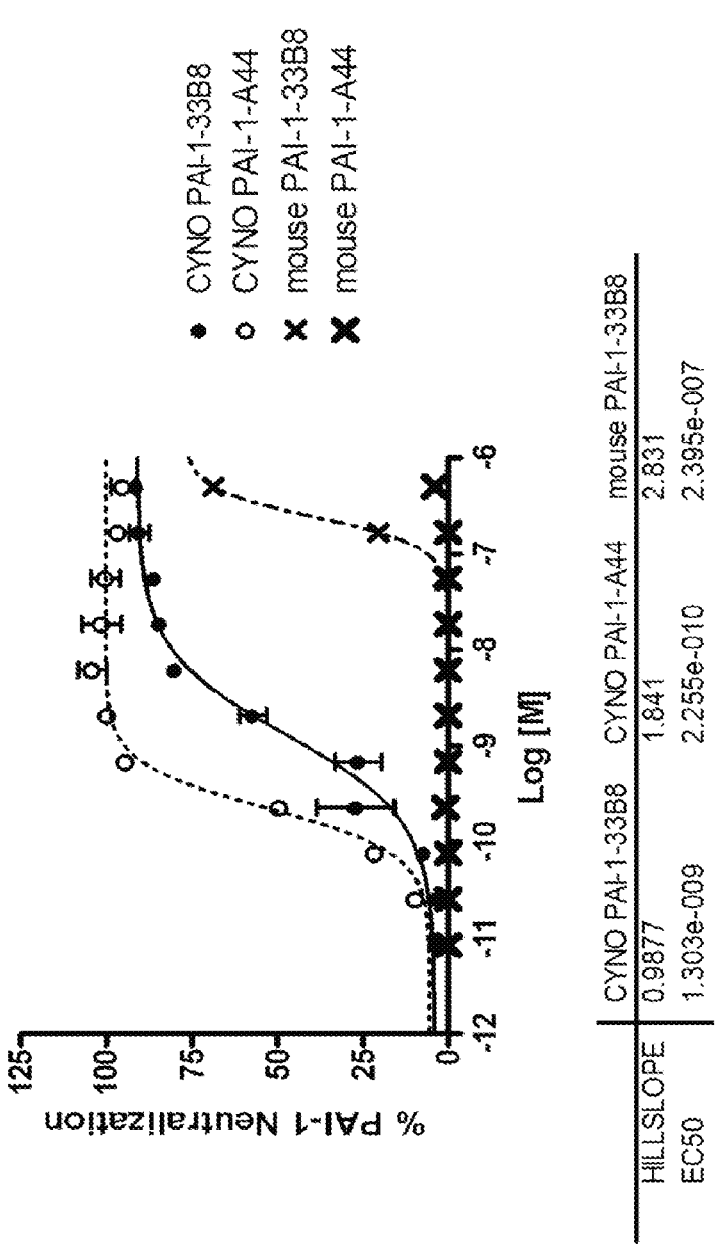
FIG. 7 depicts neutralization of cynomolgus (cyno) and mouse PAI-1 blocking activity of human tPA by A44 and 33B8 (commercially available) antibodies in the chromogenic assay described in Example 4.

Orthologs of human PAI-1 inhibiting human tPA were tested in the two step chromogenic assay system. Titration of orthologs was performed as described above for human PAI-1 (see FIG. 6 for representative curves of titrations) and tPA activity was determined by chromogenic method (see FIG. 7 for representation curves for 33B8 and A44 against cyno and mouse PAI-1). Final concentration of human tPA used in the assay was 1.4 nM. 12.5 ul active PAI-1 (56 nM) was incubated with an equal volume of either PBS contain-ing 1% BSA or with serial 3-fold dilutions of antibody starting at 2 uM. The mixture was allowed to react in the wells of a 96-well microtiter plate for 30 minutes at room temperature. Then 25 ul of tPA (14 nM) was added to the wells and incubated for 15 minutes at room temperature. To finalize reaction 200 ul tPA substrate S2288 (Chromogenix) (1.25 mM) was added to the mixture. Ortholog PAI-1 was obtained from Molecular Innovations: mouse PAI-1 (wild type active fraction; cat #MPAI); rat PAI-1 (wild type active fraction; cat #RPAI); and rabbit PAI-1 (stable mutant; cat #RbPAI-191L) cyno PAI-1 (active cyno PAI-1) was pro-duced in-house in *E. coli*. Because of the poor off-rates of the rabbit and rat orthologs in the Biacore screening (data not shown), screening of the antibodies against these orthologs was not performed.

TABLE 7

Activity of Antibodies against Orthologs and Glycosylation States of PAI-1 in Functional Chromogenic Assay

| Clone ID | Isotype | PAI-1 Ortholog and Glycosylation Status | | | |
|---|---|---|---|---|---|
| | | non-gly hPAI-1 | gly hPAI-1 | non-gly cPAI-1 | non-gly mPAI-1 |
| A37 | IgG1 | +/– | – | – | – |
| A39 | IgG1 | – | +++ | – | – |
| A41 | IgG1 | +/– | – | – | – |
| A44 | IgG1 | +++ | +++ | +++ | – |
| A47 | IgG1 | nd | – | – | – |
| A71 | IgG1 | +++ | +++ | +++ | – |
| A75 | IgG2a | +++ | +++ | +++ | – |
| A83 | IgG1 | nd | +/– | +/– | – |
| A89 | IgG2b | – | – | – | – |
| A98 | IgG1 | nd | nd | nd | nd |
| A105 | IgG1 | +++ | +++ | +++ | – |
| A107 | IgG1 | +/– | – | – | – |
| A113 | IgG1 | – | – | – | – |
| A119 | IgG2a | – | – | – | – |
| B18 | IgG1 | + | + | + | – |
| B28 | IgG2b | – | +++ | – | – |
| B29 | IgG1 | – | – | – | – |
| B32 | IgG1 | nd | – | – | – |
| B58 | IgG1 | nd | + | + | – |
| B89 | IgG1 | nd | – | – | – |
| B99 | IgG2a | nd | + | + | – |
| B105 | IgG1 | – | – | – | – |
| B109 | IgG1 | +++ | +++ | +++ | – |
| B118 | IgG1 | + | + | + | – |
| C26 | IgG1 | ++ | ++ | ++ | + |
| C45 | IgG2b | +++ | +++ | +++ | – |
| C61 | IgG1 | + | + | + | – |
| C66 | IgG1 | + | + | + | – |
| C69 | IgG1 | ++ | ++ | ++ | – |
| C79 | IgG2b | +/– | +/– | +/– | – |
| C109 | IgG2b | +/– | +/– | +/– | – |
| C118 | IgG1 | ++ | ++ | ++ | – |
| C145 | IgG2b | ++ | ++ | ++ | – |
| D4 | IgG2a | + | ++ | + | – |
| D12 | IgG1 | + | + | + | – |
| D13 | IgG1 | – | – | – | – |
| D15 | IgG1 | + | + | + | – |
| D31 | IgG1 | ++ | ++ | ++ | – |
| D33 | IgG1 | – | – | – | – |
| D37 | IgG2a | – | – | – | – |
| D48 | IgG2a | – | +/– | – | – |
| D52 | IgG1 | + | + | + | – |
| Ell | IgG1 | ++ | ++ | ++ | – |
| E16 | IgG1 | +++ | +++ | +++ | – |
| E21 | IgG2b | +++ | +++ | +++ | – | h = human,
c = cynomolgus monkey,
m = mouse,
nd = not determined
"–" = no activity,
"+/–" = partial activity,
"+" = slight activity,
"++" = moderate activity,
"+++" = strong activity One or more antibodies from each fusion demonstrated ability to block both cyno and human PAI-1 inhibitory function in this assay, with about 14 antibodies having moderate to strong blocking activity. A39 and B28 had a unique profile in that these two antibodies blocked glycosylated hPAI-1 but had no activity against human or cyno non-glycosylated PAI-1. None of the antibodies were able to block mouse PAI-1 activity efficiently (within 10 fold of the human PAI-1) except for C26.

Example 7: Mechanism of Action for Monoclonal Antibodies

Monoclonal antibodies can inhibit PAI-1 by three different mechanisms: a) by steric hindrance, b) by converting PAI-1 into a latent conformation upon binding, and c) by converting PAI-1 into a substrate for tPA conformation instead of the inhibitor ("substrate conformation"). PAI-1 makes a covalent bond with tPA upon interaction with serine protease.

Figure 8:
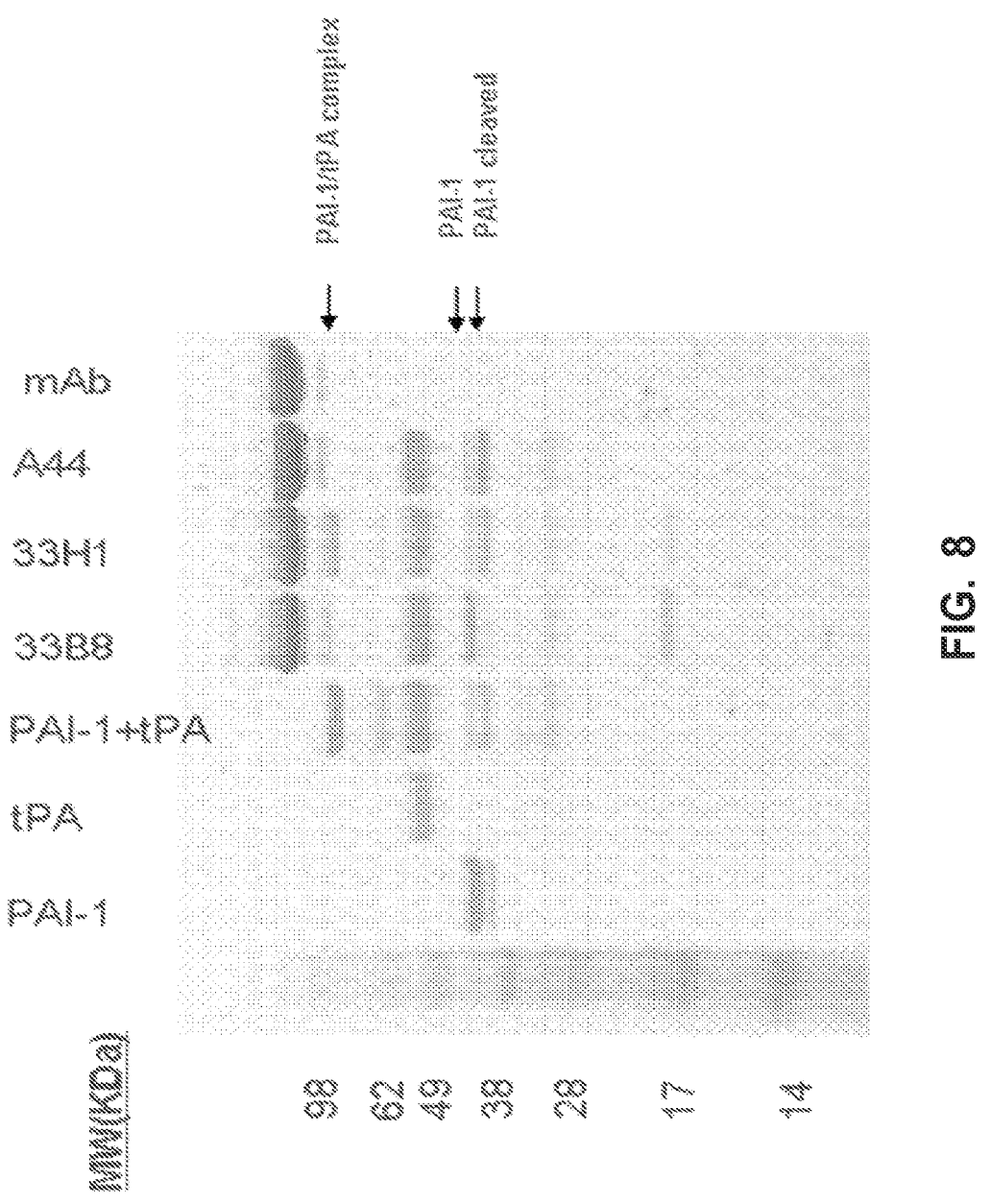
FIG. 8 depicts SDS-Page analysis of the mechanism of action for antibodies 33H8 (converts PAI-1 from active to latent confirmation), 33H1 (converts PAI-1 from active to substrate conformation) and A44 to block the interaction of PAI-1 with tPA. Lane 1: molecular weight standards; Lane 2: PAI-1 only; Lane 3: tPA only; Lane 4: PAI-1 in the presence of tPA; Lane 5: 33B8+PAI-1+tPA; Lane 6: 33H1+PAI-1+tPA; Lane 7: A44+PAI-1+tPA; Lane 8: mAb is an isotype control antibody.
Figure 9:
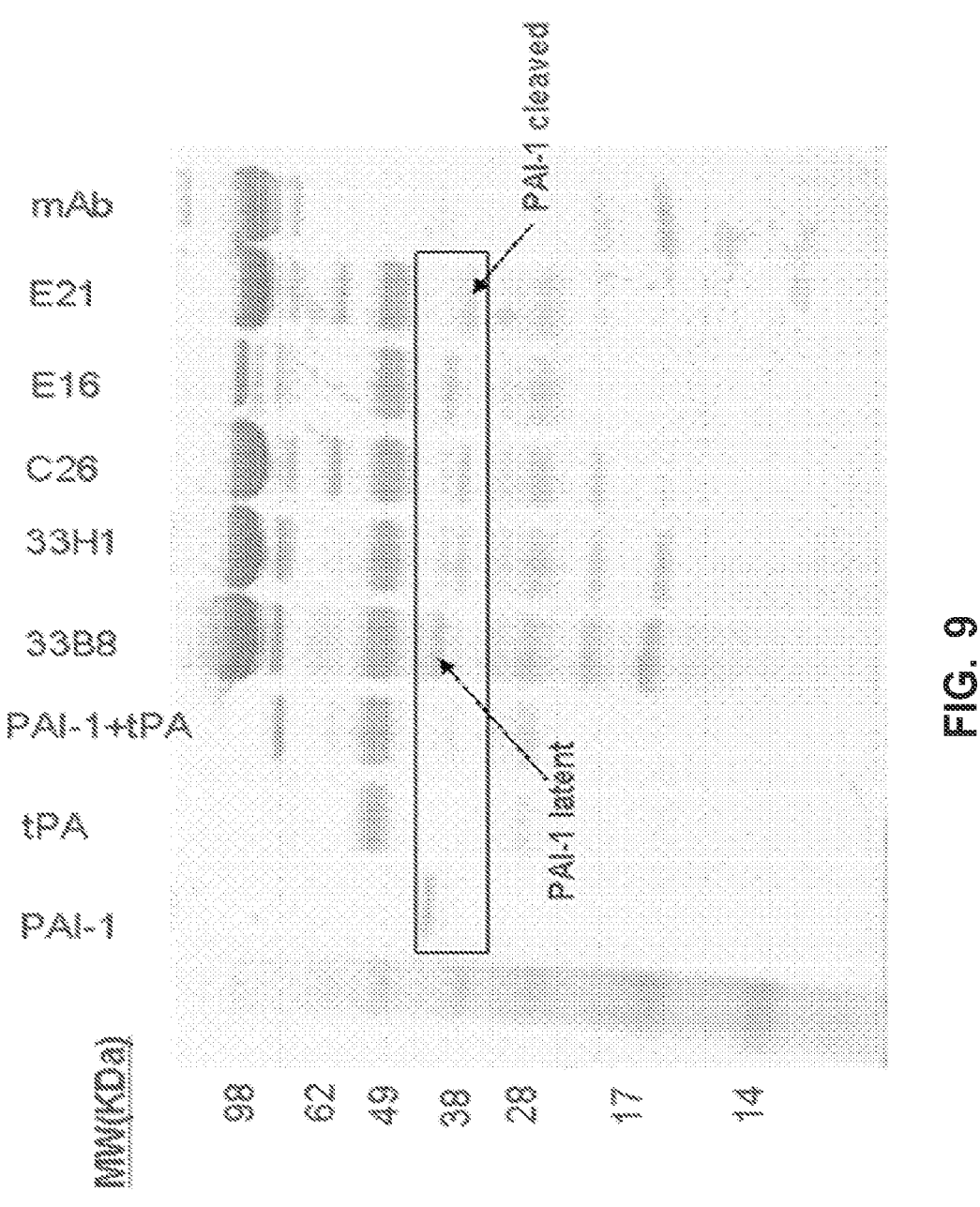
FIG. 9 depicts SDS-Page analysis of the mechanism of action for antibodies 33H8 (converts PAI-1 from active to latent confirmation), 33H1 (converts PAI-1 from active to substrate conformation) and antibodies developed from fusions C26, E16 and E21 to block the interaction of PAI-1 with tPA. Lane 1: molecular weight standards; Lane 2: PAI-1 only; Lane 3: tPA only; Lane 4: PAI-1 in the presence of tPA; Lane 5: 33B8+PAI-1+tPA; Lane 6: 33H1+PAI-1+tPA; Lane 7: C26+PAI-1+tPA; Lane 8: E16+PAI-1+tPA; Lane 9: E21+PAI-1+tPA; Lane 10: mAb is an isotype control antibody.
Figure 10:
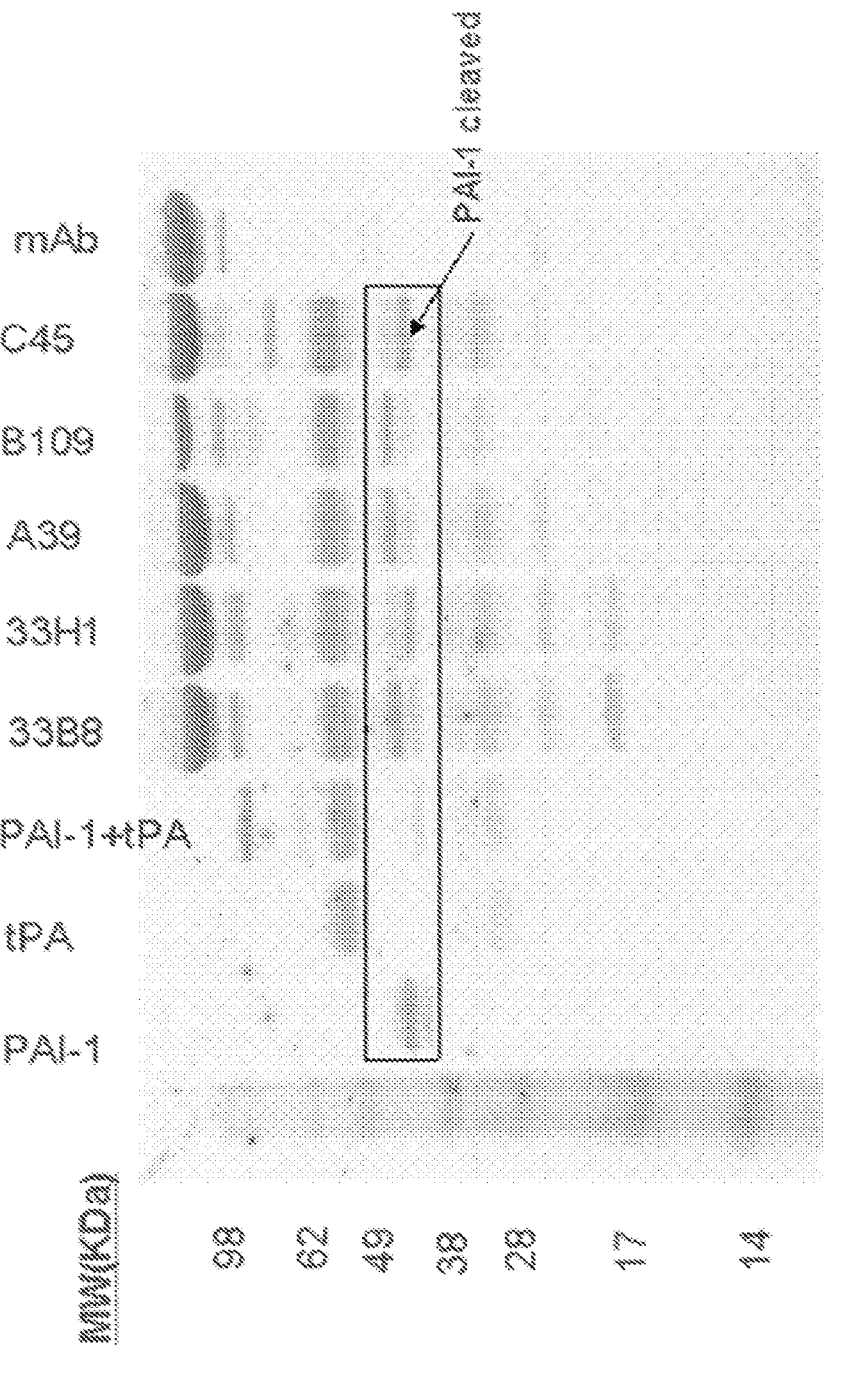
FIG. 10 depicts SDS-Page analysis of the mechanism of action for antibodies 33H8 (converts PAI-1 from active to latent confirmation), 33H1 (converts PAI-1 from active to substrate conformation) and antibodies developed from fusions A39, B109 and C45 to block the interaction of PAI-1 with tPA. Lane 1: molecular weight standards; Lane 2: PAI-1 only; Lane 3: tPA only; Lane 4: PAI-1 in the presence of tPA; Lane 5: 33B8+PAI-1+tPA; Lane 6: 33H1+PAI-1+tPA; Lane 7: A39+PAI-1+tPA; Lane 8: B109+PAI-1+tPA; Lane 9: C45+PAI-1+tPA; Lane 10: mAb is an isotype control antibody.

The chromogenic assay and SDS-PAGE techniques were used to identify antibody mechanism of action. A reaction between monoclonal antibody (or control antibodies), PAI-1 and tPA was carried out as described above for the functional chromogenic assay. Samples were mixed with Laemmli sample buffer and loaded on SDS-PAGE gel under non-reducing conditions and ran for 30 minutes. Afterwards, the gels were stained with Coomassie blue to visualize proteins, complexes and the cleaved form of PAI-1. Control monoclonal antibodies with known mechanism of action were used as comparators. 33B8 is known to convert PAI-1 into a latent conformation and 33H1 is known to convert PAI-1 into a substrate conformation. This assay could positively identify the substrate conformation but was unable to distinguish between latent conformation or steric hindrance. Representative SDS-gels are shown in FIGS. 8, 9 and 10.

TABLE 8

Mechanism of Action of Monoclonal Antibodies

| Antibody | Mechanism of Action |
|---|---|
| A44 | Converts PAI-1 from Active → Substrate Conformation |
| C26 | Converts PAI-1 from Active → Substrate Conformation |
| C45 | Converts PAI-1 from Active → Substrate Conformation |
| E21 | Converts PAI-1 from Active → Substrate Conformation |
| A39 | Converts PAI-1 from Active → Latent Conformation or Steric Hindrance |
| B109 | Converts PAI-1 from Active → Latent Conformation or Steric Hindrance |
| E16 | Converts PAI-1 from Active → Latent Conformation or Steric Hindrance |

A44, C26, C45 and E21 block PAI-1 activity by converting PAI-1 form the active conformation to the substrate conformation. A39 and B109 have a different mechanism of action, but the assay was unable to distinguish whether these antibodies block PAI-1 activity by changing PAI-1 from the active conformation to the latent conformation or by steric hindrance.

Example 8: Purified Antibody Binding Kinetics

In kinetics measurement, the antibodies were evaluated in reverse at 25° C. In the reverse assay, PAI-1 antibodies were captured to the anti-mouse IgG Fc antibody surface prepared on CM5 chip followed by injecting the serial 2× dilutions of PAI-1 proteins (human or cyno) starting at 40 nM. A high flow rate was chosen at 50 ul/min to avoid mass transportation limitation. Two thousand seconds was allowed for dissociation time to accommodate for the slow off rate of the selected antibodies. The chip was regenerated by glycine-HCl, pH 1.7 buffer after each round of antibody-PAI-1 binding. Kinetics data analysis was performed using Biacore BIAevaluation software. The sensorgrams were double-referenced by subtracting the reference flow cell values and the blank buffer values. The sensorgrams were fitted by using the simulated kinetics 1:1 (Langmuir) model with local Rmax. The data for the antibodies tested are shown below in Table 9.

TABLE 9

| | Binding Kinetics by Biacore Reverse Assay | | | |
| | human PAI-1 | | cyno PAI-1 | |
| Antibody | Dissociation Rate kd (1/s) | Affinity KD (M) | Dissociation Rate kd (1/s) | Affinity KD (M) |
| --- | --- | --- | --- | --- |
| A39 | 7.09E−05 | 1.16E−11 | ND | ND |
| A44 | 1.49E−05 | 3.76E−12 | <=1.0E−6 | <=1.0E−13 |
| A75 | 4.76E−04 | 1.20E−10 | ND | ND |
| A105 | 1.64E−04 | 4.23E−11 | ND | ND |
| B28 | 4.61E−04 | 6.5E−10 | ND | ND |

ND = not determined

Binding kinetics of representative antibodies were further analyzed and compared in Biacore forward assay with vitronectin and PAI-1 complex. In the forward assay, human vitronectin protein was immobilized onto the CM5 chip in flow cells Fc1-Fc4 by amine coupling. Human PAI-1 was then captured to the vitronectin surface in flow cells Fc2-Fc4 as ligand. Fc1 was reserved as reference cell. The antibodies were diluted 2× starting from 40 nM and injected to Fc1-4. Kinetics data analysis was performed using Biacore BIAevaluation software. The sensorgrams were first double-referenced by subtracting the reference cell values and the blank buffer values, and then fitted by 1:1 (Langmuir) model was used with global Rmax.

TABLE 10

| Kinetics of A44 binding to human vitronectin captured human PAI-1 in Biacore forward assay | | |
| | kd (1/s) | KD (M) |
| --- | --- | --- |
| A44 binding to Vn captured hPAI-1 | <=1.0E−6 | <=1.0E−12 |

Data in Table 10 indicated that A44 binds free human PAI-1as well as PAI-1 in vitronectin complex.

Example 9: Functional Assay in Primary Human Cells

To further investigate each antibody's ability to restore downstream plasmin production by primary human cells, a plasmin generation assay was used. Only antibodies that showed high potency in the chromogenic assay and good affinity in Biacore were used tested in this assay.

On day 1, human primary hepatic stellate cells (Sciencell CA, cat no SC5300) were plated at 20000 cells/well in starvation medium (DMEM Gibco+glutamax-1 4.5 g/L D-Glucose, Pyruvate (31966-021), 0.2% Fetal Bovine Serum gold PAA (A11-152)) at 37° C. under 5% CO2. On day 2, to neutralize PAI-1 activity, antibodies were pre-incubated with recombinant PAI-1 (Molecular Innovation, cat #IGLYHPAI-A, recombinant Glycosylated human PAI-1, final concentration 5 nM) for 15 minutes at room temperature. At the same time, tPA (Molecular Innovations (cat #HTPA-TC), 5 nM in DMEM without red phenol) was incubated with cells for 15 minutes at 37° C. After washing unbound tPA, PAI-1/mAb mixtures were added on the cells and then residual tPA activity was measured by adding and glu-Plasminogen/Substrate mixture (Glu-Pg: Sigma cat #9001-91-6; 0.5 μM final concentration) and plasmin chromogenic substrate: (CBS00.65 Stago cat #00128, 0.5 mM final concentration).

Plasminogen activation to plasmin is detected by kinetic reading every 45 seconds of A405/492 nm using spectrophotometer (IEMS, Thermofisher) thermostated at 37° C. Biolise software (Thermofischer) calculates the maximal rate of chromogenic substrate cleavage: plasmin generation expressed as Vmax: maximal rate of A405/492 nm per min (mDO/min) calculated. PAI-1 inhibition is then calculated with tPA alone as reference (100% inhibition) and PAI-1 (without mAb, as no inhibition) and plotted using Biostat speed software to calculate $IC_{50}$ and Imax.

TABLE 11

| Plasminogen Generation in Human Primary Hepatic Stellate Cells | | | |
| Antibody | $IC_{50abs}$ mean ± sem (nM) | $I_{max}$ mean (%) | n |
| --- | --- | --- | --- |
| A44 | 3.32 ± 0.34 | 97 | 7 |
| A39 | 5.4 ± 0.8 | 99 | 3 |
| A71 | 8.61 ± 3.6 | 90 | 3 |
| A75 | 22.6 ± 8.2 | 66 | 4 |
| A105 | 27 ± 7.8 | 88 | 3 |
| B28 | 7.28 ± 2.7 | 90 | 3 |
| B109 | 6.11 ± 0.88 | 94 | 3 |
| C26 | Inactive | n/a | 2 |
| C45 | 6.5 ± 1.11 | 97 | 4 |
| E16 | 4.74 ± 2.27 | 95 | 3 |
| E21 | Inactive | n/a | 3 |
| 33H1 | 22.92 ± 12 | 56 | 3 |
| 33B8 | Inactive | n/a | 3 | n/a = not applicable

Example 10: Antibody Binding Epitope Exploration by Biacore Competition Assay A selected group of anti-PAI-1 antibodies with superior binding and blocking activities were explored for their potential binding epitopes in Biacore competition assays. In the assays, the newly identified antibodies as well as several commercially available anti-PAI-1 antibodies with known binding site on human PAI-1 were set up to compete for binding to human PAI-1 protein. Each antibody was immobilized onto a flow cell in Biacore CM5 chip using standard amine coupling reaction. All tested antibodies except for clone B28 retained binding site activity after amine coupling. Human PAI-1 protein was captured to the immobilized antibody on the chip followed by injection of each antibody as analyte. Only the analyte antibodies that have different binding sites on human PAI-1 from the immobilized antibody will show additional binding signals in Biacore. The competition experiments were repeated twice for each immobilized antibody and the results are show in the following Table.

TABLE 12

Summary of Binding Epitopes from Biacore competition assay

| | | Analyte Antibody | | | | | | | | | | | |
|---|---|---|---|---|---|---|---|---|---|---|---|---|---|
| | | 33H1 | 33B8 | A44 | 31C9 | A71 | A75 | B109 | B28 | C45 | C26 | E16 | E21 |
| Immobilized | 33H1 | c/c | b/c | b/b | b/b | b/b | b/b | b/b | b/b | b/b | c/c | b/b | b/c |
| Antibody | 33B8 | b/b | c/c | b/b | b/c | b/b | b/b | b/b | p/b | b/b | b/b | b/b | b/b |
| | A44 | b/b | b/b | c/c | b/b | b/b | b/b | b/b | b/b | c/c | b/b | c/c | b/b |
| | 31C9 | nt | nt | nt | nt | nt | nt | nt | nt | nt | nt | nt | nt |
| | A71 | b/b | b/c | b/b | b/b | c/c | c/c | b/b | b/b | b/b | b/b | b/b | b/b |
| | A75 | b/b | p/p | b/b | p/p | c/c | c/c | b/b | b/b | b/b | b/b | b/b | b/b |
| | B109 | b/b | c/c | b/b | b/b | b/b | b/b | c/c | c/c | b/b | b/b | b/c | b/b |
| | B28 | — | — | — | — | — | — | — | — | — | — | — | — |
| | C45 | b/b | p/b | c/c | b/b | b/b | b/b | b/b | b/b | c/c | b/b | b/b | b/b |
| | C26 | b/c | p/c | b/b | b/b | b/b | b/b | b/b | b/c | b/b | c/c | b/b | c/c |
| | E16 | b/b | p/b | b/c | b/b | b/b | p/b | b/b | b/c | b/b | b/b | c/c | b/b |
| | E21 | b/c | b/c | b/b | b/c | b/c | b/b | b/b | b/c | b/b | b/c | b/b | c/c | p = partial binding by the analyte antibody,
c = competition by the analyte antibody,
b = binding by the analyte antibody;
"—" = no PAI-1 binding to the immobilized antibody;
nt = not tested When A44 is immobilized and binds PAI-1, C45 (analyte antibody) is unable to bind to PAI-1 that is bound by A44. Therefore, C45 competes for the same binding site that A44 binds on PAI-1 (denoted in Table 12 as "c/c") or A44 binding to PAI-1 interferes with C45 binding to PAI-1. This analysis is confirmed when the experiment is repeated in the reverse order. Specifically, when C45 is the immobilized antibody and is bound to PAI-1, A44 as the analyte antibody is unable to bind the PAI-1 that is bound to C45 (denoted in Table 12 as "c/c"). In a similar analysis, A71 and A75 compete for the same site on PAI-1. The Biacore analysis confirmed that A44 and C45, as well as A71 and A75, compete with or to interfere with each other when binding to PAI-1.

Conversely, the commercially available antibodies, 33H1 and 33B8, do not compete with A44. When A44 is the immobilized antibody and is bound to PAI-1, both 33H1 and 33B8 are able to still bind to the PAI-1 that is bound to A44 (denoted as "b/b" in Table 12). This is confirmed in the reverse experiment. When PAI-1 is bound to immobilized 33H1 or immobilized 33H8, A44 is still able to bind to PAI-1. Thus, the commercial antibodies 33H1 and 33B8 do not compete with or interfere with A44 binding to PAI-1.

Interestingly, some immobilized antibodies (i.e., B109) blocked analyte antibody (i.e., 33B8) from binding to the captured PAI-1 protein; but, when switching the positions of the immobilized antibody to the analyte antibody (e.g., flipping the pair on the chip), the antibody pair no longer competed for binding with each other to PAI-1. For example, when B109 was the immobilized antibody bound to PAI-1, 33B8 was unable to bind PAI-1. However, when 33B8 was the immobilized antibody binding PAI-1, B109 was able to bind PAI-1. One possible explanation for this result is that when the immobilized antibody is bound to PAI-1, PAI-1 may shift to an unfavorable conformation for the second or analyte antibody and prevents the analyte antibody from binding (for instance, when B109 is the immobilized antibody and 33B8 is the analyte antibody). However, when the antibody pair is reversed, the immobilizing antibody may bind in such a manner that PAI-1 conformation is relatively unchanged, thus allowing the analyte antibody to bind to the bound PAI-1 (i.e., the analyte antibody B109 is able to bind PAI-1 that is bound by the immobilized antibody 33B8). Therefore, the competition observed between 33B8 and B109 was not due to overlapping binding sites on PAI-1 but likely due to a conformational change in PAI-1 when bound to B109.

Another interesting observation was that B28 lost binding to human PAI-1 when immobilized via amine coupling, suggesting B28's CDR regions involve amino acids with primary amine group(s).

Example 11: Selection of Mouse Monoclonal Antibody for Humanization

Table 13 shows a summary of the in vitro data characterizing the most active monoclonal antibodies from the five fusions performed. Based on these data, A44 was selected for humanization because A44 was the most potent antibody in the chromogenic assay and in plasmin generation while having the highest affinity in Biacore.

TABLE 13

Summary of Monoclonal Antibody Affinity and Potency against Human Glycosylated PAI-1

| Antibody | Chromogenic Assays (nM) | Plasmin Generation (nM) | Affinity Kd (M) | Mechanism of Action |
|---|---|---|---|---|
| A39 ( IgG1/k) | 1.70, 1.00 | 5.4 | 1.16E−11 | SH or latent |
| A44 ( IgG1/k) | 1.66, 1.50, 1.70 | 3.32 | 4.20E−14 | substrate |
| A71 ( IgG1/k) | Approx. 4.00 | 8.61 | ND | SH or latent |
| A75 ( IgG2a/k) | 3.00 | 22.6 | 1.20E−10 | SH or latent |
| A105 ( IgG1/k) | 7.00 | 27.0 | 4.20E−11 | SH or latent |
| B28 ( IgG2b/k) | 1.80 | 7.28 | 6.5E−10 | SH or latent |
| B109 ( IgG1/k) | 0.23 | 6.11 | ND | SH or latent |
| C26 ( IgG1/k) | 5.00 | Inactive | ND | substrate |
| C45 (IgG2b) | 0.5 | 10.6 | ND | substrate |
| E16 (IgG1) | 1.1 | 4.74 | ND | SH or latent |
| E21 (IgG2b) | 1.3 | 216.0 | ND | substrate |

SH = steric hindrance;
ND = not determined

The heavy and light chain sequences shown in Table 1 are aligned in FIG. 12 and CDRs, as defined by IMGT, are highlighted in bold. Based on the in vitro data presented in the Table 13, A44 was selected for humanization.

Example 12: Engineering of the Anti-PAI-1 A44
Fab: Humanization, Stabilization and Mutation of
Unwanted Sequence Motifs Several approaches discussed below were taken to humanize, stabilize and optimize the sequence motifs of the A44 murine antibody against PAI-1.

1) Humanization

The humanization protocol used has been described in PCT/US08/74381 (US20110027266), herein incorporated by reference in its entirety. The variable light (VL) and variable heavy (VH) sequences of murine A44 were used to build a homology model of anti-PAI-1 A44 light chain (LC) and heavy chain (HC) in Molecular Operating Environment (MOE; v. 2010.10; Chemical Computing Group). The following templates were used: light chain framework—1D5I (94% identity in the framework regions), heavy chain framework—3KSO (96% identity in the framework regions), L1-1D5I (94% identity), L2-1D5I (94% identity), L3-1AXS (72% identity), H1-1IC7 (82% identity), H2-1MBU (68% identity) and H3-2WDB (62% identity). The H3 loop was particularly difficult to model since Trp is the first residue. 2WDB, although a shorter loop, also has a Trp at the beginning of the loop and the same Phe-Asp-Tyr sequence at the end of the H3 loop. The side-chains of Glu-105 (LC) and His-99 were rebuilt and the subsequent model was energy minimized using the standard procedures implemented in MOE. A molecular dynamics (MD) simulation of the minimized 3D homology model of the murine A44 was subsequently performed, with constraints on the protein backbone at 500 K temperature for 1.1 nanoseconds (ns) in Generalized Born implicit solvent. Ten diverse conformations were extracted from this first MD run every 100 picoseconds (ps) for the last 1 ns. These diverse conformations were then each submitted to a MD simulation, with no constraints on the protein backbone and at 300 K temperature, for 2.3 ns. For each of the 10 MD runs, the last 2,000 snapshots, one every ps, from the MD trajectory were then used to calculate, for each murine A44 amino acid, its root mean square deviations (rmsd) compared to a reference medoid position. By comparing the average rmsd on the 10 separate MD runs of a given amino-acid to the overall average rmsd of all A44 murine amino-acids, one decides if the amino-acid is flexible enough, as seen during the MD to be considered as likely to interact with T-cell receptors and responsible for activation of the immune response. 37 amino-acids were identified as flexible in the murine A44 antibody, excluding the CDR and its immediate 5 Avicinity.

The motion of the 62 most flexible murine A44 amino acids, during the 20 ns (10×2 ns), were then compared to the motion of the corresponding flexible amino-acids of 49 human germline homology models, for each of which were run the 10×2 ns MD simulations. The 49 human germline models were built by systematically combining the 7 most common human germline light chains (vk1, vk2, vk3, vk4, vlambda1, vlambda2, vlambda3) and 7 most common human germline heavy chains (vh1a, vh1b, vh2, vh3, vh4, vh5, vh6). The vk1-vh2 human germline antibody showed 0.58 4D similarity of its flexible amino-acids compared to the flexible amino-acids of the murine A44 antibody; the vk1-vh2 germline antibody was therefore used to humanize A44 antibody focusing on the flexible amino-acids. The vlambda3-vh4 human germline showed the second highest 4D similarity, 0.57, and was also used as the basis for humanization of the A44 antibody. For the pair wise amino-acid association between murine A44 and vk1-vh2 amino-acids, the 2 sequences were aligned based on the optimal 3D superposition of the alpha carbons of the 2 corresponding homology models. The pair wise amino-acid association between murine A44 and vlambda3-vh4 was performed in a similar manner. FIG. 13 shows the alignment of murine A44 light chain with vk1 and vlambda3. FIG. 14 shows the alignment of murine A44 heavy chain with vh2 and vh4.

2) Stabilization a) Knowledge-Based Approach

The amino-acids of the light and heavy chains with low frequency of occurrence vs. their respective canonical sequences, excluding the CDRs, were proposed to be mutated into the most frequently found amino-acids (ΔΔGth>0.5 kcal/mol; (E. Monsellier, H. Bedouelle. J. Mol. Biol. 362, 2006, p. 580-593)). This first list of consensus mutations for the LC and HC has been restricted to the amino-acids found in the closest human germline (vk1-vh2). Suggested changes in the immediate vicinity of the CDRs (5 Angstroms "Vernier" zone (J. Mol. Biol. 224, 1992, p. 487-499)) were removed from consideration. This resulted in two stabilizing mutations in the LC (see Table 15) and five stabilizing mutations in the HC (see Table 16). Other criteria were taken into account to consider these mutations for potentially stabilizing the anti-PAI-1 A44 antibody. These criteria were a favorable change of hydropathy at the surface or a molecular mechanics based predicted stabilization of the mutant. Also, additional stabilizing mutations reported to be successful in the literature (E. Monsellier & H. Bedouelle, J. Mol. Biol., 362, 2006, p. 580-593; B. J. Steipe et al. J. Mol. Biol, 1994, 240, 188-192) and were considered (see Tables 17 & 18), however, no additional mutations were suggested.

TABLE 15

| Stabilizing Changes Proposed in Light Chain | | | |
|---|---|---|---|
| Residue | Proposed Change | Calculated ΔΔGth | Accept Change |
| Lys-3 | Val | 2.23998 | No - not in germline |
| Met-11 | Leu | 0.766432 | Already changed in humanization |
| Tyr-12 | Ser | 2.04389 | Already changed in humanization |
| Leu-36 | Val | 2.17091 | No - Vernier |
| Lys-42 | Gln | 0.939652 | No - not in germline |
| Thr-46 | Leu | 2.01966 | No-Vernier |
| Gln-69 | Thr | 2.16357 | No-Vernier |
| Tyr-80 | Ala | 2.92454 | Already changed in humanization |
| Met-83 | Leu | 2.57007 | Already changed in humanization |
| Gly-84 | Ala | 0.597822 | Yes |
| Ile-85 | Thr | 1.27255 | Yes |

TABLE 16

| Stabilizing Changes Proposed in Heavy Chain | | | |
|---|---|---|---|
| Residue | Proposed Change | Calculated ΔΔGth | Accept Change |
| Glu-1 | Gln | 0.562423 | Yes |
| Met-2 | Val | 3.41361 | No - Vernier |
| Glu-6 | Gln | 0.655069 | No - Not in germline |
| Pro-9 | Ala | 0.505324 | No - Not in germline |
| Ser-10 | Glu | 2.40018 | Already changed in humanization |
| Gln-16 | Ala | 1.11244 | No - Not in germline |
| Thr-17 | Ser | 1.79135 | No - Not in germline |
| Leu-18 | Val | 0.760243 | No - Not in germline |
| Ser-19 | Lys | 1.20539 | No - Not in germline |

TABLE 16-continued

| Stabilizing Changes Proposed in Heavy Chain | | | |
|---|---|---|---|
| Residue | Proposed Change | Calculated ΔΔGth | Accept Change |
| Thr-21 | Ser | 1.3289 | No - Not in germline |
| Ser-23 | Lys | 1.82798 | No - Not in germline |
| Val-24 | Ala | 1.35286 | No - Not in germline |
| Thr-25 | Ser | 1.72008 | Yes |
| Ile-37 | Val | 1.66985 | No - Not in germline |
| Arg-38 | Lys | 0.568427 | No - Not in germline |
| Lys-39 | Gln | 2.27769 | Yes |
| Phe-40 | Arg | 1.81199 | No - Not in germline |
| Asn-43 | Lys | 1.42568 | Already changed in humanization |
| Lys-44 | Gly | 2.01606 | Already changed in humanization |
| Tyr-47 | Trp | 2.62805 | No - Vernier |
| Met-48 | Ile | 1.67766 | No - Vernier |
| Pro-61 | Glu | 1.08569 | No - Not in germline |
| Ser-62 | Lys | 0.840485 | No - Not in germline |
| Leu-63 | Phe | 1.25428 | No - Not in germline |
| Arg-66 | Lys | 0.528008 | No - Not in germline |
| Ile-67 | Ala | 1.93707 | No - Vernier |
| Ser-68 | Thr | 1.36475 | Yes |
| Ile-69 | Leu | 0.550185 | No - Vernier |
| Arg-71 | Val | 0.61536 | No - Vernier |
| Asn-72 | Asp | 3.40632 | Yes |
| Thr-73 | Lys | 0.5597 | No - Vernier |
| Lys-75 | Ser | 0.81321 | No - Not in germline |
| Asn-76 | Ser | 0.744463 | No - Not in germline |
| Gln-77 | Thr | 1.30652 | No - Not in germline |
| Tyr-78 | Ala | 2.54699 | No - Vernier |
| Val-85 | Leu | 1.71111 | No - Not in germline |
| Thr-87 | Ser | 1.30394 | No - Not in germline |
| Thr-90 | Ser | 0.557686 | No - Not in germline |
| Thr-92 | Val | 1.13795 | No - Not in germline |

TABLE 17

| Combinations of stabilizing mutations evaluated | | |
|---|---|---|
| Combination* | Additional changes suggested | Accept Change |
| L1 (40–>P & 42–>Q) | None - neither changed | No changes |
| L2 (45–>K) | None - already K45 | None |
| L3 (74–>T) | None - already T74 | None |
| L4 (76–>S) | None - already S76 | None |
| L5 (84–>A, 85–>T) | None - already changed in stabilization | None |
| H1 (15–>G) | None - not in germline | None |
| H2 (61–>E, 62–>Lys, 63–>Phe) | None in germline | None |
| H3 (86–>T, 87–>S, 88–>E) | 87 and 88 not in germline | None |
| S1 (L1 & L5) | None | No |
| S2 (H1 & H3) | None | No |

*Note:
Sequential numbering used to refer to residues

TABLE 18*

| Stabilization mutations evaluated | | |
|---|---|---|
| Light Chain Residue* | Additional changes suggested | Accept Change |
| 15–>L | V15–>L | No - V15 in Vk1 germline |
| 90–>Q | None - already Q90 | None |
| 32–>Y | None - already Y32 | None |

TABLE 18*-continued

| Stabilization mutations evaluated | | |
|---|---|---|
| Light Chain Residue* | Additional changes suggested | Accept Change |
| 106–>I | None - already I106 | None |
| 63–>S | None - already S63 | None |
| 21–>I | None - already M21 | None |

*Note:
Sequential numbering used to refer to residues b) 3D and MD-Based Approaches 3D and MD-based approaches have been previously reported (Seco J., Luque F. J., Barril X., J. Med. Chem. 2009 Apr. 23:52(8):2363-71; Malin Jonsson et al., J. Phys. Chem. B 2003, 107:5511-5518). Hydrophobic regions of the antibody were explicitly identified by analyzing the molecular dynamics simulation of the Fab in a binary solvent (20% isopropanol in water, 20 ns production simulation). Additional analysis using a hydrophobic surface map within Schrodinger's maestro software (v. 8.5.207) was completed. The protein surface analyzed by these two methods is quite hydrophilic. Even with both these techniques, no residues contributing to any hydrophobic patches on the surfaces were present therefore, no anti-aggregation mutations were suggested.

3) Humanization by Grafting

Humanization using grafting techniques has previously been reported (P. T. Jones, P. H. Dear, J. Foote, M. S. Neuberger, G. Winter, Nature 1986, 321:522-525). The humanization started by identifying the two closest human germlines to anti-PAI1 A44 variable domain light and heavy chains. This was done by performing a BLAST search vs. all the human germlines which were systematically enumerated (all possible combinations of the V & J domains for the kappa and lambda chains; V, D and J domains for the heavy chains). The BLAST searches were performed using an intranet application linked to the Sequence Information Retrieval and Analysis (SIRA) service provide by the National Center for Biotechnology Information (NCBI).

The closest human germline were identified with 70% and 67% sequence identity to anti-PAI1 A44 variable domain light and heavy chains, respectively. Using the internal VBASE germline sequences, the light chain was found to be close to V□I-018 (approximately 64% identity) locus and the heavy chain was close to 4-30 (approximately 69% identity) locus of the VH4 sub-family. CDR regions (based on Kabat) and Vernier residues are indicated in italics for mA44 light chain (A44LC) and for IGVK1-33-01_IGKJ4-01 (IGVK1). Vernier residues as defined in J. Mol. Biol., 1992, 224, 487 are underlined. The humanizing mutations (in boldface) were obtained by performing a pairwise comparison of the two aligned sequences, excluding the CDR & Vernier zone residues (also underlined in murine) as defined above. T46L and Q69T from the murine light chain and M2V in the murine heavy chain (Vernier zone residue) were mutated to the predominantly conserved human germline sequence as one part of the humanization by grafting approach (LC5a, HC5a). In another variant, these three Vernier zone residues were retained as seen in the original murine sequence (LC5b, HC5b).

```
mA44 - Light chain
                                      (SEQ ID NO: 141)
DIKMTQSPSS MYASLGERVT ITCKASQDIN SYLSWLQQKP

GKSPKTLIYR ANRSVDGVPS RFSGSGSGQD YSLTISSLEY

EDMGIYYCLQ YDEFPPTFGG GTKLEIK

IGKV1-33-01_IGKJ4-01
                                      (SEQ ID NO: 107)
DIQMTQSPSS LSASVGDRVT ITCQASQDIS NYLNWYQQKP

GKAPKLLIYD ASNLETGVPS RFSGSGSGTD FTFTISSLQP

EDIATYYCQQ YDNLPLTFGG GTKVEIK

MA44 - Heavy chain
                                      (SEQ ID NO: 140)
EMQLQESGPS LVKPSQTLSL TCSVTGDSMT NGYWNWIRKF

PGNKLEYMGY ITYSGSTYYN PSLKGRISIT RNTSKNQYYL

QLSSVTTEDT ATYYCARWHY GSPYYFDYWG QGTTLTVSS

IGHV4-59-02_IGHD6-13-0_IGHJ4-02
                                      (SEQ ID NO: 108)
QVQLQESGPG LVKPSETLSL TCTVSGGSVS SYYWSWIRQP

PGKGLEWIGY IYYSGSTNYN PSLKSRVTIS VDTSKNQFSL

KLSSVTAADT AVYYCARGYS SSWYYFDYWG QGTLVTVSS
```

The next closest human germline was identified with 59% and 58% sequence identity to anti-PAI1 A44 variable domain light and heavy chains, respectively. Using the internal VBASE germline, this light chain is found to be close to VκIII-L6 (~56% identity) locus and the heavy chain close to 6-01 locus of the VH6 sub-family. CDR regions (based on Kabat) and Vernier regions and are indicated in italics. Vernier regions (as defined in *J. Mol. Biol.,* 1992, 224, 487) and underlined. The humanizing mutations were obtained by performing a pairwise comparison of the 2 aligned sequences, excluding the CDR & Vernier zone residues (also underlined in murine) as defined above and are shown in boldface.

```
mA44 - Light Chain
                                      (SEQ ID NO: 141)
DIKMTQSPSS MYASLGERVT ITCKASQDIN SYLSWLQQKP

GKSPKTLIYR ANRSVDGVPS RFSGSGSGQD YSLTISSLEY

EDMGIYYCLQ YDEFPPTFGG GTKLEIK

IGKV3-11-02_IGKJ4-01
                                      (SEQ ID NO: 143)
EIVLTQSPAT LSLSPGERAT LSCRASQSVS SYLAWYQQKP

GQAPRLLIYD ASNRATGIPA RFSGSGSGRD FTLTISSLEP

EDFAVYYCQQ RSNWPLTFGG GTKVEIK mA44 - Heavy Chain
(SEQ ID NO: 140)
EMQLQESGPS LVKPSQTLSL TCSVTGDSMT N..GYWNWIR

KFPGNKLEYM GYIT..YSGS TYYNPSLKGR ISITRNTSKN

QYYLQLSSVT TEDTATYYCA RWHYGSPYYF DYWGQGTTLT

VSS
```

```
IGHV6-1-02_IGHD6-13-01_IGHJ4-02
                                      (SEQ ID NO: 144)
QVQLQQSGPG LVKPSQTLSL TCAISGDSVS SNSAAWNWIR

QSPSRGLEWL GRTYYRSKWY NDYAVSVKSR ITINPDTSKN

QFSLQLNSVT PEDTAVYYCA RGYSSSWYYF DYWGQGTLVT

VSS
```

4) Mutation of Unwanted Sequence Motifs

The following motifs of sequences were considered: Asp-Pro (acid labile bond), Asn-X-Ser/Thr (glycosylation, X=any amino-acid but Pro), Asp-Gly/Ser/Thr (succinimide/ iso-asp formation in flexible regions), Asn-Gly/His/Ser/Ala/ Cys (exposed deamidation sites), and Met (oxidation in exposed areas). The VL & VH domains of murine anti-PAI1 A44 possess two potential glycosylation sites: $N^{12}RS$ (in CDR2) in the LC and $N^{72}TS$ in the HC. One exposed deamidation site is present in CDR1 of the HC ($N^{31}G$). Three potential sites of succinimide formation were identified in the original murine sequence: $D^{56}G$ (end of CDR2) in the LC, and $D^{27}S$ (in CDR1) and $D^{89}T$ in the HC. The LC problematic motifs, $N^{12}RS$ and $D^{56}G$, are both in CDR2. Since these mutations occur in a CDR, they were addressed by mutation in two proposed engineered sequences below (LC2 and LC4). $N^{12}$ was conservatively mutated to Gln and $D^{56}$ was mutated to Glu. There are four existing problematic residues in the HC. The first two occur in CDR1: the potential succinimide formation site, $D^{27}S$, and the deamidation site $N^{31}G$. Two additional problematic motifs also occur in the third framework region. In CDR1, $D^{27}$ was mutated to an E to avoid the formation of succinimide, while $N^{31}$ was altered to a Q. $N^{72}$ and $D^{89}$ were altered to Q and E, respectively. These problematic motifs were addressed in engineered sequences HC2a and HC4 described below. The HC2b variant contains only the mutation of the $N^{31}G$ deamidation site.

The resulting humanized sequences were blasted for sequence similarity against the IEDB database (found on the world wide web at immuneepitope.com, version June 2009; Vita R., Zarebeski L., Greenbaum J. A., Emami H., Hoof I., Salimi N., Damle R., Sette A., Peters B. The immune epitope database 2.0 Nucleic Acids Res. 2010, January, 38 (Database issue):D854-62. Epub 2009, Nov. 11) to ensure that none of the sequences contain any known human B- or T-cell epitopes (sequence identity of 70% used as cut-off for the results obtained through BLAST search and considering only the results from human species). DeClerck, et al. (International Publication No. WO 2002034776) have disclosed antibody binding epitopes of PAI-1, none of which are problematic for the epitopes disclosed herein.

For the murine A44 LC, there is one human epitope from Kirschmann et al. (The Journal of Immunology, 1995, 155, 5655-5662). It possesses ~71% identity over a 14 amino acid stretch as seen below. The subject sequence was a partial sequence that had not been verified by mass spectrometry. No binding data is reported for this peptide. This epitope was seen in all the LC variants proposed. No potentially problematic epitopes were identified when a similar search was performed for the HC.

5) Original Sequences of Anti-PAI1 Variable Domains

CDRs are highlighted in bold and Vernier regions are (as defined by Foote & Winter, J. Mol. Biol., 1992, 224:487-499) are underlined.

Light Chain (SEQ ID NO: 142)
  1 DIKMTQSPSS MYASLGERVT ITCKASQDIN SYLSWLQQKP GKSPKTLIYR

51 ANRSVDGVPS RFS*GSGSG*QD YSLTISSLEY EDMGIYYCLQ YDEFPPTFGG

101 GTKLEIKRAD AAPTVSIF

Germinality index=70% with IGKV1-33-01_IGKJ4-01
[V☐I-O18]

Heavy Chain (SEQ ID NO: 140)
  1 EMQLQESGPS LVKPSQTLSL TCSVTGD*SMT* NGYWNWIRKF PGNKLE*YMG*Y

51 ITYSGSTYYN PSLKGR*IS*IT R*NT*SKN*QY*YL QLSSVTTEDT ATYYC*AR*WHY

101 GSPYYFDY*W*G QGTTLTVSS

Germinality index=67% with IGHV4-59-02_IGHD6-137-01_IGHJ4-02 [VH4 4-30]

Figure 16:
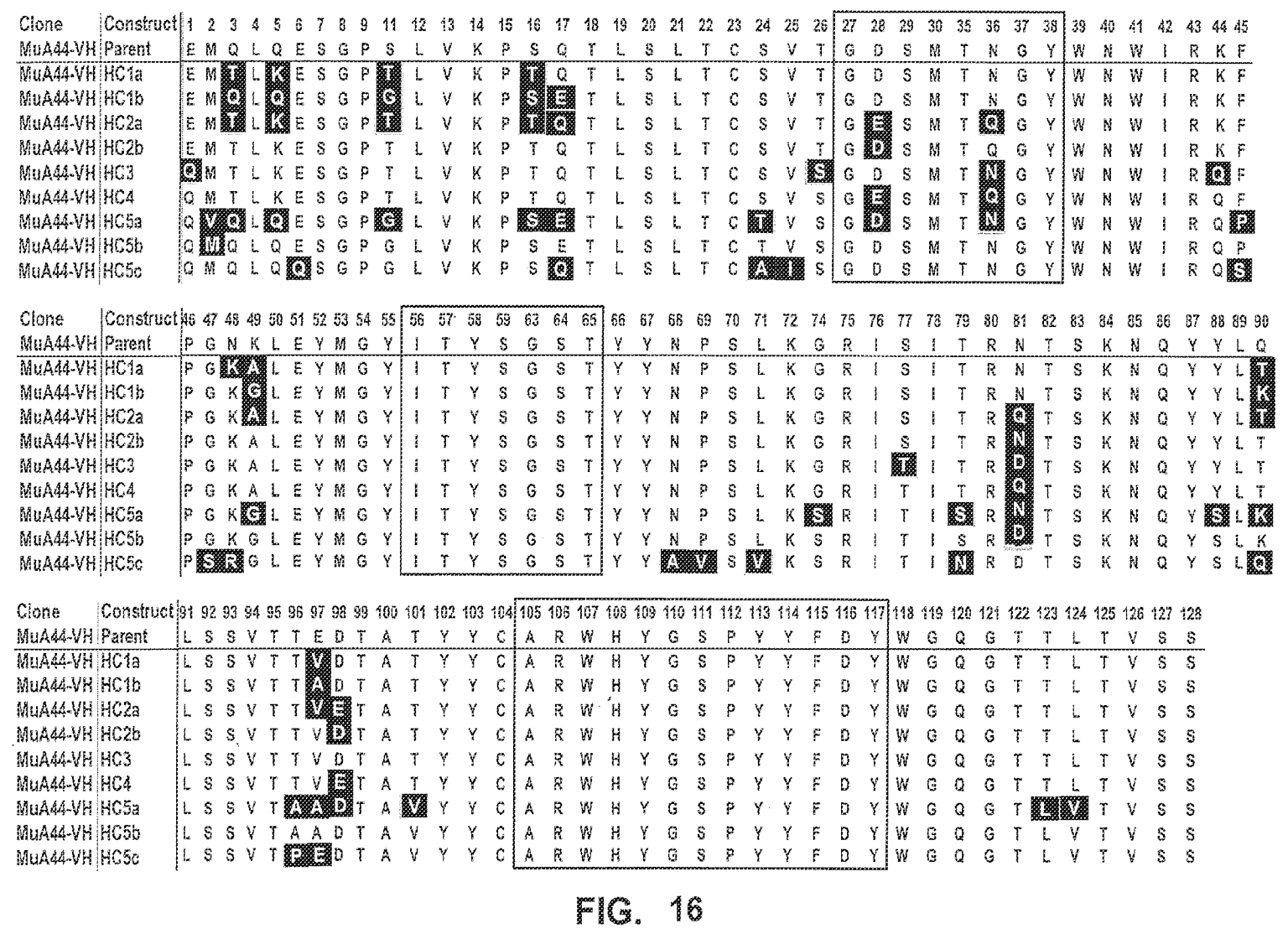
Figure 17:
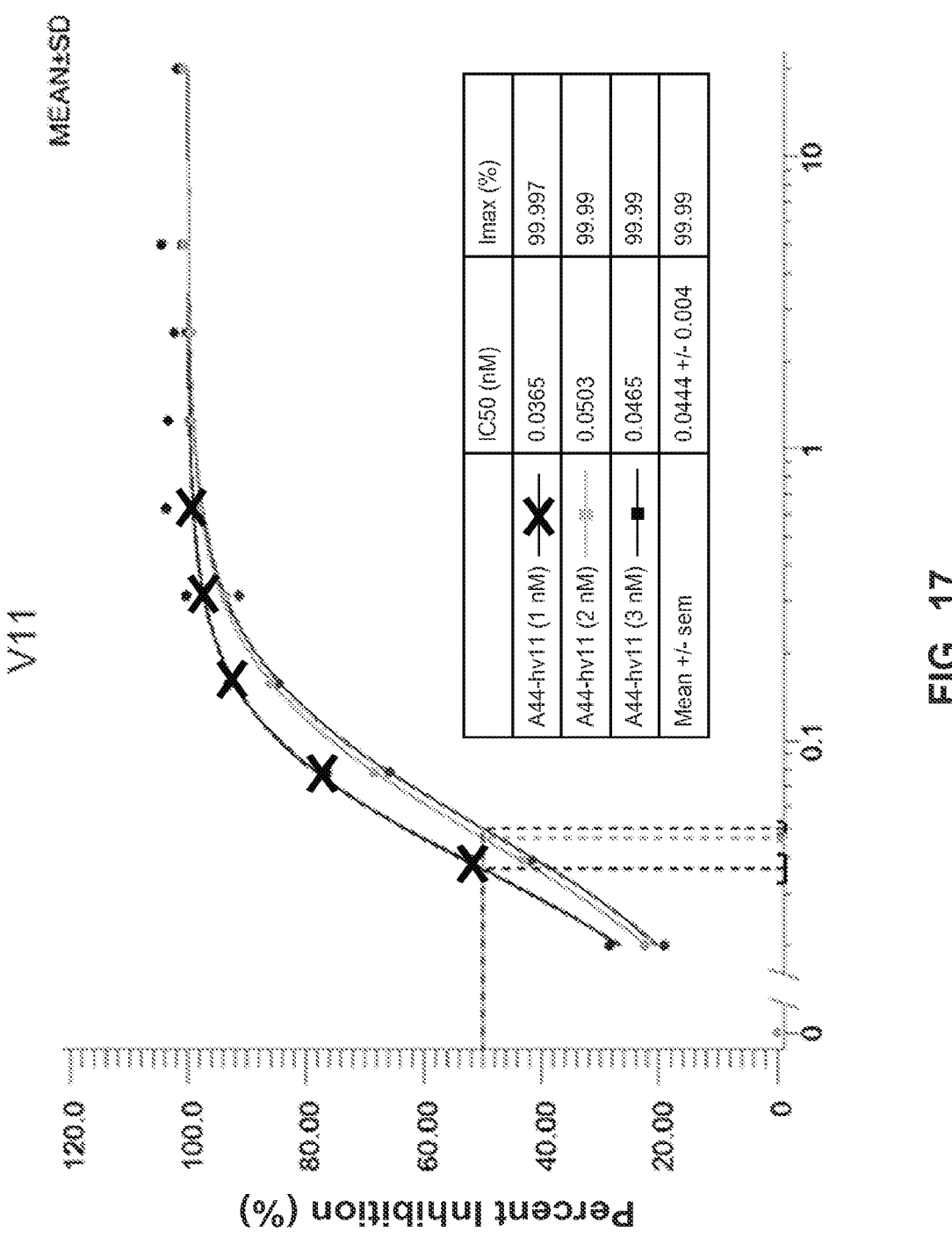
FIG. 17 depicts percent inhibition of PAI-1 activity was plotted as a function of mAb concentration and IC50 was determined Imax using Biostat speed software.
Figure 18:
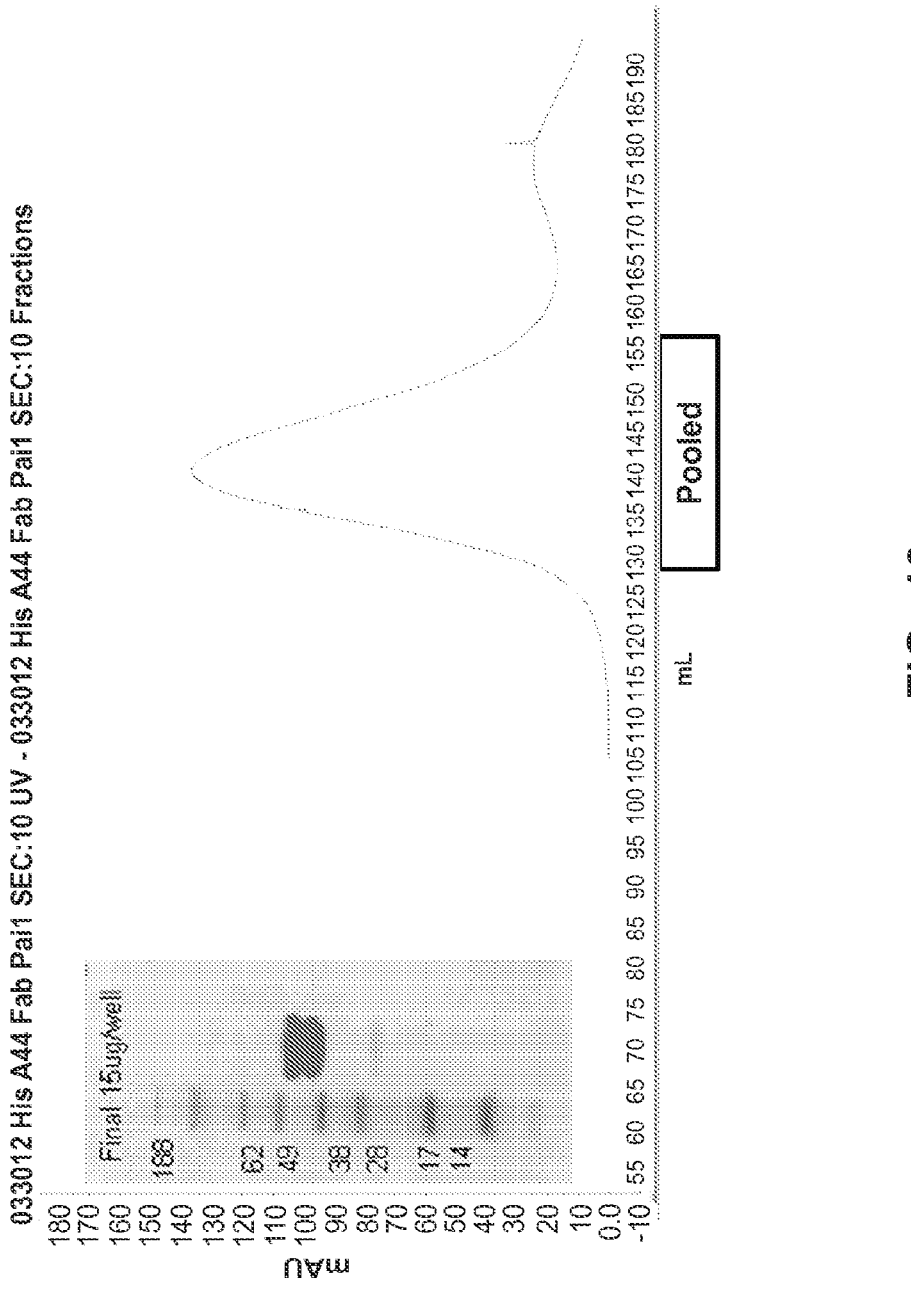
FIG. 18 depicts purification of homogeneity recombinant 6-His tagged Fab A44.

6) Engineered Sequences 4D humanization and grafting approaches were applied to the closest two human germline sequences a) Engineered Light Chain Sequences LC1a contains seven mutations derived from the 4D humanization method using the closest germline sequence, vk1. LC1b has 12 mutations derived from the 4D humanization to the second closest human germline sequence, vl3. LC2 contains 2 additional mutations in CDR2 as compared to LC1a. These mutations address a potential glycosylation site ($N^{52}RS$) and a potential site of succinimide formation ($D^{56}G$). LC3 contains the mutations from the 4D humanization to the closest germline sequence with an additional 2 stabilizing mutations. LC4 combines the humanizing, stabilizing and unwanted motif mutations. CDRs and vernier zones are in italics, vernier residues are underlined, humanizing mutations are in boldface, problematic motifs are in double strikethrough and stabilizing mutations are shown in lower case. FIGS. 16 and 17 show summaries of the mutations.

LC1a(SEQ ID NO: 91):
  1 D*I*K*M*TQSPSS LSASVGDRVT YTC*KASQDIN SYLSW*LQQKP GKSP*K*TLIYR

51 *ANRSVDGVPS* RFS*GSGSG*QD *YSLTISSL*QP EDLGIYYC*LQ YDEFPPT*FGG

101 GTKLEIK

No additional human epitopes for sequence LC1a found in IEDB database. LC1a germinality index=76% with IGKV1-33-01_IGKJ4-01 [VκI-O18].

LC1b (SEQ ID NO: 92):
  1 D*I*K*M*TQSPSS VSVSPGQTVT ITC*KASQDIN SYLSW*LQQKP GQSP*K*TLIYR

51 *ANRSVDGVPS* RFS*GSGSG*QD *YSLTISSL*QA* MDE**GIYYC*LQ YDEFPPT*FGG

101 GTKLTIK

In addition to the epitope described in section 4 above, K39PGQSPKTLI has 70% sequence identity to KPGQP-PRLLI (Kirschmann et al. J. Immun., 1995, 155, 5655-5662). This peptide is reported to have an IC50>100,000 nM against all the HLA-DR alleles for which it was tested. LC1b germinality index=67% with IGKV1-33-01_IGKJ4-01 [VκI-O18].

LC2 (SEQ ID NO: 93):
  1 D*I*K*M*TQSPSS LSASVGDRVT ITC*KASQDIN SYLSW*LQQKP GKSP*K*TLIYR

51 A̶*RS*V̶GVPS RFS*GSGSG*QD *YSLTISSL*QP* EDLGIYYC*LQ YDEFPPT*FGG

101 GTKLEIK

No additional human epitopes for sequence LC2 were found in IEDB database.
LC2 germinality index=76% with IGKV1-33-01_IGKJ4-01 [VκI-O18].

```
LC3 (SEQ ID NO: 94):
  1 DIKMTQSPSS LSASVGDRVT ITCKASQDIN SYLSWLQQKP GKSPKTLIYR
 51 ANRSVDGVPS RFSGSGSGQD YSLTISSLQP EDLatYYCLQ YDEFPPTFGG
101 GTKLEIK
```

No additional human epitopes for sequence LC3 were found in IEDB database. LC3 germinality index=78% with IGKV1-33-01_IGKJ4-01 [VκI-O18].

```
LC4 (SEQ ID NO: 95):
  1 DIKMTQSPSS LSASVGDRVT ITCKASQDIN SYLSWLQQKP GKSPKTLIYR

51 A-RSVGVPS RFSGSGSGQD YSLTISSLQP EDLatYYCLQ YDEFPPTFGG

101 GTKLEIK
```

No additional human epitopes for sequence LC4 were found in IEDB database. LC4 germinality index=78% with IGKV1-33-01_IGKJ4-01 [VκI-O18].

```
LC5a (SEQ ID NO: 96):
  1 DIQMTQSPSS LSASVGDRVT ITCKASQDIN SYLSWLQQKP GKAPKLLIYR

51 ANRSVDGVPS RFSGSGSGTD YTFTISSLQP EDIATYYCLQ YDEFPPTFGG

101 GTKVEIK
```

In addition to the epitope described in section 4 above, A43PKLLIYRAN has 80% sequence identity to APKLLI-YAASSL (Kirschmann et al. J. Immun., 1995, 155, 5655-5662). The molecular weight was not determined on this peptide and no binding data was reported. LC5a germinality index=85% with IGKV1-33-01_IGKJ4-01 [VκI-O18].

```
LC5b (SEQ ID NO: 97):
  1 DIQMTQSPSS LSASVGDRVT ITCKASQDIN SYLSWLQQKP GKAPKTLIYR

51 ANRSVDGVPS RFSGSGSGQD YTFTISSLQP EDIATYYCLQ YDEFPPTFGG

101 GTKVEIK
```

No additional human epitopes for sequence LC5b were identified in IEDB database.
LC5b germinality index=83% with IGKV1-33-01_IGKJ4-01 [VκI-O18].

```
LC5c (SEQ ID NO: 98):
  1   EIVMTQSPAT LSLSPGERAT LSCKASQDIN SYLSWLQQKP GQAPRTLIYR

51   ANRSVDGIPA RFSGSGSGQD YTLTISSLEP EDFAVYYCLQ YDEFPPTFGG

101   GTKVEIK
```

Figure 15:
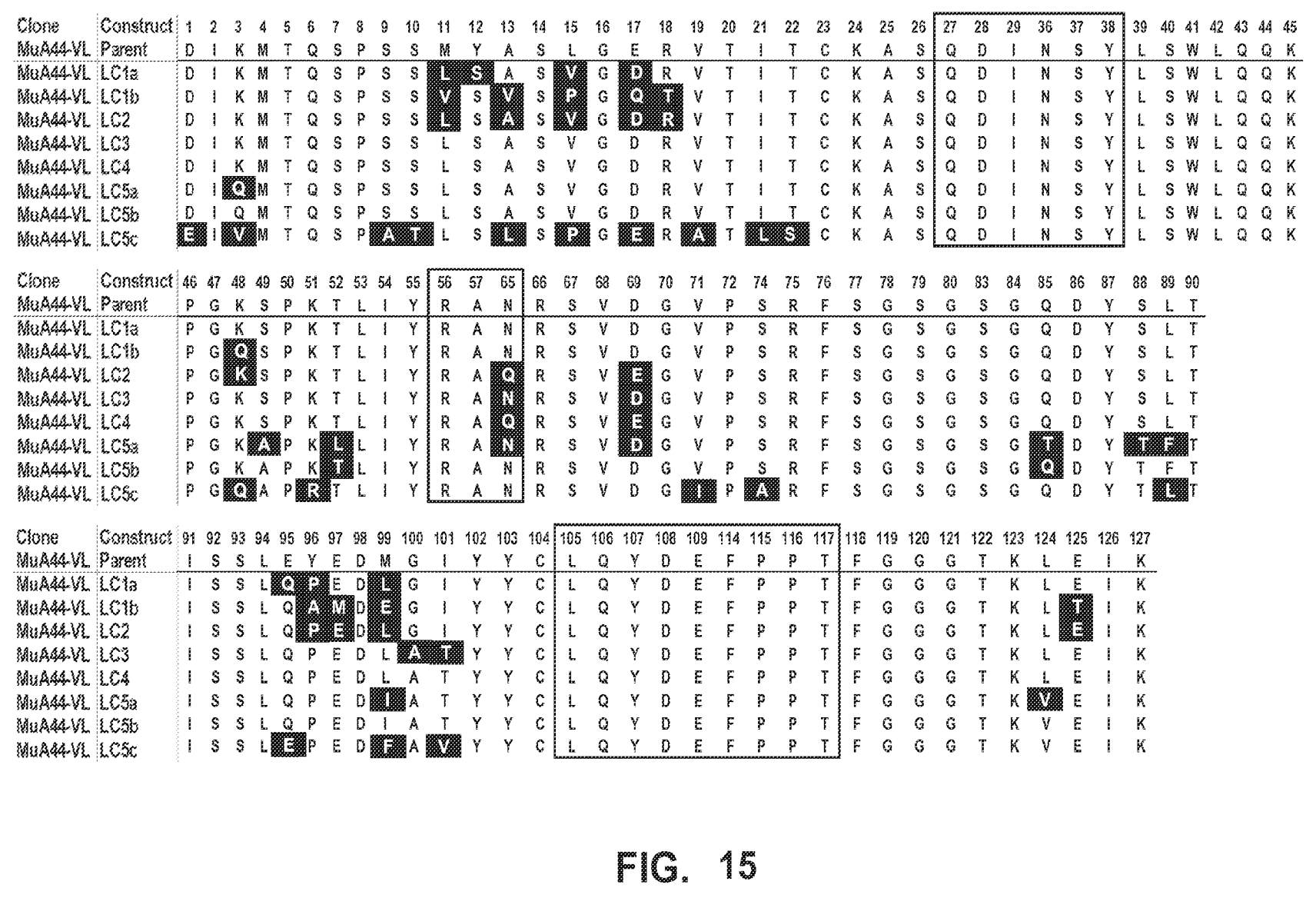

In addition to the epitope described in section 4 above, K$^{39}$PGQAPRTLI has 80% sequence identity to KPGQP-PRLLI (Kirschmann et al. J. Immun., 1995, 155, 5655-5662). This peptide is reported to have an IC50>100,000 nM against all the HLA-DR alleles for which it was tested. LC5c germinality index=79% with IGKV3-11-02_IGKJ4-01 [VκIII-L6]. A schematic of all light chain mutations is shown in FIG. 15.

b) Engineered Heavy Chain Sequences

HC1a contains eight mutations derived from the 4D humanization method to the closest human germline sequence. HC1b contains six mutations derived from the 4D humanization method to the $2^{nd}$ a closest germline sequence. HC2a contains four additional mutations when compared to HC1a to address unwanted sequence motifs. HC2b only addresses the deamidation site in CDR1 (N$^{31}$G). HC3 contains the humanizing mutations from HC1a with an additional five stabilizing mutations. HC4 contains humanizing mutations from HC1a, stabilizing mutations from HC3 and the mutations addressing problematic motifs from HC2a. CDRs and vernier zones are in italics, vernier residues are underlined, humanizing mutations are in boldface, problematic motifs are in double strikethrough and stabilizing mutations are shown in lower case.

HC1a (SEQ ID NO: 82):

```
  1    EMTLKESGPT LVKPTQTLSL TCSVTGDSMT NGYWNWIRKF PGKALEYMGY

51    ITYSGSTYYN PSLKGRISIT RNTSKNQYYL TLSSVTTVDT ATYYCARWHY

101    GSPYYFDYWG QGTTLTVSS
```

No human epitopes were identified for sequence HC1a in IEDB database. HC1a germinality index=68% with IGHV4-31-03_IGHD6-25-01_IGHJ4-02.

HC1b (SEQ ID NO: 83):

```
  1    EMQLQESGPG LVKPSETLSL TCSVTGDSMT NGYWNWIRKF PGKGLEYMGY

51    ITYSGSTYYN PSLKGRISIT RNTSKNQYYL KLSSVTTADT ATYYCARWHY

101    GSPYYFDYWG QGTTLTVSS
```

No human epitopes were identified for sequence HC1b in IEDB database. HC1b germinality index=73% with IGHV4-31-03 IGHD6-25-01 IGHJ4-02.

HC2a (SEQ ID NO: 84):

```
  1    EMTLKESGPT LVKPTQTLSL TCSVTGESMT QGYWNWIRKF PGKALEYMGY

51    ITYSGSTYYN PSLKGRISIT RQTSKNQYYL TLSSVTTVET ATYYCARWHY

101    GSPYYFDYWG QGTTLTVSS
```

No human epitopes were identified for sequence HC2a in IEDB database. HC2a germinality index=67% with IGHV4-31-03_IGHD6-25-01_IGHJ4-02.

HC2b (SEQ ID NO: 85):

```
  1    EMTLKESGPT LVKPTQTLSL TCSVTGDSMT QGYWNWIRKF PGKALEYMGY

51    ITYSGSTYYN PSLKGRISIT RNTSKNQYYL TLSSVTTVDT ATYYCARWHY

101    GSPYYFDYWG QGTTLTVSS
```

No human epitopes were identified for sequence HC2b in IEDB database. HC2b germinality index=67% with IGHV4-31-03_IGHD6-25-01_IGHJ4-02.

HC3 (SEQ ID NO: 86):

```
  1    qMTLKESGPT LVKPTQTLSL TCSVsGDSMT NGYWNWIRqF PGKALEYMGY

51    ITYSGSTYYN PSLKGRItIT RdTSKNQYYL TLSSVTTVDT ATYYCARWHY

101    GSPYYFDYWG QGTTLTVSS
```

No human epitopes were identified for sequence HC3 in IEDB database. HC3 germinality index=72% with IGHV4-31-03 IGHD6-25-01 IGHJ4-02.

```
HC4 (SEQ ID NO: 87):
    1    qMTLKESGPT LVKPTQTLSL TCSVsGESMT GGYWNWIRqF PGKALEYMGY

51    ITYSGSTYYN PSLKGRItIT MGTSKNQYYL TLSSVTTVST ATYYCARWHY

101    GSPYYFDYWG QGTTLTVSS
```

No human epitopes were identified for sequence HC4 in IEDB database. HC4 germinality index=70% with IGHV4-31-03_IGHD6-25-01_IGHJ4-02.

```
HC5a (SEQ ID NO: 88):
    1    QVQLQESGPG LVKPSETLSL TCTVSGDSMT NGYWNWIRQP PGKGLEYMGY

51    ITYSGSTYYN PSLKSRITIS RNTSKNQYSL KLSSVTAADT AVYYCARWHY

101    GSPYYFDYWG QGTLVTVSS
```

No human epitopes were identified for sequence HC5a in IEDB database. HC5a germinality index=84% with IGHV4-59-02_IGHD6-13-01_IGHJ4-02 [VH4 4-59].

```
HC5b (SEQ ID NO: 89):
    1    QMQLQESGPG LVKPSETLSL TCTVSGDSMT NGYWNWIRQP PGKGLEYMGY

51    ITYSGSTYYN PSLKSRITIS RDTSKNQYSL KLSSVTAADT AVYYCARWHY

101    GSPYYFDYWG QGTLVTVSS
```

No human epitopes were identified for sequence HC5b in IEDB database. HC5b germinality index=84% with IGHV4-59-02_IGHD6-13-01_IGHJ4-02 [VH4 4-59].

```
HC5c (SEQ ID NO: 90):
    1    QMQLQQSGPG LVKPSQTLSL TCAISGDSMT NGYWNWIRQS PSRGLEYMGY

51    ITYSGSTYYA VSVKSRITIN RDTSKNQYSL QLSSVTPEDT AVYYCARWHY

101    GSPYYFDYWG QGTLVTVSS
```

No human epitopes were identified for sequence HC5c in IEDB database. HC5c germinality index=78% with IGHV6-1-02_IGHD6-13-01_IGHJ4-02 [VH6 6-01].

A schematic of all heavy chain mutations is shown in FIG. 16.

c) Combinations of Heavy and Light Chain Variant Sequences

For grafting, three versions for the light chain (LC5a, LC5b, LC5c) and three versions of the heavy chain (HC5a, HC5b, HC5c) were created. LC5a contains 16 mutations derived from grafting to the closest human germline sequence and retaining the murine CDR and most of the murine Vernier zone residues. Two murine Vernier residues, T46 and N69 are not present in any human germline sequence and were conservatively mutated. LC5b contains 14 mutations derived from grafting to the closest human germline sequence and retained the murine CDR and all the murine Vernier zone residues. LC5c contains 22 mutations derived from grafting to the second closest human germline sequence and retained the murine CDR and all the murine Vernier zone residues.

HC5a contains 20 mutations derived from grafting to the closest human germline sequence and retained the murine CDR and most of the murine Vernier zone residues with the exception of M2V. Met occurs with a very low propensity at this position in human germline sequences. HC5b contains 20 mutations derived from grafting to the closest human germline sequence and retained the murine CDR and all the murine Vernier zone residues. HC5c contains 23 mutations derived from grafting to the second closest human germline sequence and retained the murine CDR and all the murine Vernier zone residues.

Ten combinations were prepared in total (summarized in Table 19):

LC1a×HC1a (mutations addressing 4D humanization based on the closest germline sequence)

LC1b×HC1b (mutations addressing 4D humanization based on the $2^{nd}$ a closest germline sequence)

LC2×HC2a (mutations addressing 4D humanization and unwanted sequences)

LC2×HC2b (mutations addressing 4D humanization and unwanted sequences)

LC1a×HC2b (mutations addressing 4D humanization and unwanted sequences)

LC3×HC3 (mutations addressing 4D humanization and stabilization)

LC4×HC4 (mutations addressing 4D humanizing, unwanted sequences and stabilization)

LC5a×HC5a (mutations addressing humanization by grafting retaining CDRs and incorporating 3 conservative Vernier modifications)

LC5b×HC5b (mutations addressing humanization by grafting retaining CDRs and Vernier regions)

LC5c×HC5c (mutations addressing humanization by grafting retaining CDRs and Vernier regions)

TABLE 19

Summary of the Ten LC × HC Combinations

|  | LC1a (H) | LC1b (H) | LC2 (H + UM) | LC3 (H + S) | LC4 (H + UM + S) | LC5a (G) | LC5b (G) | LC5c (G) |
|---|---|---|---|---|---|---|---|---|
| HC1a (H) | X(1) | | | | | | | |
| HC1b (H) | | X(2) | | | | | | |
| HC2a (H + UM) | | | X(3) Low | | | | | |
| HC2b (H + UM) | X(4) | | X(5) | | | | | |
| HC3 (H + S) | | | | X(11) | X(6) | X(12) | | |
| HC4 (H + UM + S) | | | | | X(7) Low | | | |
| HC5a (G) | | | | | | X(8) | | |
| HC5b (G) | | | X(13) | | X(14) | | X(9) | |
| HC5c (G) | | | | | | | | X(10) Low |

H = humanizing;
UM = unwanted motifs;
S = stabilizing;
G = grafting
Low = low expression levels
Number within the ( ) indicates the variant number;
note:
variants 11-14 were added following characterization of the original ten variants (variants 1-10)

TABLE 21

Mutations of the eight LC variants of the anti-PAI1 A44 antibody

| LC Sequential Numbering | LC1a (H) | LC1b (H) | LC2 (H − UM) | LC3 (H + S) | LC4 (H − UM + S) | LC5a (G) | LC5b (G) | LC5c (G) |
|---|---|---|---|---|---|---|---|---|
| Asp1 | | | | | | | | Glu |
| Lys3 | | | | | | Gln | Gln | Val |
| Ser9 | | | | | | | | Ala |
| Ser10 | | | | | | | | Thr |
| Met11 | Leu | Val | Leu | Leu | Leu | Leu | Leu | Leu |
| Tyr12 | Ser | Ser | Ser | Ser | Ser | Ser | Ser | Ser |
| Ala13 | | Val | | | | | | Leu |
| Leu15 | Val | Pro | Val | Val | Val | Val | Val | Pro |
| Glu17 | Asp | Gln | Asp | Asp | Asp | Asp | Asp | |
| Arg18 | | Thr | | | | | | |
| Val19 | | | | | | | | Ala |
| Ile21 | | | | | | | | Leu |
| Thr22 | | | | | | | | Ser |
| Lys42 | | Gln | | | | | | Gln |
| Ser43 | | | | | | Ala | Ala | Ala |
| Lys45 | | | | | | | | Arg |
| Thr46 | | | | | | Leu | | |
| Asn52 | | | Gln | | Gln | | | |
| Asp56 | | | Glu | | Glu | | | |
| Val58 | | | | | | | | He |
| Ser60 | | | | | | | | Ala |
| Gln69 | | | | | | Thr | | |
| Ser72 | | | | | | Thr | Thr | Thr |
| Leu73 | | | | | | Phe | Phe | |
| Glu79 | Gln | Gln | Gln | Gln | Gln | Gln | Gln | |
| Tyr80 | Pro | Ala | Pro | Pro | Pro | Pro | Pro | Pro |
| Glu81 | | Met | | | | | | |
| Met83 | Leu | Glu | Leu | Leu | Leu | He | He | Phe |
| Gly84 | | | | Ala | Ala | Ala | Ala | Ala |
| Ile85 | | Thr | | | Thr | Thr | Thr | Val |
| Leu104 | | | | | | Val | Val | Val |
| Glu105 | | Thr | | | | | | |
| Number of mutations | 7 | 12 | 9 | 9 | 11 | 16 | 14 | 22 |

H = humanizing;
UM = unwanted motifs;
S = stabilizing;
G = grafting

TABLE 22

Mutations of the nine HC variants of the anti-PAI1 A44 antibody

| HC Sequential Numbering | HC1a (H) | HC1b (H) | HC2a (H − UM) | HC2b (H − UM) | HC3 (H + S) | HC4 (H − UM + S) | HC5a (G) | HC5b (G) | HC5c (G) |
|---|---|---|---|---|---|---|---|---|---|
| Glu1 | | | | | Gln | Gln | Gln | Gln | Gln |
| Met2 | | | | | | | Val | | |
| Gln3 | Thr | | Thr | Thr | Thr | Thr | | | |
| Glu5 | Lys | | Lys | Lys | Lys | Lys | | | Gln |
| Ser10 | Thr | Gly | Thr | Thr | Thr | Thr | Gly | Gly | Gly |
| Ser15 | Thr | | Thr | Thr | Thr | Thr | | | |
| Gln16 | | Glu | | | | | Glu | Glu | |
| Ser23 | | | | | | | Thr | Thr | Ala |
| Val24 | | | | | | | | | He |
| Thr25 | | | | | Ser | Ser | Ser | Ser | Ser |
| Asp27 | | | Glu | | | Glu | | | |
| Asn31 | | | Gln | Gln | | Gln | | | |
| Lys39 | | | | | Gln | Gln | Gln | Gln | Gln |
| Phe40 | | | | | | | Pro | Pro | Ser |
| Gly42 | | | | | | | | | Ser |
| Asn43 | Lys | Lys | Lys | Lys | Lys | Lys | Lys | Lys | Arg |
| Lys44 | Ala | Gly | Ala | Ala | Ala | Ala | Gly | Gly | Gly |
| Asn60 | | | | | | | | | Ala |
| Pro61 | | | | | | | | | Val |

TABLE 22-continued

Mutations of the nine HC variants of the anti-PAI1 A44 antibody

| HC Sequential Numbering | HC1a (H) | HC1b (H) | HC2a (H – UM) | HC2b (H – UM) | HC3 (H + S) | HC4 (H – UM + S) | HC5a (G) | HC5b (G) | HC5c (G) |
|---|---|---|---|---|---|---|---|---|---|
| Leu63 | | | | | | | | | Val |
| Gly65 | | | | | | | Ser | Ser | Ser |
| Ser68 | | | | Thr | | Thr | Thr | Thr | Thr |
| Thr70 | | | | | | | Ser | Ser | Asn |
| Asn72 | | | Gln | | Asp | Gln | | Asp | Asp |
| Tyr79 | | | | | | | Ser | Ser | Ser |
| Gln81 | Thr | Lys | Thr | Thr | Thr | Thr | Lys | Lys | |
| Thr87 | | | | | | | Ala | Ala | Pro |
| Glu88 | Val | Ala | Val | Val | Val | Val | Ala | Ala | |
| Asp89 | | | Glu | | | Glu | | | |
| Thr92 | | | | | | | Val | Val | Val |
| Thr114 | | | | | | | Leu | Leu | Leu |
| Leu115 | | | | | | | Val | Val | Val |
| Number of mutations | 8 | 6 | 12 | 9 | 13 | 16 | 20 | 20 | 23 |

H = humanizing;
UM = unwanted motifs;
S = stabilizing;
G = grafting

In summary, ten variants were generated during the humanization process. These variants were expressed and characterized in several in vitro assays as described below.

7) Characterization of Humanization Variants

Based on the in silico modeling presented in the above example, ten variants were generated (variants 1-8 by 4D humanization and variants 9-10 by CDR grafting; variants 3 and 10 were created on the second closest germline). The variable region of the light chain and heavy chain DNA of humanized A44 were prepared for HEK293 expression. Proteins were generated after cloning the corresponding DNA into pXL plasmids (New England Biolabs; NheI/Eco47III for the HC, NheI/BsiWI for the LC). Humanized sequences were codon optimized for HEK expression and gene synthesized by GeneArt (subsidiary of Life Technologies). The resulting plasmids were co-transfected and transiently expressed in FreeStyle™293 Expression System (Invitrogen, Cat #K9000-01). Variants 3 and 10 were very poorly expressed and were not further pursued. All other variants were expressed and purified using Protein A columns. Analytical gels showed partial glycosylation (about 5-10%) of the light chains in variants 6 and 9 and heavy chains in variants 5 and 7 (data not shown). The remaining eight variants were tested in the chromogenic assay using hPAI and plasmin generation assay in human stellate cells using human glycosylated PAT. Results are shown in Table 23.

TABLE 23

Characterization of humanization variants in plasmin generation and chromogenic assay

| mAb | Plasminogen Activation | | Chromogenic Assay |
|---|---|---|---|
| | IC50 (nM) | Y50% | IC50 (nM) |
| A44 | 3.17 | 45.99 | 0.44 |
| A44-hv1 | 3.12 | 44.99 | 0.49 |
| A44-hv2 | Not determined | Not determined | 0.60 |
| A44-hv4 | Inactive | 26.00 | 0.52 |
| A44-hv5 | Not determined | Not determined | 1.11 |
| A44-hv6 | 1.78 | 56.94 | 0.82 |
| A44-hv7 | Not determined | Not determined | 0.59 |

TABLE 23-continued

Characterization of humanization variants in plasmin generation and chromogenic assay

| mAb | Plasminogen Activation | | Chromogenic Assay |
|---|---|---|---|
| | IC50 (nM) | Y50% | IC50 (nM) |
| A44-hv8 | Inactive | 11.00 | 0.76 |
| A44-hv9 | 1.9 | 46.53 | 0.86 |

Variants 6 and 9 showed the best potency in the plasmin generation assay but had partial (5-10%) glycosylation in the light chain. Based on these results, new variants 11-14 were produced using combinations of heavy chains from variants 6 and 9 and light chains from variants 5 and 7. Table 24 summarizes all the variants created.

TABLE 24

Humanization variants

| Variant # | Description | SEQ ID NOs |
|---|---|---|
| A44-hv1 | LC1a × HC1a | 109 |
| A44-hv2 | LC1b × HC1b | 110 |
| A44-hv3 | LC2 × HC2a | 111 |
| A44-hv4 | LC1a × HC2b | 112 |
| A44-hv5 | LC2 × HC2b | 113 |
| A44-hv6 | LC3 × HC3 | 114 |
| A44-hv7 | LC4 × HC4 | 115 |
| A44-hv8 | LC5a × HC5a | 116 |
| A44-hv9 | LC5b × HC5b | 117 |
| A44-hv10 | LC5c × HC5c | 118 |
| A44-hv11 | LC2 × HC3 | 119 |
| A44-hv12 | LC4 × HC3 | 120 |
| A44-hv13 | LC2 × HC5b | 121 |
| A44-hv14 | LC4 × HC5b | 122 |

TABLE 25

| | DNA Sequence Humanization variants | |
| --- | --- | --- |
| | Gene | Protein |
| HC1a | GAGATGACCCTGAAAGAGTCCGGCCCCACCCTGG<br>TCAAACCCACCCAGACCCTGAGCCTGACCTGCAG<br>CGTGACCGGCGACAGCATGACCAACGGCTACTGG<br>AACTGGATCCGGAAGTTCCCCGGCAAGGCCCTCG<br>AGTACATGGGCTACATCACCTACAGCGGCAGCAC<br>CTACTACAACCCCAGCCTGAAGGGCCGGATCAGC<br>ATCACCCGGAACACCAGCAAGAACCAGTACTACC<br>TGACCCTGTCCAGCGTG<br>(SEQ ID NO: 123) | EMTLKESGPTLVKPTQTLSL<br>TCSVTGDSMTNGYWNWIRK<br>FPGKALEYMGYITYSGSTYY<br>NPSLKGRISITRNTSKNQYYL<br>TLSSVTTVDTATYYCARWH<br>YGSPYYFDYWGQGTTLTVSS<br>(SEQ ID NO: 82) |
| HC1b | GAGATGCAGCTGCAGGAAAGCGGCCCTGGCCTG<br>GTCAAACCCAGCGAGACACTGAGCCTGACCTGCA<br>GCGTGACCGGCGACAGCATGACCAACGGCTACTG<br>GAACTGGATCCGGAAGTTCCCCGGCAAGGGCCTC<br>GAGTACATGGGCTACATCACCTACAGCGGCAGCA<br>CCTACTACAACCCCAGCCTGAAGGGCCGGATCAG<br>CATCACCCGGAACACCAGCAAGAACCAGTACTAC<br>CTGAAGCTGTCCAGCGTG<br>(SEQ ID NO: 124) | EMQLQESGPGLVKPSETLSL<br>TCSVTGDSMTNGYWNWIRK<br>FPGKGLEYMGYITYSGSTYY<br>NPSLKGRISITRNTSKNQYYL<br>KLSSVTTADTATYYCARWH<br>YGSPYYFDYWGQGTTLTVSS<br>(SEQ ID NO: 83) |
| HC2a | GAGATGACCCTGAAAGAGTCCGGCCCCACCCTGG<br>TCAAACCCACCCAGACCCTGAGCCTGACCTGCAG<br>CGTGACCGGCGAGAGCATGACCCAGGGCTACTGG<br>AACTGGATCCGGAAGTTCCCCGGCAAGGCCCTCG<br>AGTACATGGGCTACATCACCTACAGCGGCAGCAC<br>CTACTACAACCCCAGCCTGAAGGGCCGGATCAGC<br>ATCACCCGGCAGACCAGCAAGAACCAGTACTACC<br>TGACCCTGTCCAGCGTG<br>(SEQ ID NO: 125) | EMTLKESGPTLVKPTQTLSL<br>TCSVTGESMTQGYWNWIRK<br>FPGKALEYMGYITYSGSTYY<br>NPSLKGRISITRQTSKNQYYL<br>TLSSVTTVETATYYCARWH<br>YGSPYYFDYWGQGTTLTVSS<br>(SEQ ID NO: 84) |
| HC2b | GAGATGACCCTGAAAGAGTCCGCCCCCACCCTGG<br>TCAAACCCACCCAGACCCTGAGCCTGACCTGCAG<br>CGTGACCGGCGACAGCATGACCCAGGGCTACTGG<br>AACTGGATCCGGAAGTTCCCCGGCAAGGCCCTCG<br>AGTACATGGGCTACATCACCTACAGCGGCAGCAC<br>CTACTACAACCCCAGCCTGAAGGGCCGGATCAGC<br>ATCACCCGGAACACCAGCAAGAACCAGTACTACC<br>TGACCCTGTCCAGCGTG<br>(SEQ ID NO: 126) | EMTLKESGPTLVKPTQTLSL<br>TCSVTGDSMTQGYWNWIRK<br>FPGKALEYMGYITYSGSTYY<br>NPSLKGRISITRNTSKNQYYL<br>TLSSVTTVDTATYYCARWH<br>YGSPYYFDYWGQGTTLTVSS<br>(SEQ ID NO: 85) |
| HC3 | CAGATGACCCTGAAAGAGTCCGGCCCCACCCTGG<br>TCAAACCCACCCAGACCCTGAGCCTGACCTGCAG<br>CGTGTCCGGCGACAGCATGACCAACGGCTACTGG<br>AACTGGATCCGGCAGTTCCCCGGCAAGGCCCTCG<br>AGTACATGGGCTACATCACCTACAGCGGCAGCAC<br>CTACTACAACCCCAGCCTGAAGGGCCGGATCACC<br>ATCACCCGGGACACCAGCAAGAACCAGTACTACC<br>TGACCCTGAGCAGCGTG<br>(SEQ ID NO: 127) | QMTLKESGPTLVKPTQTLSL<br>TCSVSGDSMTNGYWNWIRQ<br>FPGKALEYMGYITYSGSTYY<br>NPSLKGRITITRDTSKNQYYL<br>TLSSVTTVDTATYYCARWH<br>YGSPYYFDYWGQGTTLTVSS<br>(SEQ ID NO: 86) |
| HC4 | CAGATGACCCTGAAAGAGTCCGGCCCCACCCTGG<br>TCAAACCCACCCAGACCCTGAGCCTGACCTGCAG<br>CGTGTCCGGCGAGAGCATGACCCAGGGCTACTGG<br>AACTGGATCCGGCAGTTCCCCGGCAAGGCCCTCG<br>AGTACATGGGCTACATCACCTACAGCGGCAGCAC<br>CTACTACAACCCCAGCCTGAAGGGCCGGATCACC<br>ATCACCCGGCAGACCAGCAAGAACCAGTACTACC<br>TGACCCTGAGCAGCGTG<br>(SEQ ID NO: 128) | QMTLKESGPTLVKPTQTLSL<br>TCSVSGESMTQGYWNWIRQ<br>FPGKALEYMGYITYSGSTYY<br>NPSLKGRITITRQTSKNQYYL<br>TLSSVTTVETATYYCARWH<br>YGSPYYFDYWGQGTTLTVSS<br>(SEQ ID NO: 87) |
| HC5a | CAGGTGCAGCTGCAGGAAAGCGGCCCTGGCCTGG<br>TCAAACCCAGCGAGACACTGAGCCTGACCTGCAC<br>CGTGTCCGGCGACAGCATGACCAACGGCTACTGG<br>AACTGGATCCGGCAGCCCCCTGGCAAGGGCCTCG<br>AGTACATGGGCTACATCACCTACAGCGGCAGCAC<br>CTACTACAACCCCAGCCTGAAGTCCCGGATCACC<br>ATCAGCCGGAACACCAGCAAGAACCAGTACAGC<br>CTGAAGCTGAGCAGCGTG<br>(SEQ ID NO: 129) | QVQLQESGPGLVKPSETLSL<br>TCTVSGDSMTNGYWNWIRQ<br>PPGKGLEYMGYITYSGSTYY<br>NPSLKSRITISRNTSKNQYSL<br>KLSSVTAADTAVYYCARWH<br>YGSPYYFDYWGQGTLVTVSS<br>(SEQ ID NO: 88) |
| HC5b | CAGATGCAGCTGCAGGAAAGCGGCCCTGGCCTGG<br>TCAAACCCAGCGAGACACTGAGCCTGACCTGCAC<br>CGTGTCCGGCGACAGCATGACCAACGGCTACTGG<br>AACTGGATCCGGCAGCCCCCTGGCAAGGGCCTCG<br>AGTACATGGGCTACATCACCTACAGCGGCAGCAC<br>CTACTACAACCCCAGCCTGAAGTCCCGGATCACC | QMQLQESGPGLVKPSETLSL<br>TCTVSGDSMTNGYWNWIRQ<br>PPGKGLEYMGYITYSGSTYY<br>NPSLKSRITISRDTSKNQYSL<br>KLSSVTAADTAVYYCARWH<br>YGSPYYFDYWGQGTLVTVSS |

TABLE 25-continued

| DNA Sequence Humanization variants | | |
|---|---|---|
| | ATCAGCCGGGACACCAGCAAGAACCAGTACAGC<br>CTGAAGCTGAGCAGCGTG<br>(SEQ ID NO: 130) | (SEQ ID NO: 89) |
| HC5c | CAGATGCAGCTGCAGCAGAGCGGCCCTGGCCTGG<br>TCAAACCCAGCCAGACCCTGAGCCTGACCTGCGC<br>CATCAGCGGCGACAGCATGACCAACGGCTACTGG<br>AACTGGATCCGGCAGAGCCCCAGCAGAGGCCTCG<br>AGTACATGGGCTACATCACCTACAGCGGCAGCAC<br>CTACTACGCCGTGTCCGTGAAGTCCCGGATCACC<br>ATCAACCGGGACACCAGCAAGAACCAGTACAGC<br>CTGCAGCTGAGCAGCGTG<br>(SEQ ID NO: 131) | QMQLQQSGPGLVKPSQTLSL<br>TCAISGDSMTNGYWNWIRQ<br>SPSRGLEYMGYITYSGSTYY<br>AVSVKSRITINRDTSKNQYSL<br>QLSSVTPEDTAVYYCARWH<br>YGSPYYFDYWGQGTLVTVSS<br>(SEQ ID NO: 90) |
| LC1a | GACATCAAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGAGCCCCAAG<br>ACCCTGATCTACCGGGCCAACCGCAGCGTGGACG<br>GCGTGCCAAGCAGATTTTCCGGCAGCGGCAGCGG<br>CCAGGACTACAGCCTGACCATCAGCAGCCTGCAG<br>CCCGAGGACCTGGGCATC<br>(SEQ ID NO: 132) | DIKMTQSPSSLSASVGDRVTI<br>TCKASQDINSYLSWLQQKPG<br>KSPKTLIYRANRSVDGVPSRF<br>SGSGSGQDYSLTISSLQPEDL<br>GIYYCLQYDEFPPTFGGGTK<br>LEIK<br>(SEQ ID NO: 91) |
| LC1b | GACATCAAGATGACCCAGAGCCCCAGCAGCGTGT<br>CCGTGTCTCCTGGCCAGACCGTGACCATCACATG<br>CAAGGCCAGCCAGGACATCAACAGCTACCTGAGC<br>TGGCTGCAGCAGAAGCCCGGCCAGTCCCCCAAGA<br>CCCTGATCTACCGGGCCAACCGCAGCGTGGACGG<br>CGTGCCAAGCAGATTTTCCGGCAGCGGCAGCGGC<br>CAGGACTACAGCCTGACCATCAGCAGCCTGCAGG<br>CCATGGACGAGGGCATC<br>(SEQ ID NO: 133) | DIKMTQSPSSVSVSPGQTVTI<br>TCKASQDINSYLSWLQQKPG<br>QSPKTLIYRANRSVDGVPSRF<br>SGSGSGQDYSLTISSLQAMD<br>EGIYYCLQYDEFPPTFGGGT<br>KLTIK<br>(SEQ ID NO: 92) |
| LC2 | GACATCAAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGAGCCCCAAG<br>ACCCTGATCTACCGGGCCAGCGGAGCGTGGAAG<br>GCGTGCCAAGCAGATTCAGCGGCAGCGGCTCCGG<br>CCAGGACTACAGCCTGACCATCAGCAGCCTGCAG<br>CCCGAGGACCTGGGCATC<br>(SEQ ID NO: 134) | DIKMTQSPSSLSASVGDRVTI<br>TCKASQDINSYLSWLQQKPG<br>KSPKTLIYRAQRSVEGVPSRF<br>SGSGSGQDYSLTISSLQPEDL<br>GIYYCLQYDEFPPTFGGGTK<br>LEIK<br>(SEQ ID NO: 93) |
| LC3 | GACATCAAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGAGCCCCAAG<br>ACCCTGATCTACCGGGCCAACCGCAGCGTGGACG<br>GCGTGCCAAGCAGATTTTCCGGCAGCGGCAGCGG<br>CCAGGACTACAGCCTGACCATCAGCAGCCTGCAG<br>CCCGAGGACCTGGCCACC<br>(SEQ ID NO: 135) | DIKMTQSPSSLSASVGDRVTI<br>TCKASQDINSYLSWLQQKPG<br>KSPKTLIYRANRSVDGVPSRF<br>SGSGSGQDYSLTISSLQPEDL<br>ATYYCLQYDEFPPTFGGGTK<br>LEIK<br>(SEQ ID NO: 94) |
| LC4 | GACATCAAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGAGCCCCAAG<br>ACCCTGATCTACCGGGCCCAGCGGAGCGTGGAAG<br>GCGTGCCAAGCAGATTCAGCGGCAGCGGCTCCGG<br>CCAGGACTACAGCCTGACCATCAGCAGCCTGCAG<br>CCCGAGGACCTGGCCACC<br>(SEQ ID NO: 136) | DIKMTQSPSSLSASVGDRVTI<br>TCKASQDINSYLSWLQQKPG<br>KSPKTLIYRAQRSVEGVPSRF<br>SGSGSGQDYSLTISSLQPEDL<br>ATYYCLQYDEFPPTFGGGTK<br>LEIK<br>(SEQ ID NO: 95) |
| LC5a | GACATCCAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGGCCCCCAAG<br>CTGCTGATCTACCGGGCCAACCGCAGCGTGGACG<br>GCGTGCCAAGCAGATTTTCCGGCAGCGGCTCCGG<br>CACCGACTACACCTTCACCATCAGCAGCCTGCAG<br>CCCGAGGATATCGCCACC<br>(SEQ ID NO: 137) | DIQMTQSPSSLSASVGDRVTI<br>TCKASQDINSYLSWLQQKPG<br>KAPKLLIYRANRSVDGVPSR<br>FSGSGSGTDYTFTISSLQPEDI<br>ATYYCLQYDEFPPTFGGGTK<br>VEIK<br>(SEQ ID NO: 96) |
| LC5b | GACATCCAGATGACCCAGAGCCCCAGCAGCCTGA<br>GCGCCAGCGTGGGCGACAGAGTGACCATCACATG<br>CAAGGCCAGCCAGGACATCAACAGCTACCTGAGC<br>TGGCTGCAGCAGAAGCCCGGCAAGGCCCCCAAG | DIQMTQSPSSLSASVGDRVTI<br>TCKASQDINSYLSWLQQKPG<br>KAPKTLIYRANRSVDGVPSR<br>FSGSGSGQDYTFTISSLQPEDI |

TABLE 25-continued

| DNA Sequence Humanization variants |
| --- |

|  | ACCCTGATCTACCGGGCCAACCGCAGCGTGGACG<br>GCGTGCCAAGCAGATTTTCCGGCAGCGGCAGCGG<br>CCAGGACTACACCTTCACCATCAGCAGCCTGCAG<br>CCCGAGGATATCGCCACC<br>(SEQ ID NO: 138) | ATYYCLQYDEFPPTFGGGTK<br>VEIK<br>(SEQ ID NO: 97) |
| --- | --- | --- |
| LC5c | GAGATCGTGATGACCCAGAGCCCCGCCACCCTGT<br>CTCTGAGCCCTGGCGAGAGAGCCACCCTGAGCTG<br>CAAGGCCAGCCAGGACATCAACAGCTACCTGAGC<br>TGGCTGCAGCAGAAGCCCGGCCAGGCCCCCAGA<br>ACCCTGATCTACCGGGCCAACAGAAGCGTGGACG<br>GCATCCCCGCCAGATTCAGCGGCAGCGGCTCCGG<br>CCAGGACTACACCCTGACCATCAGCAGCCTGGAA<br>CCCGAGGACTTCGCCGTG<br>(SEQ ID NO: 139) | EIVMTQSPATLSLSPGERATL<br>SCKASQDINSYLSWLQQKPG<br>QAPRTLIYRANRSVDGIPARF<br>SGSGSGQDYTLTISSLEPEDF<br>AVYYCLQYDEFPPTFGGGTK<br>VEIK<br>(SEQ ID NO: 98) |

| Protein |
| --- |

| CH | ASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPEL<br>LGGPSVFLFPPKPKDTLMISRTPEVTCVVVDVSHEDPEVKFNWYVDGVEVHNAKTKP<br>REEQYNSTYRVVSVLTVLHQDWLNGKEYKCKVSNKALPAPIEKTISKAKGQPREPQV<br>YTLPPSRDELTKNQVSLTCLVKGF (SEQ ID NO: 99) |
| --- | --- |
| CL | RTVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC<br>(SEQ ID NO: 100) |

All variants, except poorly expressed variants 3 and 10, were tested in Biacore against human and cyno PAI-1 and Vitronectin-PAI-1 complex. The data is presented in Table 26.

TABLE 26

| Characterization of humanization variants in a Biacore | | | |
| --- | --- | --- | --- |
|  | ka1 (1/Ms) | kd 1 (1/s) | KD (M) |
| Vitronectin Chip/Human PAI-1 | | | |
| mAb/hPAI-1/Vn | | | |
| A44 parental* | 5.68E+06 | 2.29E−04 | 4.04E−11 |
| A44-hv1* | 1.10E+07 | 5.55E−04 | 5.26E−11 |
| A44-hv2** | 2.99E+06 | 4.03E−04 | 1.35E−10 |
| A44-hv4* | 4.59E+06 | 8.80E−05 | 1.92E−11 |
| A44-hv5* | 2.72E+06 | 2.76E−05 | 1.02E−11 |
| A44-hv6* | 4.38E+06 | 5.68E−05 | 1.33E−11 |
| A44-hv7** | 4.14E+06 | 3.94E−04 | 9.64E−11 |
| A44-hv8* | n/a | n/a | n/a |
| A44-hv9* | 6.36E+06 | 1.03E−04 | 1.70E−11 |
| A44-hv11* | 7.66E+06 | 1.22E−04 | 1.56E−11 |
| A44-hv12* | 5.15E+06 | 8.14E−05 | 1.61E−11 |
| A44-hv13** | 2.40E+06 | 4.36E−04 | 1.79E−10 |
| A44-hv14* | 4.06E+06 | 3.95E−05 | 9.57E−12 |
| Vitronectin Chip/Cyno PAI-1 | | | |
| mAb/cPAI-1/Vn | | | |
| A44 parental* | 3.98E+06 | 2.75E−04 | 6.96E−11 |
| A44-hv1** | 3.37E+06 | 8.27E−03 | 2.45E−09 |
| A44-hv2** | 2.30E+06 | 3.14E−04 | 1.37E−10 |
| A44-hv4** | 2.26E+05 | 1.70E−04 | 7.52E−10 |
| A44-hv5* | 3.40E+06 | 1.11E−04 | 3.26E−11 |
| A44-hv6* | 5.26E+06 | 2.51E−05 | 5.01E−12 |
| A44-hv7** | 2.50E+06 | 2.39E−04 | 9.56E−11 |
| A44-hv8* | n/a | n/a | n/a |
| A44-hv9* | 6.51E+06 | 1.34E−04 | 2.15E−11 |
| A44-hv11** | 1.56E+06 | 6.00E−04 | 3.87E−10 |
| A44-hv12* | 4.26E+06 | 2.35E−04 | 5.69E−11 |
| A44-hv13** | 2.12E+06 | 2.43E−04 | 1.15E−10 |
| A44-hv14* | 5.86E+06 | 2.13E−04 | 3.86E−11 |

TABLE 26-continued

| Characterization of humanization variants in a Biacore | | | |
| --- | --- | --- | --- |
|  | ka1 (1/Ms) | kd 1 (1/s) | KD (M) |
| Anti-human IgG Fc chip/human PAI-1 | | | |
| mAb/hPAI-1* | | | |
| A44-hv11/hPAI-1 | 1.57E+06 | 6.68E−05 | 4.25E−11 |
| A44-hv12/hPAI-1 | 1.62E+06 | 6.70E−05 | 4.14E−11 |
| A44-hv13/hPAI-1 | 1.54E+06 | 2.52E−05 | 1.64E−11 |
| A44-hv14/hPAI-1 | 1.25E+06 | 3.42E−05 | 2.70E−11 |
| Anti-human IgG Fc chip/cyno PAI-1 | | | |
| mAb/cPAI-1* | | | |
| A44-hv11/hPAI-1 | 1.87E+06 | 5.60E−05 | 3.00E−11 |
| A44-hv12/hPAI-1 | 2.24E+06 | 5.45E−05 | 2.44E−11 |
| A44-hv13/hPAI-1 | 1.89E+06 | 5.08E−05 | 2.70E−11 |
| A44-hv14/hPAI-1 | 2.32E+06 | 2.69E−05 | 1.15E−11 | n/a means the variant did not bind effectively to vitronectin/PAI-1 complex

*1:1 molecular interaction model

**Two state reaction (conformation change) model

Biacore data did not reveal significant differences between humanized variants. All humanized variants, except variant 8, showed affinity to both cyno PAI-1 and human PAI-1 and PAI-1 complexed to vitronectin within an acceptable range. In comparison to parental A44, humanization did not appear to change antibody affinity.

Although affinity and potency of the humanized variants didn't differ significantly in the chromogenic and Biacore assays, the ability of the variants to restore plasmin generation in the cellular assays was significantly lower than parental mouse antibody for some variants (see Table 27 summarizing comparison of chromogenic assay and cellular assay below). Humanized variants 11-14 were tested for the ability to block PAI-1 in the cellular assay.

TABLE 27

Characterization of humanization variants
11-14 in plasmin generation

| mAb | IC50 (nM) | Y50% | n |
|---|---|---|---|
| | | Plasminogen Activation | |
| A44 | 3.13 | 79.79 | 6 |
| A44-hv11 | 2.01 | 85.82 | 6 |
| A44-hv12 | 1.99 | 76.70 | 6 |
| A44-hv13 | 1.82 | 71.10 | 6 |
| A44-hv14 | 1.82 | 61.22 | 6 |
| A44-hv9 | 1.51 | 50.92 | 4 |
| A44-hv1 | 2.08 | 58.50 | 2 |

Variants 11 through 14 showed good potency in the plasmin generation assay and were further characterized in additional in vitro assays.

8) Characterization of Humanization Variants in Human Liver

Additional screening of the humanized variants 11-14 was performed using endogenously produced human PAI-1 from human plasma and human fibrotic liver samples.

PAI-1 activity was evaluated by measuring the ability of this serpin to form a stable complex with urokinase immobilized on 96 well plates. After washing unbound PAI-1, uPA-PAI-1 complexes were detected by the use of polyclonal antiPAI-1 antibodies. The bound polyclonal anti-PAI-1 antibodies (which is proportional to active PAI-1 in the sample) was then detected by using a horseradish peroxidase conjugated secondary antibody (Molecular Innovation Cat. No. HPAIKT). Various concentrations of A44 humanized variants were incubated for 15 minutes at room temperature with either human or cynomolgus recombinant PAI-1 (0.31 nM final concentration) and then tested for functional active PAI-1 by uPA-PAI-1 complex using the ELISA described above. Samples were compared to a human PAI-1 standard. Human plasma from high BMI patients with high active PAI-1 levels were diluted 4-fold and were incubated with increasing amounts of A44 humanized variants. Remaining active PAI-1 levels were determined using uPA-PAI-1 complex detection by ELISA. Cyno recombinant PAI-1 neutralization was also tested by plasmin generation to confirm cross-reactivity.

frozen at −80° C. Total protein concentration using standard BCA assay and active & total PAI-1 levels (determined by UK-PAI complex ELISA provided by Mol Innov Cat No HPAIKT & Cat No MPAIKT-TOT) were performed following manufacturer instructions by plotting standard human PAI-1 concentration vs A450 nm using Biostat Calibration software. Increasing concentrations of A44 humanized variants incubated with liver lysate diluted to 2.5 nM of active PAI-1 were evaluated as described previously and data analyzed. Inhibition of PAI-1 activity (PAI-1 activity without mAb being 0% inhibition, no significant and dose-dependent inhibition of PAI-1 occurred with IgG1) was calculated for each mAb concentration. Percent inhibition of PAI-1 activity was plotted as a function of mAb concentration and IC50 was determined Imax using Biostat speed software. Data is shown in FIG. 17 and in Table 29.

TABLE 29

PAI-1 activity neutralization by A44-hv11 in human liver

| | IC50 (nM) | Imax (%) |
|---|---|---|
| A44-hv11 (1 nM) | 0.0365 | 99.997 |
| A44-hv11 (2 nM) | 0.0503 | 99.99 |
| A44-hv11 (3 nM) | 0.0465 | 99.99 |
| Mean +/− sem | 0.0444 +/− 0.004 | 99.99 |

Based on the above data, A44-hv11 was selected for further characterization in additional structural studies and additional in vitro and in vivo studies.

Example 13: Humanization of APG Antibody by Grafting

Humanization using grafting techniques has previously been reported (P. T. Jones, et al., *Nature* 1986, 321:522-525). The humanization of the anti-PAI1 murine antibody APG began with the murine light chain (SEQ ID NO: 148) and murine heavy chain (SEQ ID NO: 149) from German Patent App. No. DE2000153251; this murine antibody is also described in Debrock et al., *Biochimica et Biophysica Acta*, 1337(2):257-266 (1997). Identifying the germline and canonical classes of the HC and LC chain of the murine antibody yielded muIGHV1-39 and muIGKV14-111,

TABLE 28

Humanized variant ability to block endogenous PAI-1 activity

| hPAI-1 Standard | | | hPlasma TH1782 | | | | Cyno PAI-1 | | |
|---|---|---|---|---|---|---|---|---|---|
| IC50(nM) | Y50% | n | mAb | IC50(nM) | Y50% | N | IC50(nM) | Y50% | n |
| 1.31E−01 | 50.80 | 2 | A44-hv11 | 1.57E−02 | 37.50 | 2 | 4.24E−02 | 50.80 | 2 |
| 1.14E−01 | 53.45 | 2 | A44-hv12 | 3.35E−03 | 37.68 | 2 | 2.66E−02 | 53.45 | 2 |
| 1.66E−01 | 52.82 | 2 | A44-hv13 | 3.11E−02 | 61.35 | 2 | 2.81E−02 | 52.82 | 2 |
| 5.63E−02 | 52.47 | 2 | A44-hv14 | 5.86E−02 | 73.90 | 2 | 2.87E−02 | 52.47 | 2 |

Human fibrotic liver samples (provided by Biopredic International, Rennes, France from surgical resection of hepatic colon metastasis) were homogenized as follows: weighed frozen liver samples were homogenized in dry tubes containing ceramic beads (Cat No 03961-1-003, Bertin Technology, France) using Precellys homogeniser (Bertin Technology, France; 4° C., 2×30 seconds at 6800 rpm) and then dissolved using 1 ml/g of lysis buffer (NaCl 1.5M in TBS—Tris Buffer Solution 0.1M Tris+0.15M NaCl pH7.4). After centrifugation at 4° C. at 5000 g for 10 min, the liver lysate in the supernatant was harvested and stored respectively. Next the list of close human germlines to anti-PAI1 APG variable domain light and heavy chains were identified and ranked by percent identity. Both steps were done by performing a BLAST search vs. all the human germlines which were systematically enumerated (all possible combinations of the V & J domains for the kappa and lambda chains; V, D and J domains for the heavy chains). The BLAST searches were performed using the IMGT/DomainGapAlign tool provided at http://www.imgt.org. (See Ehrenmann, et al. Cold Spring Harbor Protocols 2011.6 (2011)). The closest human germlines were identified with 67.4% and 63.3% sequence identity to anti-PAI1 APG variable domain light and heavy chains, respectively. Using the IMGT database, the light chain was found to be close to HuIGKV1-33 and the heavy chain was close to HuIGHV1-46. The closest human germline to the anti-PAI1 APG variable domain heavy chain with a matching canonical class was found to be HuIGHV7-4-1 with a sequence identity of 62.2%.

CDR regions (based on a combination of Kabat and IMGT for APG) and Vernier residues are indicated in italics for the parent murine APG (mAPG) light chain (SEQ ID NO: 148), IGKV1-33-01_IGKJ4-01 (IGKV1a) (SEQ ID NO: 107) and for GKV1-33-01_IGKJ2-02 (IGKV1b) (SEQ ID NO: 150) (see Table 30, below). Vernier residues as defined in Foote, et al. *J. Mol. Biol.* 224(2):487-99 (1992) are underlined. The humanizing mutations (in boldface) were obtained by performing a pairwise comparison of the two aligned sequences, excluding the CDR & Vernier zone residues (also underlined in mAPG sequences, Table 30) as defined above. No further engineering was performed on the murine APG antibody. These humanized antibodies were named APGv2 and APGv4.

TABLE 30

| APG humanization sequences | |
| --- | --- |
| APG Light Chain | DIKLTQSPSS MYASLGERVT ITCKASQDIY SYLSWFQQKP GKSPKTLIYR ANRLIDGVPS RFSGSGSGQD YSLTISSLEY EHMGIYYCLQ YDEFPFTFGS GTKLEIK (SEQ ID NO: 148) |
| APG Heavy Chain | QVKLQESGPE LVKPGASVKI SCKASGYSFT DYNMNWVKQS KGKSLEWIGI IHPNSGTTTY NQKFKGKATL TVDQSSSTAY LQLNSLTSED SAVYYCARSK LRFFDYWGQG TTVTVSS (SEQ ID NO: 149) |
| IGKV1-33-01_IGKJ4-01 (IGKV1a) | DIQMTQSPSS LSASVGDRVT ITCQASQDIS NYLNWYQQKP GKAPKLLIYD ASNLETGVPS RFSGSGSGTD FTFTISSLQP EDIATYYCQQ YDNLPLTFGG GTKVEIK (SEQ ID NO: 107) |
| IGKV1-33-01_IGKJ2-02 (IGKV1b) | DIQMTQSPSS LSASVGDRVT ITCQASQDIS NYLNWYQQKP GKAPKLLIYD ASNLETGVPS RFSGSGSGTD FTFTISSLQP EDIATYYCQQ YDNLPCSFGQ GTKLEIK (SEQ ID NO: 150) |
| IGHV7-4-1-02_IGHJ4-03 | QVQLVQSGSELKKPGASVKVSCKASGYTFTSY AMNWVRQAPGQGLEWMGWINTNTGNPTYAQGF TGRFVFSLDTSVSTAYLQISSLKAEDTAVYYC ARxxxxxYFDYWGQGTLVTVSS (SEQ ID NO: 151) |
| IGHV1-46-01_IGHJ4-03 | QVQLVQSGAEVKKPGASVKVSCKASGYTFTSY YMHWVRQAPGQGLEWMGIINPSGGSTSYAQKF QGRVTMTRDTSTSTVYMELSSLRSEDTAVYYC ARxxxxxYFDYWGQGTLVTVSS (SEQ ID NO: 152) |
| APGv2_VL2 | DIQLTQSPSS LSASVGDRVT ITCKASQDIY SYLSWFQQKP GKAPKTLIYR ANRLIDGVPS RFSGSGSGQD YTFTISSLQP EDIATYYCLQ YDEFPFTFGQ GTKLEIK (SEQ ID NO: 153) |
| APGv2_VH2 | QVQLVQSGSE LKKPGASVKV SCKASGYSFT DYNMNWVRQA PGQGLEWIGI IHPNSGTTTY NQKFKGRAVL SVDQSVSTAY LQISSLKAED TAVYYCARSK LRFFDYWGQG TLVTVSS (SEQ ID NO: 154) |

TABLE 30-continued

| APG humanization sequences | |
| --- | --- |
| APGv4_VH4 | QVQLVQSGAE VKKPGASVKV SCKASGYSFT DYNMNWVRQA PGQGLEWIGI IHPNSGTTTY NQKFKGRATL TVDQSTSTAY MELSSLRSED TAVYYCARSK LRFFDYWGQG TLVTVSS (SEQ ID NO: 155) |

Engineered Sequences 4D humanization and grafting approaches were applied to the human germline sequence matches described above. For the engineered light chain sequences, APGv2 contains the murine light chain CDRs grafted into the human IGKV1-33 germline (APGv2 germinality index=94% with IGKV1-33-01_IGKJ2-01). For the engineered heavy chain sequences, APGv2 and APGv4 contain the murine heavy chain CDRs grafted into the human IGHV7-4-1 and IGHV1-46 germlines respectively (APG_VH2 germinality index=91% with IGHV7-4-1-02_IGHD6-25-01_IGHJ4-02; APG_VH4 germinality index=91% with IGHV1-46-01_IGHD6-25-01_IGHJ4-02). See Table 30 above.

Combinations of Heavy and Light Chain Variant Sequences

For grafting, one version of the light chain (APGv2_VL2; SEQ ID NO: 153) and two versions of the heavy chain (APGv2_VH2; SEQ ID NO: 154 and APGv4_VH4; SEQ ID NO: 155) were created. APG_VL2 contains 15 mutations derived from grafting to the closest human germline sequence and retaining the murine CDR and Vernier zone residues. APG_VH2 contains 21 mutations derived from grafting to the closest human germline sequence with a matching canonical class and retaining the murine CDR and Vernier zone residues. APG_VH4 contains 20 mutations derived from grafting to the closest human germline sequence and retaining the murine CDR and Vernier zone residues. The delimitations of the CDRs for this grafting protocol are loosely based on the various different definitions available in the literature.

APG_VL2×APG_VH2 (mutations addressing humanization by grafting retaining CDRs and Vernier regions)

APG_VL2×APG_VH4 (mutations addressing humanization by grafting retaining CDRs and Vernier regions)

Two mAPG variants were generated during this humanization campaign, which were named APGv2 and APGv4. These variants were expressed and characterized in several in vitro assays as described below.

Example 14: Affinity Kinetics for APG Antibodies by Surface Plasmon Resonance

Affinity to human glycosylated PAI-1 (GLYHPAI-A, Molecular Innovation) was investigated by Surface Plasmon Resonance (SPR) for mouse APG and the two humanized variants (APGv2 & APGv4) using a Biacore 2000 instrument (GE Healthcare, Uppsala, Sweden).

Figure 19:
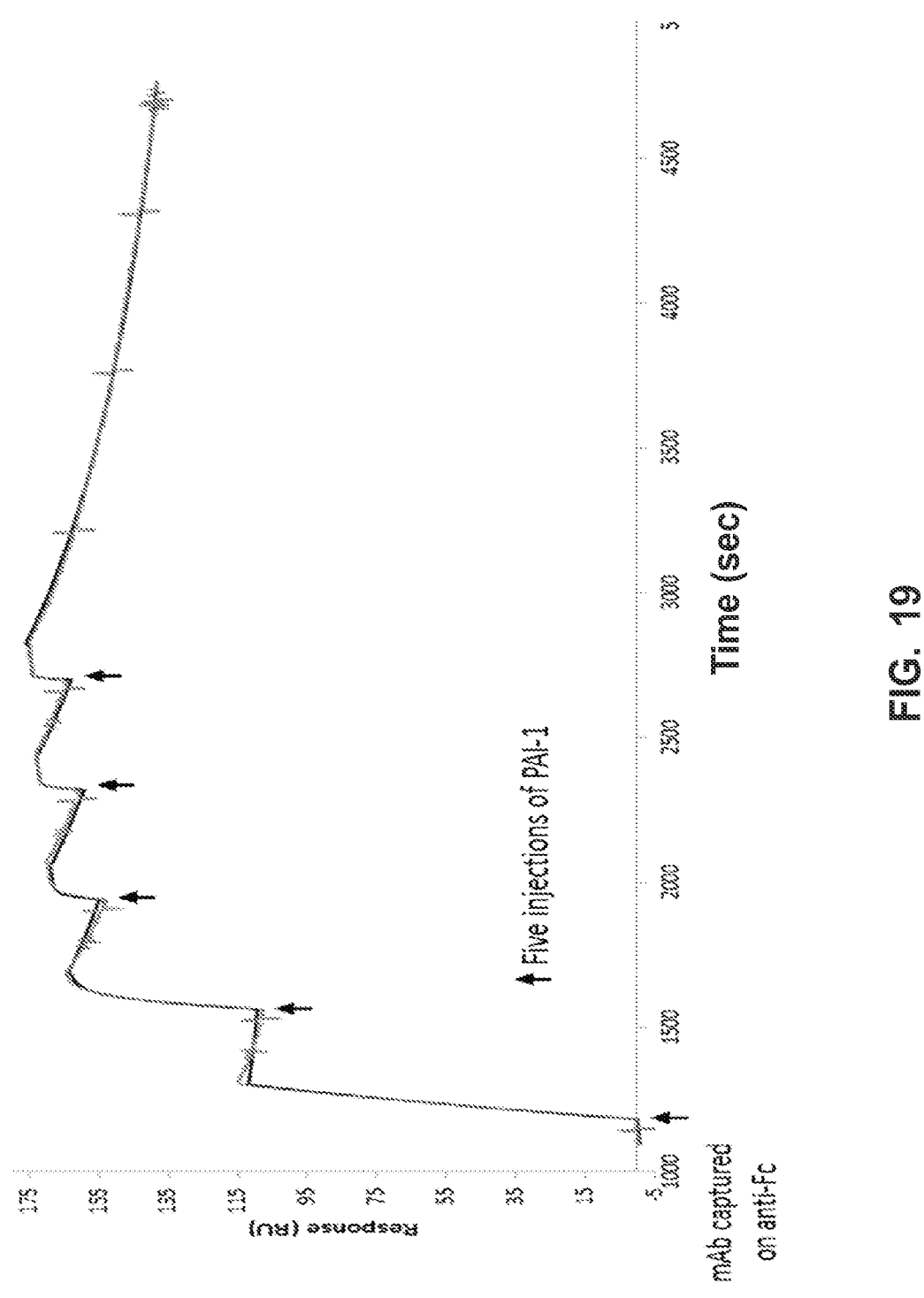
FIG. 19 depicts SPR analysis with Biacore 2000 using single kinetic analysis of human PAI-1 glycosylated binding to immobilized APG antibody. A sensogram from single-cycle kinetic is shown in grey. Fit model is shown in black.

First, the surface of a Sensor Chip CM5 (GE Healthcare, Uppsala, Sweden) was prepared using routine amine coupling for the capture of the mouse and human anti-Fc (Anti-human IgG (Fc) antibody & Anti-mouse IgG antibody kits, GE Healthcare). All monoclonal antibodies (mAbs) were diluted to 5 nM using HBS-EP running buffer. Each purified mAb was captured for three minutes on a different flow cell surface. Human PAI-1 was injected at various concentrations (2.5, 5, 10, 20 and 40 nM) with short dissociation times in between and a long dissociation time at the end (contact time: 120 seconds, short dissociation: 90 seconds; long dissociation: 1800 seconds, flow rate: 50 µl/min). The chip was regenerated by glycine-HC1, pH 1.7 buffer after each round of antibody-PAI-1 binding. Kinetics data analysis was performed using Biacore BIAevaluation software. The sensorgrams were double-referenced by subtracting the reference flow cell values and the blank buffer values. The sensorgrams were fitted by using the simulated kinetics 1:1 (*Langmuir*) model with local Rmax. (see FIG. 19). The data for the three APG antibodies are shown in Table 31.

TABLE 31

| Binding Kinetics by Biacore Reverse Assay | | | |
| --- | --- | --- | --- |
| | human PAI-1 | | |
| Antibody | ka (M⁻¹s⁻¹) | Dissociation Rate kd (1/s) | Affinity KD (M) |
| APG | 3.82E+06 | 4.32E−04 | 1.131E−10 |
| APGv2 | 6.58E+06 | 2.69E−04 | 4.080E−11 |
| APGv4 | 9.48E+06 | 3.59E−04 | 3.800E−11 |

Example 15: Characterization of APG Antibodies in Human Plasma

The mouse APG and the humanized variants APGv2 and APGv4 were screened for their ability to block PAI-1 according to the functional assays disclosed herein (see, e.g., Examples 6 and 9, above). Briefly, PAI-1 activity was evaluated by the ability of this serpin to form stable complex with urokinase immobilized on 96 well plates. After washing unbound PAI-1, uPA-PAI-1 complexes were detected by the use of polyclonal antiPAI-1 antibodies. The bound polyclonal anti-PAI-1 antibodies (which is proportional to active PAI-1 in the sample) was then detected using a horseradish peroxidase conjugated secondary antibody according to manufacturer instructions (Molecular Innovation, Cat #HPAIKT).

Various concentrations of APG humanized variants (APGv2, APGv4) or parental mouse APG antibodies were incubated for 15 min at room temperature with undiluted human plasma having a high active PAI-1 level. Remaining active PAI-1 level was determined using uPA-PAI-1 complex detection by ELISA as described above (see, e.g., Example 6) and according to the manufacturer instruction.

Figure 20:
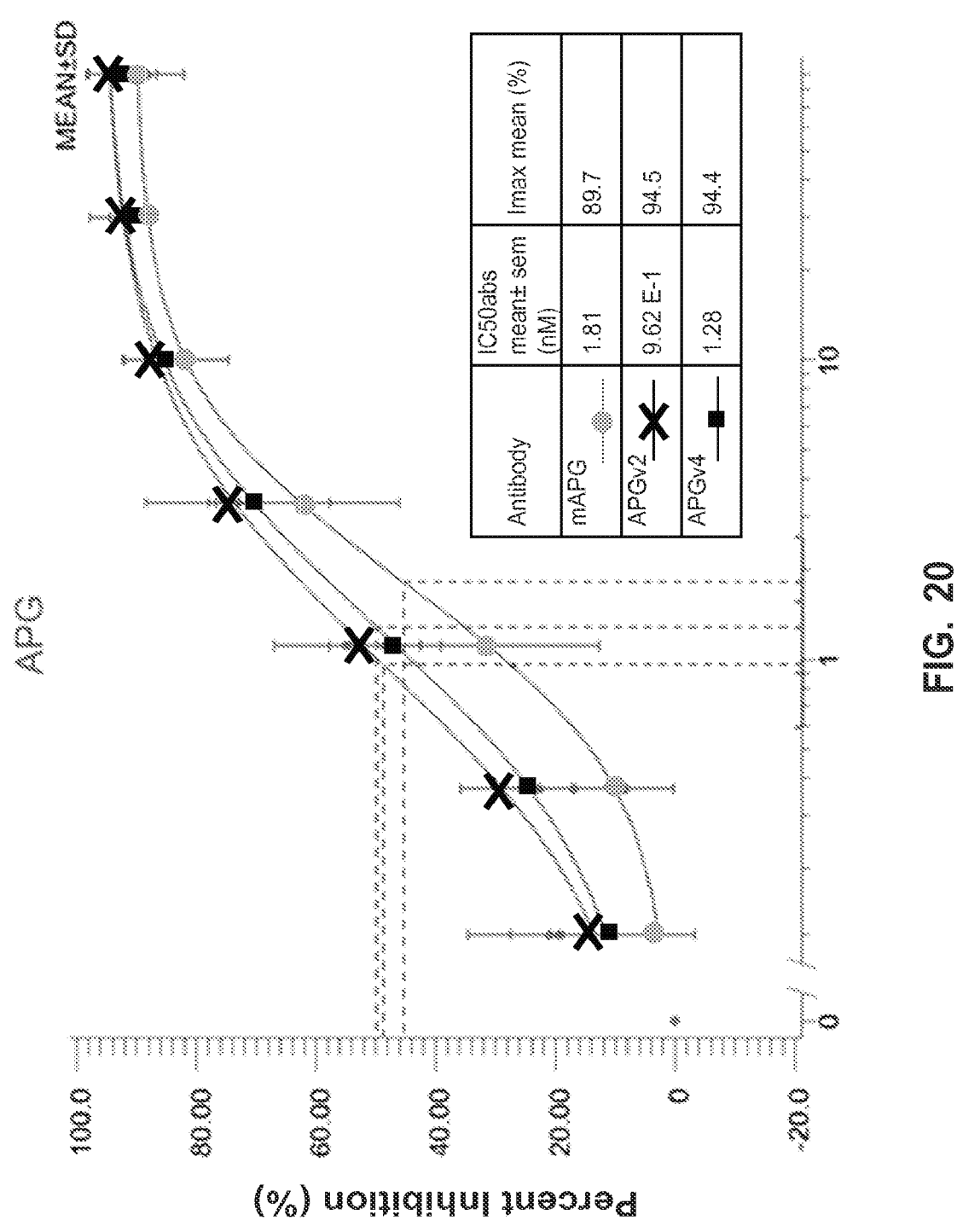
FIG. 20 depicts human plasma PAI-1 neutralization by APG, APGv2, and APGv4 antibodies as determined by UK-PAI-1 complex formation detection by ELISA. Percent inhibition of PAI-1 activity was plotted as a function of concentration of APG, APGv2, or APGv4 antibodies.

Inhibition of PAI-1 activity was calculated for each mAb concentration. Percent inhibition of PAI-1 activity was plotted as a function of concentration of APG humanized variants (APGv2, APGv4) or parental mouse APG antibody. Biostat speed software was used to determine $IC_{50}$ and $I_{max}$ after three independent experiments (in duplicate)(see FIG. 20). Data is presented below in Table 32.

TABLE 32

| Plasminogen Generation in Human Plasma | | |
| --- | --- | --- |
| Antibody | $IC_{50abs}$ mean ± sem (nM) | $I_{max}$ mean (%) |
| mAPG | 1.81 | 89.7 |
| APGv2 | 9.62E−1 | 94.5 |
| APGv4 | 1.28 | 94.4 |

Example 16: Clot Lysis Assay in Human Plasma: A44V11, mAPG, and APG Variant Activity The fibrinolytic system is often altered in patients with stroke. A clot lysis assay can be used to determine fibrinolytic activity by measuring the degree of fibrin breakdown. See generally Lindgren, A. et al. Stroke 27:1066-1071 (1996). Clot lysis assays have been described in detail elsewhere. See, e.g., Beebe, et al. *Thromb. Res.* 47:123-8 (1987); Tilley et al., *J. Vis. Exp.* 67:e3822.

The functional activity of A44V11 and other PAI-1 neutralizing antibodies was determined using a human plasma clot lysis assay. Briefly, the assay applied here induces clot formation using a mixture of Tissue Factor/Ca2+ in the presence of tPA and a concentration of PAI-1 known to inhibit clot lysis. Fibrin polymerization induces an increase of turbidimetry that was detected by absorbance measurement at 340 nm. The ability of the antibody to restore clot lysis was determined by incubating increasing doses of antibody with normal human platelet poor plasma.

Briefly, clot lysis experiments were performed in microtiter plates. Citrated human plasma (Biopredic International, Rennes, France) was incubated with anti-PAI-1 antibody or isotype controle IgG diluted in assay buffer (NaCl, Tris-HC1 pH=7.4). After 15 min incubation at room temperature, human glycosylated PAI-1 (GLYHPAI-A, Molecular Innovation) was added to a final concentration of 3 nM and incubated for an additional 10 min. t-PA (sctPA, Molecular Innovation) was then added to a final concentration of 1 nM. Clot formation was induced by an activation mix comprising Tissue Factor (Innovin®, Siemens Healthcare Diagnostics, Marburg, Germany) diluted to a final concentration of 7.5 mM in calcium assay buffer (CaCl₂).

Kinetic reading of absorbance at 340 nm was performed every 30 see for 5 hours with an iEMS microplate reader (ThermoFischer) or a SpectrostarNano (BMG Labtech). To quantify the effect on clot lysis, the area under curve (AUC) which reflects the balance between clot formation and clot lysis was calculated using GraphPad Prism Software. The restoration of clot lysis after antibody treatment was determined according to the following calculation:

$$\text{Restoration} = 100 \times \frac{AUC_{max\,lysis} - AUC_{treated}}{AUC_{no\,lysis} - AUC_{max\,lysis}}$$

$IC_{50}$ and $I_{max}$ were calculated using Biostat speed software.

The 1 nM concentration of t-PA yielded complete lysis of normal plasma within 2 hours. The 3 nM-concentration of PAI-1 inhibited t-PA-induced clot lysis. Addition of either t-PA or PAI-1 alone did not affect clot formation. Addition of neither t-PA or PAI-1 did not affect clot formation.

Figure 21:
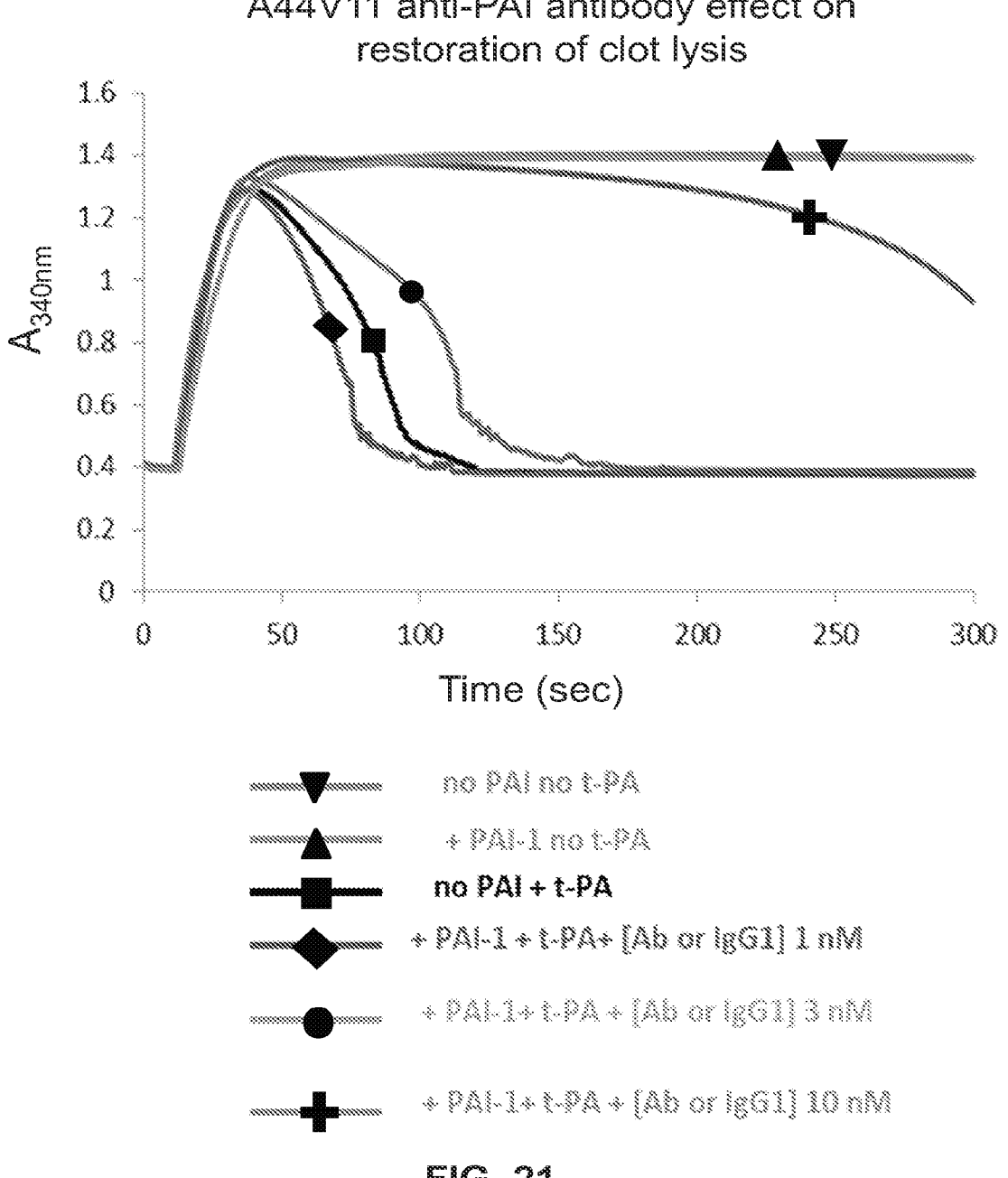
FIG. 21 depicts restoration of human plasma clot lysis by A44V11 (1, 3 or 10 nM) in the presence of tPA 1 nM and PAI-1 3 nM as detected by turbidimetry kinetic measurement by absorbance reading at 340 nm as a function of time (min).
Figure 22:
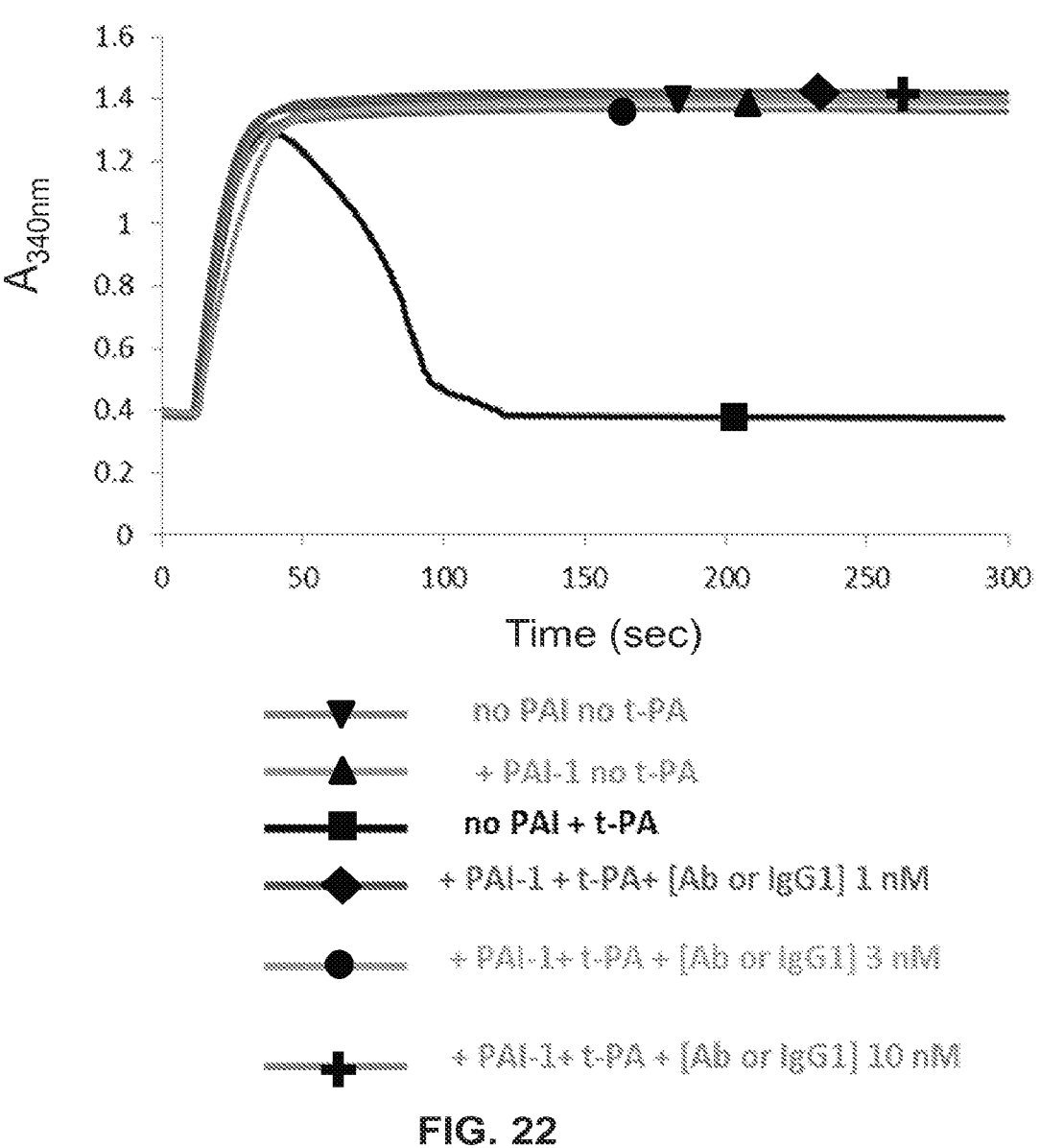
FIG. 22 depicts absence of restoration of human plasma clot lysis by human IgG1 negative controle (1, 3 or 10 nM) in the presence of tPA 1 nM and PAI-1 3 nM as detected by absorbance at 340 nm as a function of time (min).
Figure 23:
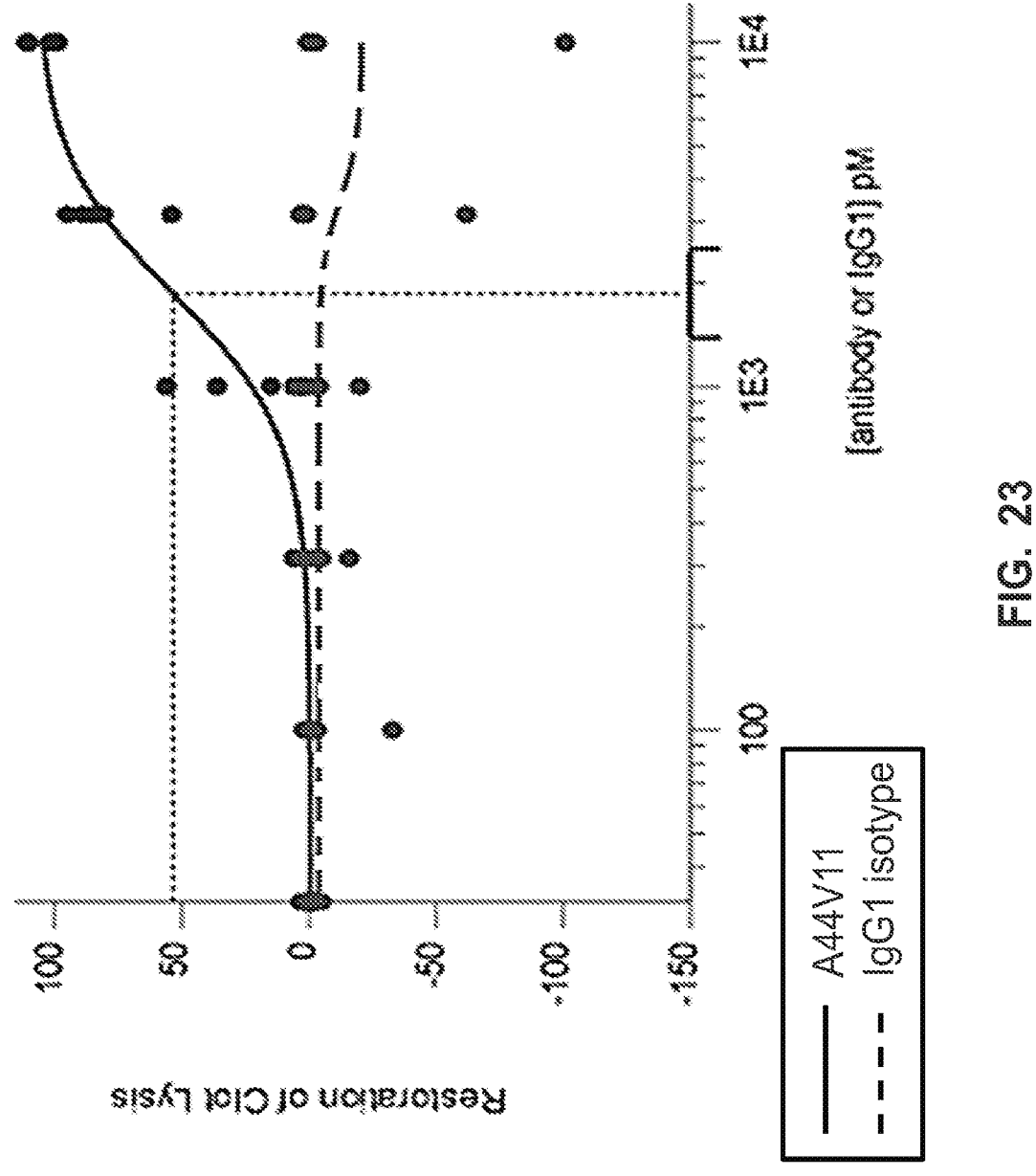
FIG. 23 depicts restoration of human plasma clot lysis by A44V 11 or human IgG1 isotype negative control at various concentrations.

The A44V11 anti-PAI-1 antibody restored human platelet poor plasma clot lysis (see FIG. 21), while the isotype IgG1 did not (see FIG. 22). A44V11 exhibited an $IC_{50}$ of 2 nM with an $I_{max}$ of 103% at 100 nM (see FIG. 23).

Figure 24:
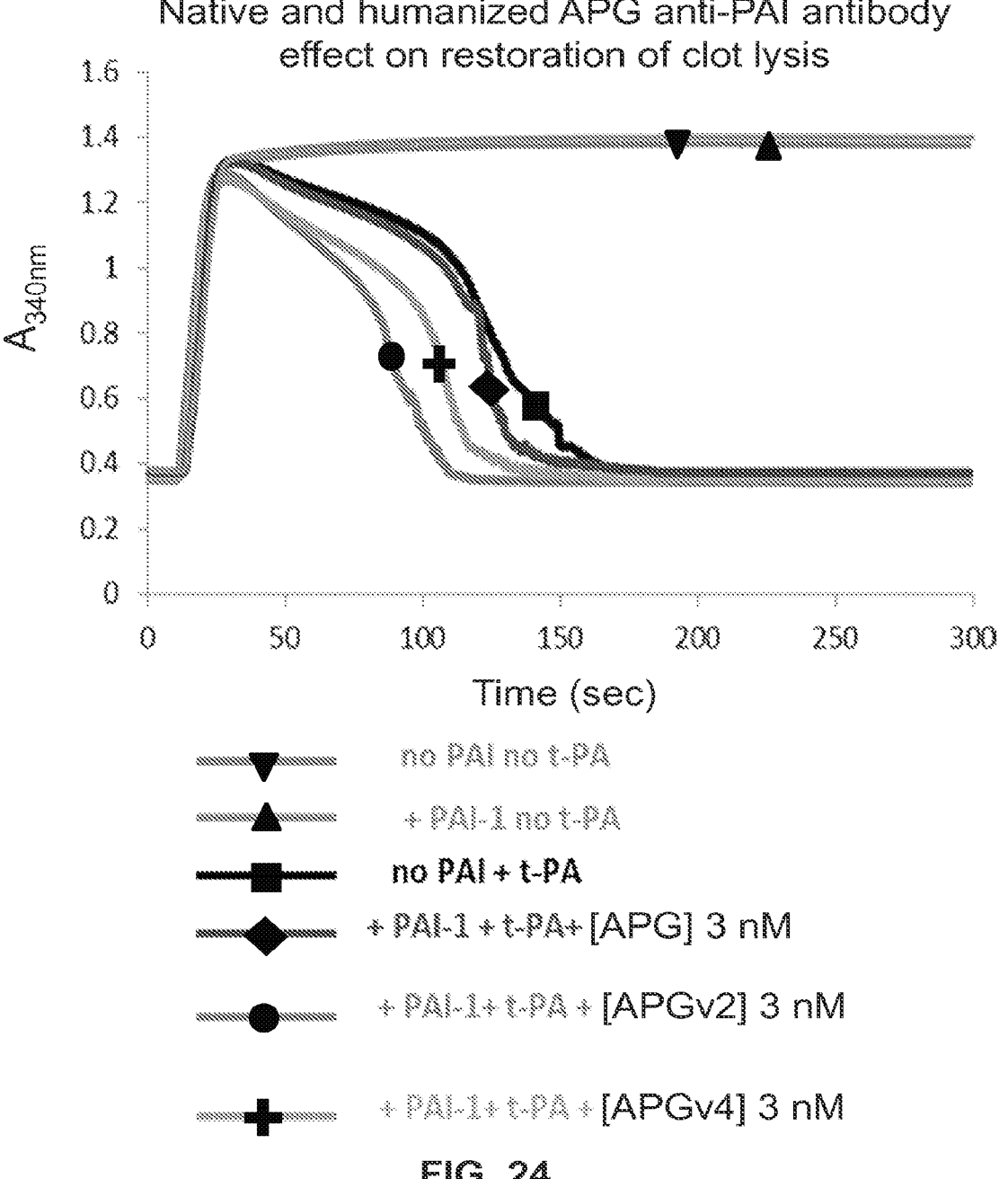
FIG. 24 depicts restoration of human plasma clot lysis by APG, APGV2 or APGV4 at 3 nM in the presence of tPA 1 nM and PAI-1 3 nM as detected by absorbance at 340 nm as a function of time (min).
Figure 25:
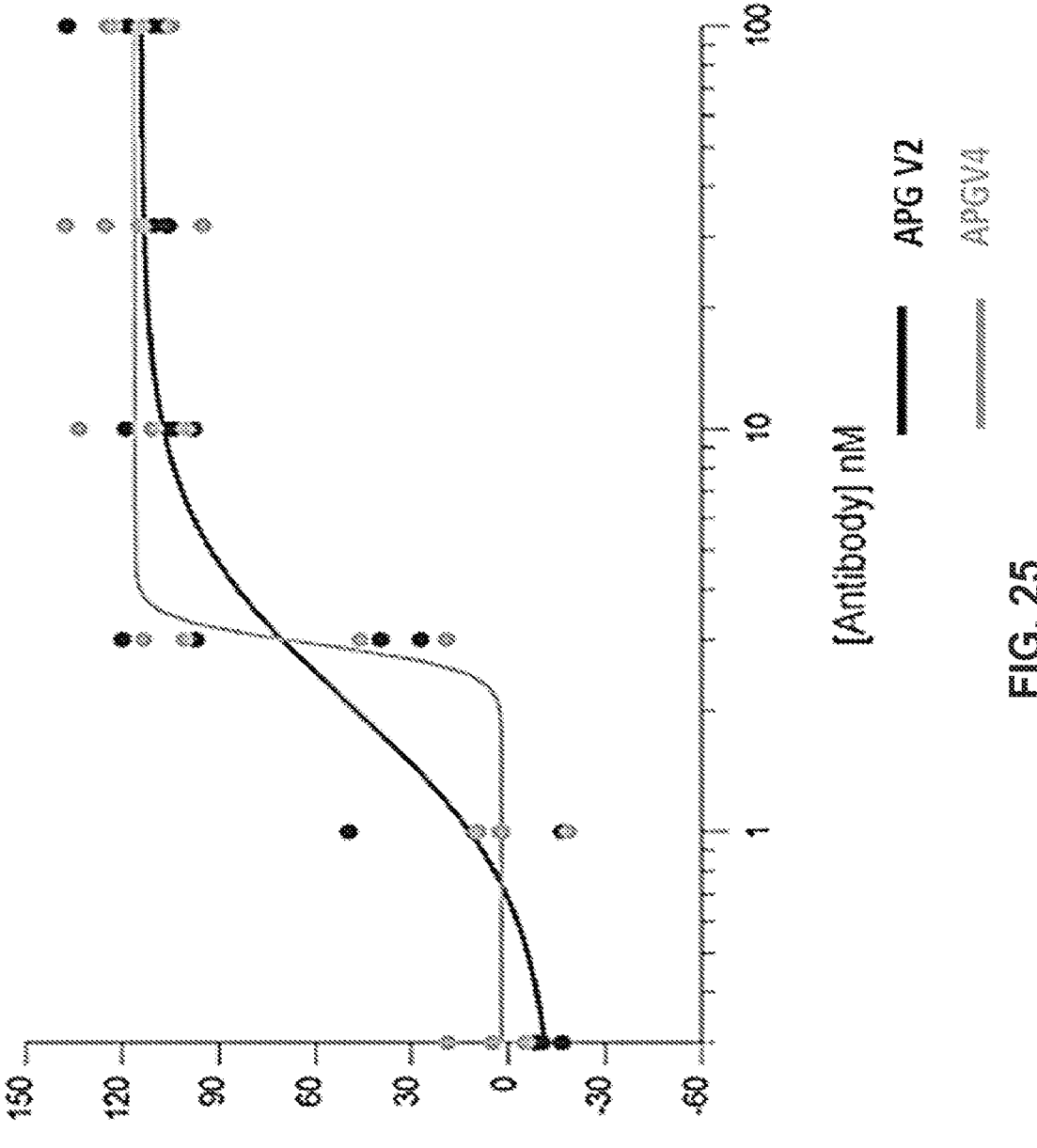
FIG. 25 depicts restoration of human plasma clot lysis by APG variant 2 and 4 at various concentrations.

The humanized variants of APG anti-PAI-1 antibody also restored human platelet poor plasma clot lysis (see FIG. 24). APGv2 exhibited an $IC_{50}$ of 2.1 nM and an $I_{max}$ of 114% at 100 nM. APGv4 exhibited an $IC_{50}$ of 2.8 nM and an $I_{max}$ of 116% at 100 nM (see FIG. 25). The clot lysis data is summarized below in Table 33.

TABLE 33

| Inhibition of clot lysis by anti-PAI-1 antibodies | | |
| --- | --- | --- |
| Antibody | $IC_{50}$ (nM) | Imax @ 100 nM |
| A44V11 | 1.38 | 113% |
| APG V2 | 2.08 | 114% |

TABLE 33-continued

| Inhibition of clot lysis by anti-PAI-1 antibodies | | |
|---|---|---|
| Antibody | IC$_{50}$ (nM) | Imax @ 100 nM |
| APG V4 | 2.82 | 116% |
| mAPG | 2.34 | 123% |

Example 17: Assessment of A44V11 Neutralization of PAI-1 in Primary Human Lung Cells The effect of antibody A44V11 on neutralization of PAI-1 was investigated in a lung cell-based system. TGFβ is considered to be the most potent and ubiquitous profibrogenic cytokine. TGFβ has been shown to induce PAI-1 expression and inhibit the activities of t-PA and plasmin as well as collagen degradation in cultured murine embryo fibroblasts (NIH3T3 cells). See Liu, R-M. Antioxid *Redox Signal.* 10(2): 303-319 (2008). Primary lung fibroblasts strains LL29 (CCL-134) and LL97A (CCL-191) from ATCC (Manassas, Virginia) were plated overnight in a 12-well plate at a concentration of 200,000 cells per well. Cells were incubated for 48 hours with A44V11 antibody or isotype control (IgG) and TGFβ (R&D Systems, Minneapolis, Minn., cat. #100-B-001) at a concentration of 5 ng/ml. After 48 hours, cell supernatants were harvested and analyzed by Western Blot for detection of PAI-1 forms with a rabbit pAb anti PAI-1 (abeam, ab66705).

Figure 26:
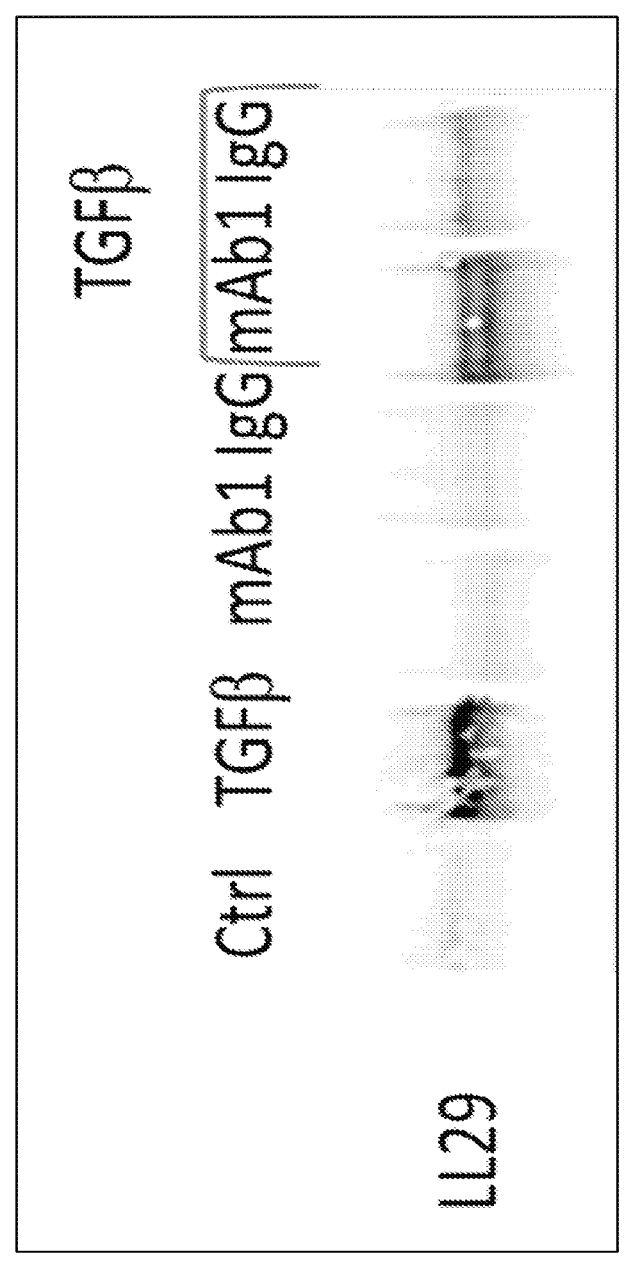
FIG. 26 depicts immunoblot anti-PAI-1 on human LL29 myofibroblast supernatants at 48H after treatment by A44V11 or IgG isotype control mAb at 50 nM and TGFβ 5 ng/ml.

Cells treated with A44V11 antibody after TGFβ stimulation display PAI-1 band as a doublet, which corresponds to the cleaved form of PAI-1 (see FIG. 26, lane 5). Cells treated with control IgG do not show this doublet formation (see FIG. 26, lane 6). This study demonstrates that treatment of primary human lung cells with A44V11 induces endogenous PAI-1 substrate conformation, which allows PAI-1 to be cleaved by protease.

Example 18: A44V11 Increases Activation of MMPs

Plasmin can activate MMPs, enzymes that can degrade most ECM proteins including collagen, the major proteinaceous component of fibrotic tissue. In this regard, plasmin is often cited as a general activator of MMPs. (See Loskutoff, et al. *J. Clin. Invest.* 106(12):1441-43 (2000)). PAI-1 decreases MMP activation and matrix degradation by blocking plasmin generation, followed by inhibition of fibroblast apoptosis. The ability of A44v11 to stimulate activation of MMPs was investigated in a lung cell-based system. Primary lung fibroblasts LL29 (CCL-134) and LL97A (CCL-191) from ATCC (Manassas, Virginia) were plated overnight in a 12-well plate at a concentration of 250,000 cells per well. Cells were incubated for 48 hours with A44V11 or isotype control (IgG) and Lys-Plasminogen (Molecular Innovation, cat. #HGPG-712) at a concentration of 0.1 µM. After 48 hours, cell supernatants were harvested and the activities of a variety of MMPs (including, for example, MMP-1, 2, 3, 7, 8, 9, 12, 13, and 14) were detected using a Sensolyte 520 Generic MMP Assay kit (AnaSpec, Fremont, CA, cat. #71158) according to the manufacturer's instructions.

Figure 27:
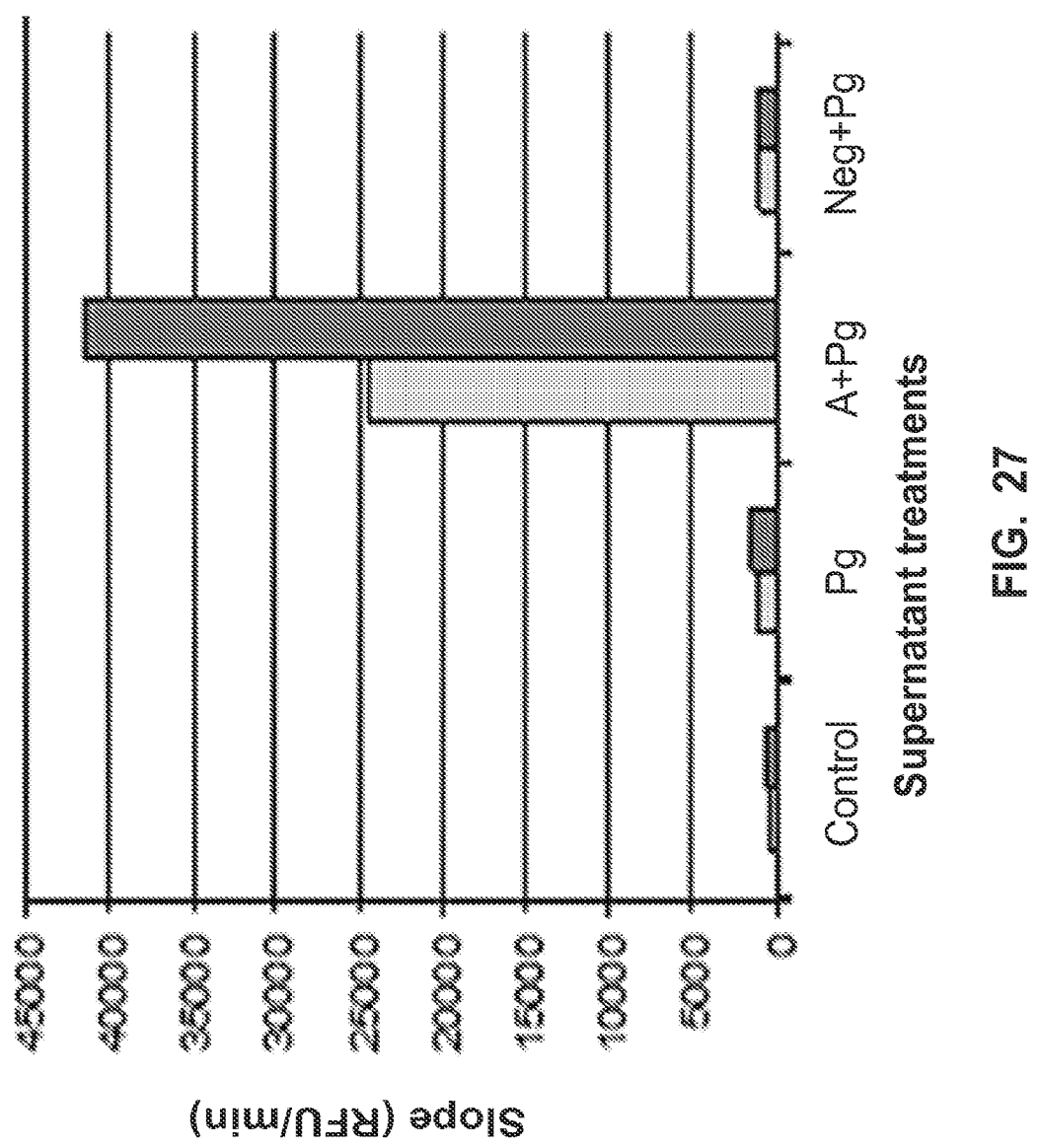
FIG. 27 depicts generic MMP activity in human primary lung fibroblasts after cell treatment for 48 hr with PBS (control), plasminogen (Pg), A44v11 and plasminogen (A+Pg) or negative human IgG and plasminogen (Neg+Pg).

As shown in FIG. 27, A44V11 stimulates the activation of plasmin-dependent MMPs in human lung fibroblasts. The chart shows two representative separate experiments. Cells treated with A44V11 and plasminogen showed substantially increased activation when compared to cells treated with an negative IgG1 antibody. This study demonstrates that A44V11 stimulates MMPs activation in a plasmin-mediated phenomenon.

Example 19: Analysis of A44V11 Potency in Lung Fibrosis Mouse Model (Bleomycin Challenge)

Experimental lung fibrosis induced by bleomycin is a well-studied model of fibrogenesis supported by ample literature. This model of pulmonary fibrosis resembles that seen in humans and has been used to assess the effects of potential therapeutic agents as well as basic research. (see, e.g., Molina-Molina et al. *Thorax* 61:604-610 (2006)). Pharmacodynamics Study in Bleomycin Treated Mice (Fibrosis Model)

Transgenic mice that express human PAI-1 (humanized PAI-1 transgenic mice) were generated by replacing the mouse PAI-1 (SERPINE1) gene CDS (exons and introns) (NCBI Ref. No. NM_008871) with the corresponding human wild type PAI-1 gene CDS (NCBI Ref. No. NM_000602.3; NC_000007.13)(see Klinger, K. W. et al. *Proc. Natl. Acad. Sci. USA* 84:8548 (1987)) under the control of the endogenous mouse PAI-1 gene regulatory sequences in C57BL/6×129 mice (The Jackson Laboratory, Bar Harbor, Maine). Molecular cloning and generation of transgenic mice are performed according to conventional techniques and according to manufacturer and breeder instructions. Expression of human PAI-1 and non-expression of mouse PAI-1 was confirmed in homozygous mice. Both mRNA and protein levels were confirmed by standard qPCR and by ELISA, respectively. Female homozygous humanized PAI-1 transgenic mice aged 8-9 weeks and weighing 22-25 g were used for these procedures. Rodent food and water were provided ad libitum.

Mice received 50 µl of Bleomycin® (Sanofi, France) dissolved in 0.9% NaCl by intra-tracheal injection via microspayer at a dose of 2 mg/kg. Control mice received 50 µl of 0.9% NaCl. For these procedures, mice were anesthetized with isoflurane (TEM, Lormont, France) by inhalation and then intubated with a 18G cannula. The cannula was connected to a ventilator fed with an oxygen/isoflurane mixture to maintain the anaesthesia. Following anesthetization, the microsprayer was introduced in the cannula for bleomycin injection directly into the lungs. Mice were then extubated and allowed to recover from anaesthesia. At day 4, after randomization in 3 groups, mice were treated once by intra-peritoneal administration of either A44v11 or negative control mouse IgG1 at 10 mg/kg in PBS (1 mg/ml).

At designated time points (day 7 or day 9) after bleomycin challenge, mice were anesthetized with a xylazine/ketamine mix and euthanized by chest opening. A blood collection was performed by intra-cardiac harvest on a citrate coated tube. Left bronchia was clamped and the left lung was removed and fixed with a fixator (FineFix®, Leica Biosystems, Buffalo Grove, IL) under controlled pressure for histological analysis A cannula was then placed into the trachea for the broncho-alveolar lavage (BAL) procedure (1.5 ml of 0.9% NaCl injected and harvest in three injections of 0.5 ml). The four lobes of the right lung were then harvested, cut in two pieces and lysed for protein analysis. All experiments were performed in accordance with European ethical lows and approved by internal ethical comity (CEPAL, sanofi).

A44V11 levels were determined using ELISA (Molecular Innovation, cat. #HPAIKT) with coated biotinylated human PAI-1 plates and detected using secondary anti mouse IgG sulfo-tag labeled (MesoScale Discovery, Gaithersburg, Maryland). For Day 7 mice treated with A44V11, the result was 200 nM in plasma, 11 nM in BALF and 12 nM in lung lysate.

Figure 28:
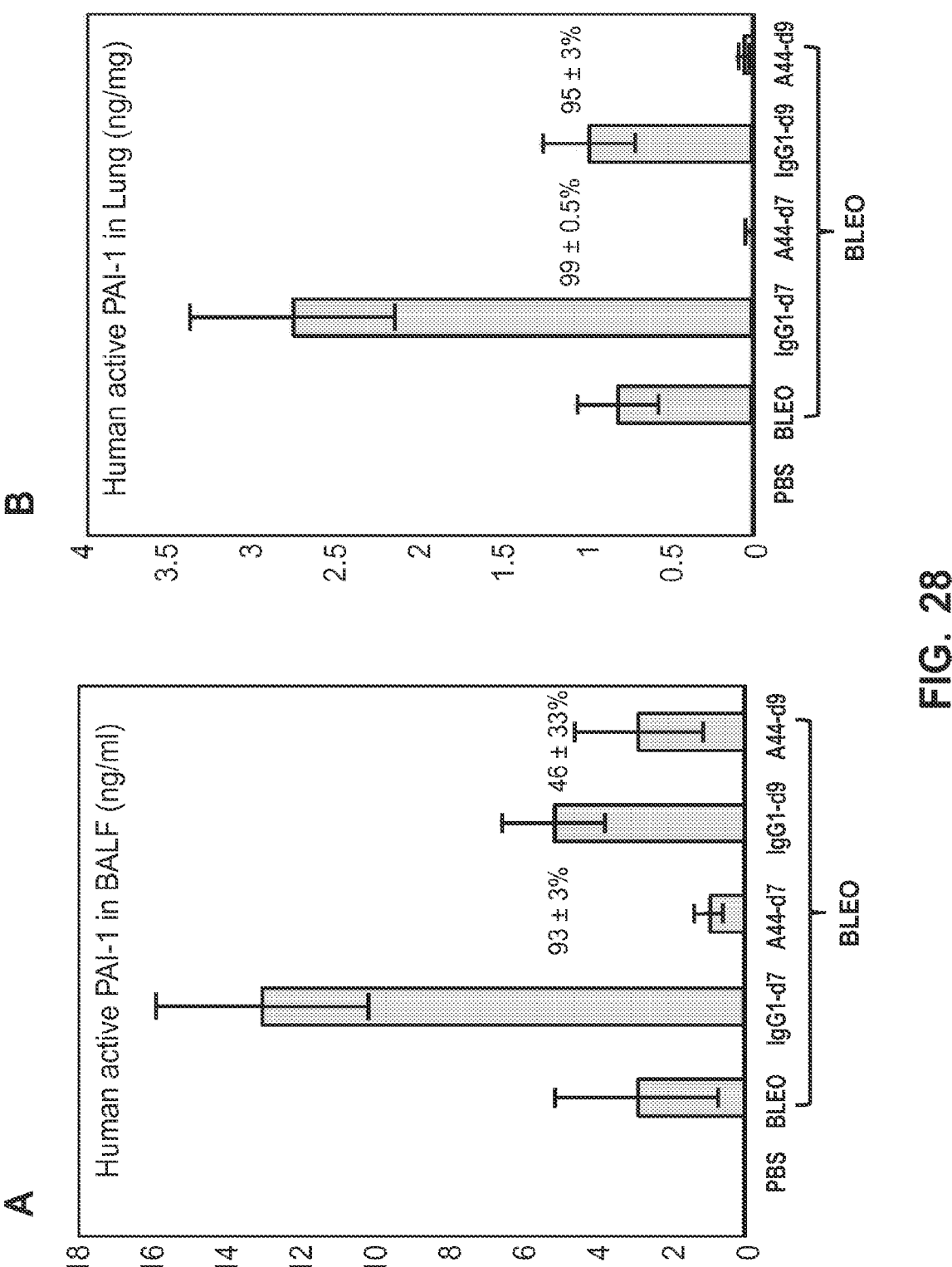
FIG. 28 depicts human active PAI-1 level in broncho-alveolar lavage fluid (BALF) (A) and in lung lysate (B) from bleomycin treated mice at day 7 and day 9 following treatment at day 4 with A44 or IgG1 at 10 mg/kg or PBS by i.p. administration. Active PAI-1 determined by ELISA (#HPAIKT Molecular Innovation). Percentage of inhibition were calculated by dividing the difference between A44 bleo and IgG bleo by the difference between IgG bleo and untreated (PBS) mice group.

As shown in FIG. 28, administration of a single intra-peritoneal dose (10 mg/kg) of A44V11 at day 4 achieves nearly full inhibition of human active PAI-1 both in BAL fluid and in lung lysate in animals sacrificed at day 7 after bleomycin challenge. For day 9 animals, A44V11 (10 mg/kg) achieves nearly full inhibition of human active PAI-1 in lung lysates, but achieves only partial inhibition in BALF.

Figure 29:
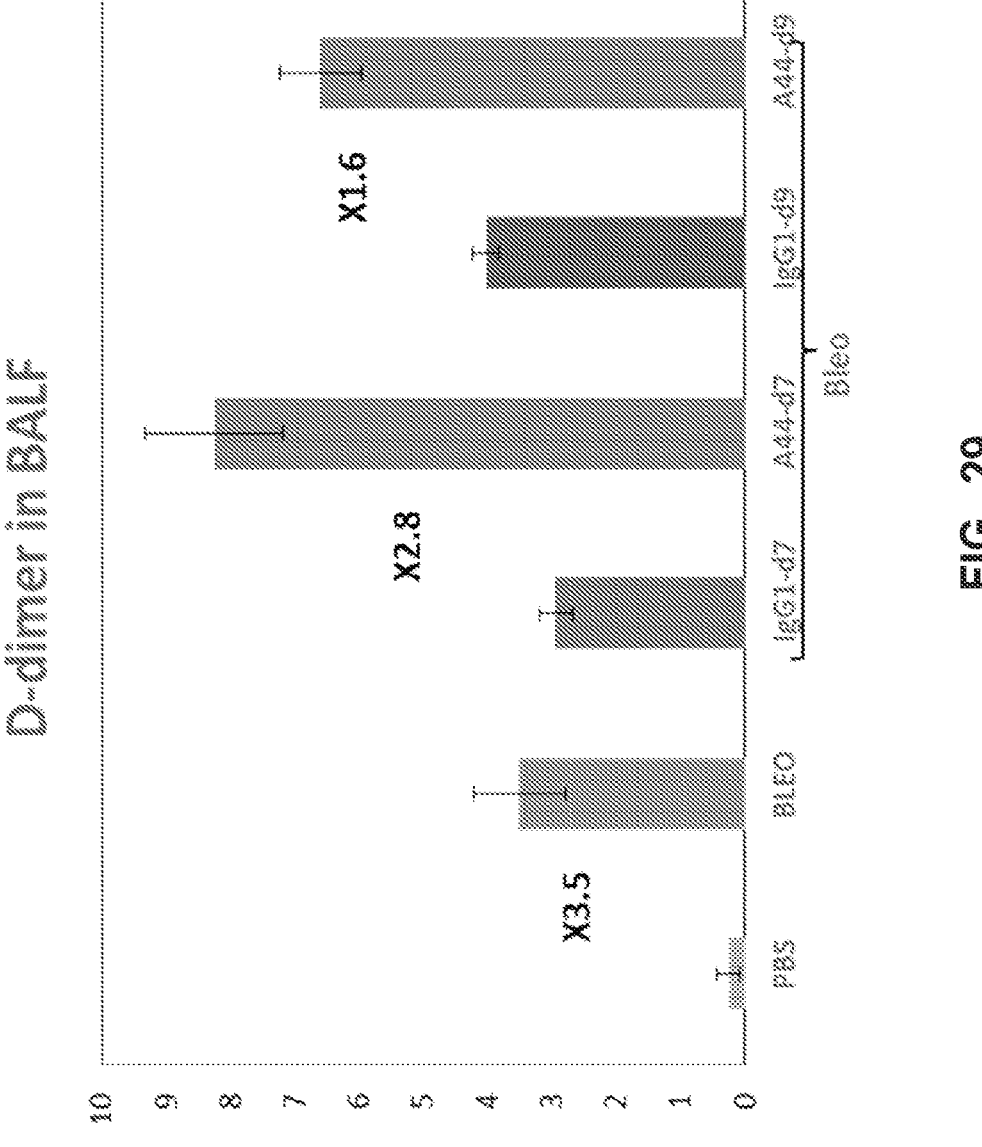
FIG. 29 depicts mouse D-Dimer level in BALF from bleomycin treated mice at day 7 and day 9 following treatment at day 4 with A44 or IgG1 at 10 mg/kg or PBS by i.p. administration as determined by ELISA (Asserachrom D-Di, Diagnostica Stago). Fold increase in D-dimer induced by A44 in comparison to IgG are indicated.

D-dimers, a fibrin degradation product, can be measured to assess the degree of fibrin breakdown. To measure fibrin degradation, the levels of D-dimer in BALF were detected by ELISA (Asserachrom D-Di, Diagnostica Stago, Asnieres, France) according to manufacturer instructions. D-dimer levels in the BALF of the A44V11-treated group were increased approximately 2.8-fold at day 7 and 1.6-fold at day 9 when compared to the IgG1 negative control group, suggesting A44V11 treatment increases fibrin degradation (see FIG. 29).

Additional studies were performed to further assess A44V11 activity in reducing fibrosis in mouse lung challenged with bleomycin. For these studies, mice were subjected to a similar protocol to the pharmacodynamy study described above, except that the study duration length was 21 days from bleomycin challenge, and treatment with antibody (either A44V11 or IgG1 control antibody at 10 mg/kg) was repeated every 3 days starting at day 4 until day 20. At day 21 after bleomycin challenge, the animals were sacrificed as described above.

Figure 30:
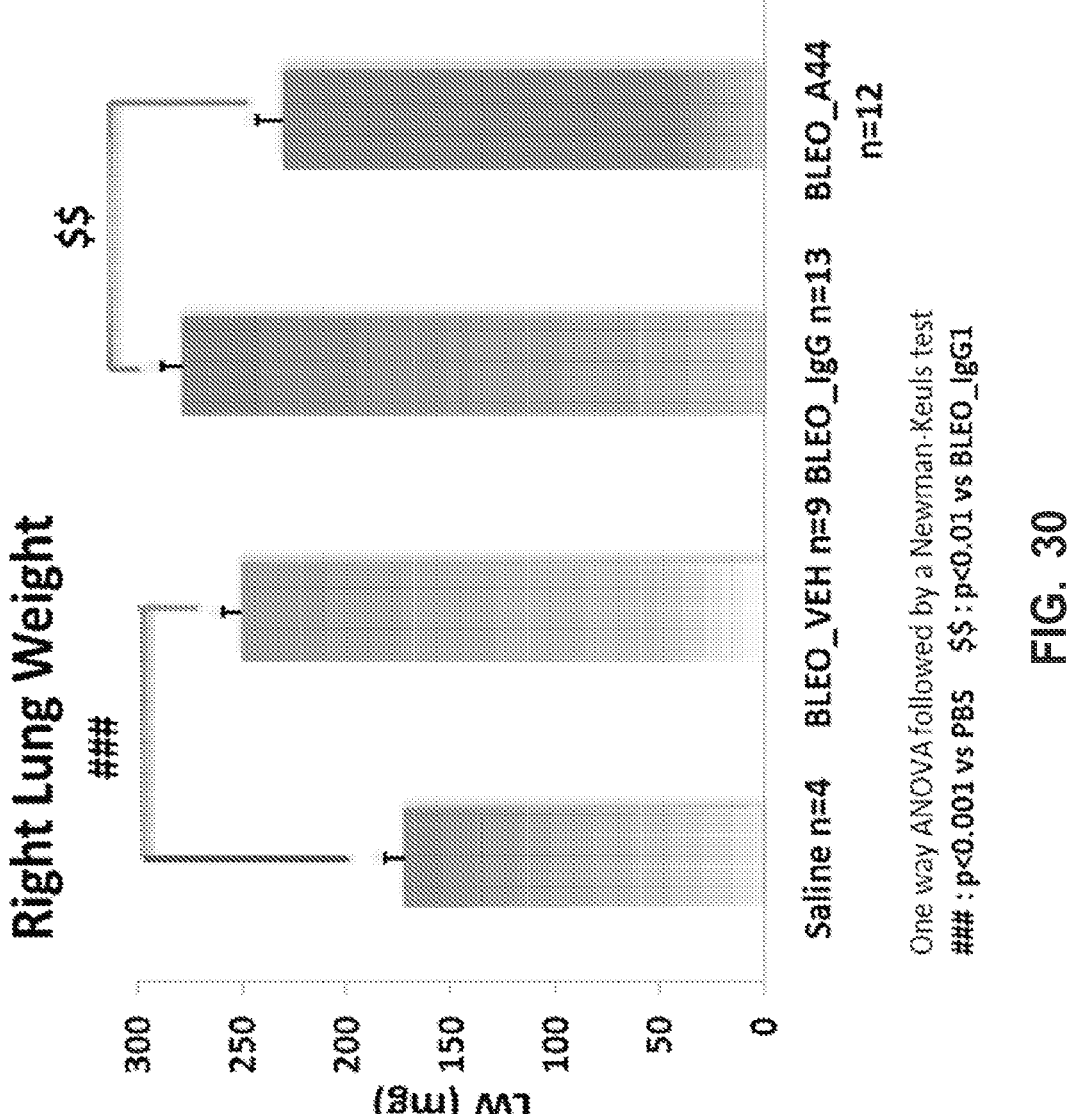
FIG. 30 depicts right lung weight from transgenic humanized mice 21 days after either saline or bleomycin treatment followed by PBS (vehicle), IgG1 or A44 10 mg/kg i.p. administration from day 4 to day 20 every 3 days.

Increase in lung weight is known to be an indicator of increased fibrosis. The right lung weight, as a measure of fibrosis, was determined for mice in all experimental groups. As shown in FIG. 30, bleomycin instillation induces an increase in right lung weight that was partially inhibited by repeated dosing of A44V11 antibody at 10 mg/kg. Repeated dosing using the IgG1 negative control antibody did not inhibit the increase in right lung weight due to bleomycin challenge. The reduction in bleomycin-induced right lung weight increase in A44V11-treated mice was statistically significant when compared to similar bleomycin-induced mice that were treated with IgG1 negative control antibody (p<0.001). Statistical analysis was performed by one-way ANOVA followed by Newman-Keuls test. This result indicates that A44V11 inhibits bleomycin-induced fibrosis in the humanized PAI-1 mouse lung, whereas a control IgG1 antibody does not.

Figure 31:
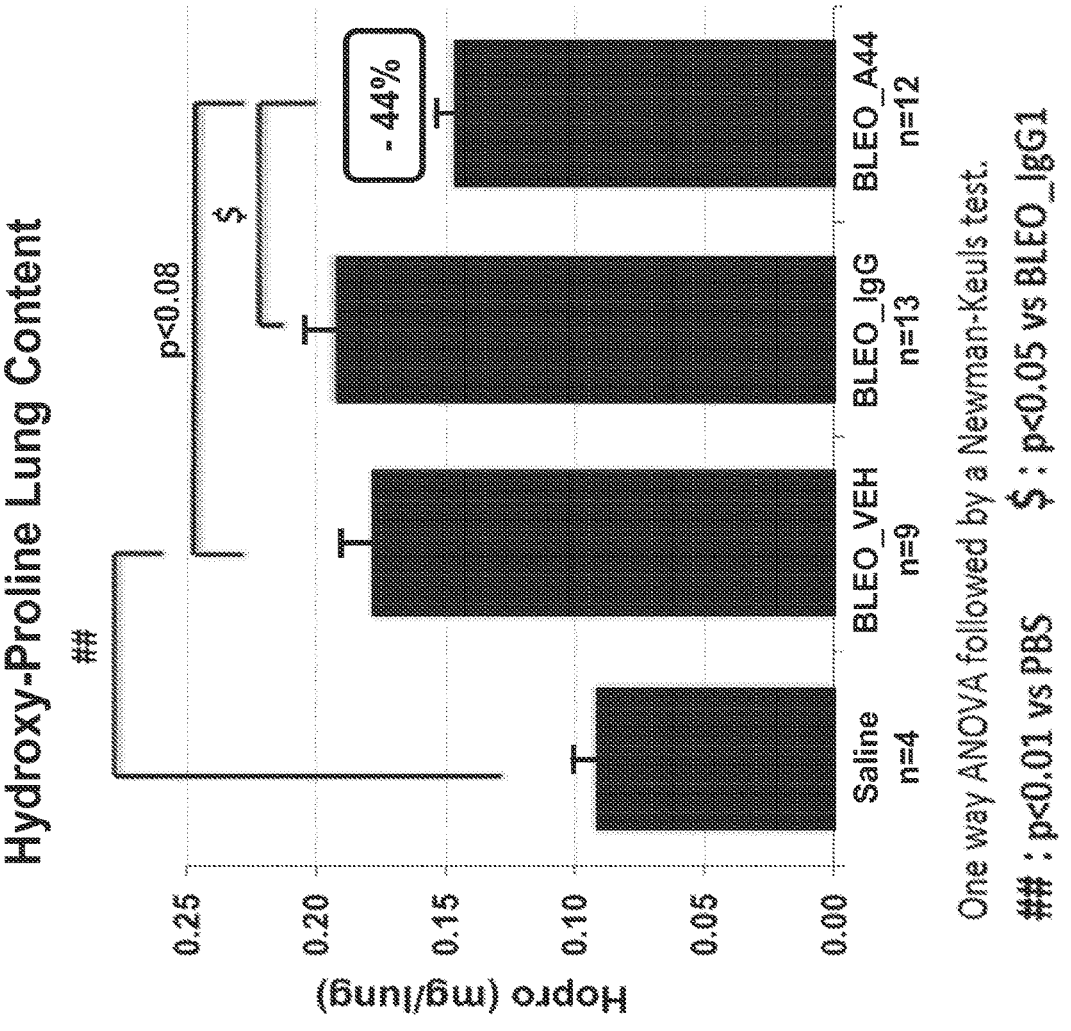
FIG. 31 depicts hydroxyproline lung content in transgenic humanized mice 21 days after either saline or bleomycin treatment followed by PBS (vehicle), IgG1 or A44 10 mg/kg i.p. administration from day 4 to day 20 every 3 days.

Collagen accumulation in the lung is another known indicator of fibrosis. To assay collagen accumulation, lung tissues from mice sacrificed at day 21 were prepared and separated by HPLC, followed by the measurement of hydroxyproline. This technique is detailed elsewhere, for example in Hattori, et al. J Clin Invest. 106(11):1341-1350 (2000). In brief, lung tissue was prepared by hydrolysis under acidic condition (6M HC1) for 22 hours at 105° C., followed by evaporation. Primary amines were blocked in the lung tissue by OPA (phthalaldehyde), and proline/hy-droxyprolines were specifically labeled using NBD (4-chloro-7-nitrobenzofurazan) (Santa Cruz Biotech., Santa Cruz, CA). Hydrolysates were then separated on Synergi™ 4 μm Hydro-RP 80 Å, LC Column 150×3 mm columns (Phenomenex, Torrance, CA, cat. #00F-4375-Y0) using HPLC (Shimazu Corp., Kyoto, Japan) under acetonitrile gradient. Standard curves of known amounts of hydroxy-proline were used as reference to quantify peak(s). A rep-resentation of the quantified data are shown in FIG. 31.

Lung collagen accumulation as detected by hydroxypro-line content was increased in bleomycin challenged animals. This increase in lung collagen accumulation was statistically reduced (p<0.08) by repeated dosing of A44V11 antibody at 10 mg/kg. (see FIG. 31). Repeated dosing using the IgG1 negative control antibody did not inhibit the increase in lung collagen accumulation due to bleomycin challenge. The reduction in bleomycin-induced collagen accumulation increase in A44V11-treated mice was statistically significant when compared to similar bleomycin-induced mice that were treated with IgG1 negative control antibody (p<0.05). A44V11-treated mice showed approximately 44% less of an increase in collagen accumulation than IgG1 control-treated mice.

Example 20: Assessment of A44V11 Activity in LPS Challenge Model in Monkeys

An acute lipopolysaccharide (LPS) challenge model in monkeys was applied to determine the PAI-1 neutralization efficacy of A44V11 in vivo. The LPS challenge model is described in Hattori, et al. J Clin Invest. 106(11):1341-1350 (2000). The activity of A44V11 mAb on PAI-1 in monkey plasma and liver samples was evaluated. Specifically, the experiment was designed to assess the impact of a high dose of LPS (100 μg/kg—IV) on plasma and tissue levels of PAI-1 in the anesthetized monkey pre-treated (24 hours before) either with A44V11 (5 mg/kg, IP) or IgG1 (negative control, 5 mg/kg, intra peritoneal administration). Experi-ments were performed in accordance with European ethical lows and approved by internal ethical comity (CEPAL, sanofi).

Cynomolgus Macaca fascicularis (male and female) weighing 4 to 9 kg were food-deprived overnight before long-term anesthesia (at least 8 hours), including IM induc-tion with Zoletil 50 (Virbac, Taguig City, Philippines) at 0.12 to 0.16 mL/kg followed by inhalation of a gaseous mix of air/oxygen and isoflurane (1 to 3%). Monkey body tempera-ture was maintained within physiological ranges using a heating pad. After catheterization, LPS (Serotype 0127-B8) was administered as a 1 min bolus in the cephalic accessory vein at a dose of 100 μg/kg (0.4 mL/kg). At various time points, blood samples and liver samples were taken. Blood samples (on citrate/EDTA) were harvested and centrifuged to isolate platelet poor plasma. Liver biopsies and terminal necropsy were stored at −80° C.

Active PAI-1, D-dimer and plasmin-α2 antiplasmin levels were determined using commercially available ELISA assays (Mol. Innovation, cat. #HPAIKT; Asserachrom D-Di-mer; Plasmin-A2 antiplasmin, Diagnostica Stago) according to manufacturer instructions.

In plasma, active PAI-1 level decreases from about 30 ng/ml to below 10 ng/ml in all monkeys administered with A44v11. (See FIG. 32(A)). There was no increase in active PAI-1 levels after LPS administration (100 ug/kg). (See FIG. 32(A). In contrast, monkeys treated with negative IgG1 control show a strong increase in active PAI-1 levels fol-lowing LPS administration, with a maximum occurring at about 4 hr (approximately 50 to about 250 ng/ml). (See FIG. 32(B)). Thus, treatment with negative IgG1 control does not reduce the active PAI-1 levels in plasma that were strongly increased after LPS administration. (See FIG. 32(B)).

Figure 33:
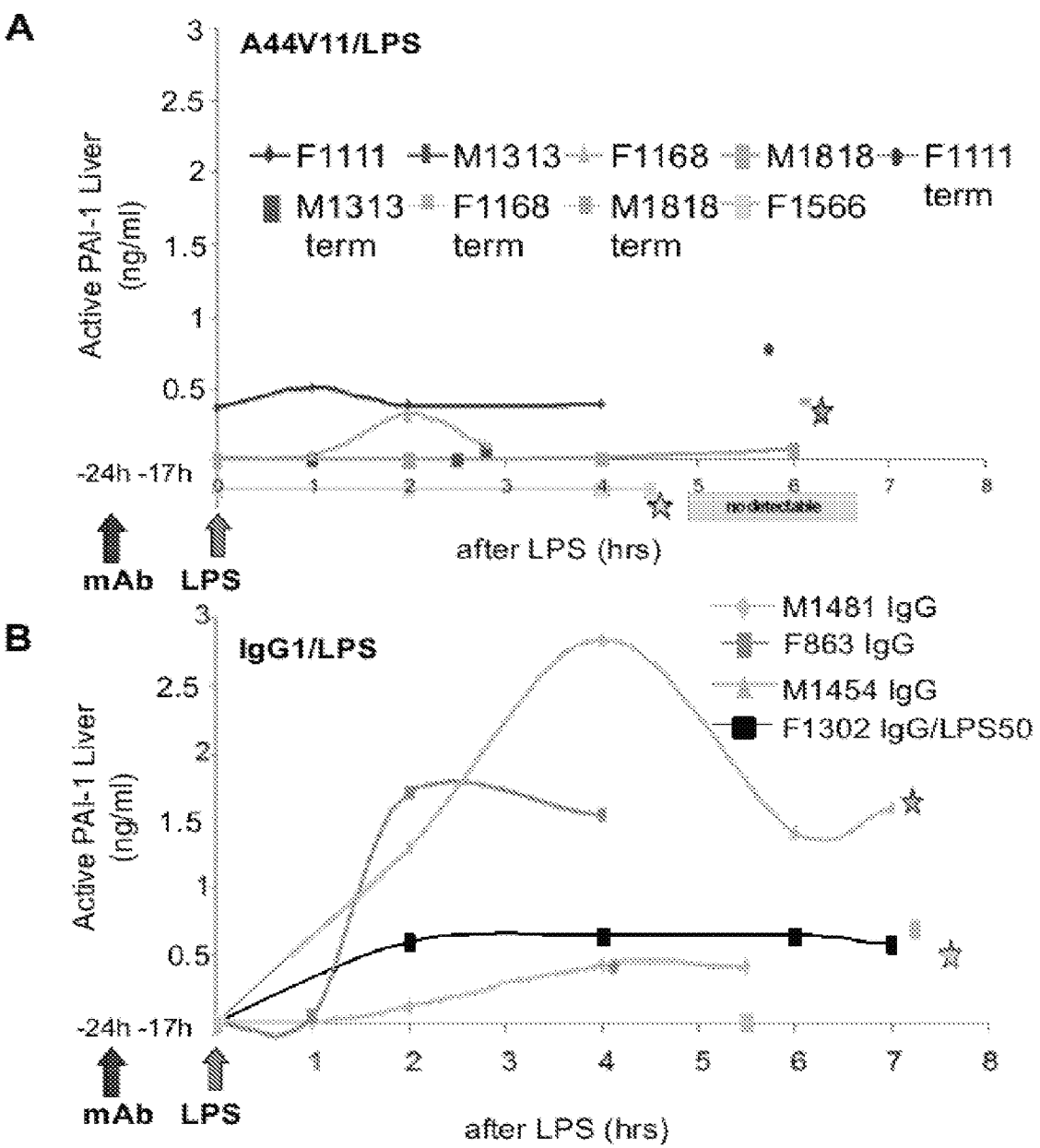
FIG. 33 depicts active PAI-1 level in liver biopsy from monkeys treated by A44V11 (A) mAb (n=5) or with IgG1 isotype control (B) (n=4) (5 mg/kg ip) 24 hours before LPS challenge (100 ug/kg iv). Liver biopsies were harvested in anesthetized monkeys at the indicated time point and active PAI-1 levels were determined in lysates using the ELISA (#HPAIKT from Molecular Innovation).

In liver biopsy lysates, a similar phenomenon was observed. Monkeys that were treated with A44V11 mAb did not show an increase in active PAI-1 levels following LPS treatment. (See FIG. 33(A)). In contrast, LPS administration induced a strong increase of active PAI-1 (up to 3 ng/mg) in liver biopsy lysates from negative IgG1 control-treated monkeys (see FIG. 33(B)).

Simultaneously to PAI-1 neutralization, the D-dimer levels in A44V11-treated monkeys (see FIG. 34(A)) was found to generally be higher than negative IgG control-treated monkeys (see FIG. 34(B)) thus suggesting that A44V11 treatment in monkeys also induces an increase of fibrin degradation in plasma.

Figure 35:
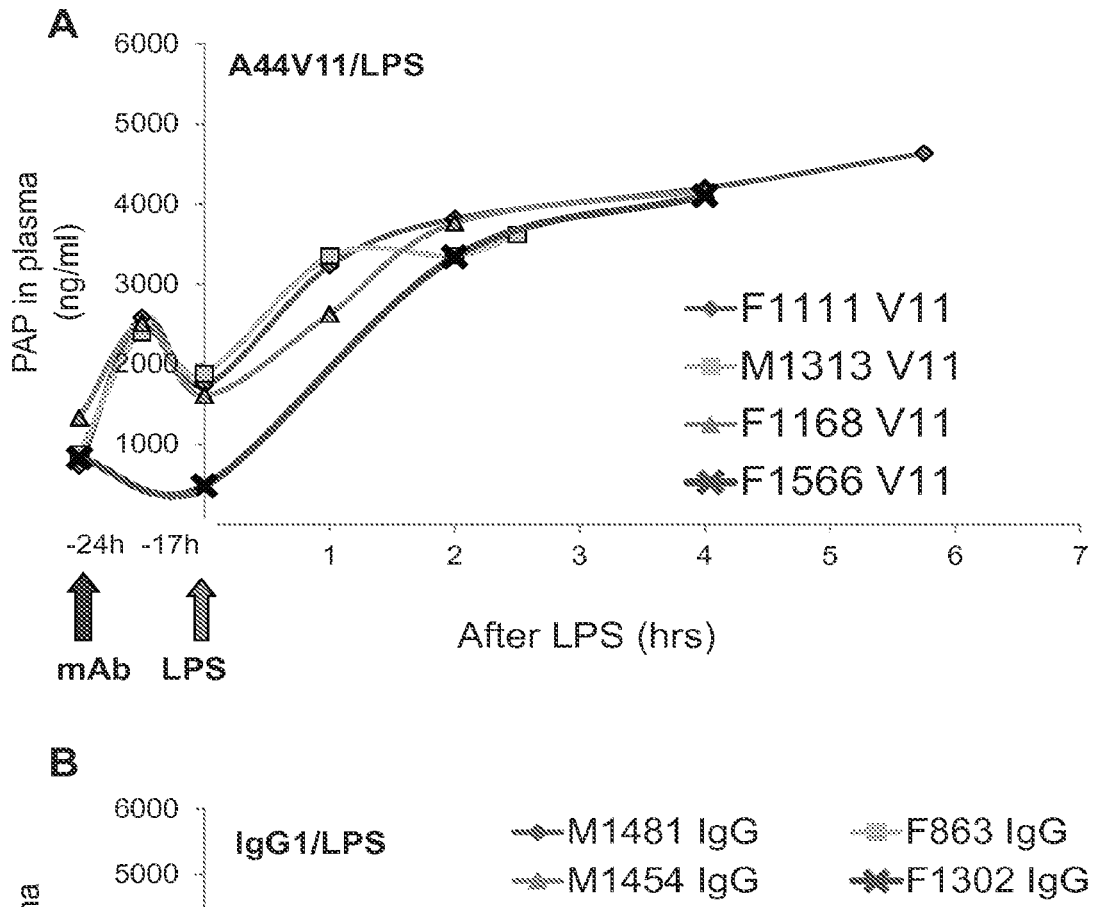
FIG. 35 depicts Plasmin-α2 Antiplasmin (PAP) complexes level in plasma from monkeys treated by A44V11 (A) mAb (n=5) or with IgG1 isotype control (B) (n=4) (5 mg/kg ip) 24 hours before LPS challenge (100 ug/kg iv). Blood samples were harvested at the indicated time point and PAP levels were determined in plasma using the ELISA (#Asserachrom PAP from Diagnostica Stago).

Finally, plasma samples of A44V11-treated monkeys showed an increased level of plasmin-α2 antiplasmin (PAP) complexes when compared to the PAP levels in negative IgG control-treated monkeys. (see FIGS. 35(A) and (B)). The increase in PAP complex and D-dimer in the presence of A44V11 indicates increases in plasmin generation.

Example 21: Assessment of A44V11 Activity in Abdominal Adhesion Mouse Model

The effect of treatment with anti-PAI-1 antibody A44V11 on the formation of adhesions was evaluated in a mouse uterine horn model of surgical injury. The mouse uterine horn approximation and electrocautery procedure disrupts the serosal surface, causes thermal damage to the uterine tissue, and approximates damaged tissue surfaces during the healing process that ultimately results in post-surgical adhesions in 100% of untreated animals. The model and surgical procedure has been previously described in Haney A. F. et al., (1993). *Fertility and Sterility*, 60(3): 550-558.

For these adhesion studies, the transgenic female mice generated above that express humanized PAI-1 transgene, approximately 9 weeks old, weighing approximately 20 g, were used. Forty-two mature transgenic female mice were divided into two groups and subjected to the surgical procedure designed to create adhesions between the uterine horns (UH), as described in detail in Haney A. F. et al., (1993). Briefly, each animal was anesthetized with isoflurane for the surgery according to IACUC guidelines, and a routine midline laparotomy was performed approximately 1.0 cm caudal to the xyphoid process. The UH were identified, approximated medially with a single 7-0 Prolene suture (Ethicon Inc., Somerville, N.J) carefully placed through the muscle wall of each horn, and the horns tied together immediately below the junction of the oviducts at the uterotubal junction. Care was taken not to damage the ovarian vascular supply. To induce electrocautery injury, a bipolar electro cautery unit was used (Valley Lab Surgistat, Solid state Electrosurgery Unit, Model No. B-20) on the medial surfaces of each uterine horn, covering an area of approximately 2×6 mm. The cautery unit was set as follows: Volts 100, 130 Hz, 50-60 Amps. A 3 mm wide cautery tip was used with pure coagulating current at a setting of 3, power was initiated, and the tissue touched for 1 second at two burn spots per horn. The muscle incision was closed with 5-0 Vicryl, BV-1 taper needle (Ethicon Inc.) in a continuous suture pattern. Skin was closed with 5-0 Prolene, BV-1 Taper needle (Ethicon Inc.), in a horizontal mattress suture pattern.

Following the creation of the UH injury, Group 1 animals were treated with a volume of 0.16 mL of an Isotype Control antibody (30 mg/kg), which was applied to the cautery burns. Group 2 animals were treated with a volume of 0.16 mL of A44V11 antibody (30 mg/kg) in the same manner. For each group, animals were euthanized at 6 hours (n=5), 72 hours (n=4), or at Day 7 (n=12). (See Table 34 below). Animals that were scheduled for euthanasia at 72 hours and Day 7 had second dose of antibody (30 mg/kg) injected intraperitoneally (IP) 48 hours after surgery.

TABLE 34

Treatment schedule for uterine horn injury studies.

| Group | Treatment | Time point Euthanized | # of Animals | Dosing (30 mg/kg) |
|---|---|---|---|---|
| Group 1 | Isotype Control mAb (0.16 mL) | 6 hours | 5 | Time 0 |
| | | 72 hours | 4 | Time 0 + 48 hours |
| | | Day 7 | 12 | Time 0 + 48 hours |
| Group 2 | Anti-PAI-1 A44 humanized mAb (0.16 mL) | 6 hours | 5 | Time 0 |
| | | 72 hours | 4 | Time 0 + 48 hours |
| | | Day 7 | 12 | Time 0 + 48 hours |

Note:
All animals had uterine horn approximated by suture and cautery burns created prior to treatment.

Efficacy Evaluation and Analysis:

Animals were euthanized at the indicated time points and the formation of adhesions was evaluated. Briefly, the length of the horns was measured from the uterine bifurcation to the approximation suture placed just below the oviducts. The two external sutures surrounding the uterine horns were removed and the length of adhesion between uterine horns was measured with the aid of a microscope, documented, and noted as present or absent (Yes/No). Also, any tissues involved in the adhesion formation will be recorded but may not be included in the length of adhesed area. The distribution of the average percent of adhesed length between uterine horns was checked for normality using the Shapiro-Wilk Test. The groups were compared with each other using Tukey Kramer analysis if normally distributed and Wilcoxon Rank-Sum analysis if not normally distributed. In all cases, a p-value≤0.05 was considered statistically significant. Animals treated with A44V11 showed significantly lower percent of length of adhesion formation between approximated uterine horns (see Table 35)

TABLE 35

Uterine Horn length measurement results.

| Group | N | % of Length with Adhesions between the Uterine Horns (Mean ± SEM) |
|---|---|---|
| Isotype Control mAb (0.16 mL) | 12 | 84 ± 3 |
| A44V11 mAb (0.16 mL) | 11 | 61 ± 7* (p = 0.02) |

Figure 36:
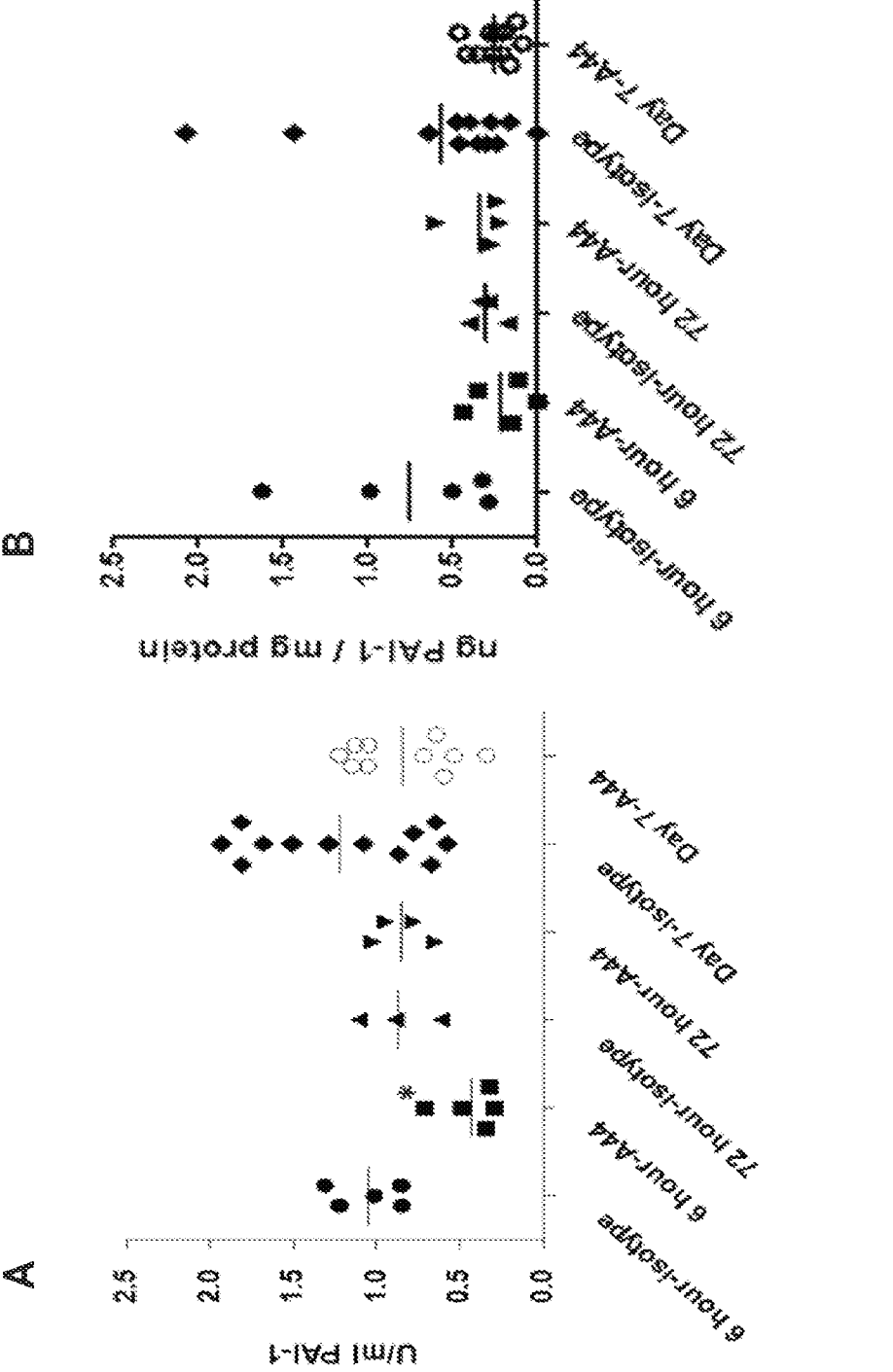
FIG. 36 depicts level of active PAI-1 in intraperitoneal fluid (IPF) and uterine horn lysates. Active PAI-1 levels in the intraperitoneal fluid (A) and uterine horn lysates (B). At the 6 hour and Day 7 time points active PAI-1 levels were lower in both intraperitoneal fluid (IPF) and Uterine Horn (UH) Lysates in the animals treated with A44V11 antibody in comparison to the isotype control antibody treated animals, no difference was observed at 72 hour time point. (*p<0.001 calculated by the Student T-test)

*p = statistically significant relative to the Isotype Control by Wilcoxon Rank Sum Analysis, Chi Square Approximation Detection of Active PAI-1 and tPA Levels Following euthanasia, animals had blood (plasma), intraperitoneal fluid (IPF), and uterine horn samples collected for evaluation. Collection of samples were performed using conventional techniques. Plasma, IPF, and uterine horn samples were evaluated for active PAI-1 and tPA levels using ELISA. (Human PAI-1 Activity ELISA kits, Cat. #HPAIKT, Molecular Innovations, Novi, MI). Data was processed using Excel, JMP, and Prism Graph pad software. In all cases, a p-value≤0.05 was considered statistically significant. At 6 hour and Day 7 time point, decreased levels of active PAI-1 were found in the IP Fluid and Uterine Horn Lysates in the animals treated with A44VI1 versus Isotype Control. (See FIG. 36). The decreased levels of active PAI-1 in the IPF at 6 hours was statistically significant result shown in IP Fluid at 6 hour time point in animals treated with A44 versus to Isotype Control (p<0.001 by Student T-test).

Example 22: Crystal Structure of Humanized Antibody A44V11

Expression and Purification of Fab A44V11

Recombinant Fab (rFab) was obtained from transiently transfected HEK293 cells, using two plasmids encoding the light chain or the C-terminal His-tagged heavy chain. After centrifugation and filtering, rFab from the cell supernatant was applied to an immobilized-metal affinity resin. After elution from the resin, the rFab was extensively dialyzed against PBS & stored at 4° C.

Source of *Macaca fascicularis* PAI-1, Referred as Cynomolgous or Cyno PAI-1:

Recombinant mature cynomolgous PAI-1 (24-402) was expressed as inclusion bodies in *E. coli* and the recombinant protein was purified using conventional methods.

Source of Human PAI-1:

Recombinant mature human PAI-1 (24-402) was purchased from Molecular Innovations Inc. (catalogue number CPAI). It was a stabilized in active conformation by introducing mutations (N150H, K154T, Q319L, M3541), as described by Berkenpas et al. (1995, EMBO J., 14, 2969-2977).

Preparation & Purification of the Complexes:

Recombinant Fab & antigen were mixed at a 1.5:1 molar ratio, incubated 30 min at room temperature, and the complexes were further purified by preparative size exclusion on a Superdex 200 PG column (GE Healthcare), equilibrated with 25 mM MES pH 6.5, 150 mM NaCl.

Crystallization of the Fab A44V11+Cyno PAI-1 Complex

The complex was concentrated to 10 mg/ml in 25 mM MES pH 6.5, 150 mM NaCl. It crystallizes in 16-24% ethanol, 100 mM Tris pH 8.5. Ethylene glycol (30%) was used as cryoprotectant. Crystals diffracted to about 3.3 Å in space group P321 (a=b=193 Å, c=144 Å) on ID29 beamline of ESRF. Data was processed with a combination of XDS and Scala (GlobalPhasing Ltd., Cambridge, UK)

Structure Determination of the Complex Fab A44V11/Cyno-PAI-1:

A model of the Fab variable domain was constructed using Prime in Maestro (Schrodinger, New York, NY). The constant domain was obtained from published structure 3FO2. Two different models of human PAI-1 were used: the latent conformation was obtained from 1LJ5, the active conformation from 1OC0. Calculation of Matthews Coefficient ($V_M$, crystal volume per unit of protein molecular weight) suggests that there are up to four complexes in the asymmetric unit ($V_M$ 2. 2 assuming a complex size of 90 kilodaltons (KD). Molecular Replacement was done using Phaser (CCP4 suite)(McCoy, et al. *J. Appl. Cryst.* 40: 658-674 (2007), which identified two monomers of latent PAI-1 and two variable domains of Fab. Additional density was clearly visible for the constant domains, which had to be placed manually. This solution, which corresponds to a $V_M$ of 4.3 (71% solvent), was also carefully examined for packing consistency. The structure was refined with Buster (GlobalPhasing) using non crystallographic symmetry, to an Rfree of 29.2% (Rfactor 25.8%). The constant domains are not stabilized by crystal packing and are poorly resolved in the electron density map.

Crystallization of the Fab A44V11+Human PA-1 Complex

Protein crystallization is a bottleneck of biomolecular structure determination by x-ray crystallography methods. Success in protein crystallization is directly proportional to the quality of the protein molecules used in the crystallization experiments, where the most important quality criteria are purity and homogeneity (both molecular and conformational) of the proteins in solution.

Initially, to determine the PAI-1/Fab mAb complex structure a native mAb A44 was used to prepare its Fab fragment by papain digestion. This Fab scaled up preparation resulted heterogeneous Fab fragments which were complexed and purified in complex with human wild type (wt) PAI-1 protein. The obtained protein complex was concentrated to 7 mg/ml concentration and screened for crystallization under 800 individual crystallization conditions at two different temperatures, 4° C. and 19° C. No crystallization hits were detected. In order to improve the protein complex homogeneity recombinant 6-His tagged Fab A44 was produced, purified and complexed with the human wild type PAI-1 protein (see FIG. 36).

The complex crystallization screening resulted first crystallization hits under 20% PEG10K+0.1M Sodium Acetate pH4.6 conditions. Crystallization optimization by conventional crystallization methods, Microseed Matrix Seeding, and in situ Trypsinolysis crystallization did not significantly improve the quality of crystals. The best obtained crystals were needle-like and were diffracting x-rays with insufficient resolution for structure determination (10 Å).

Figure 37:
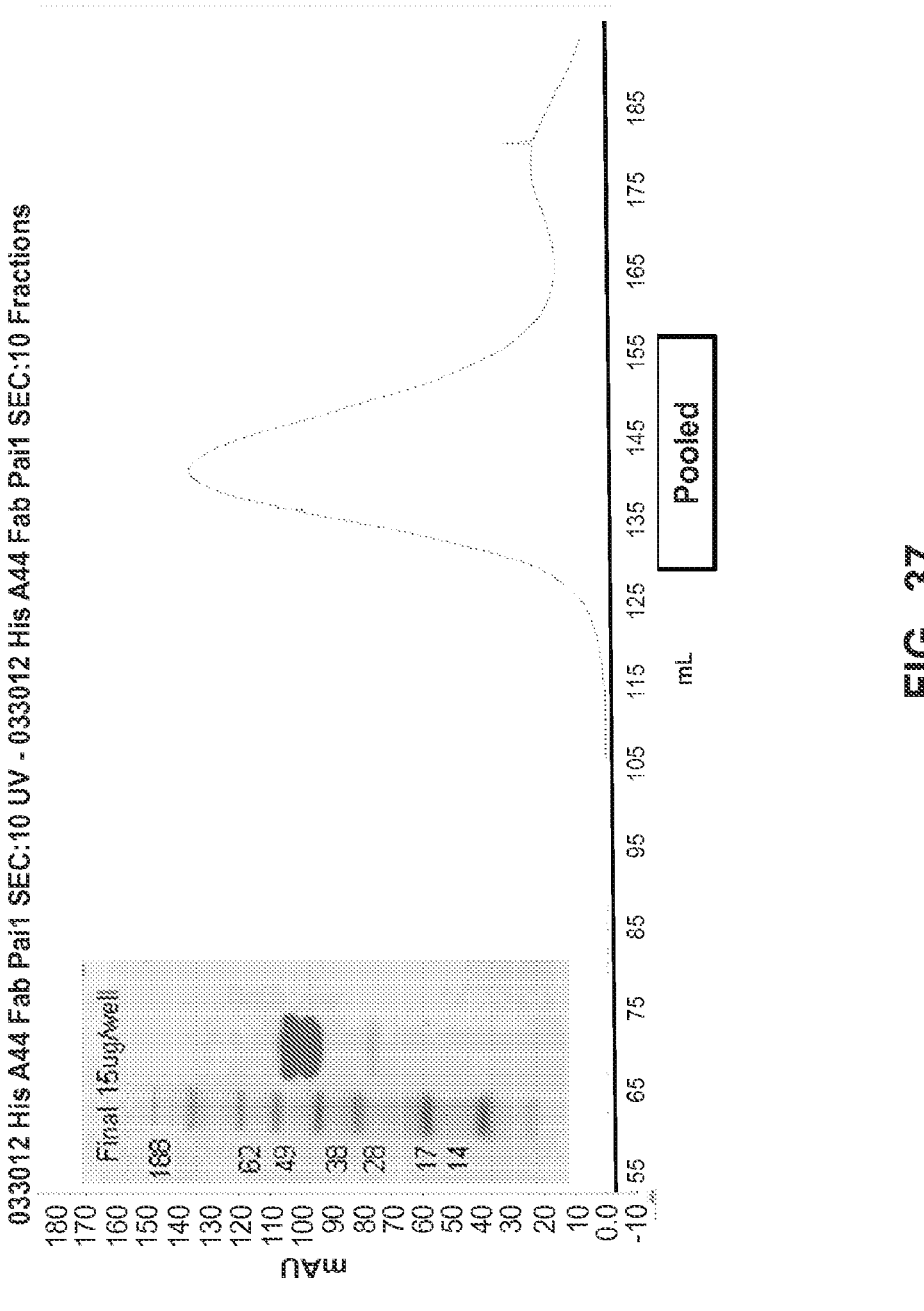
FIG. 37 depicts another example of purification of homogeneity recombinant 6-His tagged Fab A44.
Figure 38:
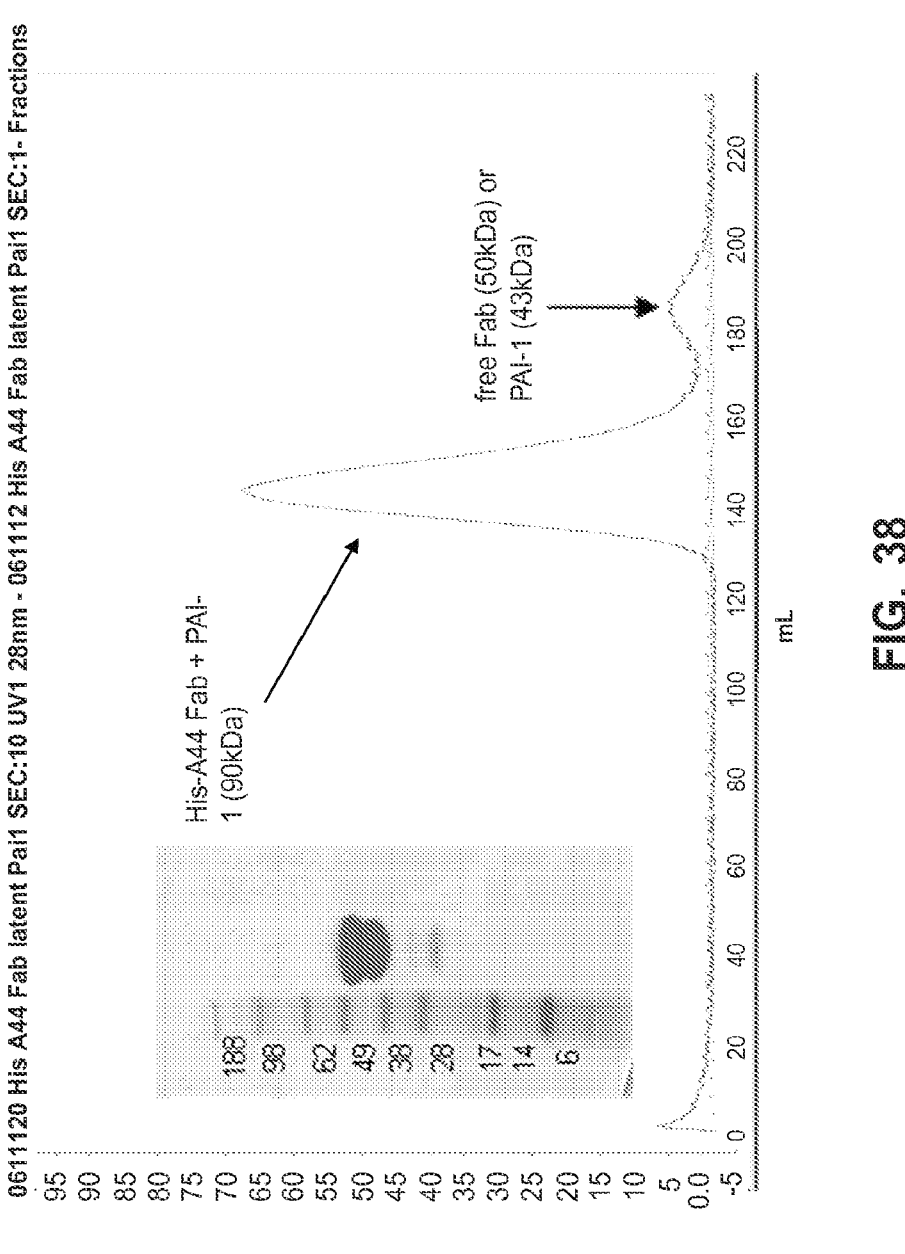
FIG. 38 depicts purification of homogeneity recombinant 6-His tagged Fab A44 complexed with the human wt PAI-1 protein.

The failure with the complex crystals crystallization could potentially be explained by the complex conformational heterogeneity. The wild type PAI-1 molecule is known to adopt three distinct conformations (active, latent, and substrate) which may interfere with crystallization. To improve the quality of the crystals, 6-His tagged A44 Fab in complex with latent PAI-1 was produced. (see FIG. 37).

The corresponding complex was produced and screened for crystallization de novo and under conditions previously used for 6-His tagged Fab A44/wt PAI-1 protein complex. The only crystallization hit out of the more than 1000 conditions tested was identified for the complex under 20% PEG3350+0.2M nH4 Acetate+4% MPD+50 mM Mes pH6 conditions (see FIG. 39(a)). After extensive optimization 3D crystals were obtained. X-Ray diffraction tests using synchrotron high intensity X-Ray beam showed no diffraction sign (see FIG. 39(b), depicting representative optimized crystals).

Figure 40:
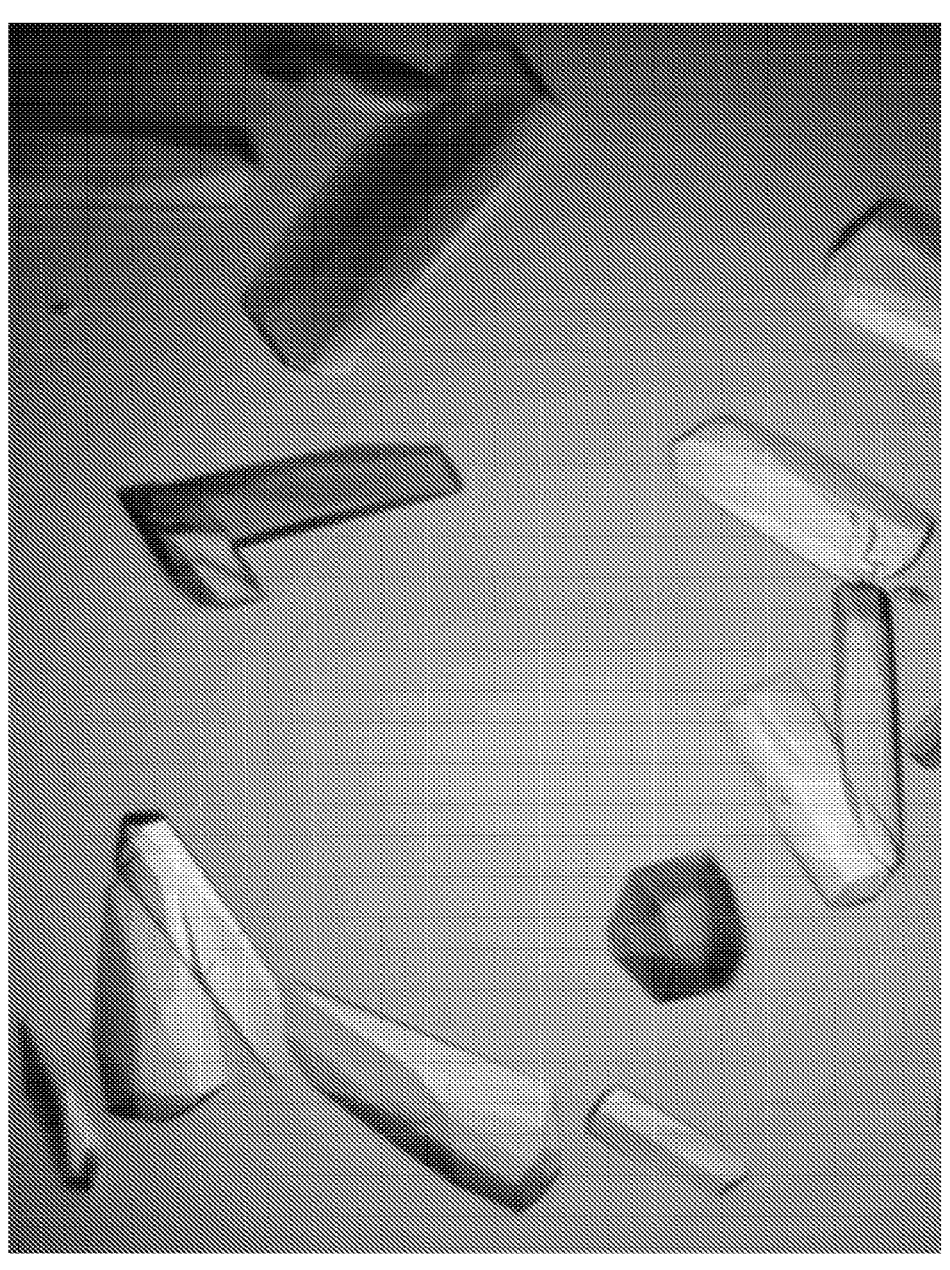
FIG. 40 depicts the rod-like single crystals of the Fab A44/PAI-1 complex.
Figure 41:
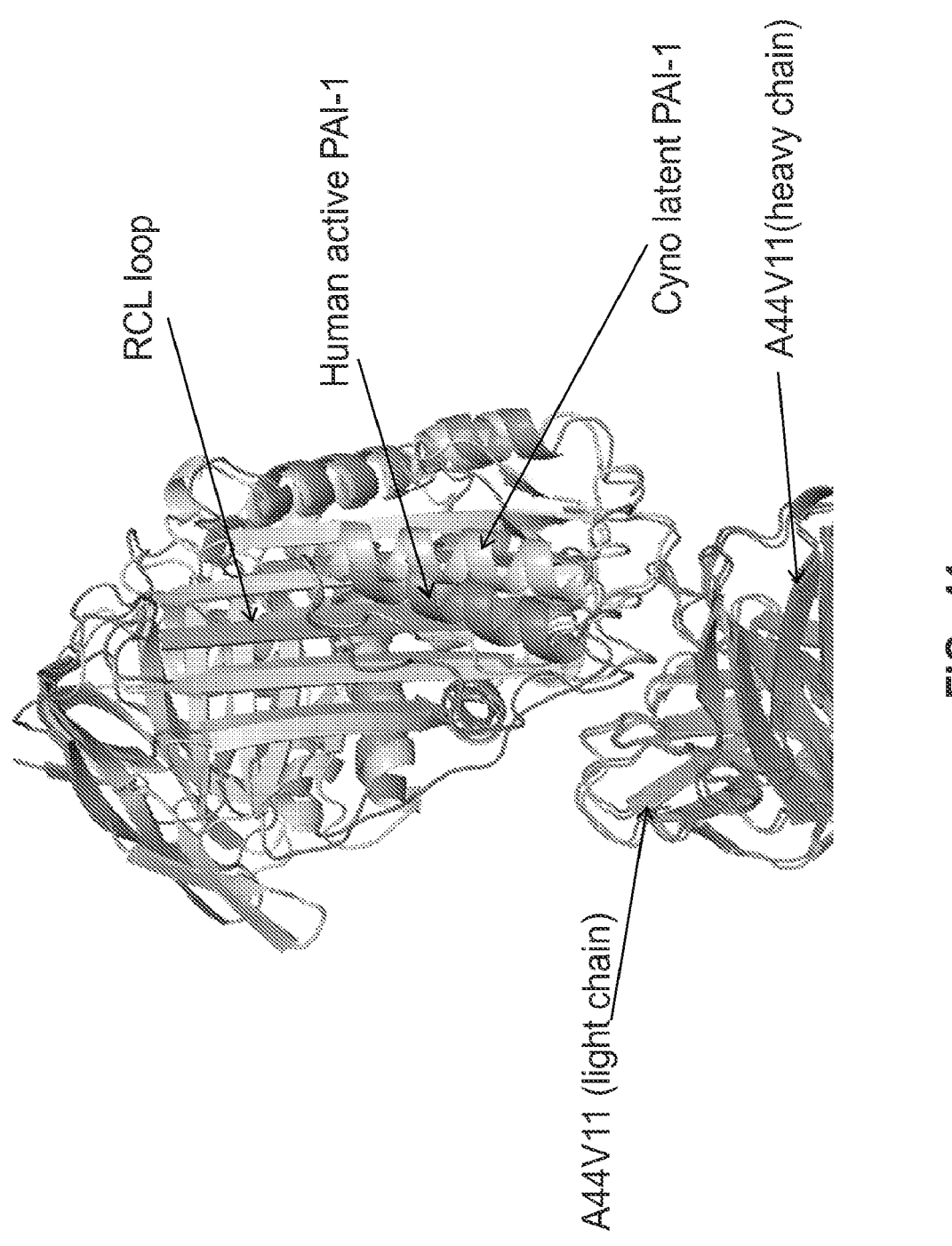
FIG. 41 depicts Fab A44 recognition the active form of human PAI-1 and the latent form of cyno PAI-1.

To reduce the flexibility of portions of the protein it was decided to produce A44 Fab fragment recombinantly but without an artificial tag such as the 6-His tag used previously. To further increase the chances for successful crystallization, an active form mutant of PAI-1 (N150H, K154T, Q319L, M3541) was purchased from Molecular Innovations (Cat. #CPAI, Novi, MI) and used for complex preparation with Fab A44 protein lacking artificial tag. The complex was concentrated to 12 mg/ml in 25 mM MES pH 6.5, 150 mM NaCl. Acceptable rod-like single crystals were obtained in 10% PEG3350, 100 mM ammonium sulfate and cryoprotected by the addition of 30% ethylene glycol (see FIG. 40). These crystals diffracted to 3.7 Å resolution, and after extensive cryoprotection optimization, resulted in an x-ray diffraction data set suitable for the structure determination (3.3 Å). A dataset was collected to 3.3 Å at beamline Proxima 1 of synchrotron SOLEIL (Saint-Aubin, France). Spacegroup is P212121 (a=105, b=152 c=298). Data was processed using XDSme scripts (XDS ref, Xdsme ref).

Structure Determination of the Complex Fab A44V11/Human-PAI-1:

Pointless (CCP4) indicated only a 40% confidence in spacegroup identification. In consequence, initial Molecular Replacement was carried out with Amore (CCP4) to test all possible space group variants of the P222 point group: P212121 was unambiguously confirmed. Final Molecular Replacement with Phaser (Phaser, CCP4) identified four dimers of active PAI-1/variable domain of Fab in the asymmetric unit. The constant domains were added manually in the electron density map. The structure was refined with Buster (GlobalPhasing) using non crystallographic symmetry, to a Rfree of 28% (Rfactor 24.1%).

Epitope and Paratope Structural Analysis

Figure 42:
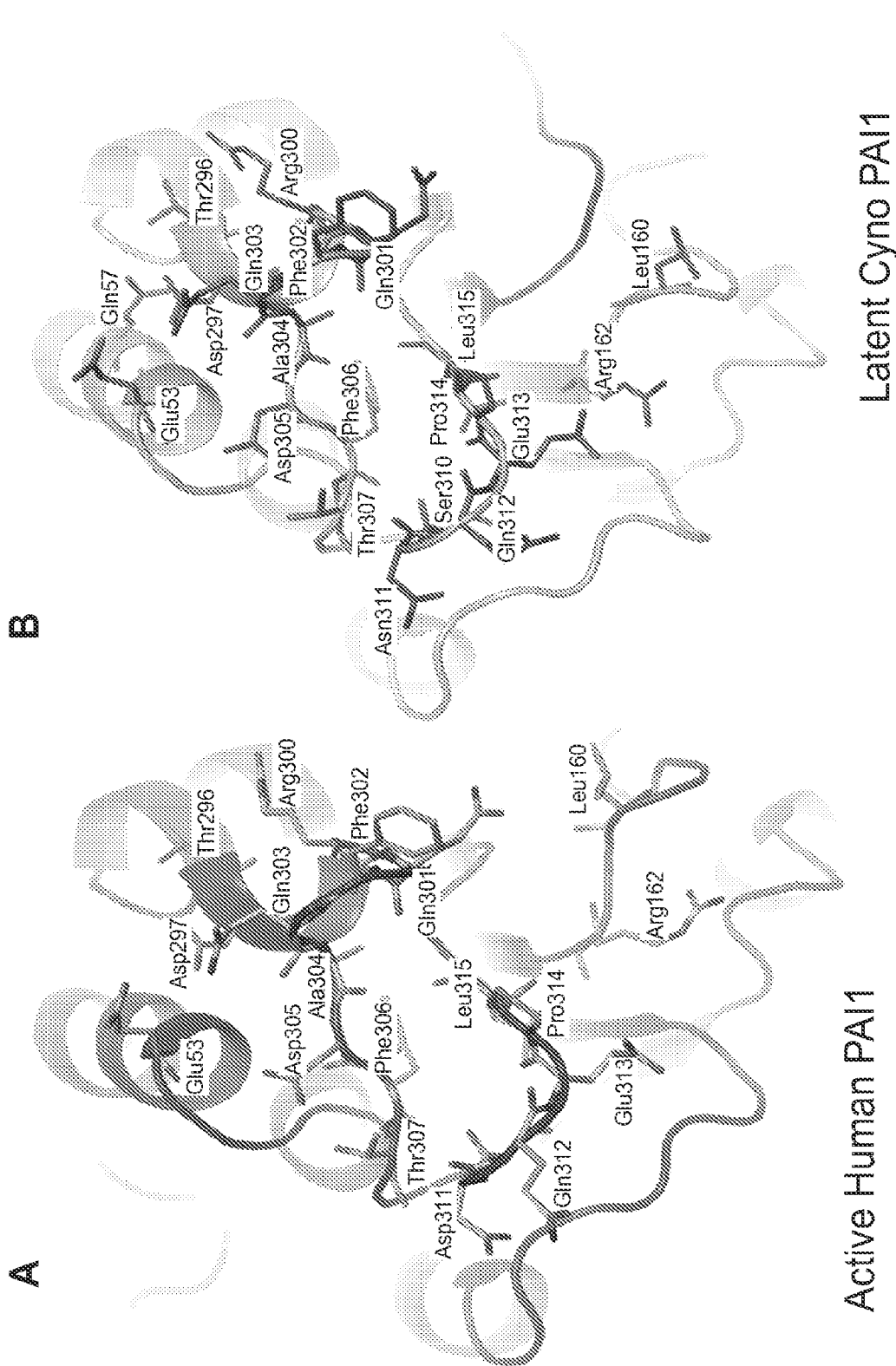
FIG. 42 depicts the PAI-1 epitope recognized by Fab A44 in (A) active human PAI-1, and (B) latent cyno PAI-1.

Epitope and paratope regions were identified as formed in the cyno and human complexes, and the complexes were compared. The crystal structures were determined to 3.3 Å for A44V 11 in complex with human and cyno PAI-1. The superimposition of both structures (see FIG. 40) shows that the paratope of A44V 11 is similar for both latent and active forms of PAI-1. Fab A44 recognized the active form of human PAI-1 and the latent form of cyno PAI-1. FIG. 42 depicts the PAI-1 epitope recognized by Fab A44 in both active human PAI-1 (FIG. 42(A)), and latent cyno PAI-1 (FIG. 42(B)). The paratope-recognizing the latent conformation is part of the paratope recognizing the active conformation.

Figure 43:
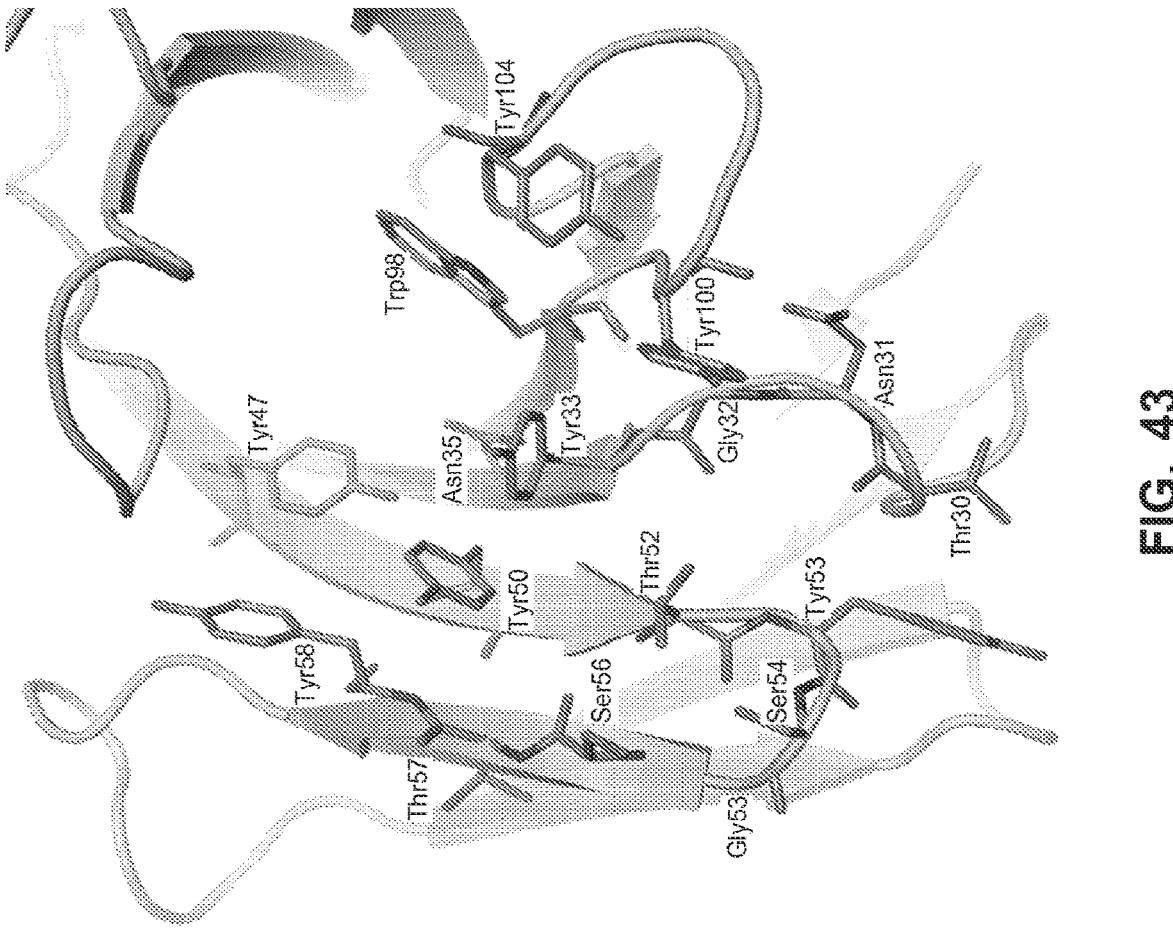
FIG. 43 depicts the heavy chain paratope of the Fab A44/PAI-1 complex.
Figure 44:
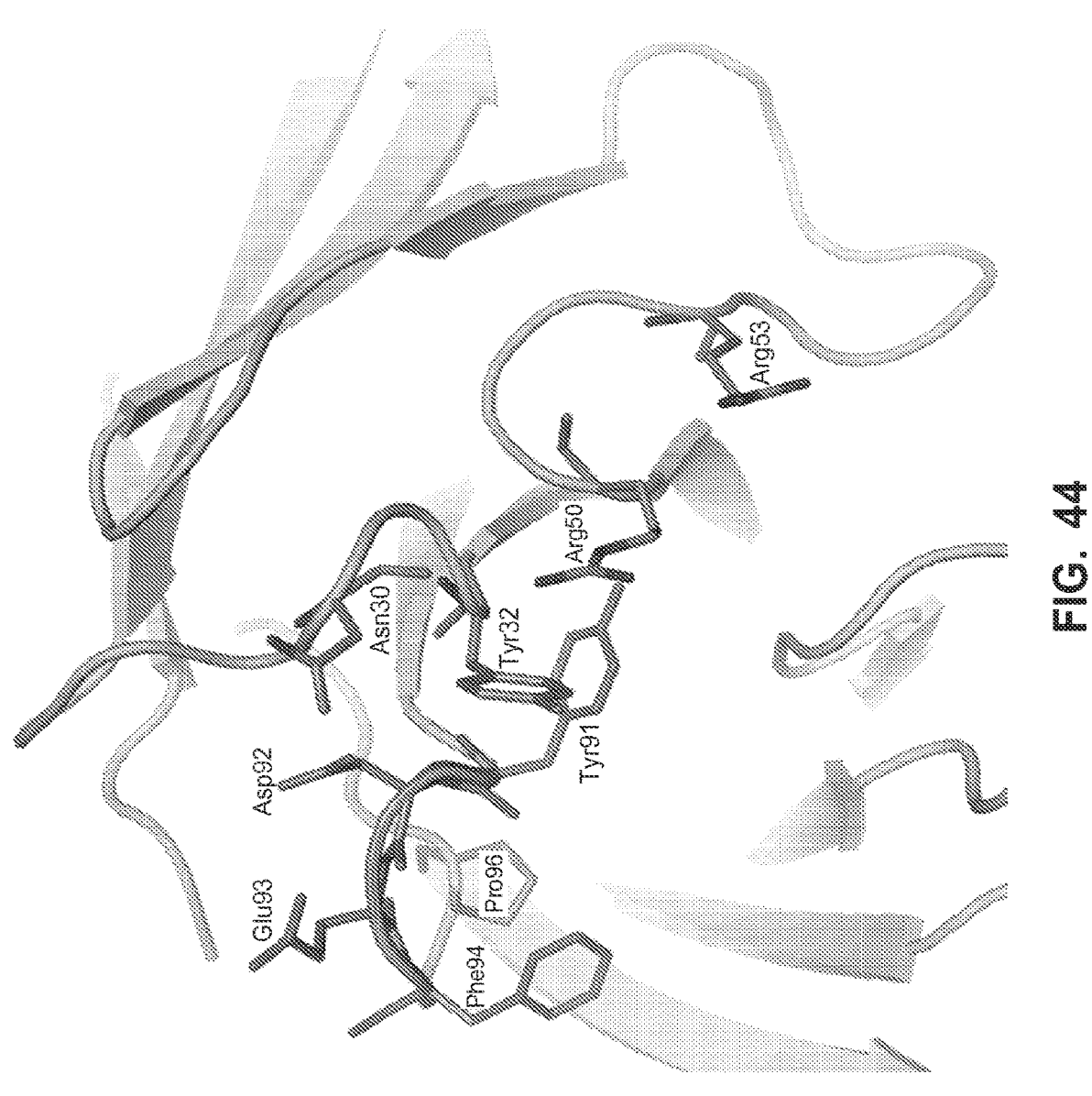
FIG. 44 depicts the light chain paratope of the Fab A44/PAI-1 complex.

PAI-1 interacts mostly with the heavy chain of A44V11, as can be seen from the analysis of the surface areas of interaction. Surface area of the interaction between active human PAI-1 and the heavy chain (average of 4 complexes) is 674 Å$^2$. Surface area of the interaction between active human PAI-1 and the light chain (average of 4 complexes) is 372 Å$^2$. Surface area of the interaction between latent cyno PAI-1 and the heavy chain (average of 2 complexes) is 703A2. Surface area of the interaction between latent cyno PAI-1 and the light chain (average of 2 complexes) is 360A2. See FIGS. 43 and 44 for depictions of the paratopes of the heavy chain and light chain, respectively.

The residues of the A44V 11 part of the paratope are shown below in Table 36. Residues in italic are involved in the interactions with active PAI-1 but not the latent form, while residues underlined are interacting only with the latent form. All other residues are involved in both interfaces.

TABLE 36

| A44V11 residues involved in paratope with PAI-1 | |
| --- | --- |
| Location | Residues |
| Heavy Chain (FIG. 43) | |
| Loop H1 | *Thr30*, Asn31, Gly32, Tyr33 and Asn35 |
| Loop H2 and neighboring β-strands | Tyr47, Tyr50, Thr52, Tyr53, Ser54, <u>Gly55</u>, Ser56, *Thr57* and *Tyr58* |
| Loop H3 | Trp98, Tyr100 and Tyr104 |
| Light Chain (FIG. 44) | |
| Loop L1: | Asn30 and Tyr32 |
| Loop L2: | Arg50 and Arg53 |
| Loop L3: | Tyr91, Asp92, *Glu93*, Phe94 and Pro96 |

Despite the different conformations of the human and cyno PAI-1 molecules, the same residues are involved in interactions with the Fab A44 (bolded residues shown below in the sequence of human PAI-1) (SEQ ID NO:1):

```
VHHPPSYVAHLASDFGVRVFQQVAQASKDRNVVFSPYGVASVLAMLQL

TTGGETQQQIQAAMGFKIDDKGMAPALRHLYKELMGPWNKDEISTTDA

IFVQRDLKLVQGFMPHFFRLFRSTVKQVDFSEVERARFIINDWVKTHT

KGMISHLLGTGAVDQLTRLVLVNALYFNGQWKTPFPDSSTHRRLFHKS

DGSTVSVPMMAQTNKFNYTEFTTPDGHYYDILELPYHGDTLSMFIAAP

YEKEVPLSALTNILSAQLISHWKGNMTRLPRLLVLPKFSLETEVDLRK

PLENLGMTDMFRQFQADFTSLSDQEPLHVALALQKVKIEVNESGTVAS

SSTAVIVSARMAPEEIIIDRPFLFVVRHNPTGTVLFMGQVMEP
```

Short-hand for the A44V11 binding epitope for human PAI-1 is as follows:

```
                                      (SEQ ID NO: 156)
      E-X-X-Q;

(SEQ ID NO: 157)
      L-X-R;

(SEQ ID NO: 158)
      T-D-X-X-R-Q-F-Q-A-D-F-T-X-X-S-D-Q-E-P-L
```

In summary, the cyno and human epitopes of PAI-1 recognizing FabA44 are identical in both conformations. Fab A44 recognizes both human and cyno PAI-1 but likely not mouse or rat PAI-1.

Example 23: Determination of A44V11 Specificity and Cross-Reactivity

To determine the specificity and reactivity of A44V11, the sequence of the A44V 11 epitope (see above) was used to search for similar epitopes in other proteins using a motif search with ScanProsite (SIB Swiss Institute of Bioinformatics) database. For additional details see Artimo, P. et al. Nucleic Acids Res. 40(W1):W597-603 (2012). All of the epitope sequence matches located in the search were related to PAI-1, suggesting that the A44V11 antibody is specific for PAI-1.

The A44V11 epitope was also compared to other known x-ray structures (3D search) using in silico profiling and molecular modeling according to Med-SuMo, which detects and compares the biochemical functions on proteins surfaces, including for example hydrogen bonds, charges, hydrophobic and aromatic groups. Med-SuMo molecular modeling is further described in Jambon, et al. *Bioinformatics* 21(20):3929-30 (2005). The 3D search of the A44V11 epitope located a similar motif in human alpha-1-antitrypsin (AAT1). However, upon further investigation, the AAT1 motif was found to have significant differences between the A44VI1 epitope, such that A44VI1 is unlikely to bind. Therefore, sequence pattern and 3D pattern analysis of the A44V 11 epitope suggests that there should be minimal cross-reactivity with other human proteins.

Figure 45:
FIG. 45 depicts a sequence alignment of the proposed A44 binding epitopes of cyno, human, rat, and mouse PAI-1. Sequences are excerpted from SEQ ID NO:1 (PAI-1 human), SEQ ID NO:162 (PAI-1 cyno), SEQ ID NO:163 (PAI-1 mouse), and SEQ ID NO:164 (PAI-1 rat).
Figure 46:
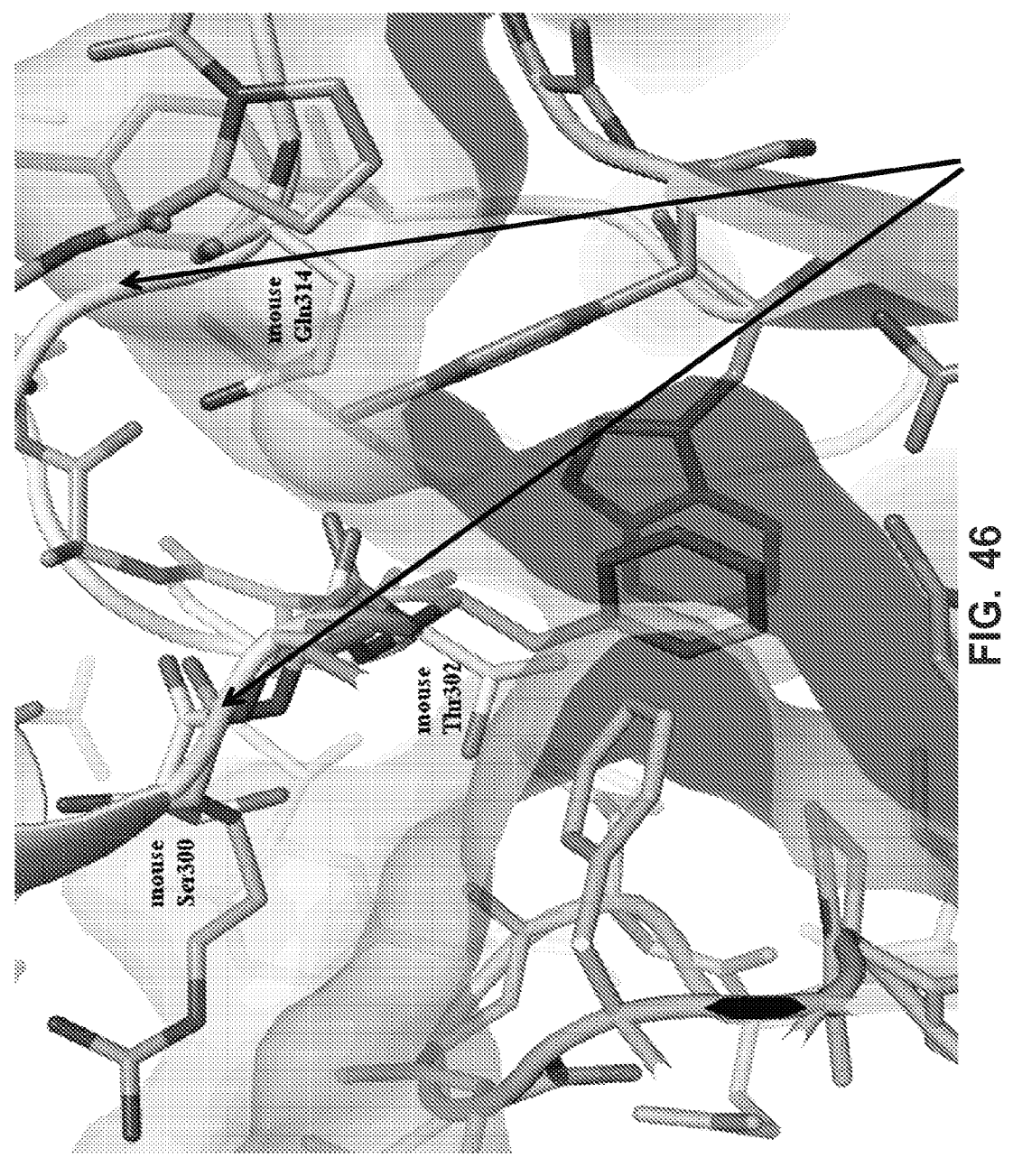
FIG. 46 depicts the comparison of the mouse PAI-1 structure with the structure of the human PAI-1/A44V11 complex.

The human and cyno PAI-1 epitopes for A44V 11 were compared to proposed epitopes from mouse and rat PAI-1. Sequences are excerpted from SEQ ID NO:1 (PAI-1 human), SEQ ID NO:162 (PAI-1 cyno), SEQ ID NO: 163 (PAI-1 mouse), and SEQ ID NO:164 (PAI-1 rat). Rat and mouse PAI-1 have respectively 75% and 79% sequence identity with human PAI-1. Alignment of the different PAI-1 sequences show significant differences between rat/mouse and human/cyno sequence in their respective epitopes, suggesting that A44VI1 is unlikely to recognize rat or mouse PAI-1 (See FIG. 45). For example, mouse PAI-1 amino acids Ser300, Thr302, Gln314 are different from the human/cyno PAI-1 counterparts. The differences in these residues represent a change in proposed epitopes, such that mouse PAI-1 cannot be recognized by A44V11. The structural comparison of the mouse PAI-1 with the structure of the complex human PAI-1/A44V11 (FIG. 46) further indicates that it should not be possible to obtain both human and mouse activity from the A44V11 antibody.

Figure 47:
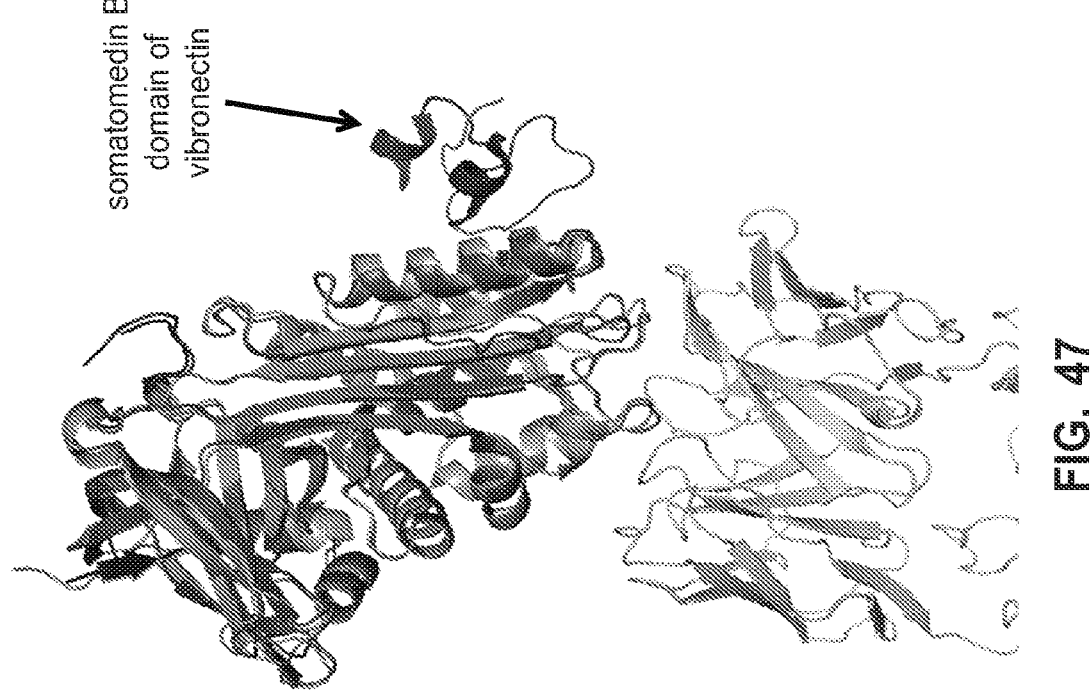
FIG. 47 shows the structure of human PAI-1/A44V11 complex and the model of vibronectin binding to PAI-1.

To further validate the identified epitope for A44V11, the human and cyno A44V11 epitopes were compared to binding regions of vibronectin. The structure of human PAI1 in complex with the somatomedin B domain of vibronectin has been published (1OC0). The structures of these two complexes were compared (see FIG. 47). The structural comparison suggests that the binding of A44V I1 will not impact PAI-1 interaction with vibronectin.

The A44Va epitope was compared to the epitopes of other published anti-PAI1 antibodies. No overlap of the A44V11 epitopes was found with other published anti-PAI-1 antibodies MA-55F4C2 and MA-33H1, which bind residues in the 128-156 region (see Debrock et al. *Thromb Haemost,* 79:597-601 (1998)).

Finally, the specificity and lack of cross-reactivity of the A44V11 antibody was confirmed by Biacore. Based on the predicted unique sequence and 3D structure of the A44V11 epitope, molecular modeling studies indicate strongly that the A44V11 is specific for human and cyno PAI-1.

Example 24: Epitope Mapping by Hydrogen/Deuterium Exchange Mass Spectrometry (HDX MS)

Hydrogen/deuterium exchange (HDX) monitored by mass spectrometry (MS) was applied to the PAI-1-binding antibodies disclosed herein to further characterize the epitopes of each antibody. HDX MS is a particularly useful technique for comparing multiple states of the same protein. Detailed methodology and applications of HDX MS to protein therapeutics are disclosed in Wei, et al., *Drug Discovery Today,* 19(1): 95-102 (2014). Briefly, if an aqueous, all-H$_2$O solvent is replaced with an isotope of hydrogen that has distinctive spectroscopic properties, then one can follow this exchange process. For most modern HDX experiments, deuterated or "heavy" water (D$_2$O) is used. In particular, the hydrogen bonded to the backbone nitrogen (also referred to as the backbone amide hydrogen) is useful for probing protein conformation. See, e.g., Marcsisin, et al. *Anal Bioanal Chem.* 397(3): 967-972 (2010). The exposed and dynamic regions of proteins will exchange quickly, while protected and rigid regions of proteins will exchange slower. All of the relevant conditions (pH, temperature, ionic strength, etc.) are kept constant, so only the difference in structure (solvent accessibility, hydrogen bonding) impacts this exchange. The interaction of the antibody with PAI-1 will block the labeling of certain portions of the antigen, thus producing a different readout based on the site of binding (epitope).

Experimental Method:

Stock solutions of cyno-PAI-1 (10 uM), cyno-PAI-1 bound to A44v11 (10 μm each) and cyno-PAI-1 bound to APGv2 (10 μm each) were prepared in PBS, pH 7.2. The protein solutions were allowed to reach binding equilibrium by incubating for 1 hour at room temperature. Based on a K$_d$ value of <50 pM, each of the antibody:antigen complexes were >99% bound under the labeling conditions described below.

Deuterium exchange, quenching, and sample injection were handled by an automated robotics system (LEAP Tech., Carrboro, NC). An aliquot of the protein solution was diluted 10-fold with labeling buffer (PBS in 99.9% D$_2$O, pD 7.2) and allowed to incubate at 20° C. for 10 sec, 1 min, 5 min, or 4 hours. At the end of the deuterium exchange time point, the labeling reaction was quenched by adding 50 μL of the labeling solution to an equal volume of pre-chilled (0° C.) 100 mM sodium phosphate, 4 M guanidine hydrochloride, 0.5 M TCEP, pH 2.5. Undeuterated controls were prepared in an identical fashion by diluting 10-fold with PBS in H$_2$O.

Each quenched sample (50 μL, 50 pmol of each protein) was immediately injected into a Waters nanoAcquity with HDX Technology (Waters Corp., Milford, MA). The proteins were digested online with a 2.1 mm×30 mm Enzymate BEH pepsin column (Waters Corp.) which was held at 20° C. All of the chromatographic elements were held at 0.0+ 0.1° C. inside the cooling chamber of the ultra-performance liquid chromatography (UPLC) system. The resulting peptides were trapped and desalted for 3 min at 100 μL/min and then separated on a 1.0×100.0 mm ACQUITY UPLC HSS T3 column (Waters Corp.) with a 12 min, 2-40% acetonitrile:water gradient at 40 μL/min. Deuterium levels were not corrected for back exchange and were reported as relative. All comparison experiments were done under identical conditions, negating the need for back exchange correction. All experiments were performed in triplicate. Peptide carryover between injections was eliminated by injecting 50 μL of 1.5 M guanidine hydrochloride, 0.8% formic acid, and 4% acetonitrile over all columns after each run.

Mass spectra were acquired with a Waters Synapt G2-Si instrument equipped with a standard electrospray source (Waters Corp.) run in HDMSe mode. Instrument settings were as follows: capillary was 3.5 kV, sampling cone was 30 V, source offset was 30 V, source temperature was 80° C., desolvation temperature was 175° C., cone gas was 50 L/hr, desolvation gas was 600 L/h, and nebulizer gas was 6.5 bar. Mass spectra were acquired over an m/z range of 50-1700. Mass accuracy was maintained through each run by simultaneous infusion of 100 fmol/uL human [Glu1]-Fibrinopeptide B through the lockmass probe.

MSE identification of the undeuterated peptic peptides was preformed using ProteinLynx Global Server software (Waters Corp.). Deuterium uptake for each peptide was determined using DynamX 2.0 software (Waters Corp.). Relative deuterium levels were calculated by subtracting the centroid of the isotopic distribution for undeuterated peptides from the corresponding centroid of the deuterium-labeled peptide. Deuterium uptake plots were generated automatically by the software.

Monitoring Deuterium Uptake for PAI-1 States

Figure 48:
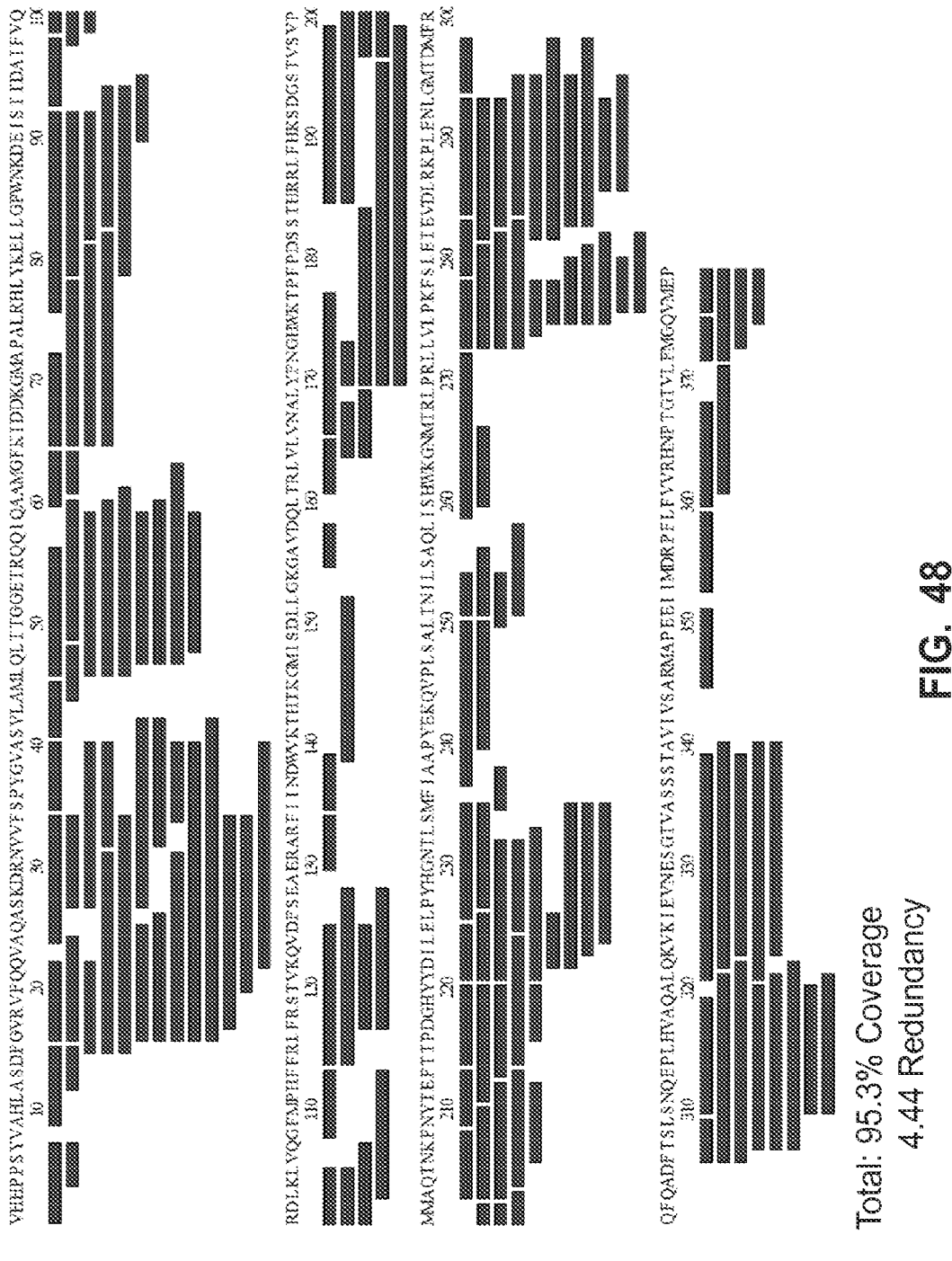
FIG. 48 depicts peptic peptide coverage of cyno-PAI-1 (SEQ ID NO:162); 95.3% sequence coverage is obtained from 150 overlapping peptic peptides.

After online pepsin digestion, 150 overlapping cyno-PAI-1 peptic peptides were identified, resulting in 95.3% sequence coverage (see FIG. 48). Deuterium uptake was monitored (from 10 see to 4 hours) in all 150 peptides for three different protein states: (1) cyno-PAI-1 alone; (2) A44v11 bound to cyno-PAI-1; and (3) APGv2 bound to cyno-PAI-1.

The majority of the cyno-PAI-1 peptides showed nearly identical deuterium uptake between the three states, which indicates that there is no interaction between cyno-PAI-1 and either mAb in these regions. See FIG. 49(A), which depicts one representative peptide region with this result (residues 139-152). In contrast, peptides incorporating residues 44-64 showed significant protection from exchange (reduced deuterium uptake) when bound to either A44v11 or APGv2

Figure 49:
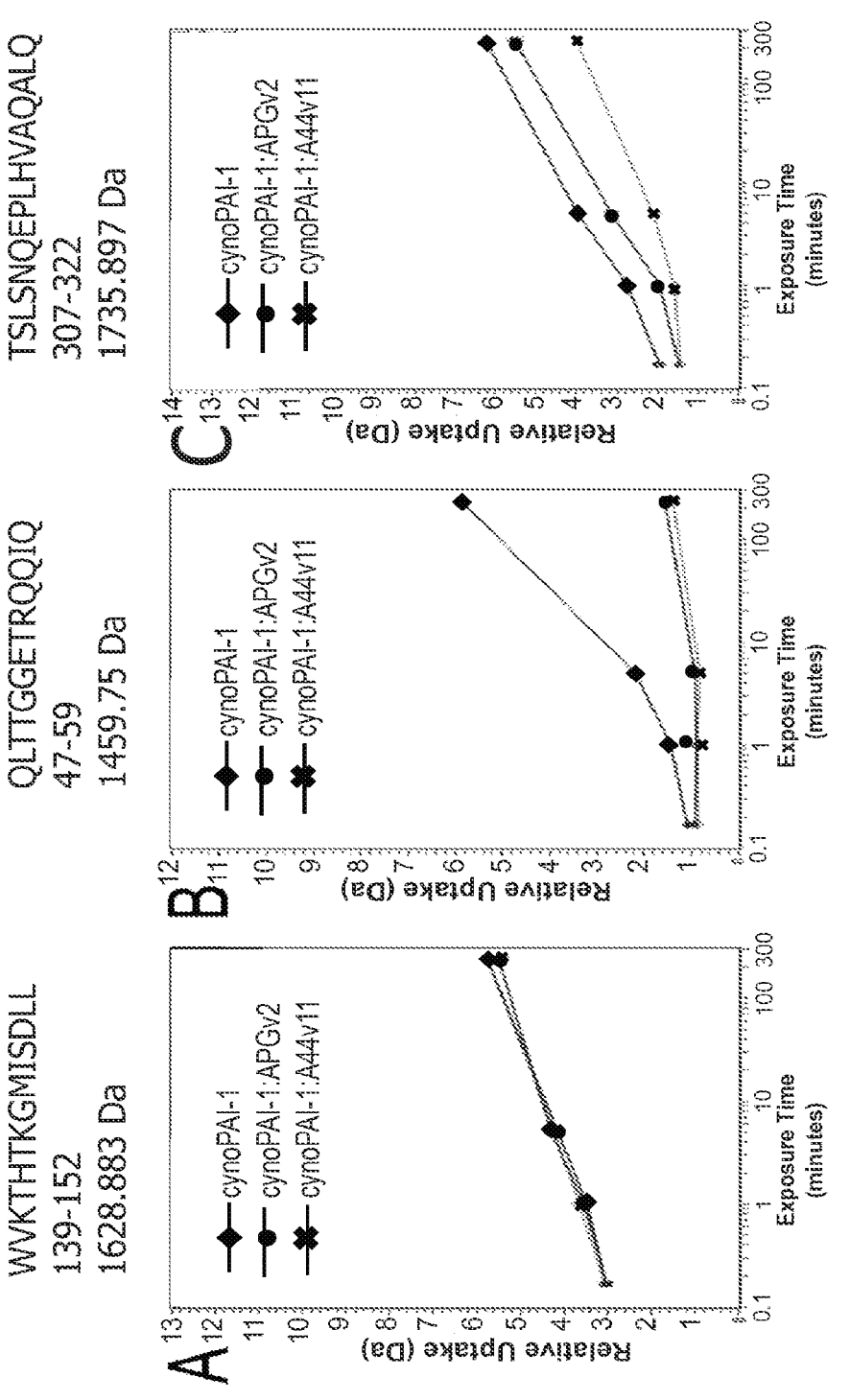
FIG. 49 depicts representative deuterium uptake plots for cyno-PAI-1 peptides in the unbound (circle lines), APGv2-bound (x-lines) and A44v11-bound (diamond lines) states. Residue ranges/positions are from SEQ ID NO: 162. (A) most of the peptic peptides showed no difference between cyno-PAI-1 alone or bound to either mAb. (B), peptides covering residues 44-64 showed similar protection from exchange in both mAb-bound states. (C), peptides incorporating residues 295-322 incorporate less deuterium in both mAb-bound states, however the magnitude of protection is greater for A44v11.

(FIG. 49(B)). In addition, peptides incorporating residues 295-322 also showed significant protection from exchange when bound to either A44v11 or APGv2 (FIG. 49(C)). For this region, the magnitude of protection was greater when cyno-PAI-1 was bound to A44v11 rather than APGv2 (See FIG. 49(C)). This indicates that A44v11 may provide greater overall protection from exchange than APGv2 when bound to cyno-PAI-1.

Comparison Studies:

For comparison studies, deuterium uptake was monitored for all of the 150 peptides generated from each of the three cyno-PAI-1 states. (See, generally, Wei, et al., *Drug Discovery Today*, 19(1): 95-102 (2014)). Data plots from each of the three states were compared to one another and a butterfly plot was generated to facilitate data interpretation (see, e.g., FIGS. 50(A), 51(A), and 52(A)). For each butterfly plot, the x-axis is the calculated peptide midpoint position, i, of each of the 150 peptides compared; the y-axis is the average relative fractional exchange (ratio).

Difference plots were also generated for each comparison between the cyno-PAI-1 states (see, e.g., FIGS. 50(B), 51(B), and 52(B)). In these plots, the deuterium uptake from one state is subtracted from the other and plotted similarly to the butterfly plots. The sum of the differences for each peptide is represented by a vertical bar. The horizontal dashed lines represent the values at which either individual measurements (+0.5 Da) or the sum of the differences (+1.1 Da) exceed the error of the measurement and can be considered as real differences between the two states. Additional details regarding this technique are disclosed in Houde D. et al., *J. Pharm. Sci.* 100(6):2071-86 (2011).

Figure 50:
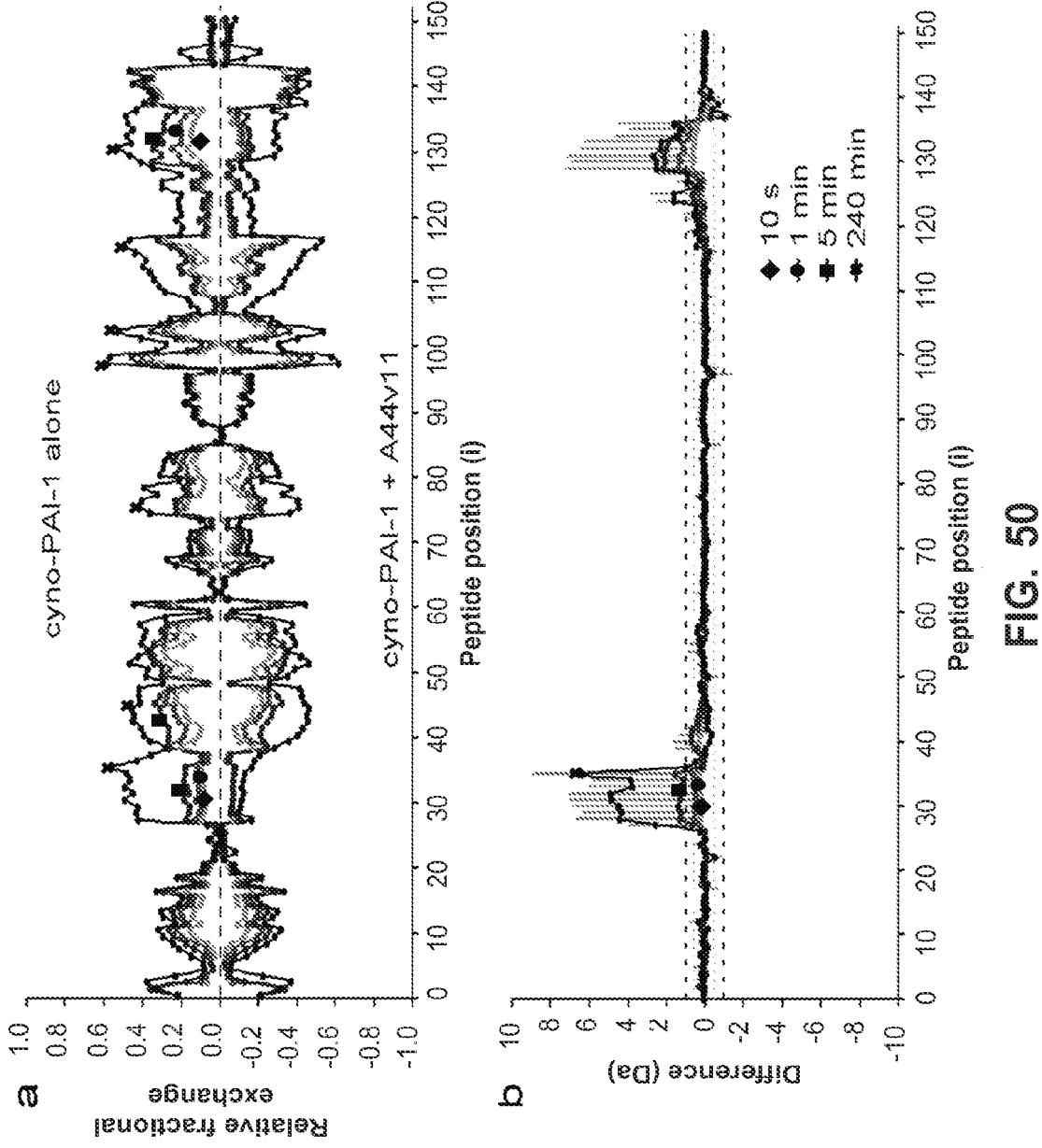
FIG. 50 depicts hydrogen/deuterium exchange (HDX) comparison of cyno-PAI-1 alone and bound to A44v11. (A), butterfly plot of the average relative fractional exchange with the unbound state above and the bound state below. The lines correspond to data acquired for the 10 sec, 1 min, 5 min, and 240 min time points. In (B), plot of the difference data (in daltons) from the above plot in (A) for cyno-PAI-1 alone or bound to A44v11.

First, cyno-PAI-1 alone was compared to the A44v11: cyno-PAI-1 bound state (FIG. 50). The butterfly plot for this comparison is shown in FIG. 50(A). The difference plot for this comparison is shown in FIG. 50(B). The observed differences between cyno-PAI-1 bound to A44v11 and free form cyno-PAI-1 are located primarily in two regions of cyno-PAI-1. One region is near the N-terminus (residues 44-64) and the other region is near the C-terminus (residues 307-321) (see FIG. 50(B)).

Figure 51:
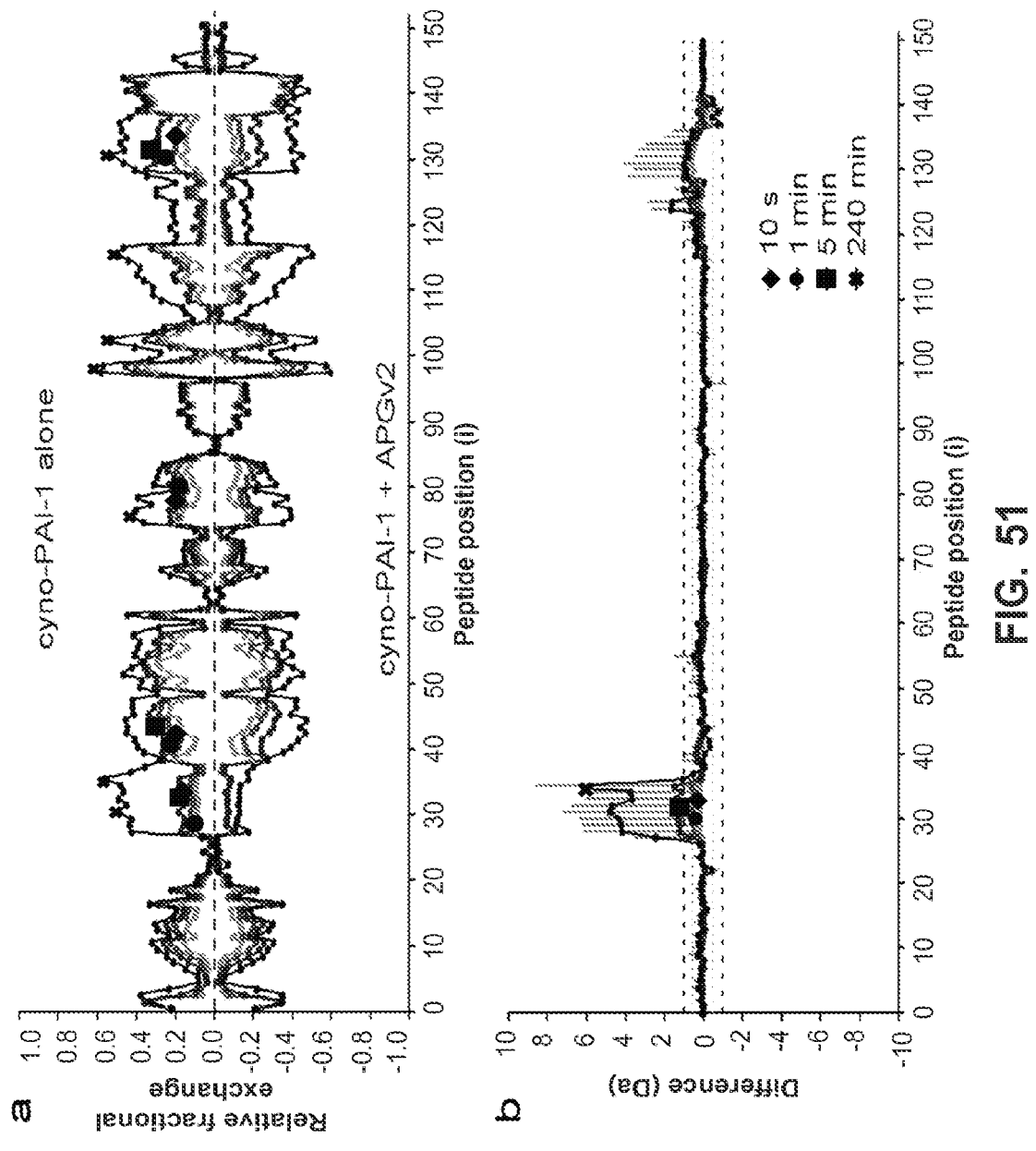
FIG. 51 depicts HDX comparison of cyno-PAI-1 alone and bound to APGv2. In (A), butterfly plot of the average relative fractional exchange with the unbound state above and the bound state below. The lines correspond to data acquired for the 10 sec, 1 min, 5 min and 240 min time points. In (B), plot of the difference data from panel (A) above for cyno-PAI-1 alone or bound to APGv2.

Next, cyno-PAI-1 alone was compared to the APGv2: cyno-PAI-1 bound state (FIG. 51). The butterfly plot for this comparison is shown in FIG. 51(A). The difference plot for this comparison is shown in FIG. 51(B). The observed differences between cyno-PAI-1 bound to APGv2 and free form cyno-PAI-1 are located primarily in two regions of cyno-PAI-1. One region is near the N-terminus and the other near the C-terminus, which is similar to the A44v11:cyno-PAI-1 result. The A44v11 and APGv2 complexes with cyno-PAI-1 share peptides showing reduced deuterium uptake when in the bound state, which may indicate that the epitopes for the two antibodies are similar.

Figure 52:
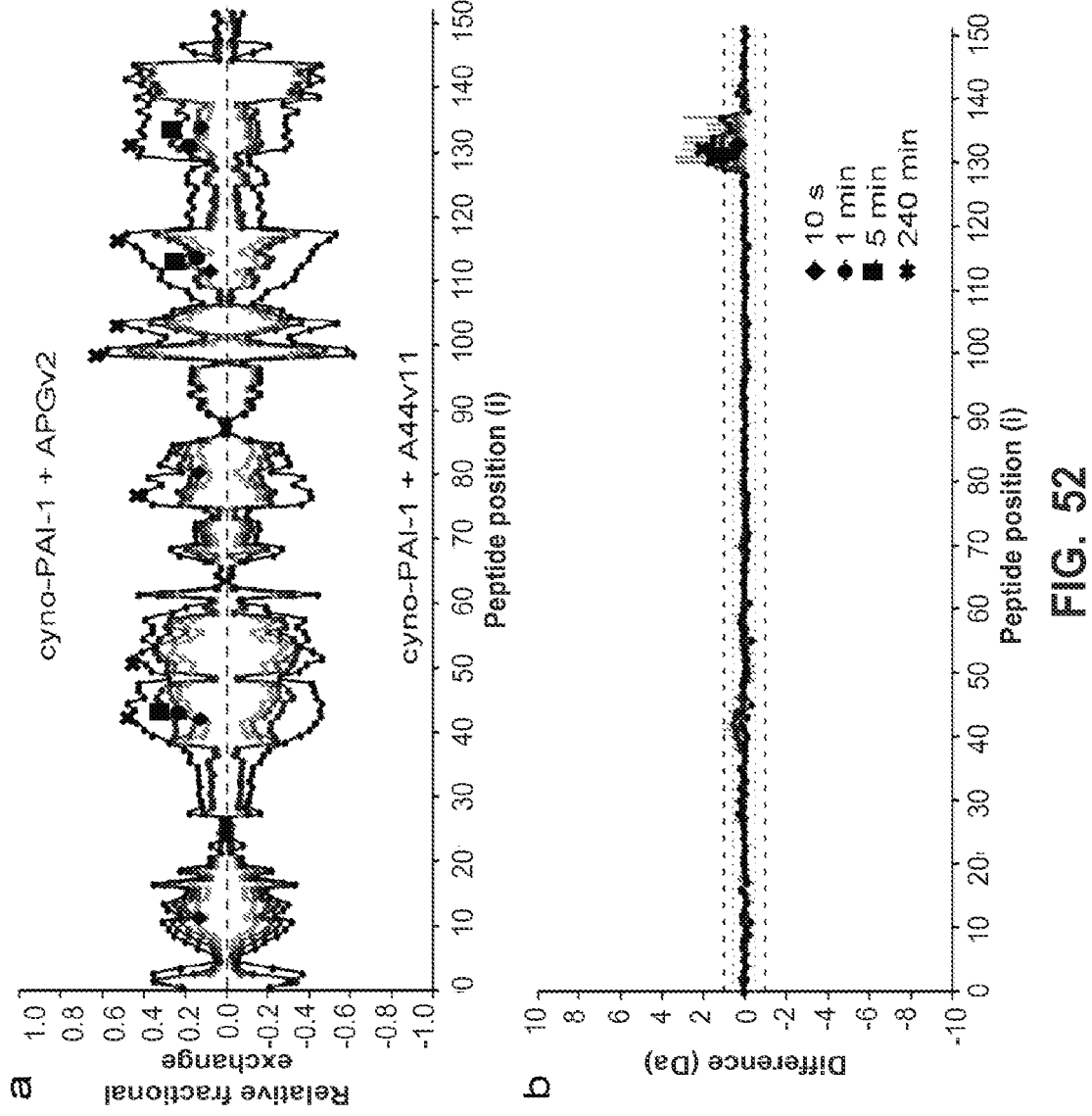
FIG. 52 depicts HDX comparison of cyno-PAI-1 bound to A44v11 and bound to APGv2. In (A), butterfly plot of the average relative fractional exchange with the APGv2 bound state above and the A44v11 bound state below. The lines correspond to data acquired for the 10 sec, 1 min, 5 min and 240 min time points. In (B), plot of the difference data from panel (A) above for cyno-PAI-1 bound to APGv2 or A44v11.

Finally, the two antibody-bound cyno-PAI-1 states were compared to each other (FIG. 52). The butterfly plot for this comparison is shown in FIG. 52(A). The difference plot for this comparison is shown in FIG. 52(B). The observed difference between A44v11:cyno-PAI-1 and APGv2:cyno-PAI-1 is located in the C-terminal region of cyno-PAI-1. (See FIG. 52(B)).

Example 25: Epitope Comparison of Antibodies A44v11 and APGv2

HDX MS was used to further define the epitopes of the A44v11 and APGv2 antibodies. By using the overlapping peptides generated in HDX MS, an antibody epitope can be refined to slightly better than peptide-level resolution (for example, see FIG. 48). The HDX MS data for the peptides which showed significant protection from exchange with A44V11 binding was further analyzed to determine the epitope for the cyno-PAI-1:A44v11 interaction. The HDX data for the A44V11 epitope of cyno-PAI-1 was found to be consistent with the epitope determined using the crystallography approach. The A44V11 epitope of cyno-PAI-1 identified using HDX MS appears in FIG. 53 (bold), and below in shorthand format:

```
                                              (SEQ ID NO: 159)
      T-T-G-G-E-T-R-Q-Q-I-Q;

(SEQ ID NO: 160)
      R-H-L;

(SEQ ID NO: 161)
      T-D-M-X-X-X-F-Q-A-D-F-T-S-L-S-N-Q-E-P-L-H-V
```

The HDX MS data for the cyno-PAI-1 peptides which showed significant protection from exchange with APGv2 binding was analyzed to further determine the epitope for the cyno-PAI-1:APGv2 interaction. The HDX MS epitope mapping data for A44v11 and APGv2 show that the epitopes are in the same region, as seen generally in FIG. 52. In the region of residues 307-321 the same peptides show protection in the antibody-bound state for both A44v11 and APGv2. However, the magnitude of protection is greater when cyno-PAI-1 is bound to A44v11 rather than APGv2 (see FIG. 49(C)). This finding is more apparent in FIG. 52(B), which depicts the difference peaks in the residue 307-321 region of cyno-PAI-1. This indicates that there are differences in the specific contacts made between cyno-PAI-1 and each of the A44V11 and APGv2 antibodies. Therefore, it appears that while the epitopes of both A44V11 and APGv2 are located in a similar region of PAI-1, the epitopes for each antibody are not the same.

---

What is claimed is:

1. An isolated nucleic acid encoding an amino acid sequence of an antibody, or an antigen-binding fragment thereof, that binds specifically to PA1-1, comprising:

(a) a heavy chain variable region comprising a heavy chain CDR1 region comprising the amino acid sequence of SEQ ID NO: 34, a heavy chain CDR2 region comprising the amino acid sequence of SEQ ID NO: 33, and a heavy chain CDR3 region comprising the amino acid sequence of SEQ ID NO: 32; and a light chain variable region comprising a light chain CDR1 region comprising the amino acid sequence of SEQ ID NO: 37, a light chain CDR2 region comprising the amino acid sequence of SEQ ID NO: 145 or SEQ ID NO: 36, and a light chain CDR3 region comprising the amino acid sequence of SEQ ID NO: 35; or (b) a heavy chain variable region comprising a heavy chain CDR1 region comprising the amino acid sequence of SEQ ID NO: 22, a heavy chain CDR2 region comprising the amino acid sequence of SEQ ID NO: 21, and a heavy chain CDR3 region comprising the amino acid sequence of SEQ ID NO: 20; and a light chain variable region comprising a light chain CDR1 region comprising the amino acid sequence of SEQ ID NO: 25, a light chain CDR2 region comprising the amino acid sequence of SEQ ID NO: 24, and a light chain CDR3 region comprising the amino acid sequence of SEQ ID NO: 23; or (c) a heavy chain variable region comprising a heavy chain CDR1 region comprising the amino acid sequence of SEQ ID NO: 28, a heavy chain CDR2 region comprising the amino acid sequence of SEQ ID NO: 27, and a heavy chain CDR3 region comprising the amino acid sequence of SEQ ID NO: 26; and a light chain variable region comprising a light chain CDR1 region comprising the amino acid sequence of SEQ ID NO: 31, a light chain CDR2 region comprising the amino acid sequence of SEQ ID NO: 30, and a light chain CDR3 region comprising the amino acid sequence of SEQ ID NO: 29; or (d) a heavy chain variable region comprising a heavy chain CDR1region comprising the amino acid sequence of SEQ ID NO: 40, a heavy chain CDR2 region comprising the amino acid sequence of SEQ ID NO: 39, and a heavy chain CDR3 region comprising the amino acid sequence of SEQ ID NO: 38; and a light chain variable region comprising a light chain CDR1 region comprising the amino acid sequence of SEQ ID NO: 43, a light chain CDR2 region comprising the amino acid sequence of SEQ ID NO: 42, and a light chain CDR3 region comprising the amino acid sequence of SEQ ID NO: 41; or (e) a heavy chain variable region comprising a heavy chain CDR 1region comprising the amino acid sequence of SEQ ID NO: 46, a heavy chain CDR2 region comprising the amino acid sequence of SEQ ID NO: 45, and a heavy chain CDR3 region comprising the amino acid sequence of SEQ ID NO: 44; and a light chain variable region comprising a light chain CDR1 region comprising the amino acid sequence of SEQ ID NO: 49, a light chain CDR2 region comprising the amino acid sequence of SEQ ID NO: 48, and a light chain CDR3 region comprising the amino acid sequence of SEQ ID NO: 47; or (f) a heavy chain variable region comprising a heavy chain CDR1region comprising the amino acid sequence of SEQ ID NO: 52, a heavy chain CDR2 region comprising the amino acid sequence of SEQ ID NO: 51, and a heavy chain CDR3 region comprising the amino acid sequence of SEQ ID NO: 50; and a light chain variable region comprising a light chain CDR1 region comprising the amino acid sequence of SEQ ID NO: 55, a light chain CDR2 region comprising the amino acid sequence of SEQ ID NO: 54, and a light chain CDR3 region comprising the amino acid sequence of SEQ ID NO: 53; or (g) a heavy chain variable region comprising a heavy chain CDR 1region comprising the amino acid sequence of SEQ ID NO: 58, a heavy chain CDR2 region comprising the amino acid sequence of SEQ ID NO: 57, and heavy chain CDR3 region comprising the amino acid sequence of SEQ ID NO: 56; and a light chain variable region comprising a light chain CDR1region comprising the amino acid sequence of SEQ ID NO: 61, a light chain CDR2 region comprising the amino acid sequence of SEQ ID NO: 60, and a light chain CDR3 region comprising the amino acid sequence of SEQ ID NO: 59; or (h) a heavy chain variable region comprising a heavy chain CDR1region comprising the amino acid sequence of SEQ ID NO: 64, a heavy chain CDR2 region comprising the amino acid sequence of SEQ ID NO: 63, and a heavy chain CDR3 region comprising the amino acid sequence of SEQ ID NO: 62; and a light chain variable region comprising a light chain CDR1 region comprising the amino acid sequence of SEQ ID NO: 67, a light chain CDR2 region comprising the amino acid sequence of SEQ ID NO: 66, and a light chain CDR3 region comprising the amino acid sequence of SEQ ID NO: 65; or (i) a heavy chain variable region comprising a heavy chain CDR1region comprising the amino acid sequence of SEQ ID NO: 70, a heavy chain CDR2 region comprising the amino acid sequence of SEQ ID NO: 69, and a heavy chain CDR3 region comprising the amino acid sequence of SEQ ID NO: 68; and a light chain variable region comprising a light chain CDR1 region comprising the amino acid sequence of SEQ ID NO: 73, a light chain CDR2 region comprising the amino acid sequence of SEQ ID NO: 72, and a light chain CDR3 region comprising the amino acid sequence of SEQ ID NO: 71; or (j) a heavy chain variable region comprising a heavy chain CDR1region comprising the amino acid sequence of SEQ ID NO: 76, heavy chain CDR2 region comprising the amino acid sequence of SEQ ID NO: 75, and a heavy chain CDR3 region comprising the amino acid sequence of SEQ ID NO: 74; and a light chain variable region comprising a light chain CDR1 region comprising the amino acid sequence of SEQ ID NO: 79, a light chain CDR2 region comprising the amino acid sequence of SEQ ID NO: 78, and a light chain CDR3 region comprising the amino acid sequence of SEQ ID NO: 77.

2. A recombinant expression vector comprising the nucleic acid of claim 1.

3. A host cell comprising the recombinant expression vector of claim 2.

4. A method of producing an antibody, or an antigen binding fragment thereof, that binds specifically to PAI-1, comprising culturing the host cell of claim 3 under conditions such that the antibody, or antigen binding fragment thereof, that binds specifically to PAI-1 is produced by the host cell.

5. The method of claim 4, wherein the antibody or antigen binding fragment thereof comprises:

a heavy chain variable region comprising a heavy chain CDR1 region comprising the amino acid sequence of SEQ ID NO: 34, a heavy chain CDR2 region comprising the amino acid sequence of SEQ ID NO: 33, and a heavy chain CDR3 region comprising the amino acid sequence of SEQ ID NO: 32; and a light chain variable region comprising a light chain CDR1 region comprising the amino acid sequence of SEQ ID NO: 37, a light chain CDR2 region comprising the amino acid sequence of SEQ ID NO: 145 or the amino acid sequence of SEQ ID NO: 36, and a light chain CDR3 region comprising the amino acid sequence of SEQ ID NO: 35.

6. The method of claim 5, wherein the antibody or antigen binding fragment thereof comprises:

a heavy chain variable region comprising a heavy chain CDR1 region comprising the amino acid sequence of SEQ ID NO: 22, a heavy chain CDR2 region comprising SEQ ID NO: 21, and a heavy chain CDR3 region comprising the amino acid sequence of SEQ ID NO: 20; and a light chain variable region comprising a light chain CDR1 region comprising the amino acid sequence of SEQ ID NO: 25, a light chain CDR2 region comprising the amino acid sequence of SEQ ID NO: 24, and a light chain CDR3 region comprising the amino acid sequence of SEQ ID NO: 23.

7. The method of claim 4, wherein the antibody or antigen binding fragment thereof comprises:

a heavy chain variable region comprising a heavy chain CDR1 region comprising the amino acid sequence of SEQ ID NO: 28, a heavy chain CDR2 region comprising the amino acid sequence of SEQ ID NO: 27, and a heavy chain CDR3 region comprising the amino acid sequence of SEQ ID NO: 26; and a light chain variable region comprising a light chain CDR1 region comprising the amino acid sequence of SEQ ID NO: 31, a light chain CDR2 region comprising the amino acid sequence of SEQ ID NO: 30, and a light chain CDR3 region comprising the amino acid sequence of SEQ ID NO: 29.

8. The method of claim 4, wherein the antibody or antigen binding fragment thereof comprises:

a heavy chain variable region comprising a heavy chain CDR1 region comprising the amino acid sequence of SEQ ID NO: 40, a heavy chain CDR2 region comprising the amino acid sequence of SEQ ID NO: 39, and a heavy chain CDR3 region comprising the amino acid sequence of SEQ ID NO: 38; and a light chain variable region comprising a light chain CDR1 region comprising the amino acid sequence of SEQ ID NO: 43, a light chain CDR2 region comprising the amino acid sequence of SEQ ID NO: 42, and a light chain CDR3 region comprising the amino acid sequence of SEQ ID NO: 41.

9. The method of claim 4, wherein the antibody or antigen binding fragment thereof comprises:

a heavy chain variable region comprising a heavy chain CDR1 region comprising the amino acid sequence of SEQ ID NO: 46, a heavy chain CDR2 region comprising the amino acid sequence of SEQ ID NO: 45, and a heavy chain CDR3 region comprising the amino acid sequence of SEQ ID NO: 44; and a light chain variable region comprising a light chain CDR1 region comprising the amino acid sequence of SEQ ID NO: 49, a light chain CDR2 region comprising the amino acid sequence of SEQ ID NO: 48, and a light chain CDR3 region comprising the amino acid sequence of SEQ ID NO: 47.

10. The method of claim 4, wherein the antibody or antigen binding fragment thereof comprises:

a heavy chain variable region comprising a heavy chain CDR1 region comprising the amino acid sequence of SEQ ID NO: 52, a heavy chain CDR2 region comprising the amino acid sequence of SEQ ID NO: 51, and a heavy chain CDR3 region comprising the amino acid sequence of SEQ ID NO: 50; and a light chain variable region comprising a light chain CDR1 region comprising the amino acid sequence of SEQ ID NO: 55, a light chain CDR2 region comprising the amino acid sequence of SEQ ID NO: 54, and a light chain CDR3 region comprising the amino acid sequence of SEQ ID NO: 53.

11. The method of claim 4, wherein the antibody or antigen binding fragment thereof comprises:

a heavy chain variable region comprising a heavy chain CDR1 region comprising the amino acid sequence of SEQ ID NO: 58, a heavy chain CDR2 region comprising the amino acid sequence of SEQ ID NO: 57, and a heavy chain CDR3 region comprising the amino acid sequence of SEQ ID NO: 56; and a light chain variable region comprising a light chain CDR1 region comprising the amino acid sequence of SEQ ID NO: 61, a light chain CDR2 region comprising the amino acid sequence of SEQ ID NO: 60, and a light chain CDR3 region comprising the amino acid sequence of SEQ ID NO: 59.

12. The method of claim 4, wherein the antibody or antigen binding fragment thereof comprises:

a heavy chain variable region comprising a heavy chain CDR1 region comprising the amino acid sequence of SEQ ID NO: 64, a heavy chain CDR2 region comprising the amino acid sequence of SEQ ID NO: 63, and a heavy chain CDR3 region comprising the amino acid sequence of SEQ ID NO: 62; and a light chain variable region comprising a light chain CDR1 region comprising the amino acid sequence of SEQ ID NO: 67, a light chain CDR2 region comprising the amino acid sequence of SEQ ID NO: 66, and a light chain CDR3 region comprising the amino acid sequence of SEQ ID NO: 65.

13. The method of claim 4, wherein the antibody or antigen binding fragment thereof comprises:

a heavy chain variable region comprising a heavy chain CDR1 region comprising the amino acid sequence of SEQ ID NO: 70, a heavy chain CDR2 region comprising the amino acid sequence of SEQ ID NO: 69, and a heavy chain CDR3 region comprising the amino acid sequence of SEQ ID NO: 68; and a light chain variable region comprising a light chain CDR1 region comprising the amino acid sequence of SEQ ID NO: 73, a light chain CDR2 region comprising the amino acid sequence of SEQ ID NO: 72, and a light chain CDR3 region comprising the amino acid sequence of SEQ ID NO: 71.

14. The method of claim 4, wherein the antibody or antigen binding fragment thereof comprises:

a heavy chain variable region comprising a heavy chain CDR1 region comprising the amino acid sequence of SEQ ID NO: 76, a heavy chain CDR2 region comprising the amino acid sequence of SEQ ID NO: 75, and a heavy chain CDR3 region comprising the amino acid sequence of SEQ ID NO: 74; and a light chain variable region comprising a light chain CDR1 region comprising the amino acid sequence of SEQ ID NO: 79, a light chain CDR2 region comprising the amino acid sequence of SEQ ID NO: 78, and a light chain CDR3 region comprising the amino acid sequence of SEQ ID NO: 77.

15. An isolated nucleic acid encoding an amino acid sequence of an antibody, or an antigen-binding fragment thereof, that binds specifically to PA1-1, comprising:

(a) a heavy chain having a heavy chain variable region comprising the amino acid sequence of SEQ ID NO: 82, and a light chain having a light chain variable region comprising the amino acid sequence of SEQ ID NO: 91; or (b) a heavy chain having a heavy chain variable region comprising the amino acid sequence of SEQ ID NO: 83, and a light chain having a light chain variable region comprising the amino acid sequence of SEQ ID NO: 92; or (c) a heavy chain having a heavy chain variable region comprising the amino acid sequence of SEQ ID NO:

84, and a light chain having a light chain variable region comprising the amino acid sequence of SEQ ID NO: 93; or (d) a heavy chain having a heavy chain variable region comprising the amino acid sequence of SEQ ID NO: 85, and a light chain having a light chain variable region comprising the amino acid sequence of SEQ ID NO: 91; or (e) a heavy chain having a heavy chain variable region comprising the amino acid sequence of SEQ ID NO: 85, and a light chain having a light chain variable region comprising the amino acid sequence of SEQ ID NO: 93; or (f) a heavy chain having a heavy chain variable region comprising the amino acid sequence of SEQ ID NO: 86, and a light chain having a light chain variable region comprising the amino acid sequence of SEQ ID NO: 94; or (g) a heavy chain having a heavy chain variable region comprising the amino acid sequence of SEQ ID NO: 87, and a light chain having a light chain variable region comprising the amino acid sequence of SEQ ID NO: 95; or (h) a heavy chain having a heavy chain variable region comprising the amino acid sequence of SEQ ID NO: 88, and a light chain having a light chain variable region comprising the amino acid sequence of SEQ ID NO: 96; or (i) a heavy chain having a heavy chain variable region comprising the amino acid sequence of SEQ ID NO: 89, and a light chain having a light chain variable region comprising the amino acid sequence of SEQ ID NO: 97; or (j) a heavy chain having a heavy chain variable region comprising the amino acid sequence of SEQ ID NO: 90, and a light chain having a light chain variable region comprising the amino acid sequence of SEQ ID NO: 98; or (k) a heavy chain having a heavy chain variable region comprising the amino acid sequence of SEQ ID NO: 86, and a light chain having a light chain variable region comprising the amino acid sequence of SEQ ID NO: 95; or (l) a heavy chain having a heavy chain variable region comprising the amino acid sequence of SEQ ID NO: 89, and a light chain having a light chain variable region comprising the amino acid sequence of SEQ ID NO: 93; or (m) a heavy chain having a heavy chain variable region comprising the amino acid sequence of SEQ ID NO: 89, and a light chain having a light chain variable region comprising the amino acid sequence of SEQ ID NO: 95; or (n) a heavy chain having a heavy chain variable region comprising the amino acid sequence of SEQ ID NO: 86, and a light chain having a light chain variable region comprising the amino acid sequence of SEQ ID NO: 93.

16. A recombinant expression vector comprising the nucleic acid of claim 15.

17. A host cell comprising the recombinant expression vector of claim 16.

18. A method of producing an antibody, or an antigen binding fragment thereof, that binds specifically to PAI-1, comprising culturing the host cell of claim 17 under conditions such that the antibody, or antigen binding fragment thereof, that binds specifically to PAI-1 is produced by the host cell.

19. The method of claim 18, wherein the antibody or antigen binding fragment thereof comprises:

a heavy chain having a heavy chain variable region comprising the amino acid sequence of SEQ ID NO: 86; and a light chain having a light chain variable region comprising the amino acid sequence of SEQ ID NO: 93.

* * * * *